(12) United States Patent
Sanmartin

(10) Patent No.: US 12,043,436 B2
(45) Date of Patent: *Jul. 23, 2024

(54) MODULAR ASEPTIC PRODUCTION SYSTEM

(71) Applicant: GLAXOSMITHKLINE INTELLECTUAL PROPERTY DEVELOPMENT LIMITED, Middlesex (GB)

(72) Inventor: Francesco Sanmartin, King of Prussia, PA (US)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/896,538

(22) Filed: Aug. 26, 2022

(65) Prior Publication Data

US 2023/0050874 A1    Feb. 16, 2023

Related U.S. Application Data

(63) Continuation of application No. 16/770,981, filed as application No. PCT/IB2018/059882 on Dec. 11, 2018, now Pat. No. 11,434,032.

(Continued)

(51) Int. Cl.
*A61L 2/04* (2006.01)
*B65B 3/00* (2006.01)
(Continued)

(52) U.S. Cl.
CPC ............... *B65B 59/04* (2013.01); *A61L 2/04* (2013.01); *B65B 3/003* (2013.01); *B65B 7/2821* (2013.01);
(Continued)

(58) Field of Classification Search
CPC ....... B65B 59/04; B65B 3/003; B65B 7/2821; B65B 43/42; B65B 55/025; A61L 2/04;
(Continued)

(56) References Cited

U.S. PATENT DOCUMENTS 2,057,367 A    10/1936  Carroll
3,082,632 A     3/1963  Paul
(Continued)

FOREIGN PATENT DOCUMENTS

DE    3209790 A1    9/1983
DE    3210964 A1    10/1983
(Continued)

OTHER PUBLICATIONS

C-Flex Bearing Corp—Pivot Bearings Brochure; Pivot Bearing Design Guide.

(Continued)

*Primary Examiner* — Timothy C Cleveland

(57) ABSTRACT

A modular production system including a plurality of production modules connected in a linear series to form a production tunnel, and collectively defining a production channel, and wherein at least one fluid inlet port defined along the production tunnel, said inlet port is in fluid communication with a pressurized fluid source, whereby influx of fluid from said fluid source through said fluid inlet port acts to maintain the fluid pressure within the production channel at a higher pressure than the atmospheric pressure outside of the production tunnel; and wherein one of said production modules positioned between said proximal-most and distal-most production modules comprises a depyrogenator and/or sterilization module, comprising a transparent tubular body, and an irradiation source positioned external to said transparent tubular body, said irradiation source capable of heating the internal environment of the depyrogenation (Continued)

and/or sterilization module to a temperature sufficient to depyrogenate or sterilize articles passing therethrough, and associated processes.

18 Claims, 61 Drawing Sheets

Related U.S. Application Data

(60) Provisional application No. 62/597,310, filed on Dec. 11, 2017.

(51) Int. Cl.
*B65B 7/28* (2006.01)
*B65B 43/42* (2006.01)
*B65B 55/02* (2006.01)
*B65B 59/04* (2006.01)

(52) U.S. Cl.
CPC ............ *B65B 43/42* (2013.01); *B65B 55/025* (2013.01); *A61L 2202/21* (2013.01)

(58) Field of Classification Search
CPC ... A61L 2/08; A61L 2/085; A61L 2/12; A61L 2/24; A61L 2202/21; A61L 2202/23
See application file for complete search history.

(56) References Cited

U.S. PATENT DOCUMENTS

| | | |
|---|---|---|
| 3,289,698 A | 12/1966 | Pierre et al. |
| 3,451,532 A | 6/1969 | Manterfield |
| 3,582,054 A | 6/1971 | Beck |
| 3,623,712 A | 11/1971 | McNeilly et al. |
| 3,656,720 A | 4/1972 | Westeren et al. |
| 3,666,086 A | 5/1972 | Brockmann |
| 3,682,208 A | 8/1972 | Fedi et al. |
| 3,811,825 A | 5/1974 | Enderlein |
| 3,871,534 A | 3/1975 | Bursk |
| 4,050,571 A | 9/1977 | Kushigian |
| 4,201,208 A | 5/1980 | Cambio, Jr. |
| 4,330,262 A | 5/1982 | Kranzl et al. |
| 4,407,406 A | 10/1983 | Norris |
| 4,669,938 A | 6/1987 | Hayward |
| 4,683,763 A | 8/1987 | Balter |
| 4,698,486 A | 10/1987 | Sheets |
| 4,803,948 A | 2/1989 | Nakagawa et al. |
| 4,857,689 A | 8/1989 | Lee |
| 4,885,947 A | 12/1989 | Balter et al. |
| 4,909,185 A | 3/1990 | Aldridge et al. |
| 4,943,234 A | 7/1990 | Sohlbrand |
| 5,054,614 A | 11/1991 | Reiss et al. |
| 5,064,614 A | 11/1991 | Reiss et al. |
| 5,108,792 A | 4/1992 | Anderson et al. |
| 5,130,093 A | 7/1992 | Wieczorek |
| 5,139,318 A | 8/1992 | Broxup |
| 5,243,867 A | 9/1993 | Polyak |
| 5,352,210 A | 10/1994 | Marrucchi |
| 5,368,648 A | 11/1994 | Sekizuka |
| 5,416,967 A | 5/1995 | Cress |
| 5,439,655 A | 8/1995 | Fedegari |
| 5,447,699 A | 9/1995 | Papciak et al. |
| 5,460,439 A | 10/1995 | Jennrich et al. |
| 5,481,088 A | 1/1996 | Peck et al. |
| 5,533,736 A | 7/1996 | Yamaga |
| 5,783,156 A | 7/1998 | Renzi et al. |
| 5,790,751 A | 8/1998 | Gronet et al. |
| 5,853,207 A | 12/1998 | Martin et al. |
| 5,892,200 A | 4/1999 | Kendall et al. |
| 5,904,065 A | 5/1999 | Koller et al. |
| 5,943,915 A | 8/1999 | Kato |
| 6,119,537 A | 9/2000 | Jost |
| 6,173,116 B1 | 1/2001 | Roozeboom et al. |
| 6,251,756 B1 | 6/2001 | Horzel et al. |
| 6,308,749 B1 | 10/2001 | Brossard et al. |
| 6,364,093 B1 | 4/2002 | LaBolt |
| 6,537,509 B2 | 3/2003 | Saint-Martin et al. |
| 6,659,115 B1 | 12/2003 | Wieczorek |
| 6,705,457 B2 | 3/2004 | Biro et al. |
| 6,749,808 B1 | 6/2004 | Huynen et al. |
| 7,938,454 B2 | 5/2011 | Buchanan et al. |
| 8,501,110 B2 | 8/2013 | Windsheimer |
| 8,517,998 B2 | 8/2013 | Proulx et al. |
| 8,662,484 B2 | 3/2014 | Valois |
| 8,837,924 B2 | 9/2014 | Tsunekawa et al. |
| 9,034,194 B2 | 5/2015 | Zadyraka et al. |
| 9,199,070 B2 | 12/2015 | Wegener et al. |
| 11,434,032 B2 * | 9/2022 | Sanmartin ............... B65B 3/003 |
| 2002/0015672 A1 | 2/2002 | Saint-Martin et al. |
| 2003/0155846 A1 | 8/2003 | Sacca |
| 2005/0034850 A1 | 2/2005 | Yoshimura et al. |
| 2005/0168117 A1 | 8/2005 | Porret |
| 2006/0071375 A1 | 4/2006 | Arai et al. |
| 2006/0246390 A1 | 11/2006 | Aoki et al. |
| 2006/0291833 A1 | 12/2006 | Timans |
| 2007/0095426 A1 | 5/2007 | Saint-Martin et al. |
| 2008/0149218 A1 | 6/2008 | Netzhammer |
| 2010/0219355 A1 | 9/2010 | Linow |
| 2010/0303389 A1 | 12/2010 | Armau et al. |
| 2011/0123178 A1 | 5/2011 | Aderhold et al. |
| 2012/0090268 A1 | 4/2012 | Krauss et al. |
| 2012/0267367 A1 | 10/2012 | Armau et al. |
| 2013/0153201 A1 | 6/2013 | Erickson et al. |
| 2013/0167442 A1 | 7/2013 | Sacca |
| 2013/0283733 A1 | 10/2013 | Py |
| 2014/0230963 A1 | 8/2014 | Simon et al. |
| 2014/0238159 A1 | 8/2014 | DiMarco et al. |
| 2014/0291995 A1 | 10/2014 | Chavrot |
| 2016/0272347 A1 | 9/2016 | Procyshyn et al. |
| 2016/0354772 A1 | 12/2016 | Nodin |

FOREIGN PATENT DOCUMENTS

| | | |
|---|---|---|
| DE | 2830589 C2 | 4/1985 |
| DE | 3510286 A1 | 9/1986 |
| DE | 3734830 A1 | 4/1989 |
| DE | 4409659 C2 | 5/1997 |
| DE | 19857142 A1 | 6/2000 |
| EP | 0312022 A2 | 4/1989 |
| EP | 0408093 B1 | 1/1991 |
| EP | 0486756 A1 | 5/1992 |
| EP | 0992246 A2 | 4/2000 |
| EP | 1593622 B1 | 7/2009 |
| EP | 2420450 A1 | 2/2012 |
| EP | 2502636 A1 | 9/2012 |
| EP | 2823828 A1 | 1/2015 |
| EP | 2881124 B1 | 1/2018 |
| FR | 2782071 B1 | 11/2000 |
| FR | 2820118 A1 | 8/2002 |
| FR | 2853552 B1 | 2/2008 |
| IT | 1230331 B | 10/1991 |
| JP | H01-190361 A | 7/1989 |
| JP | H5-57001 A | 3/1993 |
| JP | 2006115809 | 5/2006 |
| JP | 2011-230832 A | 11/2011 |
| JP | 2013-508136 A | 3/2013 |
| WO | WO1983003235 A1 | 9/1983 |
| WO | 2008022723 A1 | 2/2008 |
| WO | 2010040383 A1 | 4/2010 |
| WO | 2011/048349 A1 | 4/2011 |
| WO | 2012087981 A1 | 6/2012 |
| WO | 2014076208 A1 | 5/2014 |
| WO | 2016097265 A1 | 6/2016 |
| WO | 2016198391 A1 | 12/2016 |
| WO | 2017021125 A1 | 2/2017 |

OTHER PUBLICATIONS

EXSEV—Ceramic Bearing Catalog.
Mark Sullivan—Flexures (San Jose' Universities; downloaded from internet).

(56) References Cited

OTHER PUBLICATIONS

Mott Corp—Porous Metal General Info; Sterilizing Grade Porous Metal.
NSK—SPACEA Bearings for Special Environment.
English Abstract of JP H5-57001 A, Houshin Kagaku Sangiyoushiyo, Mar. 9, 1993.
English Abstract of JP 2011-230832 A, Shibuya Kogyo Co, Ltd., Nov. 17, 2011.

* cited by examiner

MODULAR ASEPTIC PRODUCTION SYSTEM

CROSS-REFERENCE TO RELATED APPLICATIONS

This application is filed as a Continuation of U.S. application Ser. No. 16/770,981, filed on Jun. 9, 2020, which is a 371 National Phase Application of International Application No. PCT/IB2018/059882 filed Dec. 11, 2018, which claims priority of U.S. Provisional Application No. 62/597,310 filed Dec. 11, 2017.

FIELD OF THE INVENTION

The present invention relates to a modular dry heat, aseptic production system useful in the production of products, such as containers filled with a pharmaceutical material under controlled environmental conditions, to production modules thereof, to related subcomponents, and processes and methods relating thereto. In a representative embodiment, the modular production system takes the form of an aseptic filling system for the depyrogenation and/or sterilization of articles, such as vials, filling such articles with a material, such as a pharmaceutical formulation, and sealing such filled articles in an integrated production tunnel; to component modules of such a system, and subcomponents thereof, and to related processes and methods.

BACKGROUND TO THE INVENTION

Pharmaceutical manufacturing may involve the elimination and/or neutralization of microbial contaminants and fever-inducing agents (pyrogens) from product components during the production process, as well as the preservation of a controlled production environment. Manufacturing facilities incorporate myriad systems to assure the creation and maintenance of such conditions, including quality assurance systems which monitor the production line and products being produced thereon. Such industrial manufacturing lines tend to be large, complex, expensive, and require large amounts of energy to operate.

In the manufacture of filled containers, a transport system is required to move containers through a production cycle that may include such processes as container sterilization/depyrogenation, pre-filling conditioning, filling with a given material, and sealing. These various processes are usually performed by different machines organized in lines that may be installed within rooms or different pharmaceutical grades (i.e., A, B, C, etc.) according to Good Manufacturing Practices (GMP). Such systems occupy warehouse sized spaces. Some may occupy one or more floors of such a facility. In the manufacture of vials of injectable pharmaceuticals, for instance, container transport systems are employed which involve complex conveyors, racking systems, and drive mechanisms inside a single machine and connect one machine to another.

The product sterilization/depyrogenation systems used in these aseptic production facilities may use ovens or tunnels to heat or otherwise irradiate the containers; a process which requires significant amounts of energy. Containers may also be exposed to sterilizing fluids (i.e., sterile, saturated steam in autoclaves), the distribution of which adds further complexity to such a system. The sterilized and/or pyrogen free containers may then be cooled in lower temperature environments in a cooling region of the line, prior to being moved through a further filling proceeding station, after which the filled container is sealed. These sealed containers, may then undergo further processing, such as labelling, packaging, etc.

During the sterilization/depyrogenation, pre-filling conditioning, filling, and sealing processes, industrial aseptic manufacturing demands that a sterile environment be maintained. The creation and preservation of such an environment involves attention to numerous factors, including product and equipment containment in an isolated environment, and air quality amongst others.

To establish and maintain such environments, large, complex and expensive heating, ventilation and air conditioning (HVAC) systems are required. Such filtration and air conditioning equipment occupy large amounts of physical space. Further, it tends to be expensive to install and maintain, and have high energy demands and are therefore expensive to operate. The airflow (or other gas) entering the systems may be pre-filtered, to assure impurities are removed, and re-filtered during use and recirculated to assure any particulate matter generated by the production equipment or other foreign materials within such system are removed (double filtration/undergoing double filtration process).

Processing of the articles in such production facilities may be conducted in closed, carefully maintained environments. These may involve clean rooms and sealed environmental systems. Such facilities require highly specialized equipment. Containment and environmental control are each very complex undertakings. Areas may include air lock systems, which allow operators gowned in environmentally sealed suits to enter through pressurized environments. In some instances, equipment may be enclosed in sealed housings fitted with windows, where operators access the contents thereof via access ports with long-sleeved gloves sealingly fitted thereover.

The transport systems employed to move containers in such production lines often employ conveyor belts or other transport systems, which involve frictionally interacting components. Such frictionally operating systems may undesirably create particulate ("non-viable") matter which is released into the contained environment, due to the abrasion of materials from frictionally engaged components and might end up inside the vial or container being filled. The problem of particulate generation is generally addressed by providing a full coverage of the vial/container path with a double HEPA filtered laminar flow which provides a curtain of clean air around the vial/container and keeps away the particulates generated in any part of the system. Further isolation is possible, but also adds to the complexity and expense of the containment and environmental controls involved.

The sterilization/depyrogenation process itself may involve heating ovens, tunnels or irradiation chambers, which heat or irradiate the internal environment of the sterilization or depyrogenation region of the facility to very high temperatures. This may involve very specialized engineering and technologies, having high energy demands and capital expense.

Large complex facilities typically involve longer periods of time to bring the system to production readiness, as each subsystem is sterilized and brought into operational condition. This warm-up period allows the requisite temperatures in the sterilization/depyrogenation systems to be achieved and the sterility of the line to be assured prior to commencement of article production. Substantial profit loss in terms of lost opportunity, is also found in the periods of time required to bring the equipment on-line, and the frequency and duration of down time required to maintain equipment. A production line experiencing high frictional wear, may require more frequent service and repair. Moreover, the time required to repair the equipment must take into account the complexity of the machinery involved; complex production equipment generally takes significantly longer to repair than a less complex system. Coupling these factors, with a longer period of time required to bring the complex production systems on line, and opportunity costs increase with longer down times, are disadvantages associated with complex production systems.

Further challenges presented by such production systems are that they are not readily scalable to smaller batch production levels, to relocation of production lines, nor to easy repurposing if production demands change.

The present invention seeks to address one or more of these disadvantages by providing a relatively uncomplicated modular production system, which provides one or more of the following potential advantages: reduced HVAC and air filtration needs; lowered required equipment footprint; cost advantages in terms of capital expenditures; easier maintenance; lower energy usage; and/or other benefits which will be apparent to those of ordinary skill based on the following disclosure.

SUMMARY OF THE INVENTION

The present invention relates to a modular production system, in modules used in such a system, and in components useful in and in relation to such modules, including various processes related thereto. The modular production system possesses a number of inventive aspects, including the individual functional modules, various subcomponents of the modules, assemblies of multiple modules to form production lines, to processes performed in a module or in multiple modules, and to the articles produced thereby.

In the specific embodiments described below, the modular production system is assembled as an aseptic filling system, capable of, for example: loading empty containers into the internal transport system within the production line; depyrogenating and/or sterilizing such containers; cooling the containers to a desired degree; filling the containers with one or more materials, for example, fluids, e.g., gases or liquids, medicament formulations in fluid (e.g. liquid suspensions or solutions) or solid (e.g., micronized, spray dried, or lyophilized medicament powders, or compositions) form, or other articles of manufacture; sealing filled containers with a closure (e.g., a cap compressed into an opening in the container, a seal over an opening of the container, a crimp around a portion of the container effecting a seal, or other cover); and offloading the filled and sealed sterile container.

Each module in the modular production system forms a functional subunit and includes a housing enclosing an interior cavity, and these individual module housings may be connected in series, such that the interiors of individual housings are interconnected to form an elongate tunnel arrangement.

An internal transport mechanism within several or each module may be physically or operationally coupled such that the transport systems in different modules can be operated in a synchronized fashion through this production tunnel. This synchronization of the transport systems in multiple modules allows for the coordinated movement of a moveable transport surface to precisely move articles through the production tunnel. This allows the passage of articles through each serially connected module of the assembled modular production system, exposing the articles serially to the functionality of each module. Thus, containers, such as vials, may be brought into the proximal end of the assembled production tunnel, undergo processing, such as depyrogenation and/or sterilization, subsequent cooling, filling, sealing/closure, or other desired task, within the regulated internal environment within the production tunnel.

Regulation of airflow into and from the interior of the production tunnel allows for precise control of the environment within a given module or region of the production tunnel. The conditions within the module interior are controllable, in terms of, for example, the gas content, relative pressure, temperature, and directional airflow therethrough. Generally, the pressure inside the tunnel should be different and measurable compared to the outside environment (atmospheric). Pressure may vary across the machine inside each section. Differences in pressure may not be easily measurable, but may be detected (e.g., by employing a tracer (e.g., smoke)) that will indicate the direction of the air flow and the general pressure gradient.

In contrast to existing large warehouse-like clean production facilities an industrial manufacturing lines, the system of the present invention provides significant advantages in lower expense and complexity. Modules are comparatively inexpensive, lowering equipment costs. The physical footprint of the system is a fraction of existing commercial systems, thus reducing facility square footage fixed costs. The simple construction allows for reduced maintenance costs, and reduced energy requirements of in comparison to existing commercial systems.

As the production system uses multiple module types, it affords great manufacturing flexibility. Modules may be arranged to achieve the needed process parameters. They may be rearranged when production needs change. A given module may be extracted from an assembled system and substituted with a different module type. Increased production may be achieved simply by employing a plurality of such production tunnels, operating in parallel.

These advantages in production and operational cost, scale, flexibility allow the system to employed for research lab purposes, while the industrialized standard to which the modules are designed accommodate production scales for clinical batch quantities, and multiple production systems may be constructed and operated in parallel to provide large-scale commercial manufacturing. In this aspect of the invention, while the output of one modular production system may produce 1/nth of the output of a warehouse sized facility, the significantly lower costs, size, and footprint of the modular production system, allows the use of "n" modular production systems to be employed while still being less expensive to build, operate and maintain.

An additional potential benefit to this modular system is that it provides great flexibility and adaptability. Modules may be mixed and matched depending on need, offering an advantage of adaptability. For example, a modular system designed to meter liquids into containers may be refitted to fill powders into the same container type by merely disconnecting the liquid filling module from the line and replacing it, for example with a powder filling (dosating) module.

A still further potential benefit includes that the modular production assembly and/or aseptic filling system can be entirely sterilized by dry heat. Size reduction and careful material selection are all necessary to sterilize the entire machine with dry heat (180-200° C.). The machine can be heated with any suitable device: irradiation, hot air, strip heaters etc. just by enclosing it in a lightweight and removable insulated envelop. Typically, other machines or isolators on the market can only use Vaporized Hydrogen Peroxide (VHP), which will not be accepted by regulators, such as the US Food and Drug Agency, as a sterilizing agent (just a "sanitizer", cannot achieve sterilization). As such, dry heat sterilization allows the present invention to achieve surprisingly/unexpectedly high levels of sterility/freedom of pyrogenic material assurance.

A further potential benefit is the provision of a new frictionless transport that reduces the size of the machine, eliminating the need a provide vast amounts of air to protect the critical items (vials, product, stoppers) from non-viable particles generated in the system, usually by traditional transport mechanisms.

By careful choice of materials, aspects of the invention enable one to sterilize with dry-heat the entire machine, achieving a high level of sterility assurance. Particularly, the small size of the system reduces the amount of energy and time required to achieve dry heat sterilization.

The frictionless transport system and ability to employ dry heat sterilization, allow for the elimination of unidirectional Air Flow (UDAF) employed in the standard machines, which is traditionally used to keep away the non-viable particles, but also the viable particles (microbes/spores) that might be present in the critical area. In the system of the present invention, such viable particles are inactivated by dry heat sterilization, and air exiting from the system prevents such viable particle ingress.

These and other advantages will be apparent in light of the following description of preferred embodiments of the invention.

Thus, in one aspect of the invention, includes: an article production module including: (a) a module housing, said module housing having a first end and a second end, and a channel extending between the first end and the second end; (b) an internal transport system having a stationary support and moveable support, the stationary and moveable supports having support portions extending between said first end to said second end of said housing in said channel; and (c) at least one operational component, for manipulating conditions present in the channel of the module housing.

It is a further aspect of the invention to provide article production module selected from the group comprising, consisting essentially of or consisting: an article infeed module, an article depyrogenation module, an article cooling module, article filling module, an article closure module, and/or an outfeed module.

It is a further aspect of the invention to provide a modular production system comprising, a plurality of article production modules of the present invention connected to define a production tunnel. In one embodiment of this aspect of the invention, the production tunnel comprises a plurality of article production modules selected from the group consisting of an article infeed module, an article depyrogenation module, an article cooling module, article filling module, an article closure module, and/or an outfeed module. In a further embodiment, modular production system comprises an article infeed module, operatively connected to an article depyrogenation module, connected to one or more article cooling module, connected to an article filling module, an article closure module, connected to an outfeed module.

It is a further aspect of the invention to provide an article infeed module. In one aspect of the invention the article infeed module provides infeed module comprising a) a module housing, said module housing having a first end and a second end, and a channel extending between the first end and the second end, said channel defining a confined space; (b) an internal transport system having a stationary support and moveable support, the stationary and moveable supports having support portions extending between said first end to said second end of said housing, and; (c) at least one fluid inlet into the housing channel and at least one fluid outlet from the channel, wherein an the interior of the channel defines a first atmosphere, and the environment outside the housing defines a second atmosphere, and a fluid entering the channel from the fluid inlet increases the pressure of the atmosphere in the channel in relation to the atmosphere outside the housing. In certain embodiments of this aspect of the invention, the article infeed module comprises a housing having a proximal end wall at said first end of the housing, with proximal end wall defining an article input opening aligned with an article support surface of the internal transport system. In certain embodiments, the article input opening is in the form of a mouse hole. In a further aspect of the invention, the infeed further comprises one or more air filters positioned between the airflow inlet and the interior of the channel of the module housing. In certain embodiments, the filter(s) is/are HEPA filter(s). In certain embodiments, the infeed module comprises a filter housing, and at least one filter is positioned within the filter housing. In certain embodiments, the module housing defines exhaust vents, wherein air within the chamber exist the chamber in part through said exhaust vents. In certain embodiments of the infeed module, the module housing includes article input opening and exhaust vents, and the exhaust vents are positioned such that airborne external material entering the internal module chamber through the article input opening is washed out of the internal chamber through the exhaust vents.

It is a further aspect of the invention to provide a modular housing having at least one end adapted to connect with a further modular housing. In one embodiment of this aspect of the invention, the end adapted to connect with a further modular housing includes a lip portion defining an exterior surface, and an O-ring or sealing elastomeric band which extends around the lip portion in contact with exterior surface, and acts to create of seal when compressed within a corresponding female mating surface of a connecting component. In an alternative form, the seal could be accomplished with a face seal O-ring 'squeezed' between the end faces two connected modules.

It is a further aspect of the invention, the moveable support of internal transport system comprising a drive frame, a moveable support connector and a movable support rail.

In one embodiment, the drive frame includes one of more flexible member(s) allowing for frictionless directional motion in the drive frame. In one embodiment, the drive frame includes a first flexible member allowing frictionless vertical motion, and at least one second flexible member allowing frictionless horizontal motion.

In one form, the flexible members comprise flexible plate-like lamella. In an alternative form, the flexible members are frictionless flex pivot bearing, such as cantilevered pivot bearings, double ended pivot bearings, or lamellar pivot bearings.

The drive frames of the present invention may be connected to a movable support by a moveable support connector. In one embodiment, the support connecter includes a first end fixedly mounted to the drive frame, and a second end fixedly mounted to the movable support rail. In an alternative form, support connecter includes a first end fixedly mounted to the drive frame, and a second end supporting in a non-fixed manner to the movable support rail. In an embodiment of the alternative form, one of the second end of the support connector or the movable support rail defines an extension (e.g., a raised portion, post, pin or the like) and the other of the second end of the support connector or the movable support rail defines a recess for receiving such extension, so as a non-fixedly connect the support connector and the movable support rail. In certain embodiments, the recess is shaped to correspond to the shape of the extension. In other embodiments, the recess may be shaped as a groove or channel which is larger than the extension positioned therein, such that a degree of slippage is accommodated. In a further embodiment, the recess is elongate, and the extension comprises a pin or post, such that the extension may move in the elongate recess. In a further embodiment, a low friction material is provided on or between one or more of the support connector and the movable support rail to permit slippage therebetween.

In one embodiment, the movable support rail is a single length of support rail. In an alternative embodiment, the movable support rail is composed of individual lengths of support rail, connected together. In one aspect of the invention, individual lengths of rail are connected to form a movable support rail surface by a flange on one portion being positioned in a groove in the portion to be joined thereto. In embodiments of the moveable rail of the present invention, the rail portions comprising the movable support rail are constructed of independently selected materials, wherein the materials of construction may be the same or different.

It is a further aspect of the invention, to provide a stationary support defining one or more article support surfaces. In one embodiment, the stationary support comprises a base stationary support rail for supporting the base of an article and a back stationary support rail which supports a further region of the article positioned thereon.

It is a further aspect of the present invention to provide a movable support which is movable relative to the stationary support surface to reposition articles positioned on the stationary support surface. It is an aspect of the invention that the movable support move in a plurality of dimensions relative to a support surface of the stationary support.

In a further aspect of the invention, the moveable support of internal transport system, includes a drive frame member, a portion of which is fixedly attached to the housing, and a portion of which freely extends within the housing but is not fixed to an internal surface thereof, wherein the freely extending portion is movable relative to the fixed stationary support surface. In certain embodiments, the freely extending portion includes a follower magnet, said follower magnet operatively coupled to a drive magnet external to the module housing. In certain embodiments one or more drive frames are positioned within the module, and the moveable support surface of the movable support is operative connected to the one or more drive frames. In certain embodiments, the module housing comprises a first end region at one end of the housing, and a second end region at the opposite end of the housing, and a drive frame is positioned in each of the first and seconds ends of the housing, and the moveable support surface of the movable support is operative connected to each of the drive frames.

It is a further aspect of the invention to provide an article depyrogenation module. In an embodiment of this aspect of the invention, the depyrogenation module includes a) a module housing, said module housing having an open first end and an open second end, and a channel extending between the first end and the second end, and a transparent tubular housing positioned between the first and second ends defining an elongate bore defining at least a portion of said channel; (b) an internal transport system having a stationary support and moveable support, the stationary and moveable supports having elongate support rails extending between said first end to said second end of said module housing, and; (c) an irradiation source positioned external to said tubular housing, said irradiation source generating irradiation to create an irradiation zone within said tubular housing, wherein said irradiation is sufficient cause the depyrogenation and/or sterilization of articles passing through said irradiation zone. In a still further embodiment of the invention, a reflective layer surrounds a portion of the exterior surface of the tubular housing, the reflective layer having an inwardly directed face which causes radiation to be redirected within the bore of the tubular housing. In certain embodiments of the invention, the reflective layer comprises polished metal, (e.g., aluminium, gold, silver, aluminized steel or other reflective/diffusive coatings, including nano-coatings like the silica, e.g., HRC®—Heraeus Reflective Coating, available from Heraeus Quartz America, LLC, Austin, TX, USA).

It is a further aspect of the invention to provide an article cooling module. In one aspect of the cooling module, the cooling module includes a) a module housing, said module housing having an open first end and an open second end, and a channel extending between the first end and the second end, and a tubular housing positioned between the first and second ends defining an elongate bore defining at least a portion of said channel; (b) an internal transport system having a stationary support and moveable support, the stationary and moveable supports having elongate support rails extending between said first end to said second end of said module housing, and; (c) an temperature reduction source for lowering the temperature of the internal chamber of cooling module.

In one embodiment of the cooling module, a portion of the temperature reduction source is positioned within the internal chamber of the cooling module housing. In certain embodiments of the cooling module, the temperature reduction source comprises a cooling sparger, said sparger designed to emit cold air into the interior chamber of the housing.

It is a further aspect of the invention to provide a modular production system comprising:
a plurality of production modules, each of said production housings comprising a module housing comprising a proximal end, a distal end, and a central cavity extending between said ends; and
wherein the plurality of production modules are connected in a linear series to form a production tunnel, wherein the central cavities of each module housing collectively define a production channel, wherein the proximal end of most-proximal module housings defines the proximal end of the production tunnel, and the distal end of the most-distal module housing defines the distal end of the production tunnel, and wherein the proximal and distal ends of the production tunnel each comprise an article passage port;
at least one fluid inlet port defined along the production tunnel, said inlet port is in fluid communication with a pressurized fluid source, whereby influx of fluid from said fluid source through said fluid inlet port acts to maintain the fluid pressure within the production channel at a higher pressure than the atmospheric pressure outside of the production tunnel, such that fluid flows from both the proximal and distal article passage ports to minimize entry of air into the production channel from either the proximal or the distal article passage ports;

wherein one of said production modules positioned between said proximal-most and distal-most production modules comprises a depyrogenator and/or sterilization module, said depyrogenation/sterilization module comprising a transparent tubular body defining at least a portion of the central cavity of said production module, and an irradiation source positioned external to said transparent tubular body, said irradiation source capable of heating the internal environment of the depyrogenation module to a temperature sufficient to sterilize or depyrogenate articles passing therethrough.

In such embodiment, the most proximal module housing further defines an exhaust vent positioned adjacent to said proximal article passage port, and forming vertical washout at the proximal end of the production tunnel.

In this and other embodiment, the most distal module housing further defines an exhaust vent adjacent the distal article passage port which acts as a vertical washout for air passing into the production channel from the distal article passage port.

In such embodiments, the irradiation source is a light source. In certain embodiments, the light source is capable of heating the contents of the transparent tubular housing to at least 250° C. For example, the light source may be selected from the group consisting a halogen short wave light emitter or a carbon medium wave emitter.

In such embodiments, transparent tubular housing may comprise a light transparent material, such as quartz, borosilicate of other suitable temperature tolerant transparent material.

In some embodiments of the modular production system of the present invention, the transparent tubular housing may comprise an exterior surface that is at least partially covered or coated with an insulative, conductive or reflective material. In certain embodiments, the reflective layer comprises a metallic coating or layer. In certain embodiments, the metallic coating or layer may be selected from any suitable material, including aluminium foil, an aluminized or gold coating or nanocoating.

In a further aspect of the invention, the embodiments of the depyrogenation/sterilization module of the present invention may further include a reflecting apron extending from the external surface of the transparent tubular housing toward the irradiation source, the reflecting apron acting to redirect light toward the central cavity defined through the transparent tubular housing.

The modular production system of the present invention, may further include at least one cooling module positioned distal to the depyrogenation or sterilization module. The cooling module includes a cooling sparger in fluid communication with a cold fluid source, said cooling sparger positioned in relation to the tubular housing so as to reduce the temperature of materials present within the central cavity of the cooling channel.

In one embodiment, the at least one cooling module includes a transparent tubular housing, which defines at least portion of the central cavity of the cooling module, with the cooling sparger positioned within said central cavity of said transparent tubular housing.

In one embodiment of such a cooling module, the transparent tubular housing of said at least one cooling module comprises an exterior surface, said exterior surface at least partially being covered or coated with a thermally conductive layer of material.

In a further aspect of the present invention, the modular production system may also include one or more filling modules. The filling module may be positioned distal of the depyrogenation module and proximal of the distal-most production module. Such filling module(s) may include one or more filling stations at which containers are positioned to be filled with a material.

In one embodiment of this aspect of the invention, a filling module comprises a filling housing, where the filling housing includes a filling channel through which a material is passed to be positioned within a container, when the container is positioned at the one or more filling station.

In a further aspect of the invention, the filling housing may further include a channel closure. The channel closure is being moveable between a first position, wherein said filling channel is sealed off from the central cavity of the filling module, and a second position, wherein the filling channel is in fluid communication with the central cavity of the filling module. The channel closure may be composed of any suitable closure type, of suitable material. In one embodiment, the channel closure comprises a metallic bellows.

In one embodiment of the filling housing, the filing channel is in the form of a needle channel. In a further aspect of the invention, the filling channel is adapted to receive the filling needle.

In a still further aspect of the invention, the modular production system may further include a filling mechanism as part of the filling module. The filling mechanism may be adapted to deliver a material to a container positioned within the filling module.

In certain embodiments, the filling mechanism includes a filling needle having a first end, a second end and a lumen extending therebetween. In such embodiments, the first end is in fluid communication with a source of liquid to be delivered to a container, and the second end is extendable into the central cavity of the filling module.

In embodiments of this aspect of the invention, the material delivered by the filling mechanism may be a fluid (liquid or gas) or a solid or an article of manufacture. In certain embodiments, the fluid is a liquid. For example, the liquid is may be a liquid medicament suspension or solution containing at least one active pharmaceutical ingredient. In further embodiments, the solid comprises a powder. In certain embodiments, the powder comprises an active pharmaceutical or biological ingredient. In other embodiments, the fluid is an inert gas.

In certain embodiments, the modular production system may include a plurality of filling mechanisms for filling materials into a container.

In certain of such embodiments, the plurality of filling mechanisms are adapted to deliver different materials. In certain of such embodiments, the plurality of filling mechanisms are adapted to deliver different materials to the same container.

In further embodiments, the modular production system may include a plurality of filling modules. In one aspect of this embodiment, each filling module delivers a single material, which may be the same or different from the single material delivered by another filling module in the production system.

In a further aspect of the invention, the modular production system described herein may further include a closure module. The closure module may be positioned distal to the one or more filling modules. In such embodiments, the closure module comprises a closure mechanism for sealing a container. In certain embodiments, sealing of the container is achieved by a closure, a cap, or a crimp. In certain embodiments, the closure mechanism comprises a piston, having a sealing head, which acts upon a closure, to cause the closure to seal a container.

Any suitable closure system recognizable to those of ordinary skill may be used in the closure module of the present production system. Preferably, the selected closure system is made of materials selected to withstand the pre-operational and operational thermal conditions.

In certain embodiments, the closure module includes a closure housing having a piston channel. The piston channel contains the closure piston, and further includes an accordion like sleeve comprising a first end sealingly connected to a portion of said piston, and a second end sealingly connected to a portion of the closure housing. The accordion like sleeve extends between a retracted and an extended state by movement of the piston. The accordion like sleeve acts to preserve the environmental integrity of the interior chamber of the closure module.

The closure module may further include a closure holder. The closure holder is configured to hold closures in an aligned orientation with a container, to permit the piston to extend to press the closure into position on said container to effectuate a seal therebetween.

In certain embodiments, closures are fed into the closure holder by a closure feed. In certain embodiments, the closure feed comprises a closure chute which extends into the central cavity of the closure module to feed closures into the closure holder.

In the modular production system, the modules further include an article transport system positioned within said linear production channel and extending between said proximal article passage port and said distal passage port. The article transport system is configured to move containers entering the production channel from the proximal article passage port to the proximal article passage port, using any suitable means. In certain embodiments articles move in a linear fashion. In some embodiments, articles are transported in single file fashion. Any suitable transport system recognizable to those of ordinary skill may be used in the modules of the present production system. The selected transport system is made of materials selected to withstand the pre-operational and operational thermal conditions to which they are exposed. In certain embodiments, the article transport system is composed of a plurality of transport sections which are interconnected to operate in a synchronized fashion.

In certain embodiments, the article transport system includes one or more moveable support rail sections, and one or more stationary support sections. The moveable support section moves articles progressively along the one or more stationary support sections, in a "walking beam conveyor" fashion.

In certain embodiments, the moveable support moves articles along the stationary support by lifting the article from the stationary support, moving the article a uniform horizontal distance in the distal direction, and lowering the article onto the stationary support.

In certain embodiments, the moveable support moves vertically downward relative to the article positioned on the stationary support, so as to be below the article positioned on the stationary support, before the moveable rail moves proximally a horizontal distance, before rising vertically to once more contact the article. The moveable support may move in any convenient trajectory (for example, but not limited to, a rectangular, oval, or elliptical fashion) relative to the stationary support, to transport such articles.

In a further aspect of certain embodiments of the invention, the moveable support is connected to a drive frame.

In certain embodiments, the drive frame may comprise one or more flexible components which provide for frictionless movement of the moveable support. In certain embodiments, the flexible component comprises a flexible lamella.

In certain embodiments, the flexible lamella is positioned within a pivot bearing.

In certain alternative embodiments, the drive frame includes one or more flexible vertical lamella, a front structural support, one or more horizontal flexible lamella, and a rear structural support;
  wherein said one or more vertical flexible lamella and one or more horizontal flexible lamella each comprise a first end and a second end;
  wherein said front structural support defines a first portion distanced from a second portion,
  wherein said first end of said one or more vertical flexible lamella is held in a fixed position relative to an interior wall of said module housing, and said second end of said vertical lamella is connected to the first portion of said front structural support, whereby said first vertical lamella may flex vertically;
  wherein said first end of said one or more horizontal flexible lamella is connected to the second portion of said front structural support, and said second end of said one or more horizontal lamella is connected to the rear structural support; and
  whereby flexion of the one or more vertical lamella allows vertical movement of the rear structural support, and flexion of the one or more horizontal lamella allows for horizontal movement of the rear structural support.

In a further embodiment of the drive frame, the front and rear structural supports each define a proximal side surface and a distal side surface; and the one or more horizontal lamella comprise a first and a second horizontal lamella;
  wherein the first end of the first horizontal lamella is connected to the proximal side surface of the front structural support, and the second end of the first horizontal lamella is connected to the proximal side surface of the rear structural support, and
  wherein the first end of the second horizontal lamella is connected to the distal side surface of the front structural support, and the second end of the second horizontal lamella is connected to the distal side surface of the rear structural support.

In certain embodiments, the drive frame includes one or more vertical and horizontal lamella which are components of pivot bearings, each of said pivot bearings comprising a first pivot housing portion and a second pivot housing portion, and rotational movement of one of said pivot housings relative to the other of said pivot housings about a common axis being provided by lamellar flexion.

In further embodiments, the drive frame includes one or more vertical pivot bearings, wherein the first pivot housing portion of said one or more pivot bearing is fixedly held in relation to said interior surface of tubular housing of said production module, and the second pivot housing of said pivot bearing as fixedly held by the front structural support, such that flexion of the vertical lamella within said one or more pivot bearings allows rotational movement of the front structural support in a vertical fashion.

In still further embodiments, the drive frame in such embodiments includes one or more horizontal pivot bearings, wherein the first pivot housing portion of said one or more pivot bearing is fixedly held in relation to said second portion of said front structural support, and the second pivot housing of said one or more pivot bearing is fixedly held by a portion of the structural support, such that flexion of the horizontal lamella within said one or more pivot bearings allows rotational movement of the rear structural support in a horizontal fashion.

In one aspect of the invention the rear structural support comprises proximal and distal lower arms having a front portion and a rear portion, wherein front portion of the proximal lower arm firmly holds the second pivot housing of a first front horizontal pivot bearing, and wherein the front portion of the distal lower arm firmly holds the second pivot housing of a second front horizontal pivot bearing, said pivot bearing being oriented to provide rotational pivoting at said front end of said lower proximal and distal arms to provide horizontal movement of said lower arms at their rear portions.

In some embodiments, the drive frame further includes a proximal rear horizontal pivot bearing firmly held by the rear portion of the proximal lower arm; a distal rear horizontal pivot bearing firmly held by the rear portion of the distal lower arm: and wherein the rear structural support further comprises an upper frame, said upper frame comprising a front portion adapted to connect to the moveable support rail of the internal transport system, and a rear portion defining a proximal portion which firmly secures the second pivot housing of the proximal rear horizontal pivot bearing, and a distal portion which firmly secures the second pivot housing of the distal rear horizontal pivot bearing, horizontal movement of the drive frame is accommodated by pivotal flexion in the pivot bearings fixedly held by the proximal and distal lower arms at their front and rear portions.

In one embodiment, the upper frame of the rear structural support comprises:
 a proximal upper arm, comprising a front portion and a rear portion;
 a distal upper arm, comprising a front portion and a rear portion; and
 a rear support bar, comprising a proximal end portion and a distal end portion;
 wherein the proximal end portion of the rear support bar is fixedly connected to the rear portion to the proximal upper arm, and the distal end portion of the rear support bar is fixedly connected to the rear portion to the distal upper arm, and
 wherein the proximal portion of rear portion of the upper frame is defined by the rear portion of the proximal upper arm;
 wherein the distal portion of rear portion of the upper frame is defined by the rear portion of the distal upper arm; and
 wherein said front portion of the upper frame adapted to connect to the moveable support rail of the internal transport system, is defined by one or both of the front portions of the proximal and distal upper arms.

In a further aspect of the drive frames described above, the rear structural support comprises at least one follower magnet. In certain embodiments, the follower magnet comprises a material which maintains is magnetic properties at temperatures of from 200° C. to 300° C. In certain embodiments, the follower magnet may be Samarium-cobalt.

In further embodiment of the modular production system, the system further includes one or more drive magnet positioned outside the modular housing within which is positioned said follower magnet, these drive and follower magnets are aligned, so as to allow magnetic coupling therebetween, whereby movement of said one or more drive magnets causes corresponding movement of the aligned and magnetically coupled follower magnets.

In certain embodiments of the modular production system, the one or more drive magnets are associated with one or more elongate drive axles, whereby movement of the one or more elongate drive axles results in movement of the one or more drive magnet. In such embodiment, the one or more drive axles extend parallel to the external length the modular production system.

In such embodiment, the one or more drive axles are capable of rotational movement, and linear movement, such that rotational movement causes the vertical movement of the drive magnet, and linear movement of the one or more drive axles result in the horizontal movement of the one or more drive magnets.

It certain embodiments of the invention, one or more of the one or more drive magnets comprise a rare earth magnetic material, such as samarium-cobalt or neodymium.

In a further aspect of the present invention, the invention relates to an individual production module for the performance of at least one operation, which is useful in the production of products comprising:
 a) a module housing defining an internal cavity, said module housing comprising a first end and a second end, said ends of said housing each comprising an opening, said end openings being in communication with said internal cavity, forming a channel through said housing,
 b) an internal transport system positioned within the housing, the internal transport system comprising:
 i.) a drive frame,
 ii.) a moveable article support surface attached to said drive frame, and
 iii.) a stationary article support surface,
 wherein the drive frame comprises
 (a) a first portion held in a fixed position within the housing channel,
 (b) a second portion suspended within said channel, and supporting the moveable article support surface,
 (c) at least one flexible lamella positioned between the first portion and the second portion of the drive frame, wherein flexion of the lamella permits movement of the second end of the drive frame in response to a directional force; and
 d) an operational assembly associated with said housing for performing an operation therein.

In one aspect of the production module, wherein the housing defines an end wall, having formed therein an article access opening. The article access opening may be in the form of a mouse hole, size to accommodate an article being passed into said channel.

In a further aspect of the production module, at least one of said ends is adapted for attachment to a further production module.

In certain embodiments, the production module housing comprises interconnected walls having interior and exterior surfaces, and said exterior surfaces having a first end portion adjacent the first end of said housing and a second end portion adjacent the second end of said housing, and at least one of said first or second end portions is adapted for attachment to a further production module.

In certain embodiments, the production module housing includes at least one of said housing wall end portions further includes a sealing surface extending circumferentially around the housing. In certain embodiments, the sealing surface is provided by an O-ring.

In certain embodiments, the at least one of housing wall end portions define a circumferential O-ring recess extending around the exterior surface of said housing, within which is positioned said O-ring. In such embodiments, the housing comprises interconnected walls having interior surfaces defining said housing cavity and exterior surfaces, and said walls each having a first end portion adjacent the first end of said housing and a second end portion adjacent the second end of said housing, and said first and second end portions are each adapted for attachment to a further production module.

In certain embodiments, the housing wall end portions each further comprise a sealing surface extending circumferentially around the exterior of housing. In some embodiments, one or both of said sealing surfaces is provided by one or more O-rings. In certain of these embodiments, one or both of said housing wall end portions include a circumferential O-ring recess extending around the exterior surface of said housing, within which is positioned an O-ring, said O-ring providing said sealing surface.

In certain embodiments of the invention, the modular housing includes interconnected walls having interior and exterior surfaces, and said exterior surfaces having a first end portion adjacent the first end of said housing and a second end portion adjacent the second end of said housing, wherein one of said end said portions further comprises an integral mounting sleeve, having an inner sealing surface adapted to facilitate connection to a further production module.

In certain of such embodiments, the integral mounting sleeve inner sealing surface defines an O-ring recess extending around the inner circumference of said sleeve.

In the production modules of the present invention, in use, the channel of the module housing is maintained at a higher air pressure than the atmosphere outside the module housing, such that net air flow is from the channel. In certain of such modules, the module housing may further include an air inlet, connectable to a pressurized air source to provide air flow to the channel. In certain of such modules, wherein the module housing further comprises a filter housing, said filter housing defining said air inlet. In certain of such modules, the module further includes an air filter positioned between said air inlet and said module housing channel.

In certain embodiments, the module housing further includes a filter housing, the filter housing defining said air inlet, and an air filter positioned between said air inlet and said module housing channel. In certain of such embodiments, the housing is defined by one or more wall portions having interior and exterior surfaces, wherein the interior surfaces of the wall portions define the channel through the housing.

In a still further aspect of the invention, the production module housing comprises a proximal end housing defining a proximal end housing internal cavity, a distal end housing defining a distal end housing internal cavity, and a tubular housing defining an axial bore therethrough. In such embodiments, the tubular housing is positioned between the proximal end housing and distal end housing, wherein the proximal end housing internal cavity, axial bore and distal end housing internal cavity are in fluid communication and collectively define the channel through the production module.

In certain embodiments of this aspect of the invention, the production module takes the form of a depyrogenation/sterilization module, wherein the tubular housing comprises a light radiation transparent material. In certain embodiments, the light radiation transparent material is tolerant of heat of 250 degrees Celsius or greater. The light radiation transparent material may be any suitable material, including but not limited, quartz, borosilicate, or heat tolerant glass. In certain embodiments, the light radiation transparent material is quartz.

In certain embodiments, the tubular housing comprises metal, glass or ceramic.

In certain embodiments, one or more of the end housings comprise metal, e.g., stainless steel, heat tolerant aluminium alloys and the like.

In certain embodiments, the proximal end housing and the distal end housing are each adapted for attachment to a further production module.

In certain embodiments, the proximal end housing comprises an open proximal end, top, front, bottom, and back walls, where the walls having interior and exterior surfaces, and the exterior surfaces of the walls of the proximal end housing comprise a proximal end portion; and; the distal end housing comprises an open end, and top, front, bottom, and back walls, the walls having interior and exterior surfaces, and the exterior surfaces of walls of the distal end housing comprises a distal end portion, and wherein the proximal end portion of the proximal end housing and the distal end portion of the distal end housing are each adapted for attachment to a further production module.

In certain embodiments, at least one of said proximal or distal end portions further includes a sealing surface to create a seal between adjacent modules. In certain embodiments, the sealing surface is provided by an O-ring.

In certain of such embodiments, at least one of said proximal or distal end portions defines a circumferential O-ring recess extending around the exterior surface of said end housing, within which is positioned said O-ring.

In certain embodiments, both of said proximal or distal end portions further include a sealing surface extending circumferentially around the respective end housing. In certain embodiments, the sealing surfaces are provided by an O-ring. In certain of such embodiments, each of said proximal and distal end portions define a circumferential O-ring recess extending around the exterior surface of said end housing, within which is positioned a respective O-ring.

In a still further embodiment of the production module, one of the proximal end portion or distal end portion may further comprise an integral mounting sleeve, having an inner sealing surface adapted to facilitate connection to a further production module.

In certain embodiments, the integral mounting sleeve inner sealing surface defines an O-ring recess extending around the inner circumference of said sleeve. In certain of such embodiments, a resilient O-ring is positioned the inner sealing surface O-ring recess.

In a further aspect of the depyrogenation/sterilization module of the present invention, the invention further includes an irradiation source for irradiating the tubular housing, such that articles passing through the tube are sterilized thereby. In a one aspect of the invention, the irradiation source is a light source or emitter. In such embodiments, the light source generates light radiation in a suitable wavelength to achieve the desired sterilization/depyrogenation effect. In certain embodiments, the light source generates infrared radiation. Since each material/component reacts differently to radiation, the emitter should be selected to have the best wavelength to heat up the desired containers. Usually emitters radiate in a range of wavelength, but they may be classified by their peak wavelength: short wave (1 to 2 μm), medium wave (2 to 4 μm), long wave (>4 μm). These are between the most common types of emitters, but other radiation sources outside the infrared region might be used to properly match the material of the container to be heated and/or the microbial/endotoxin content.

In certain such embodiments, the tubular housing has an exterior surface, and inner surface and the irradiation source is positioned adjacent the outer surface to direct radiation through the exterior surface of the tubular housing and the interior surface to irradiate the bore of the axial tubular housing.

In certain of such embodiments, the tubular housing has an exterior surface and further includes a reflective layer on or adjacent the exterior surface of the tubular housing, said reflective layer having a reflective surface facing the central bore of the tubular housing, such that radiation from the irradiation source passing through the housing and into the bore is redirected by the reflective surface back toward the bore of the tubular housing. In certain embodiments, the reflective layer defines an exposure window between the irradiation source and the external surface of the transparent tubular housing.

In certain further embodiments, the tubular housing further includes a reflective apron comprising a reflective underside, the reflective apron extending outward from the surface of the tubular housing adjacent the exposure window and toward the irradiation source, such that radiation from the irradiation source exiting the tubular housing through the exposure window is redirected by the reflective underside of the reflective apron back toward the bore of the tubular housing.

In certain other embodiments of the present invention, the production module further includes a cold air sparger positioned adjacent the irradiation source, wherein the cold air sparger is in fluid communication with a cold air source, and the cold air sparger comprises a tubular body provided with one of more sparger vents directed toward the irradiation source, for directing cold air from the cold air source toward the irradiation source to cool the irradiation source.

In a further aspect of the present invention, where the module housing proximal end housing and a distal end housing, and a tubular housing therebetween, the proximal end housing comprises a distal side wall defining an access opening extending therethrough, which provides fluid communication between said proximal end housing internal cavity and the central bore of the tubular housing; and wherein the distal end housing comprises a proximal side wall defining an access opening extending therethrough, providing fluid communication between said distal end housing internal cavity and the central bore of the tubular housing.

In certain embodiments, of this aspect of the invention, the module housing further includes a proximal ring shaped bracket comprising an inner circumferential surface, said an inner circumferential surface defining a central opening, said bracket being sealingly connected to the distal wall of the proximal end housing such that the ring-shaped bracket surrounds the access opening extending through the distal side wall; and a distal ring shaped bracket comprising an inner circumferential surface, said inner circumferential surface defining a central opening, said distal ring shaped bracket being sealingly connected to the proximal wall of the proximal end housing such that the distal ring shaped bracket surrounds the access opening extending through the distal side wall; and wherein said tubular housing comprises an external surface; a proximal end, the proximal end of the tubular housing sealingly positioned within the central opening of the proximal ring-shaped bracket; and a distal end, the distal end of the tubular housing sealingly positioned within the central opening of the distal ring-shaped bracket; and wherein the tubular housing is sealingly connected to each end housing, and the access openings in the distal side wall of the proximal end housing and the proximal side wall of the distal end housing provide fluid communication between the internal cavities of the end housings and axial bore of the tubular housing.

In certain of such embodiments, the module further includes:
a first O-ring, said first O-ring being compressed between the inner circumferential surface of the proximal ring shaped bracket and the exterior surface of the tubular housing at the proximal end of the tubular housing; and
a second O-ring, said second O-ring being compressed between the inner circumferential surface of the distal ring-shaped bracket and the exterior surface of the tubular housing at the distal end of the tubular housing.

In certain of such embodiments of the invention, the inner circumferential surface of the proximal ring-shaped bracket defines and O-ring recess in which is positioned a portion of the first O-ring; and the inner circumferential surface of the distal ring-shaped bracket defines an O-ring recess in which is positioned a portion of the second first O-ring.

In a further aspect of the depyrogenation/sterilization module invention, the moveable article support surface attached to said drive frame, and a stationary article support surface, each comprise a heat tolerant material. In certain of such embodiments, the moveable article support surface and the stationary article support surface, each comprise a rail extension comprising a heat tolerant material. In certain of such embodiments, the rails comprise transparent materials, such a borosilicate or quartz. In certain embodiments, the extensions comprise borosilicate.

In certain embodiments, the internal transport mechanism used in the depyrogenation/sterilization module includes:
a moveable article support surface including a proximal movable rail portion, connected to a drive frame connected to a surface of the proximal end housing, and a distal movable rail portion, connected to a drive frame connected to a surface of the distal end housing, where the movable rail extension extends from the distal end of the proximal movable rail section, and the distal end of the movable rail extension connects to the proximal end of the distal movable rail section, and where the movable rail freely extends through the bore of the tubular housing, and where the stationary article support includes a stationary article support surface base rail and a back rail, wherein the base and back rails each include a proximal base and back rail portions mounted within the proximal end housing, distal base and back rail portions mounted within the distal end housing, and stationary base rail extension extending from the distal end of the proximal base rail section and the proximal end of the back rail extension connecting to the proximal end of the distal base rail section, and where the movable rail freely extends through the bore of the tubular housing.

It is a further aspect of the present invention to provide a production module housing in the form of a cooling module, said cooling module further comprising a cold air sparger comprising a cold air sparger tube, said cold air sparger tube being positioned in the internal cavity of the module housing, said sparger tube having an external body defining an internal bore and one or more exit ports extending through said sparger body; said cold air sparger being in fluid communication with a cold air source to provide cold air through said internal bore of said sparger and out of said one or more exit ports in said sparger body and into the internal cavity of the module housing.

In certain embodiments of the cooling module, the module further includes an air filter positioned between the cold air source and the one or more exit ports in said sparger body.

In certain embodiments, the module further comprises a filter housing containing the air filter. In certain embodiments, the filter housing is affixed to or is a of component of the module housing. In certain embodiments, the filter is a HEPA filter.

In a further aspect of the present invention, the production module takes the form of a filling module, and operational assembly thereof is a filling mechanism for depositing an amount of a material into a container which is positioned upon the internal transport system within said module.

In certain embodiments, the filling module may include a filing mechanism for delivering a quantity of a liquid, a gas or a solid to a container. In certain of such embodiments, the material delivered by the filling mechanism comprises an active pharmaceutical ingredient. In certain of such embodiments, the material delivered by the filling mechanism comprises a liquid suspension or a liquid solution. In certain of such embodiments, the material delivered by the filling mechanism comprises an active pharmaceutical ingredient.

In certain of such embodiments, the production module further includes:
  a container, defining a material containment cavity, wherein said container is positionable upon a portion of said internal transport system, and is transported by the internal transport system through said channel within said module housing;
  wherein said filling mechanism further comprises a filling housing, said housing defining a filling needle channel defined therethrough and in fluid communication with said channel within said module housing, said needle channel being adapted to receive a filling needle;
  wherein said filling needle comprises an elongate body comprising a first end, a second end, and a central lumen extending therebetween to allow fluid to flow from said first end to said second end through said filling needle;
  wherein said filling needle is positionable in said filling channel such that the second end of said filling needle is positionable over or within said material containment cavity of said container.

In a further aspect of the invention, the production module takes the form of a closure module, wherein the operational assembly of the module comprises a closure mechanism for sealing a container positioned therein. In certain of embodiments of this aspect of the invention, the sealing of the container is achieved by a closure, cap, crimp.

In certain of such embodiments, the closure mechanism comprises a piston, having a sealing head, which acts upon a closure, to cause the closure to seal a container.

In certain of such embodiments, the module further comprises a closure housing defining a piston channel, and said piston channel containing said piston, further comprising an accordion like sleeve surrounding comprising a first end sealingly connected to a portion of said piston and a second end sealingly connected to a portion of the closure housing, the accordion like sleeve extending between a retracted and an extended start by movement of said piston.

In certain of such embodiments, the module further comprising a closure holder, said closure holder configured to hold closures in an aligned orientation with a container, to permit the piston to extend to press the closure into position on said container to effectuate a seal therebetween.

In a further aspect of the invention, the closures are fed into the closure holder by a closure feed.

In certain of such embodiments, the closure feed comprises a closure chute which extends into the central cavity of the closure module to feed closures into the closure holder.

In a further distinct aspect of the invention, the invention comprises a filling needle assembly including:
  an elongate filling needle, comprising a needle body having first end, a second end opposite the first end, and a central lumen extending axially through the body between the first and second end;
  a top portion, comprising a body which surrounds the first end of the elongate needle;
  an elongate, extendable sheath having a first end and a second end, an exterior surface and an interior surface, wherein the first end of the elongate sheath is sealingly connected to the top portion of the filling needle assembly and extends therefrom, such that the sheath surrounds the elongate needle; and
  a bottom portion sealingly connected to the second end of the sheath, the bottom portion comprising a body having an upper end, a lower end, and defining a needle channel extending through the upper end and the lower end, said needle channel sized to allow the elongate filling needle to extend therethrough;
  wherein the bottom portion further comprises a pierceable seal, bisecting the needle channel; so as to form a sealed environment defined by the interior surface of the elongate, extendable sheath.

In certain of such embodiments, wherein the elongate, extendable sheath is formed as an accordion, wherein alternating folds of the accordion allow the elongate sheath to occupy i) an extended position, wherein the top portion is distanced from the bottom portion, and the second end of the needle is within a sealed environment formed by the upper portion, sheath interior surface, needle channel of the lower portion, and pierceable metal seal, and ii) a retracted position, wherein the top portion is in closer proximity to the bottom portion, and the second end of the needle extends through the needle channel so as to have pierced the pierceable seal.

In a still further aspect of the invention, the invention comprises a sterilizable container for containing articles comprising:
  a container defining an interior chamber and an exit conduit comprising a mouth;
  a sealing disc positioned along the exit conduit, wherein the sealing disc seals the interior chamber of the container;
  a butterfly valve rotatable about an axle positioned within the exit conduit, between the sealing disc and the mouth,
  wherein rotation of the butterfly valve about the axle acts to shear the sealing disc, to open a passageway through the conduit between the mouth and the interior chamber of the sterilizable container.

In certain embodiments of the sterilizable container, the container and/or sealing disc is composed of a heat-tolerant material, capable of withstanding sterilization conditions. In certain of such embodiments, the heat-tolerant material of the sealing disc is metal, e.g., aluminium or stainless steel.

In a further embodiment of the sterilizable container, the butterfly valve comprises a round body having a first face and second face and an annular periphery, and said axle comprises a first axle portion and a second axle portion, said first and second axle portions extending from opposite sides of the annular periphery of the body of the valve on a common axis.

In a further embodiment of the sterilizable container, the conduit further comprises a first axle portion recess, and a second axle portion recess opposite the first axle portion recess, wherein the first axle portion is positioned within said first axle portion recess, and the second axle portion is positioned within said second axle portion recess, so as to permit rotation of said butterfly valve round body.

A still further aspect of the present invention provides for a method of using dry heat on the production system or components thereof to depyrogenated and/or sterilize the production system after assembly and before operating the system to depyrogenate and/or sterilize articles. As such, the system provides exceptionally high assurance of sterility/freedom from pyrogens through the use of dry heat.

In such further aspect of the present invention, we provide a method for the depyrogenating and/or sterilizing a modular production system prior to its use in a manufacturing articles comprising the steps of:
  a. providing a modular production system according of any one of the embodiemnts above; and
  b. exposing those portions of said modular production system defining said production channel to dry heat for a period of time, and at a temperature, sufficient to render the said portions free from pyrogen causing agents and/or sterile.

In a still further embodiment of this aspect of the invention, the method further comprising step of maintaining said production channel modular production system in a sterile and/or pyrogen free state.

It is a still further aspect of the present invention, we provide a method for the depyrogenating and/or sterilizing a production module of the present invention, this method comprising the steps of:
  a. providing one or more production module as described above; and
  b. exposing said one or more production module to dry heat for a period of time, and at a temperature, sufficient to render said one or more module so exposed free from pyrogen causing agents and/or sterile.

In a further embodiment of this aspect of the invention, the method further comprising step of maintaining each exposed module in an environment to maintain its sterile and/or pyrogen free state.

DESCRIPTION OF DRAWINGS/FIGURES

Non-limiting representative embodiments of the invention are described with reference to the following figures.

Figure 13:
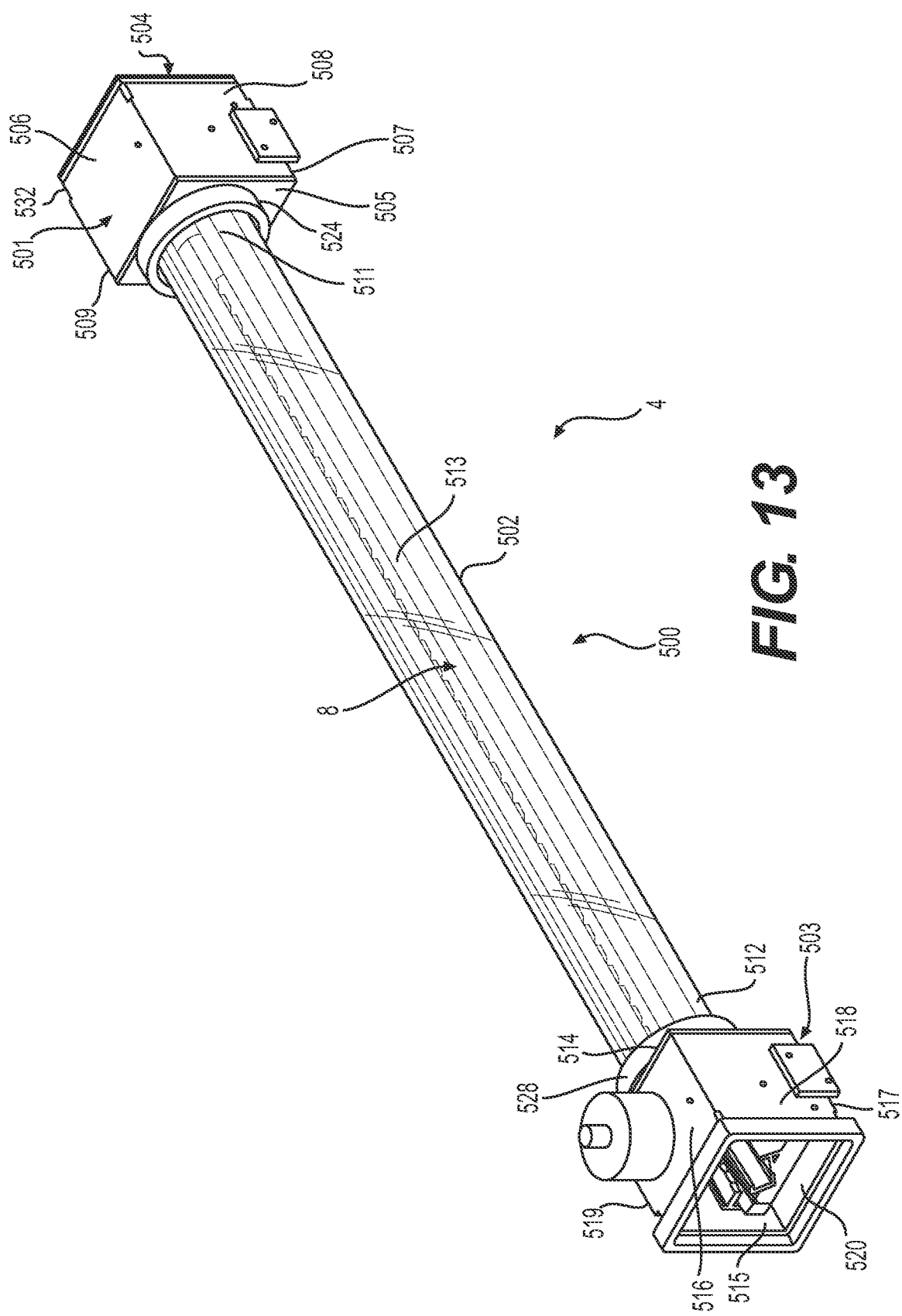
Figure 14:
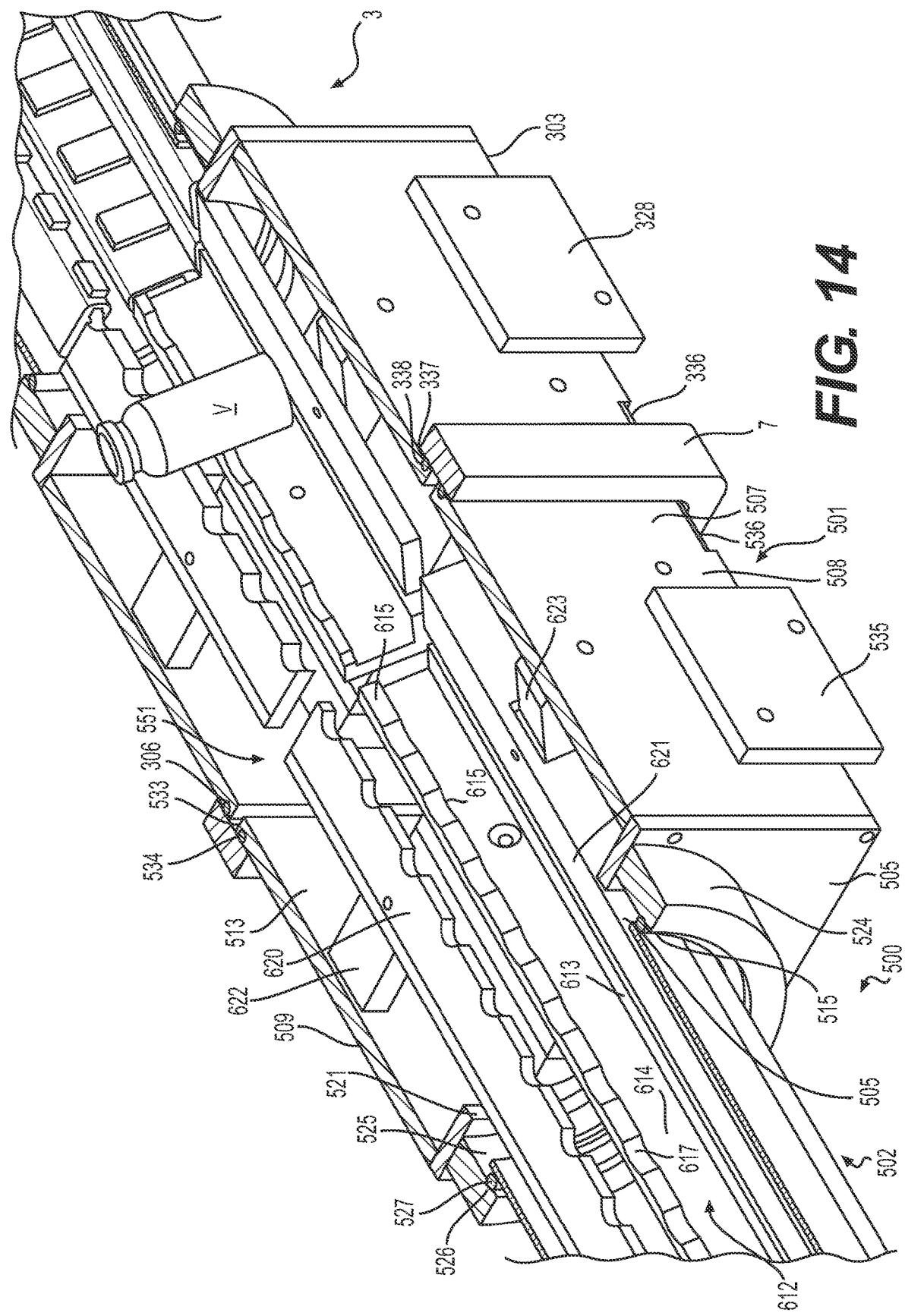
Figure 15:
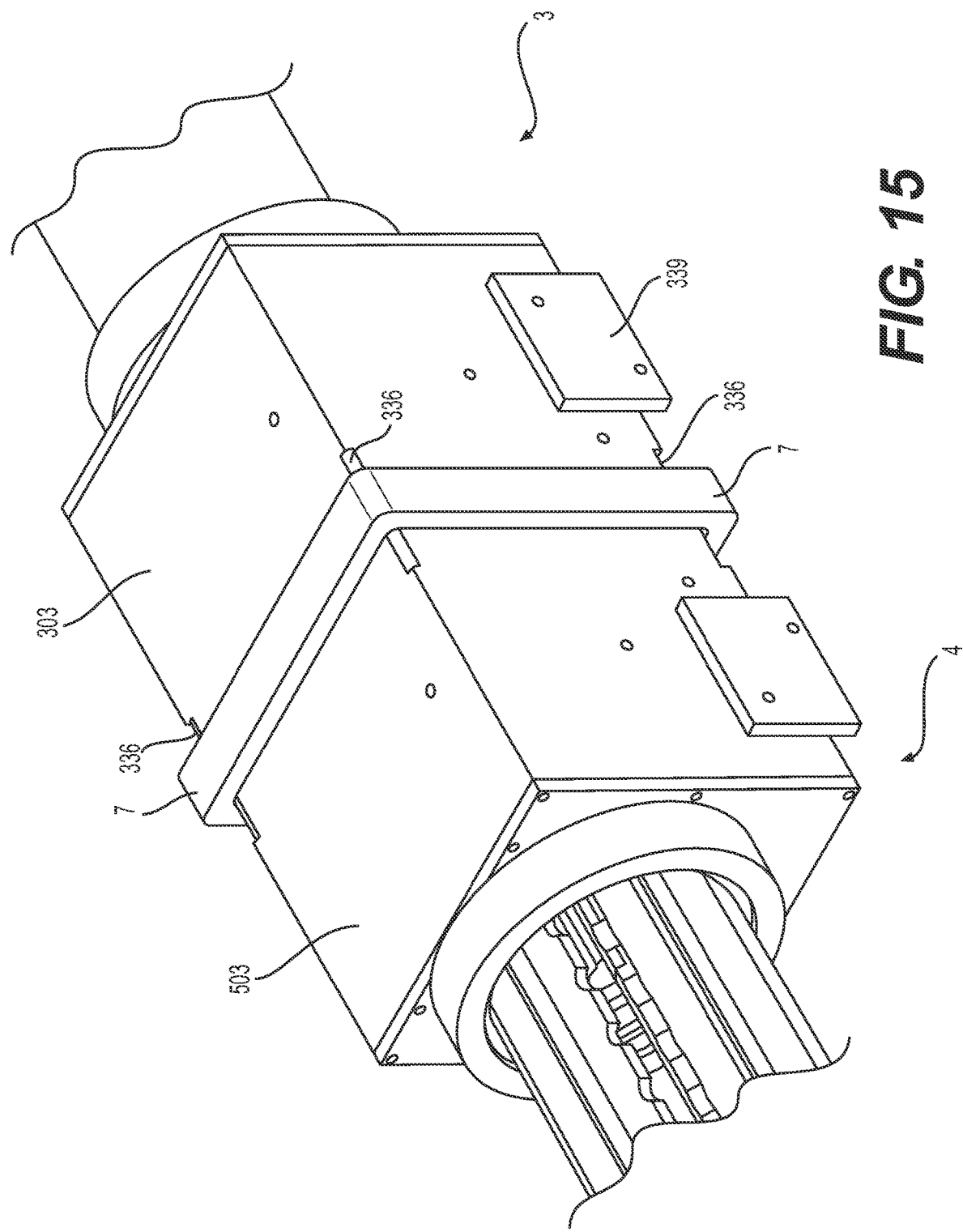
Figure 16:
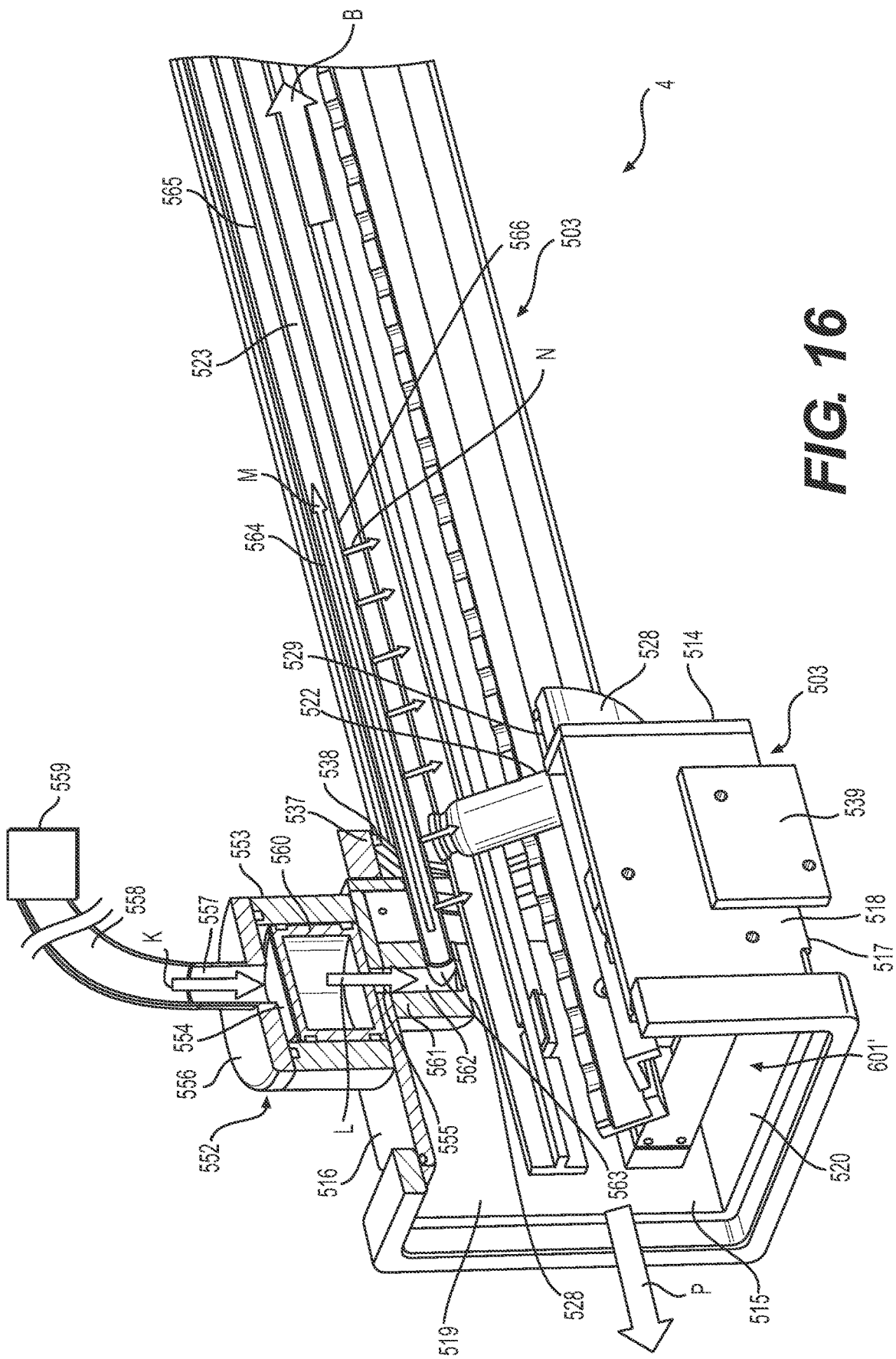
Figure 17:
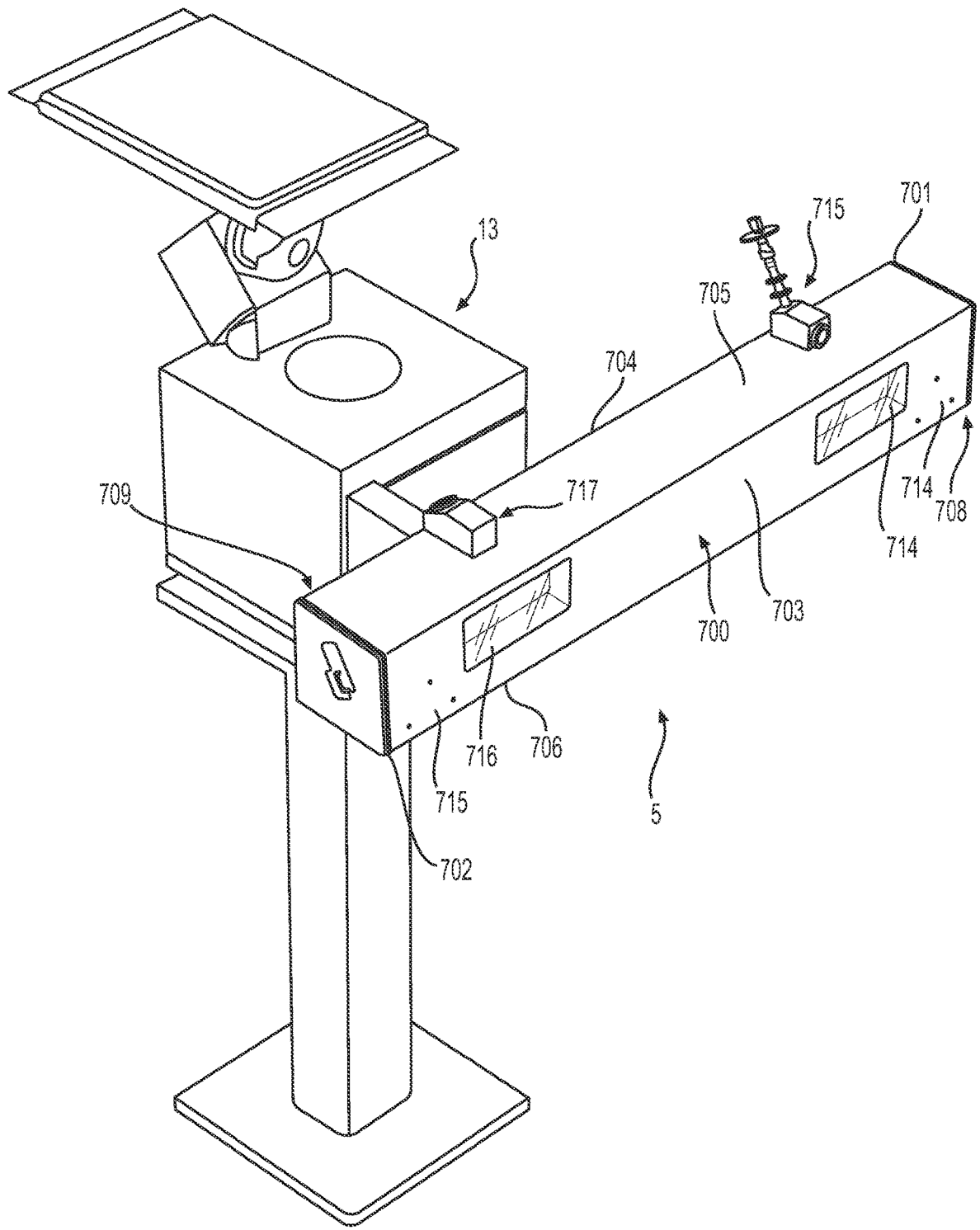
Figure 18:
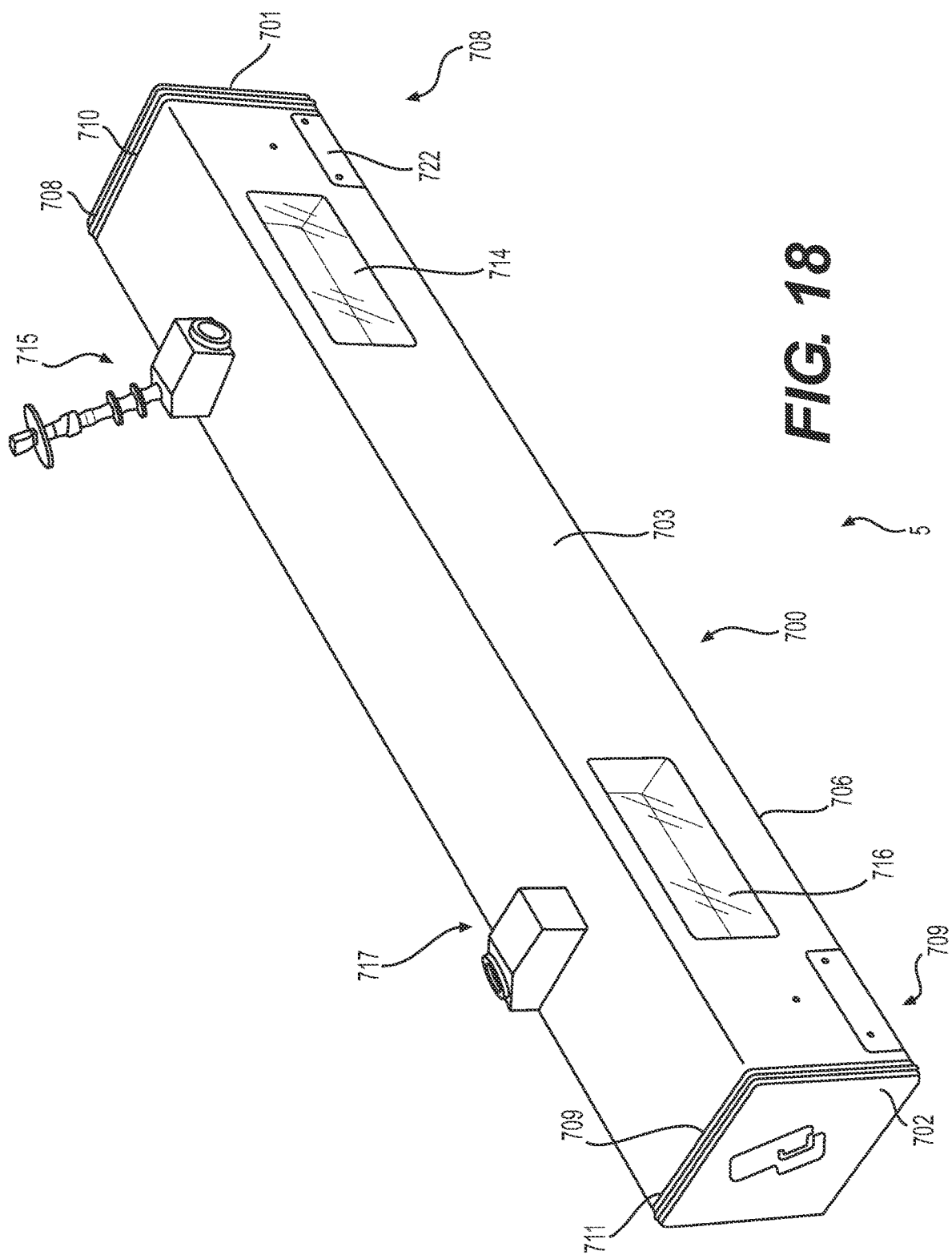
Figure 19:
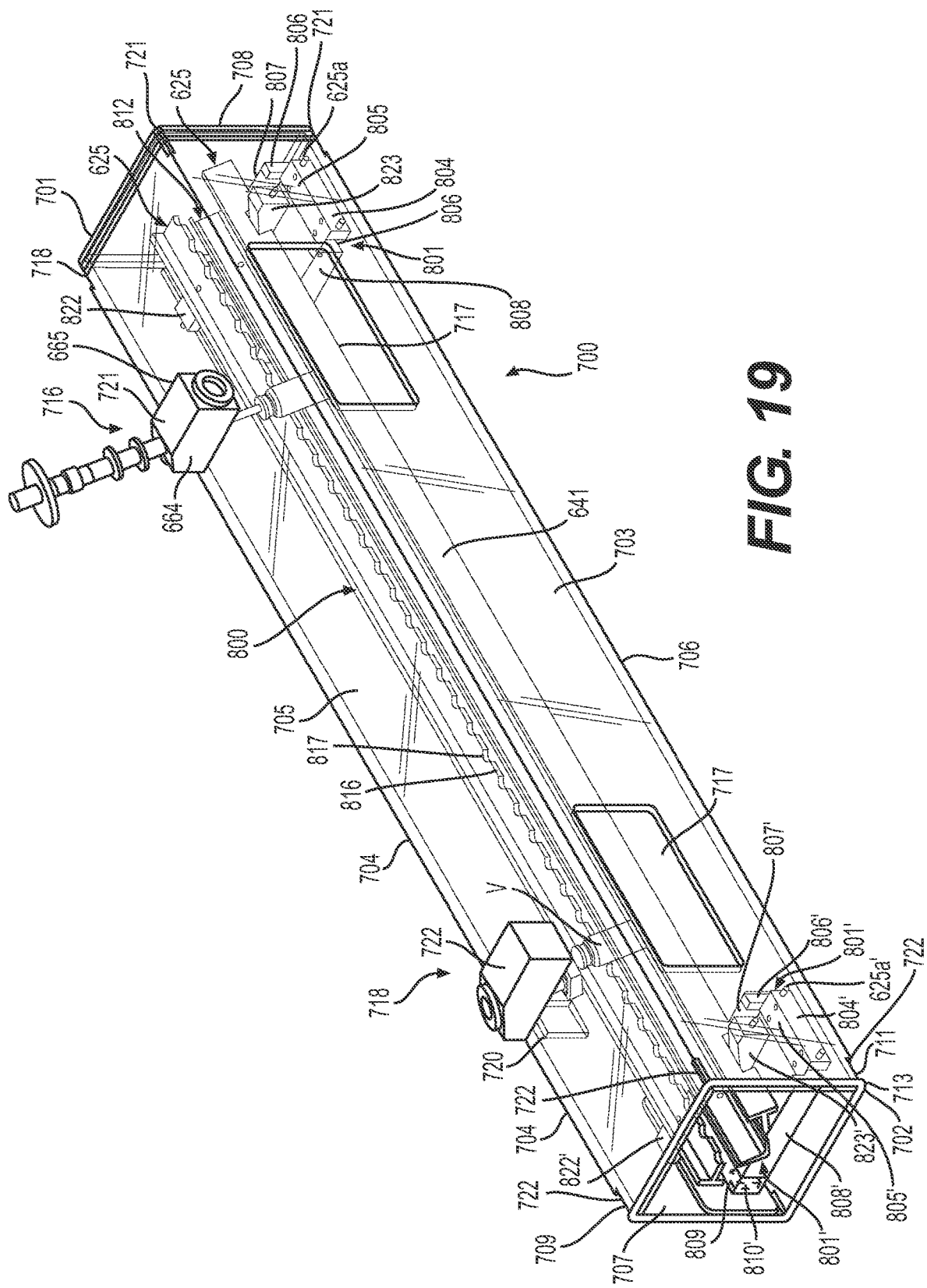
Figure 20:
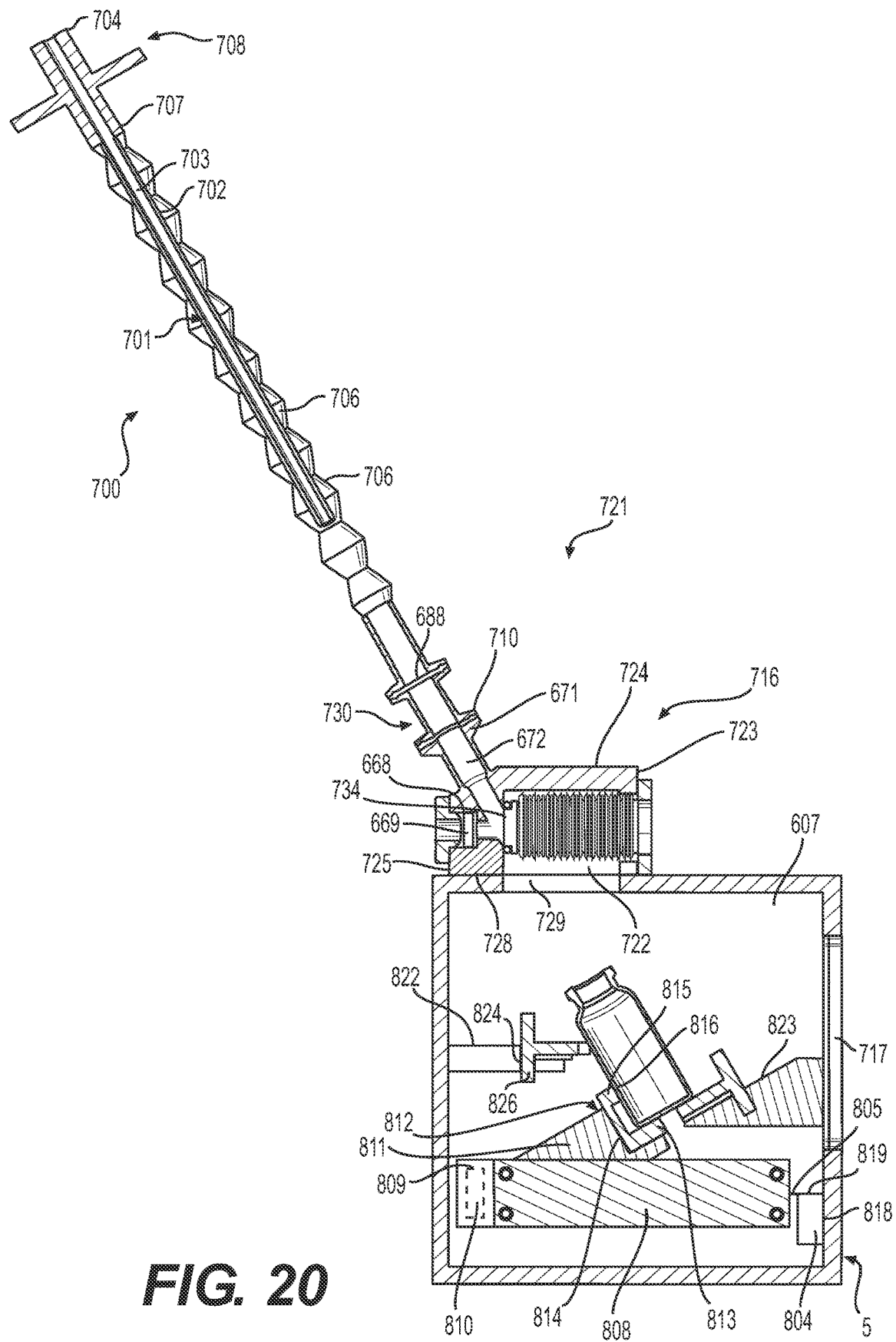
Figure 21:
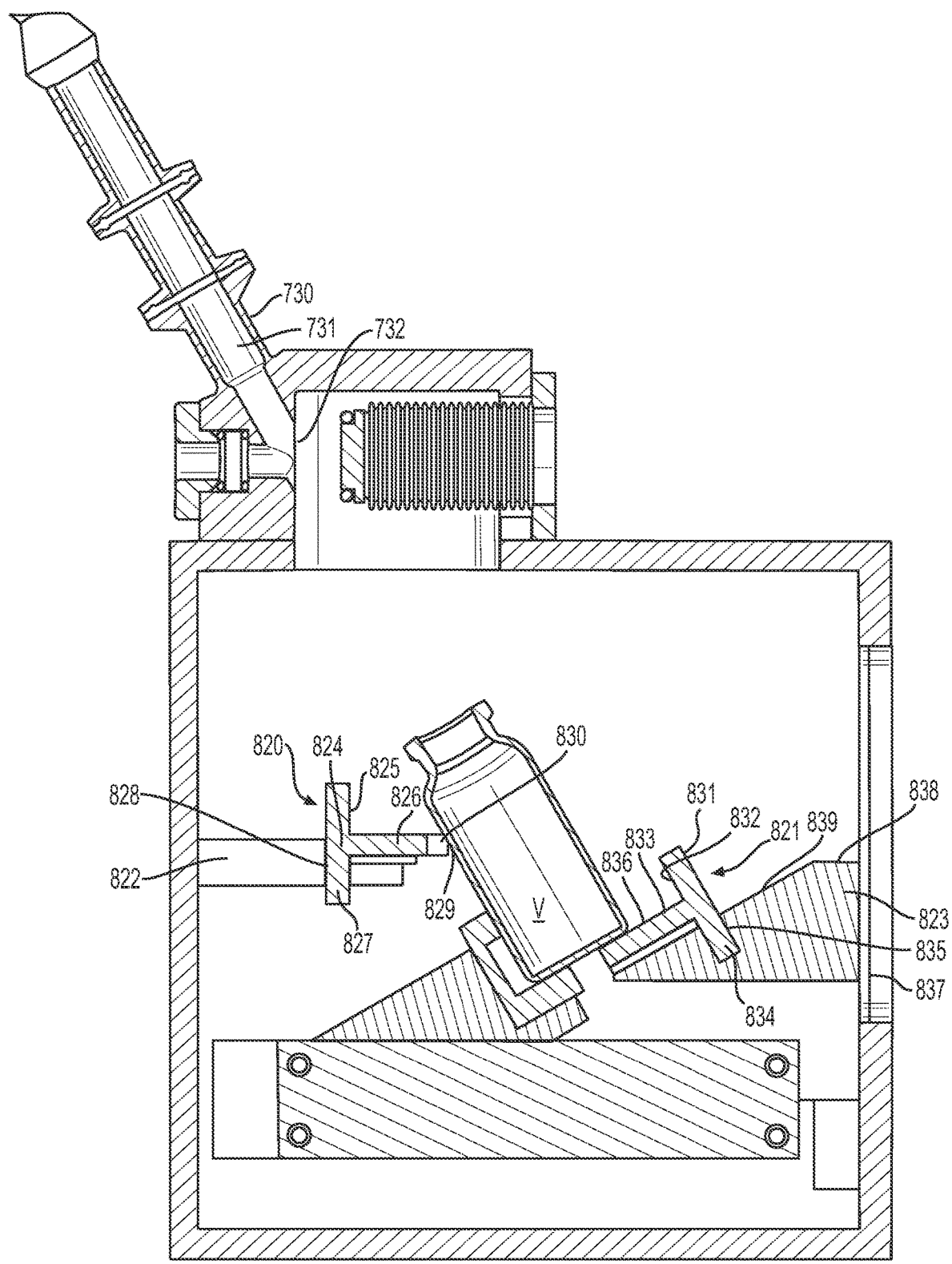
Figure 22:
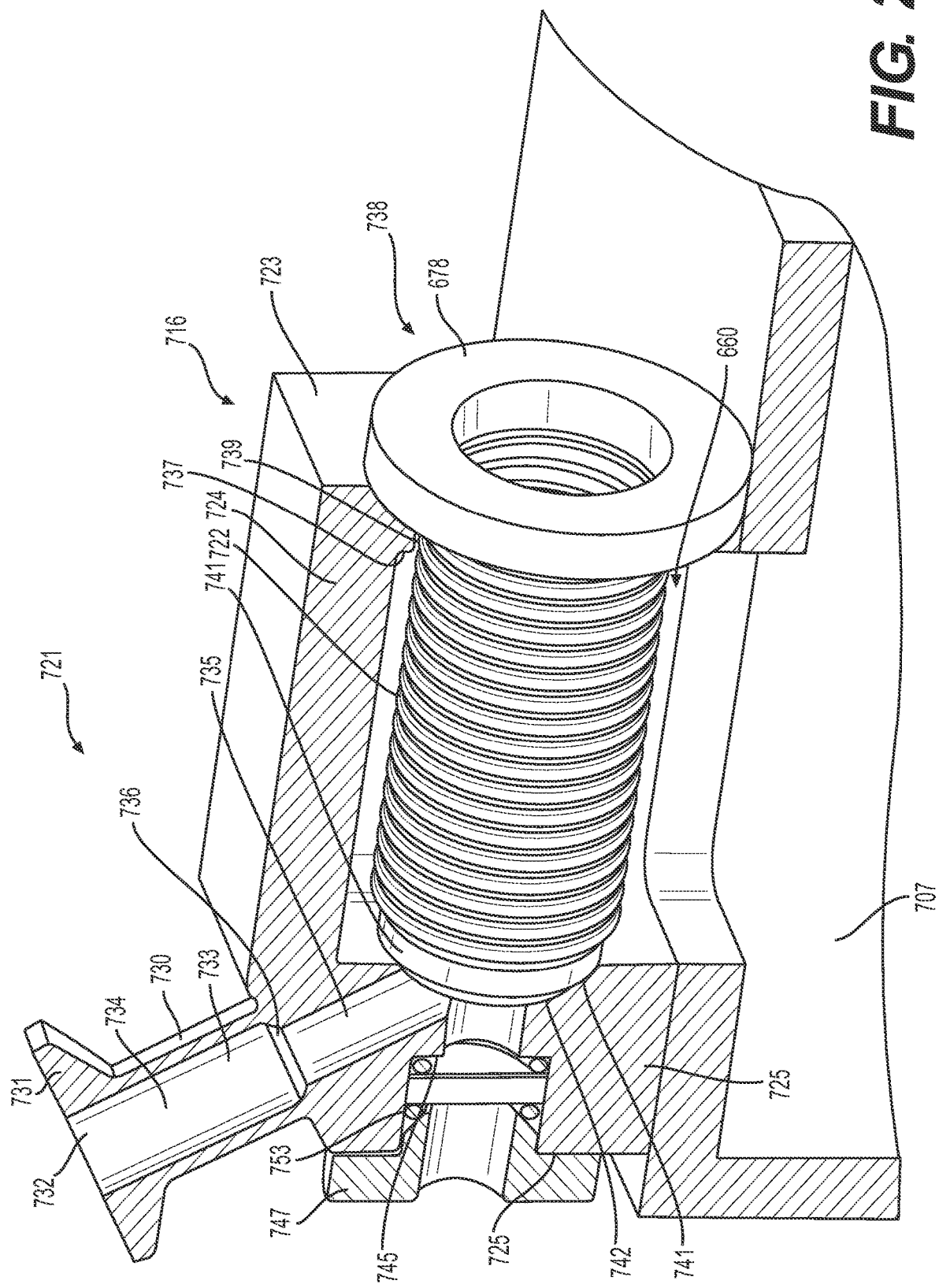
Figure 23:
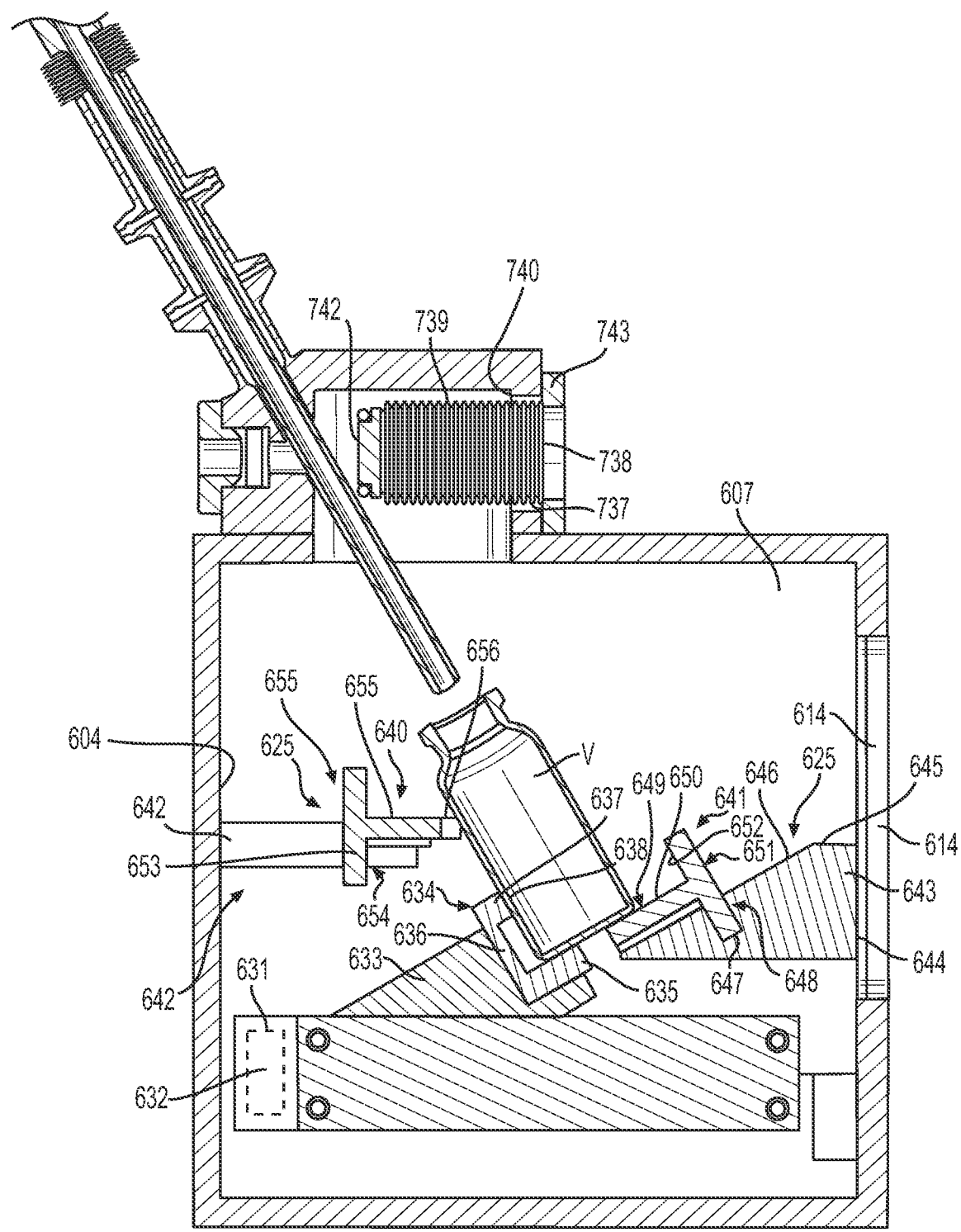
Figure 24:
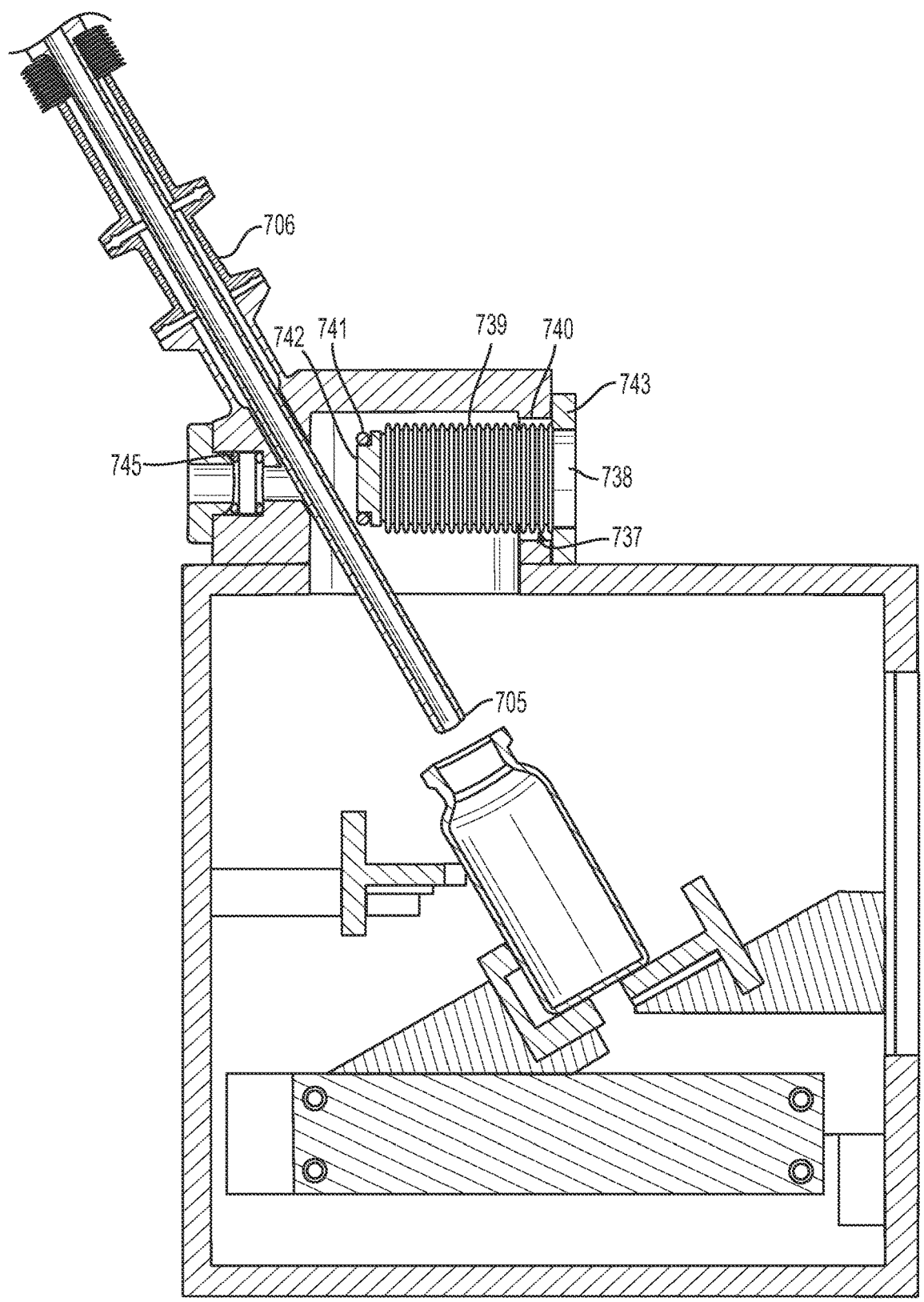
Figure 25:
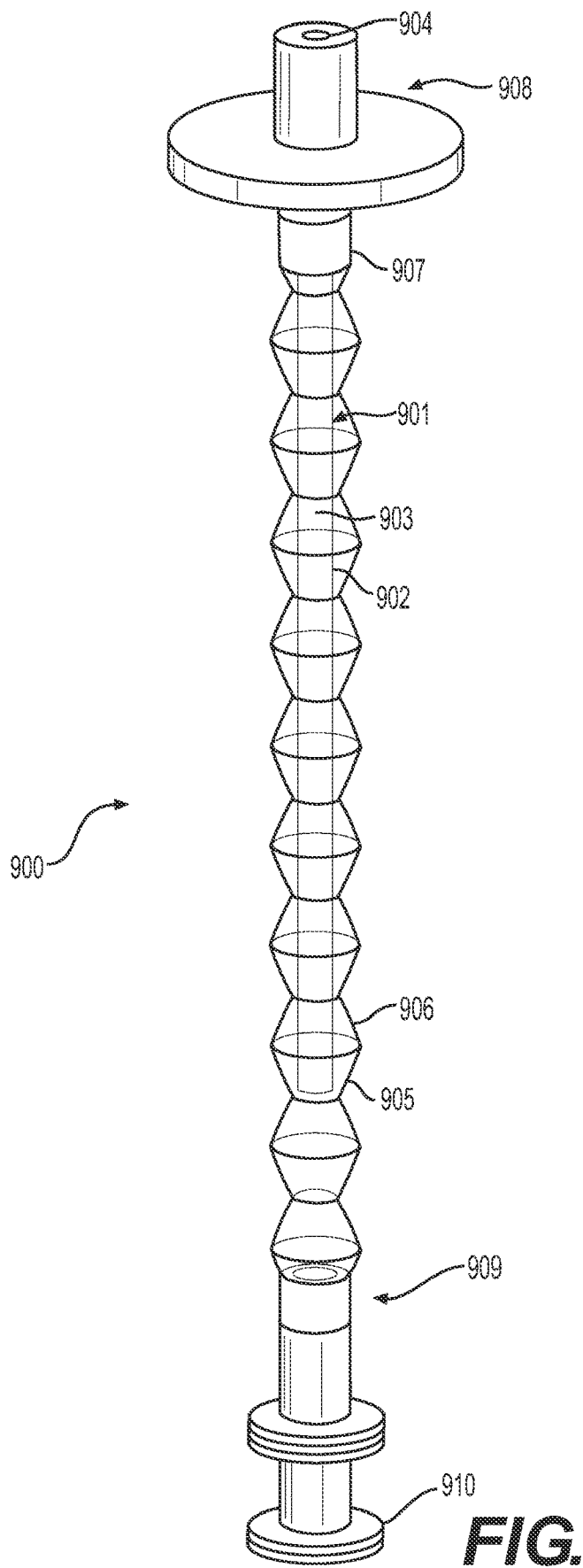
Figure 26:
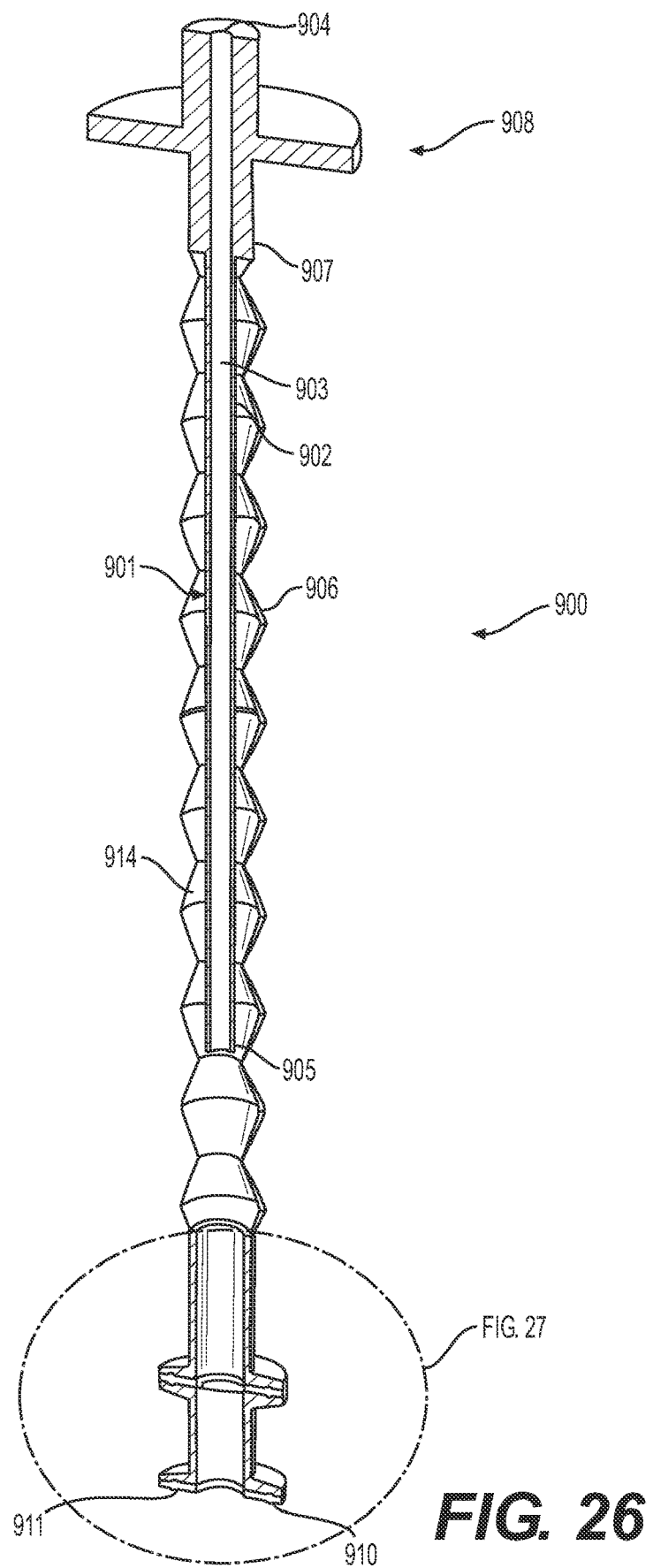
Figure 27:
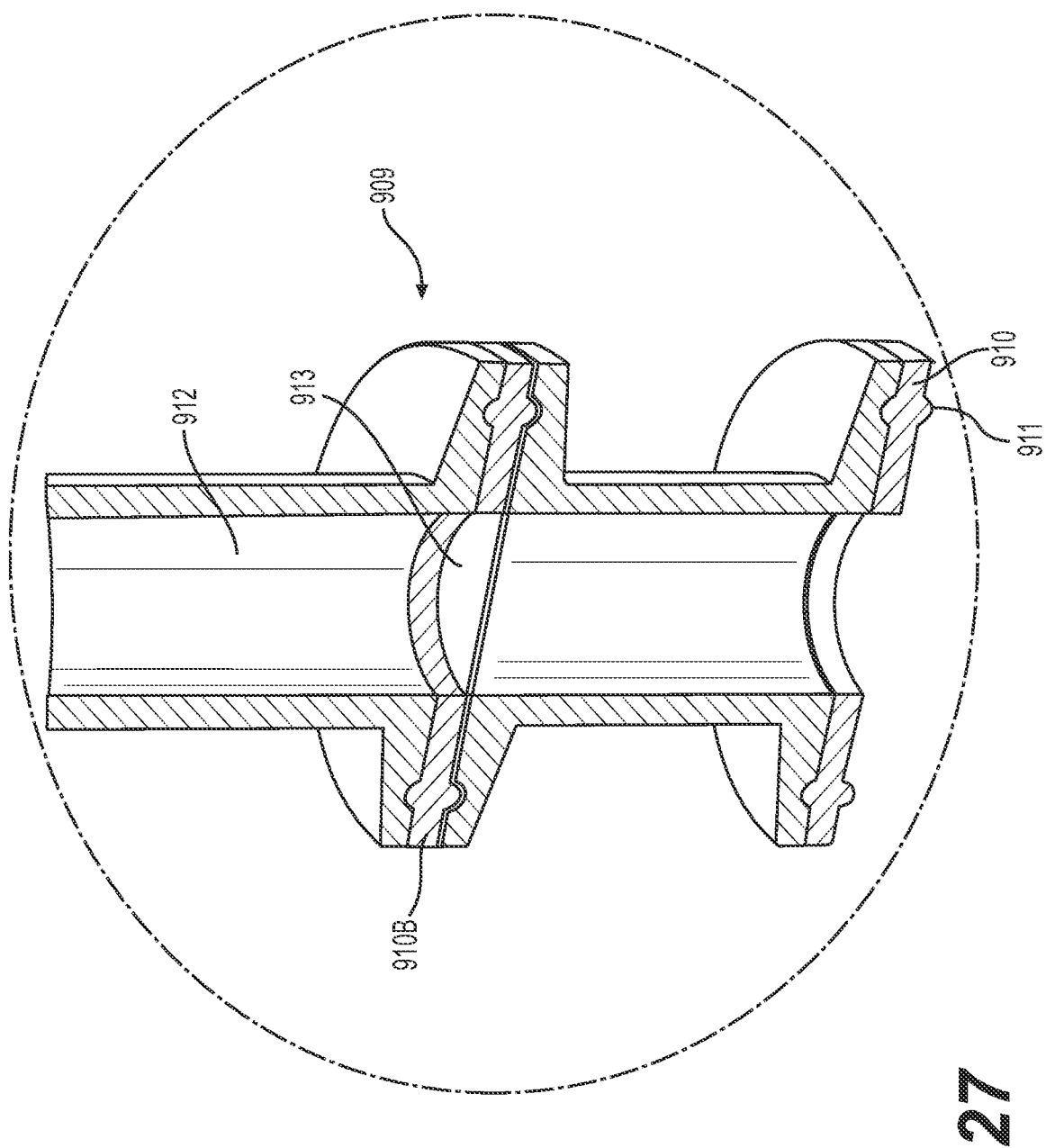
Figure 28:
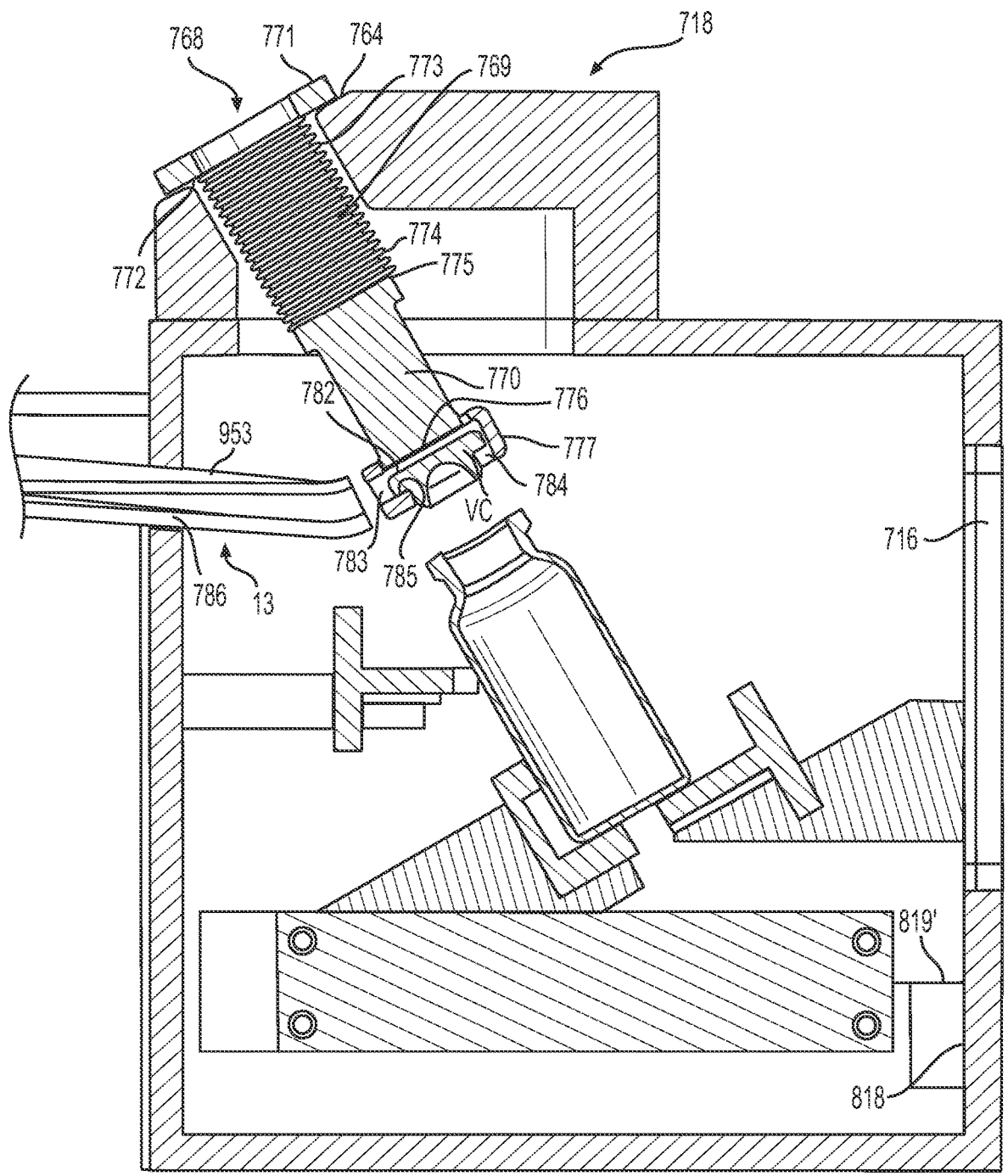
Figure 29:
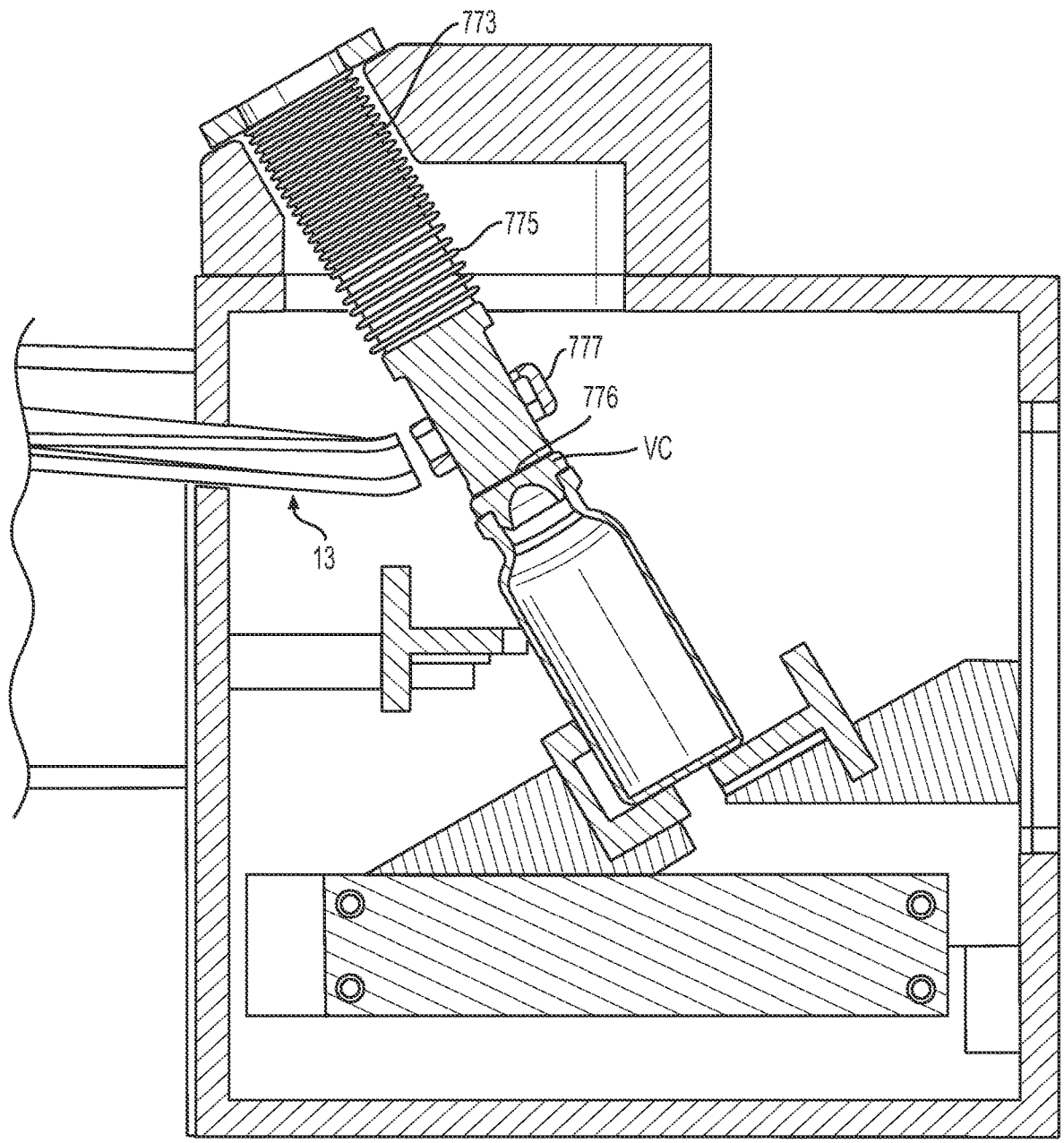
Figure 30:
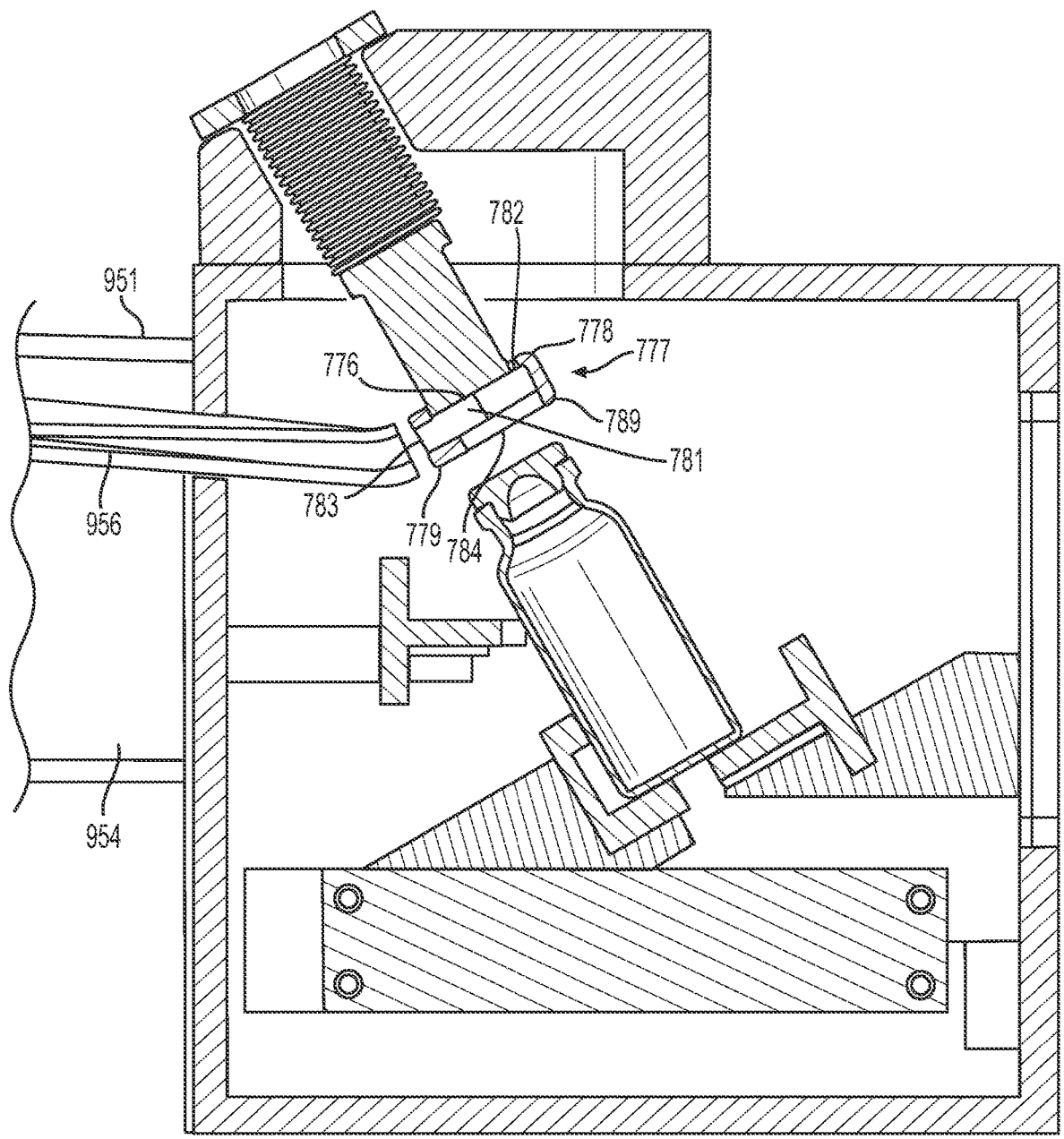
Figure 31:
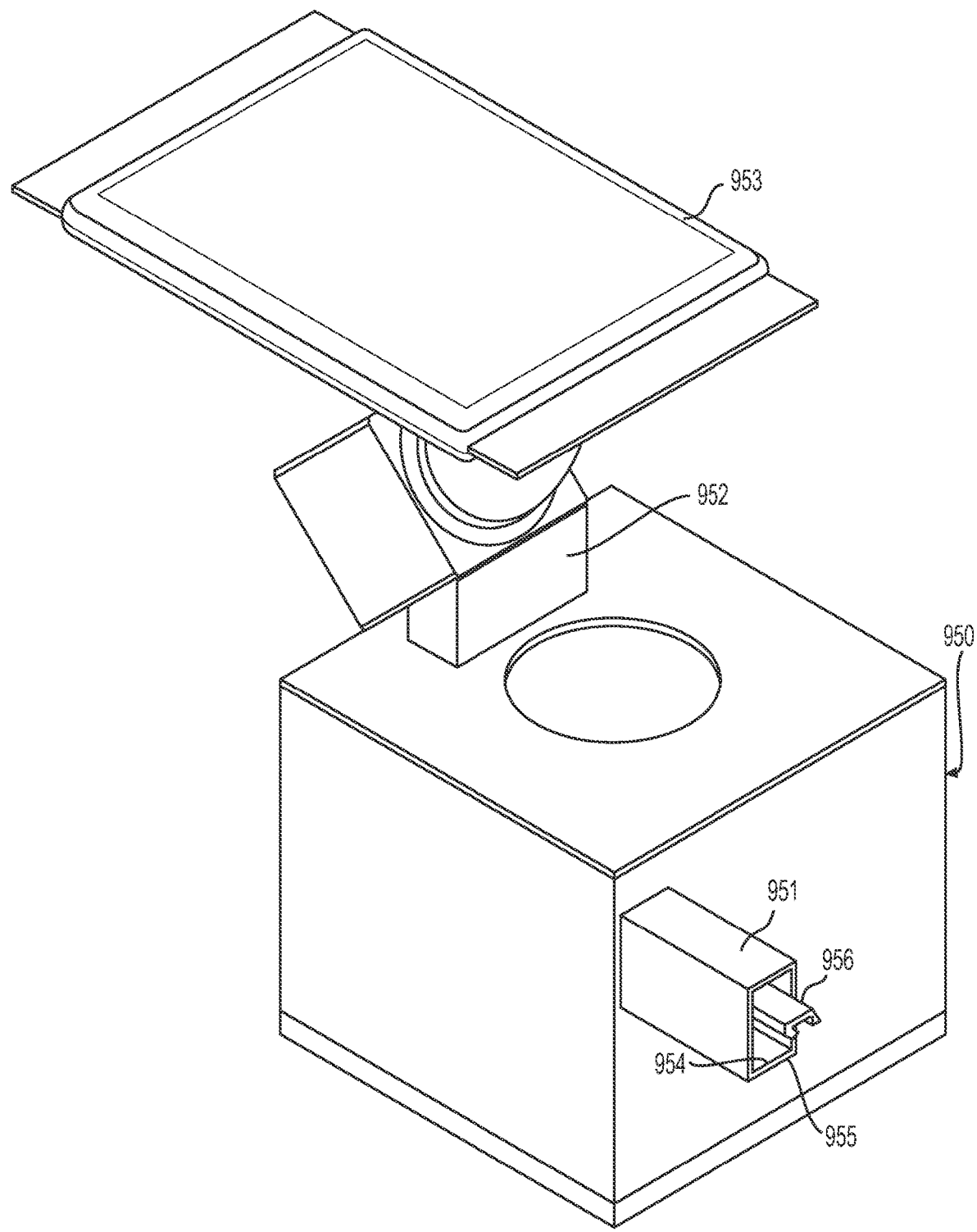
Figure 32:
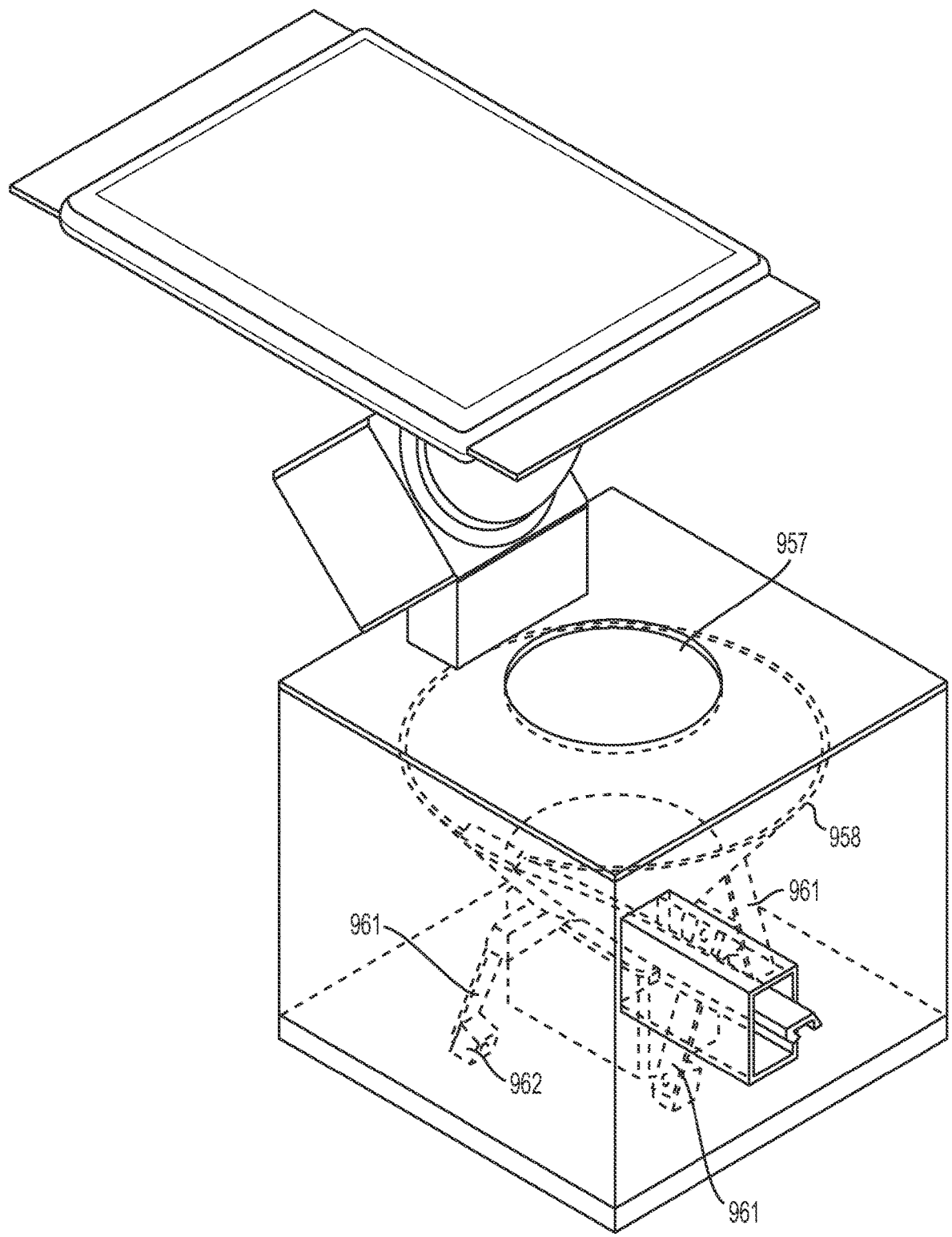
Figure 33:
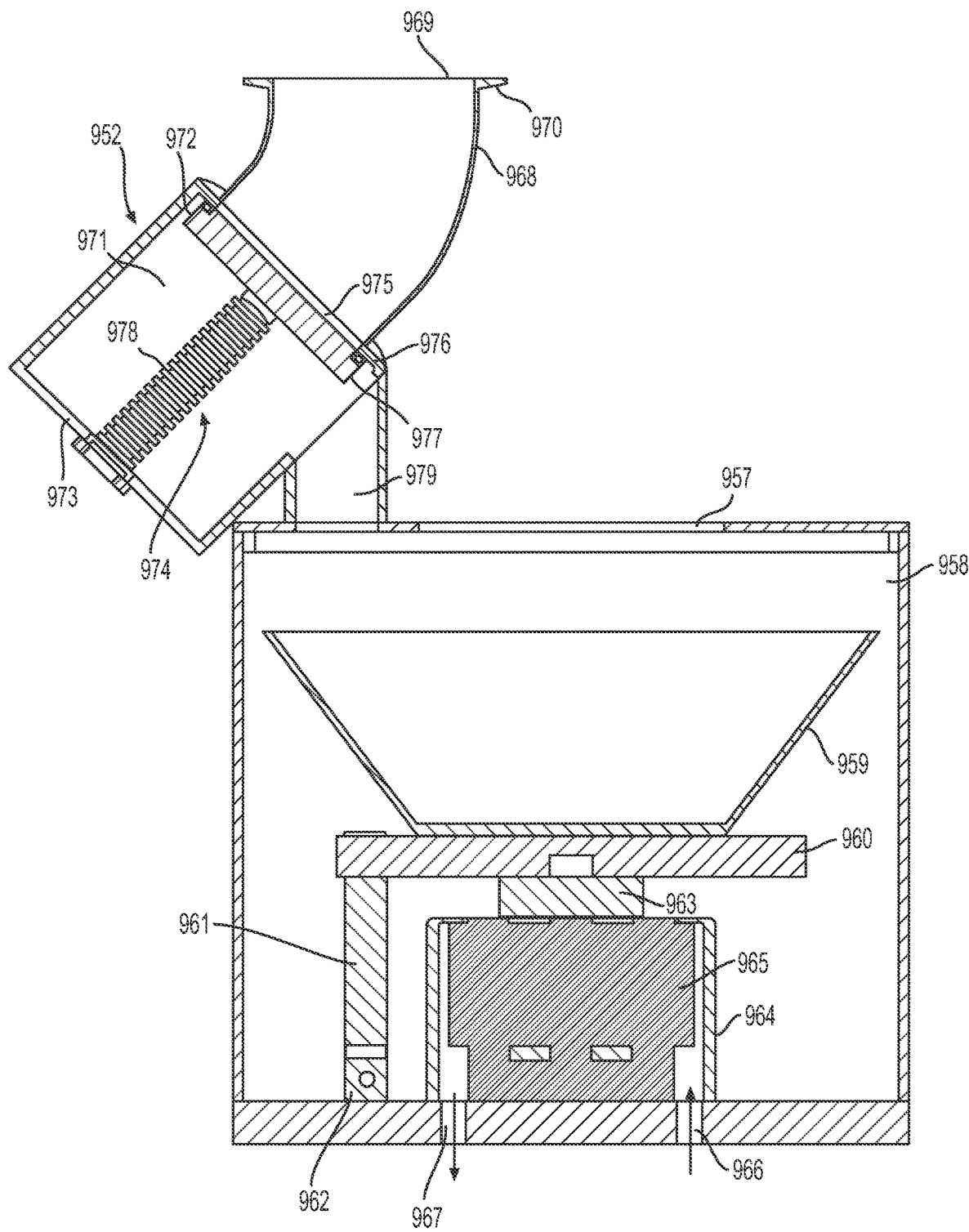
Figure 34:
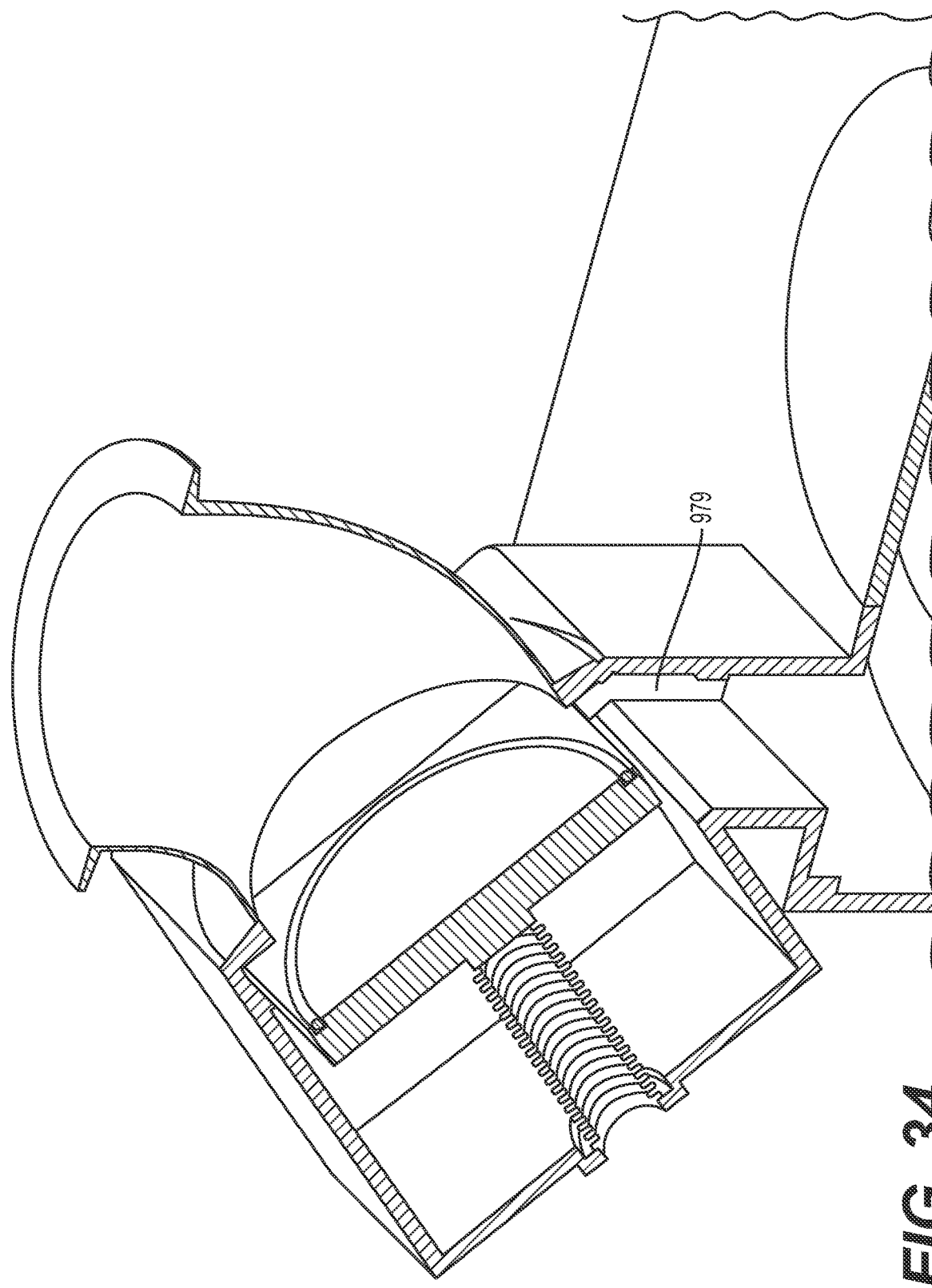
Figure 35:
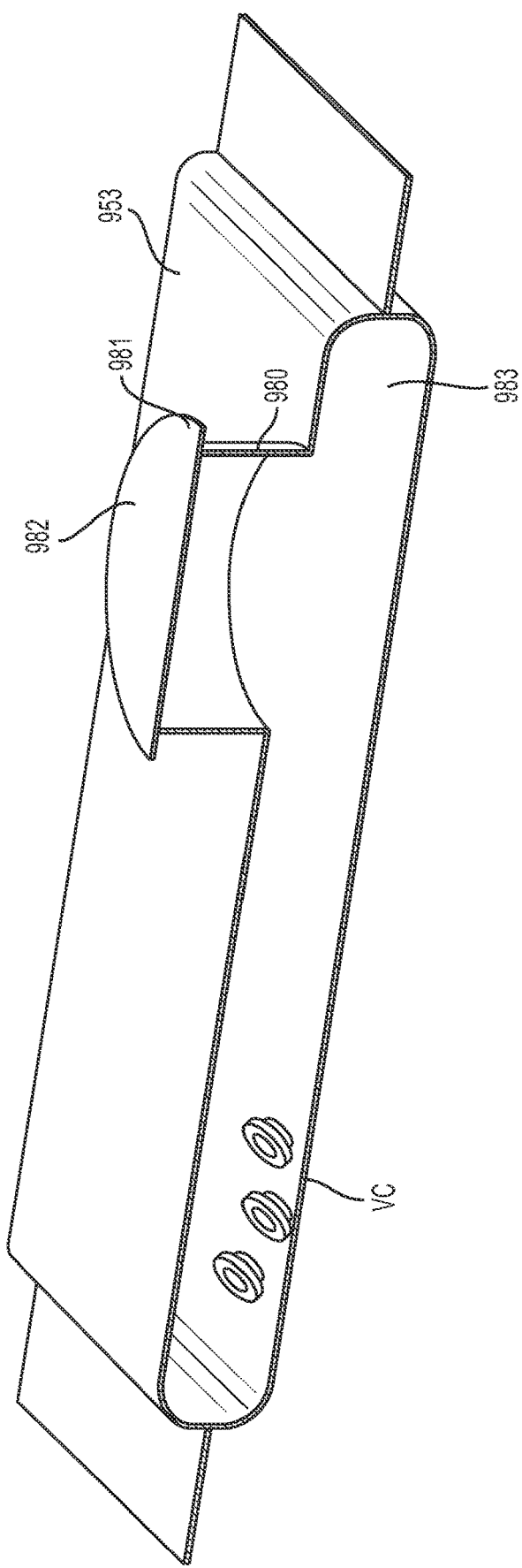
Figure 36:
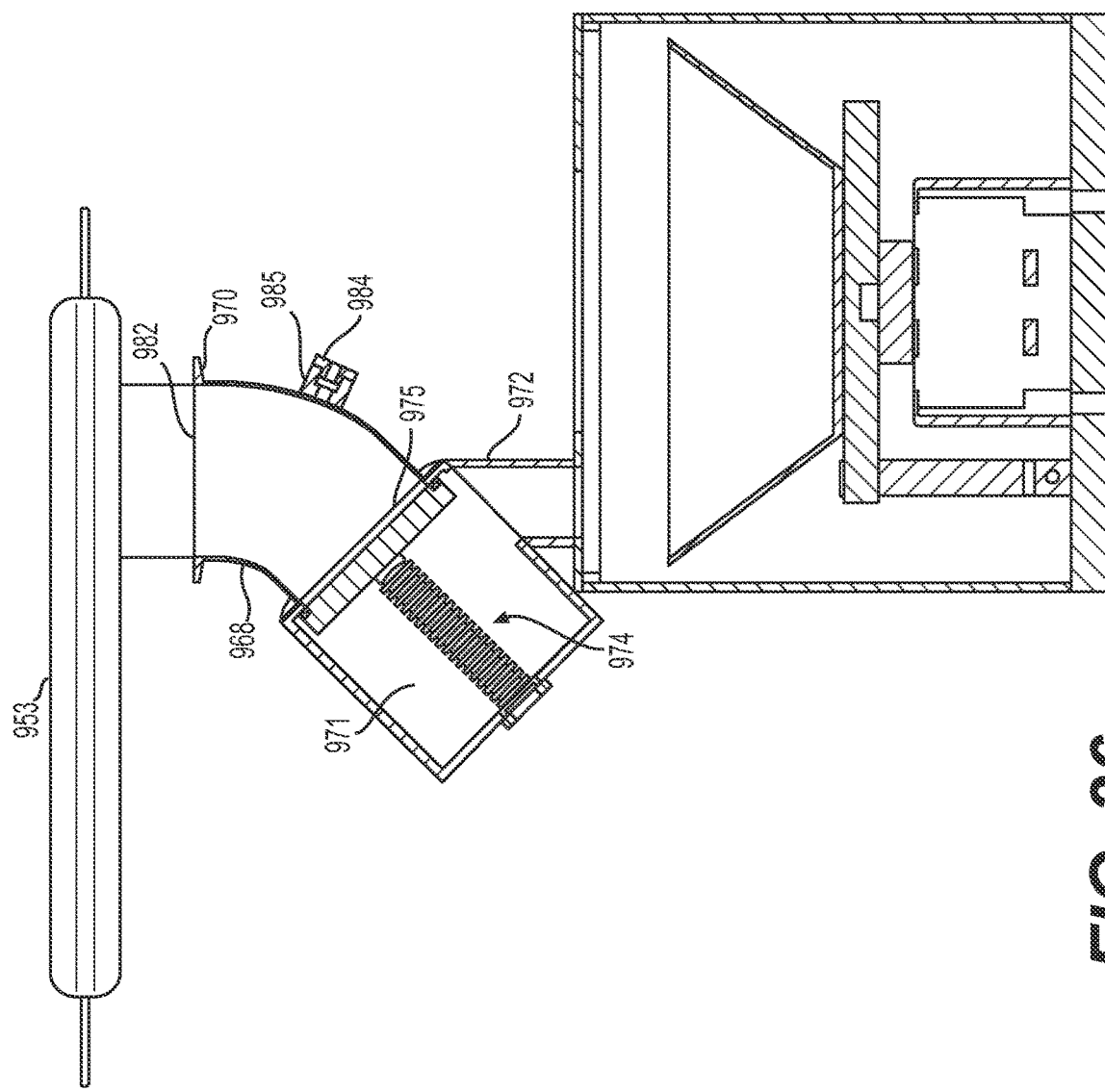
Figure 37:
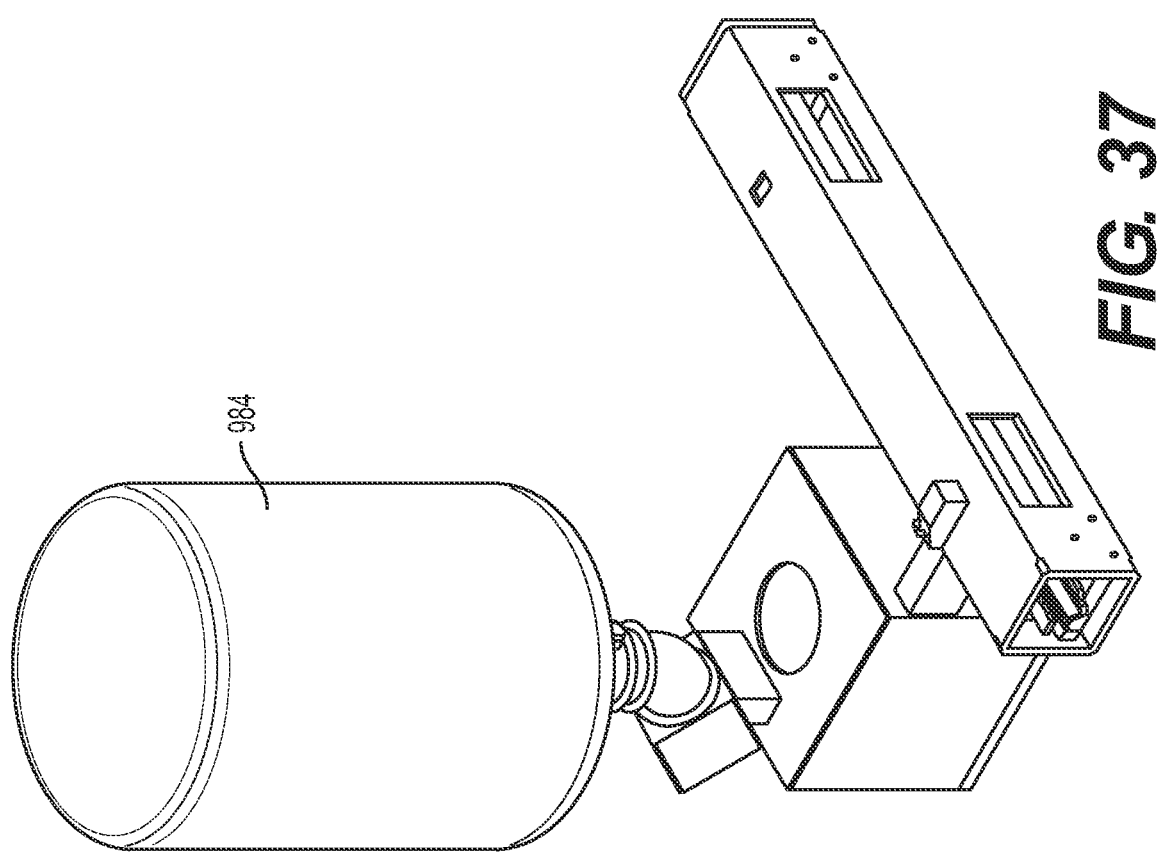
Figure 38:
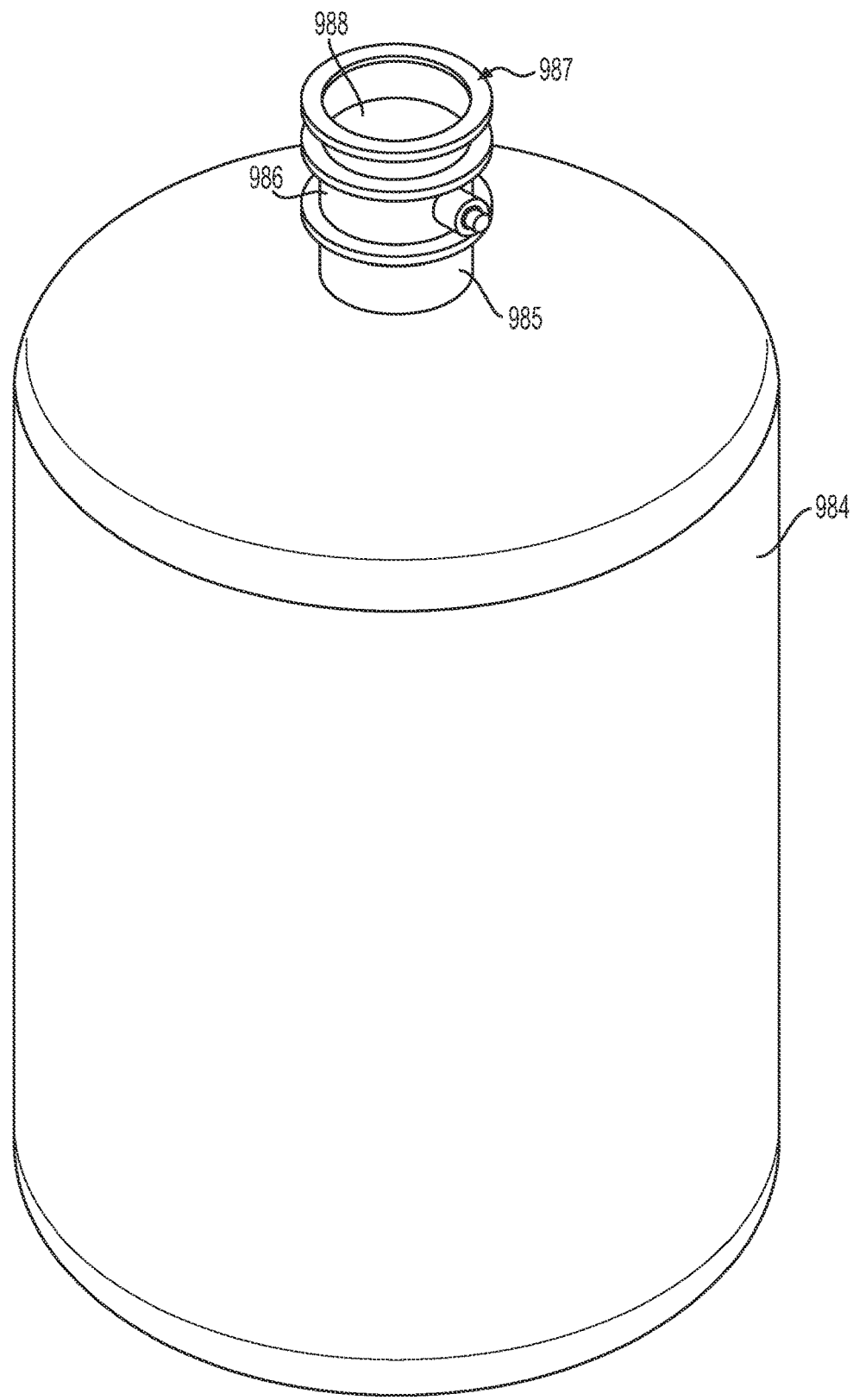
Figure 39:
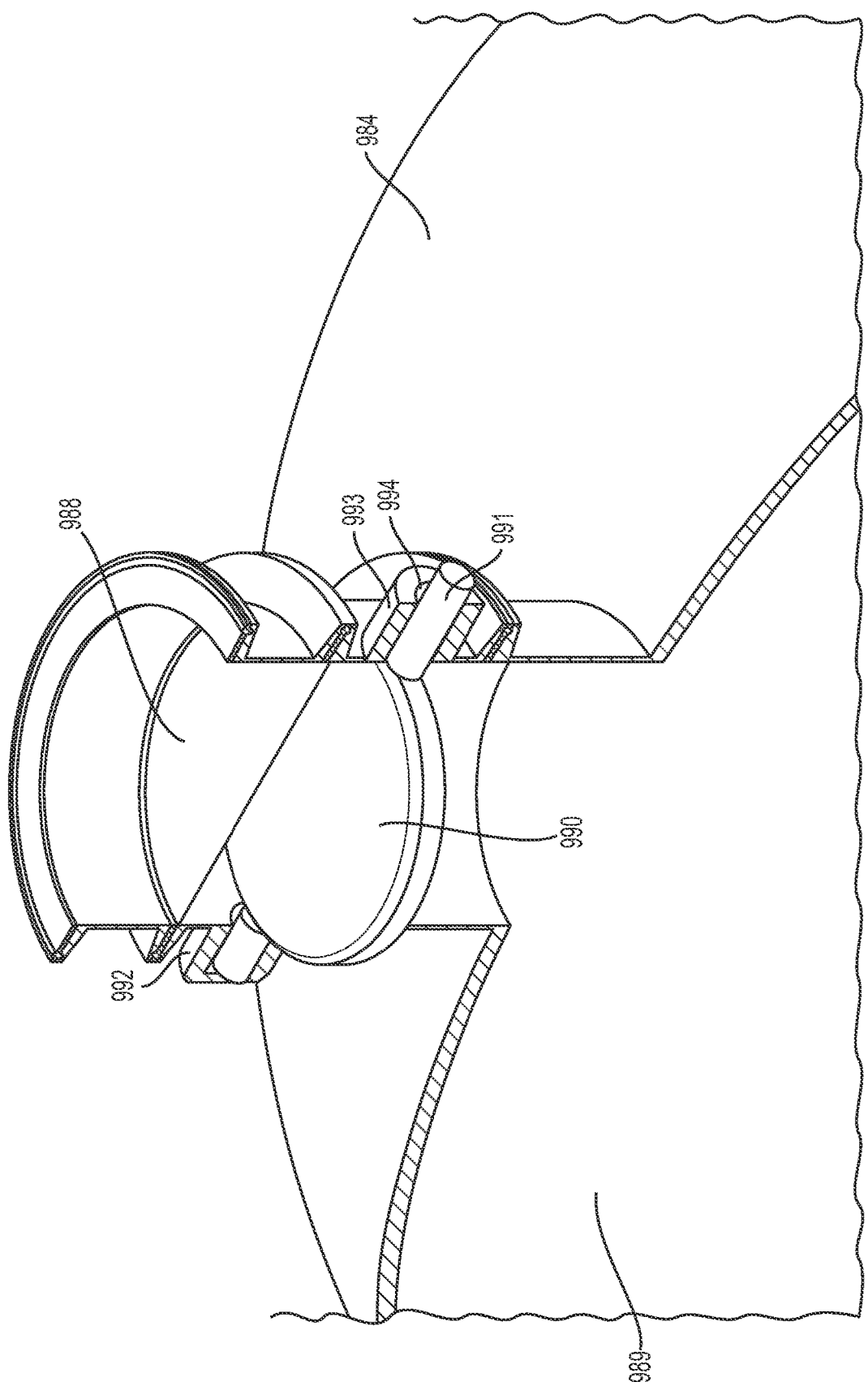
Figure 40A:
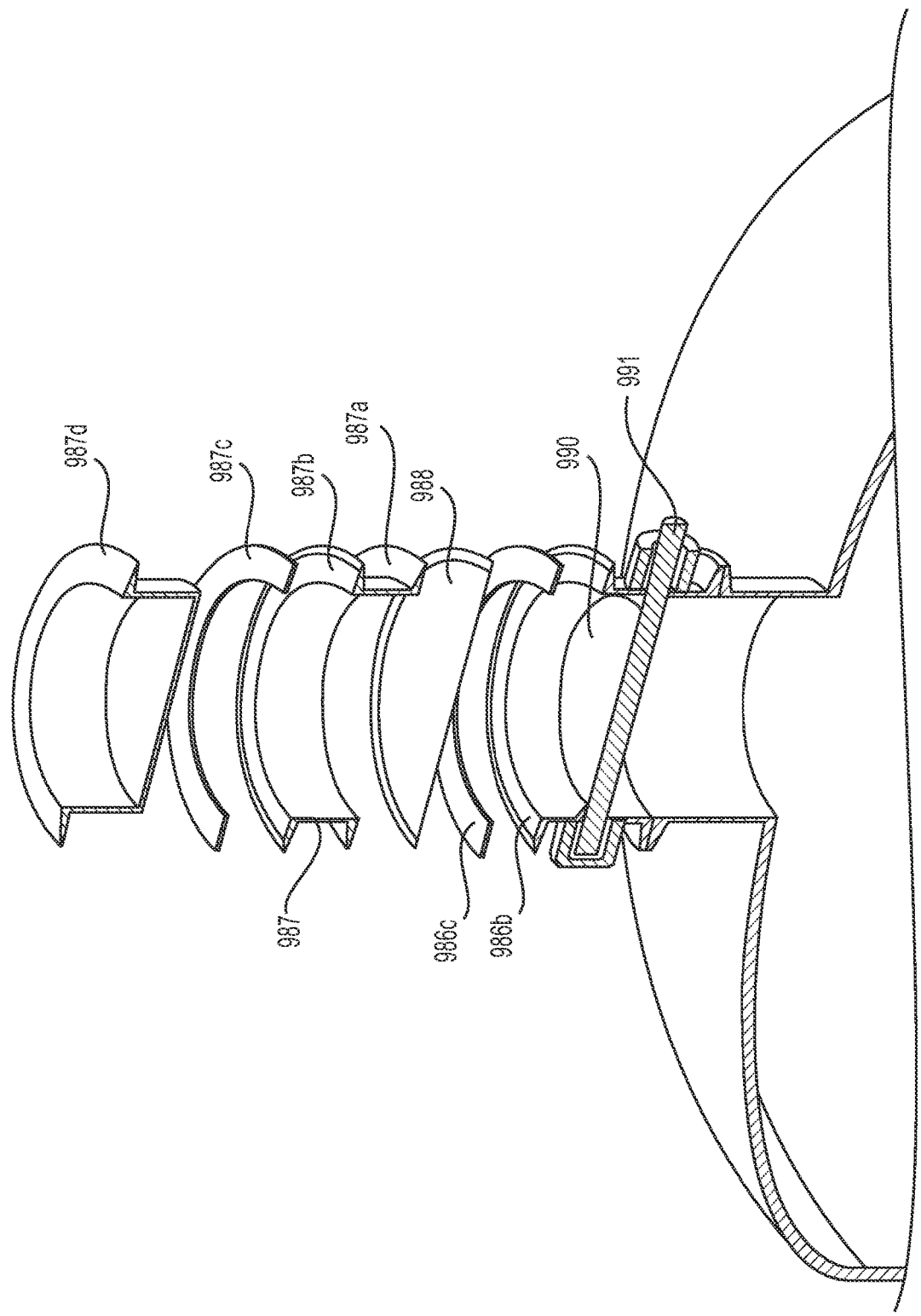
Figure 40B:
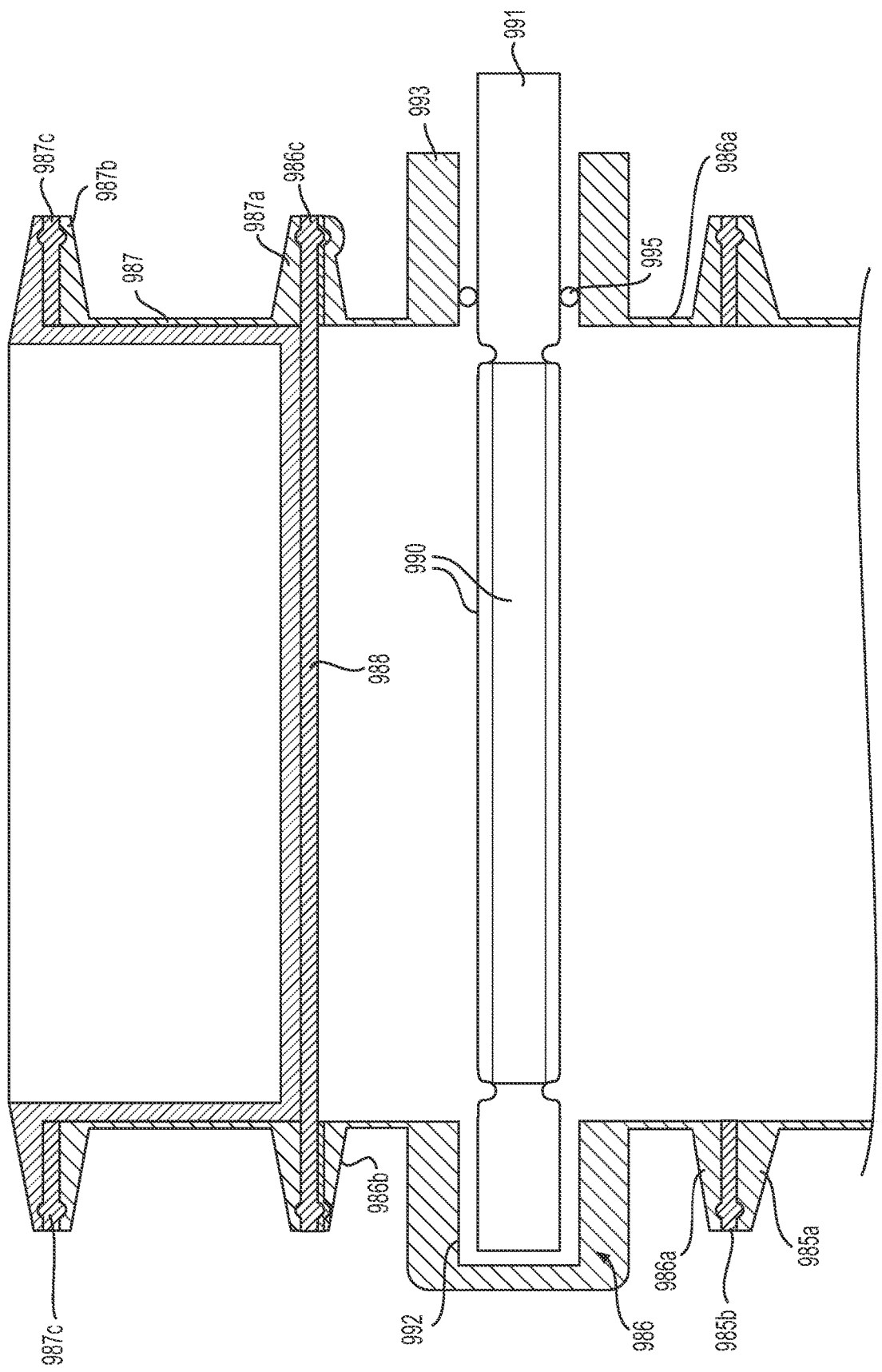
Figure 41:
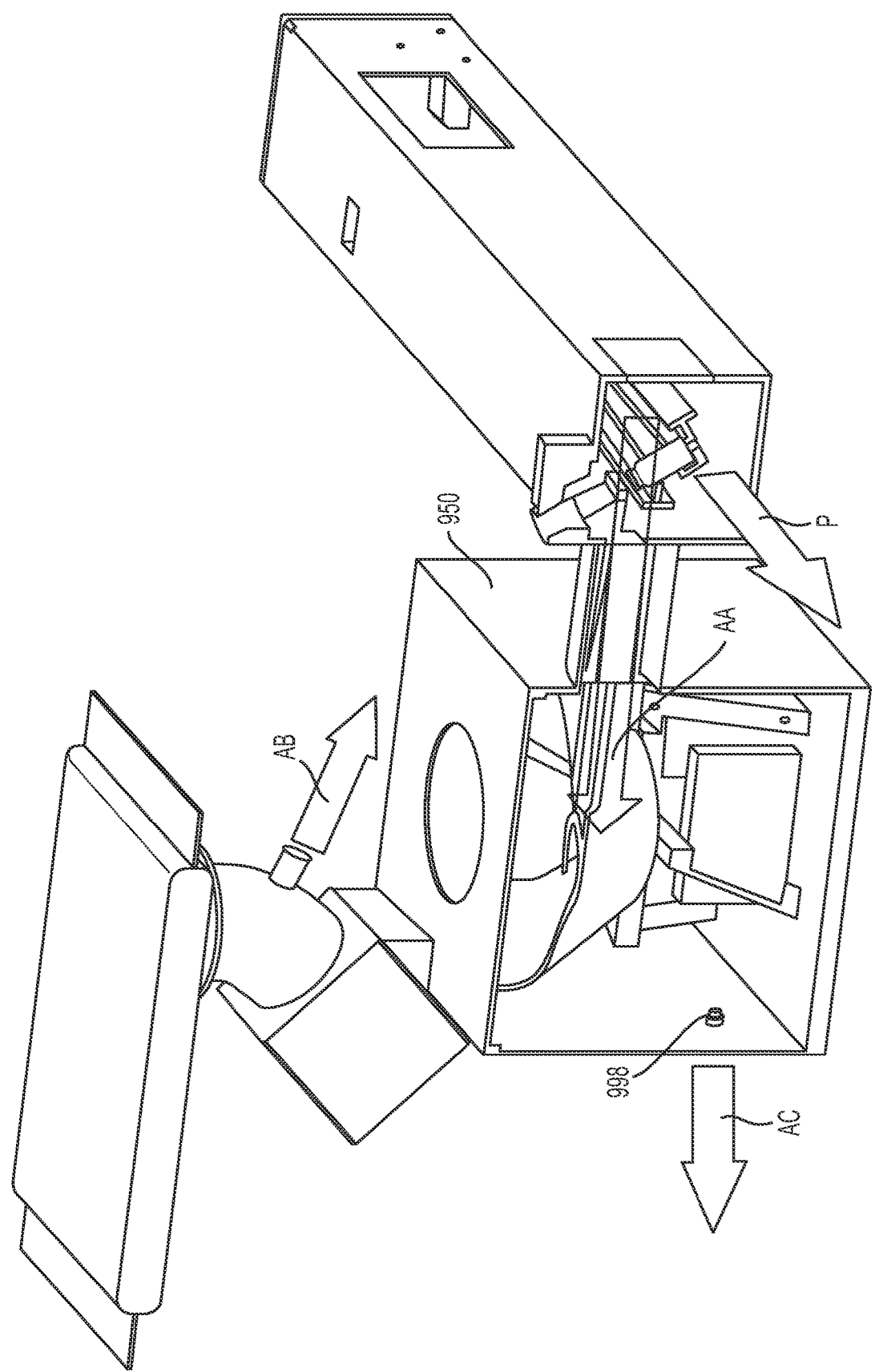
Figure 42:
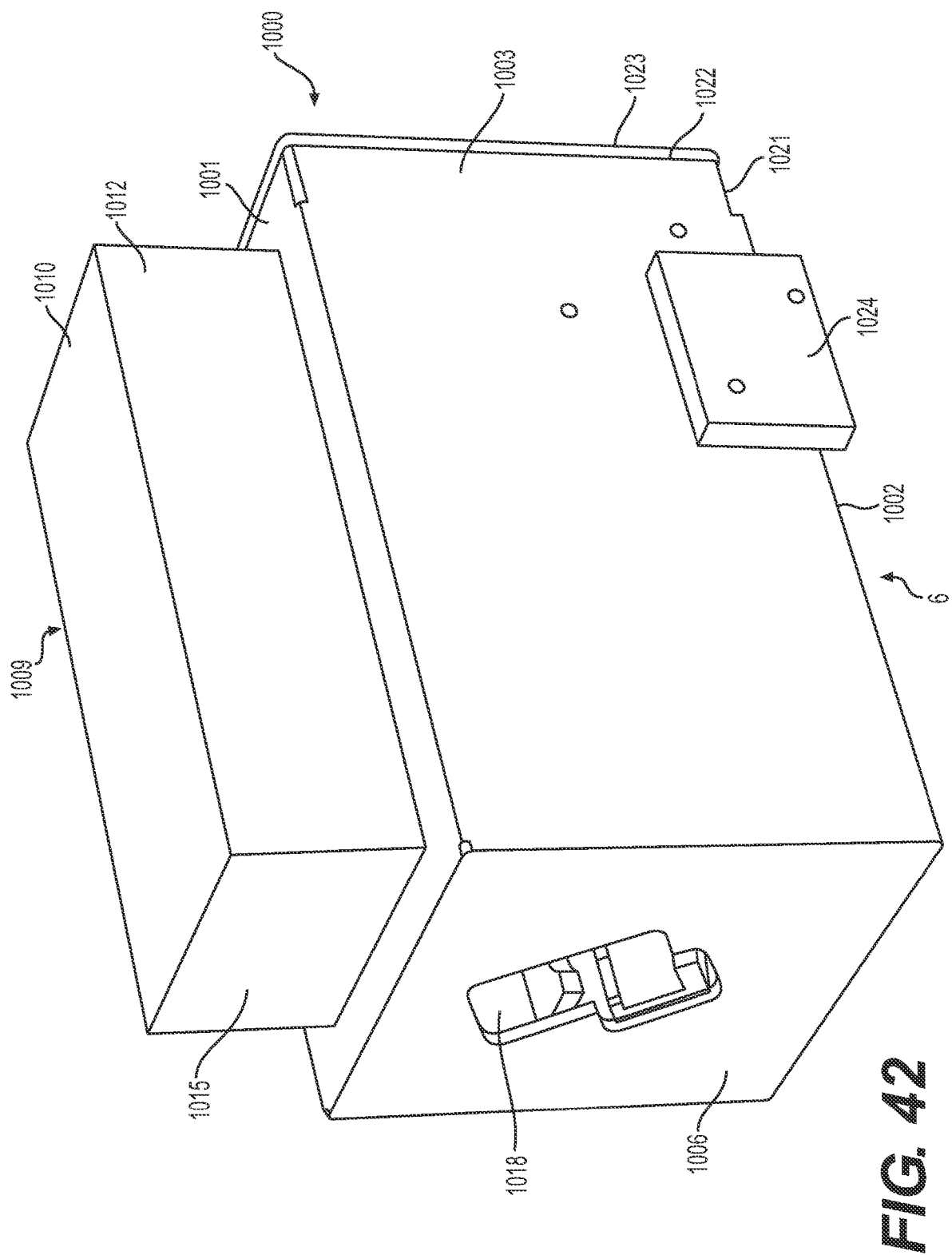
Figure 43:
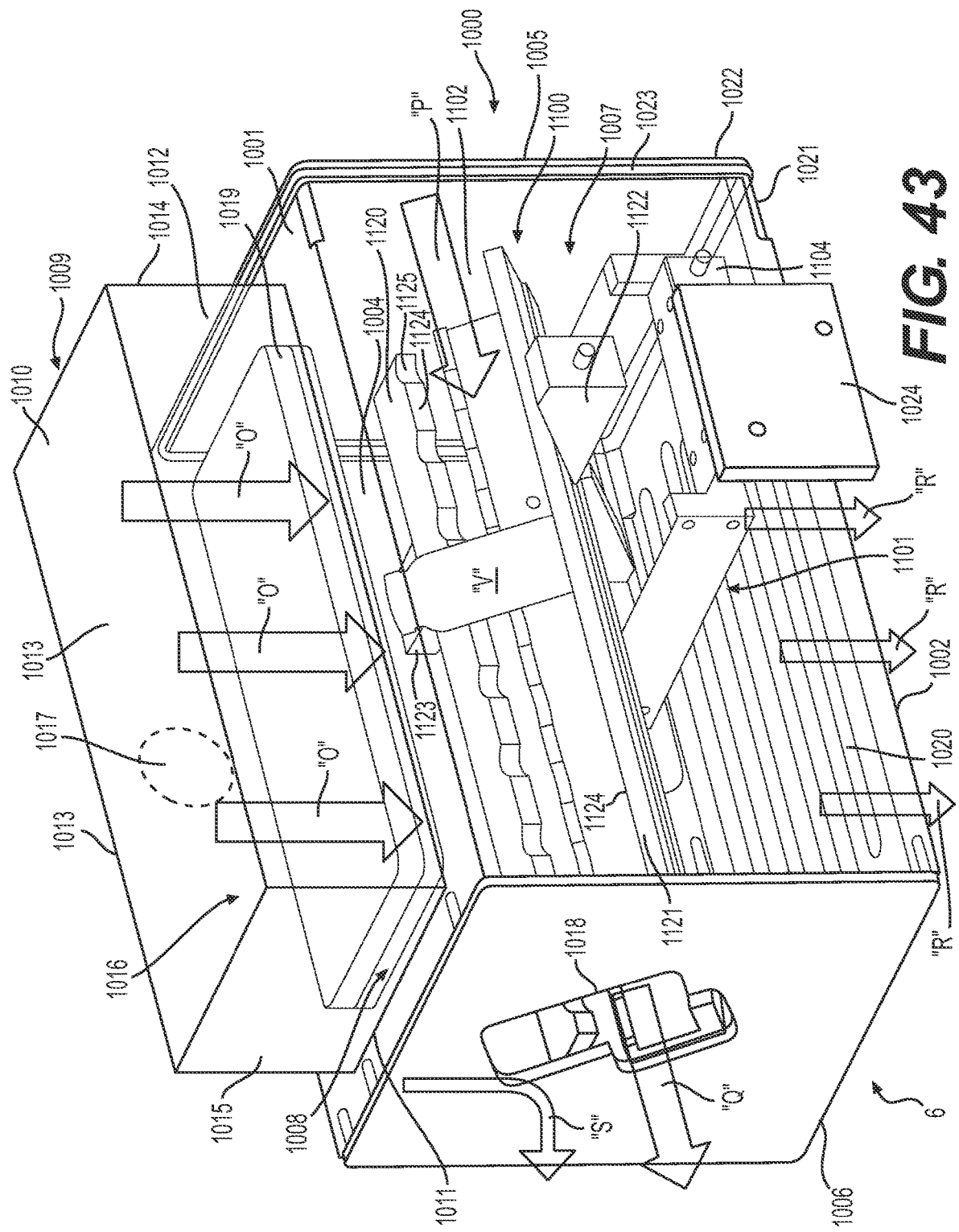
Figure 44:
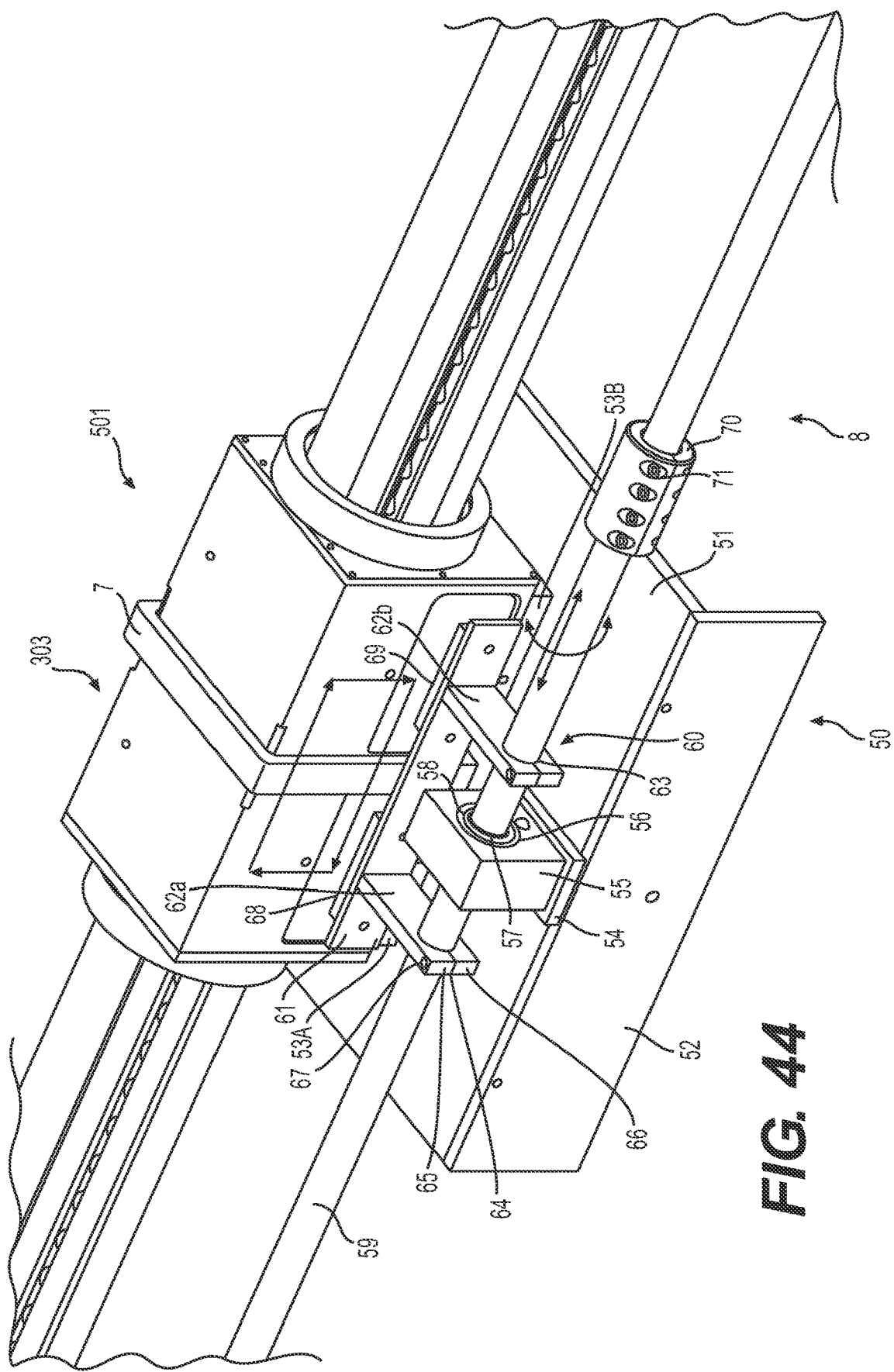
Figure 45:
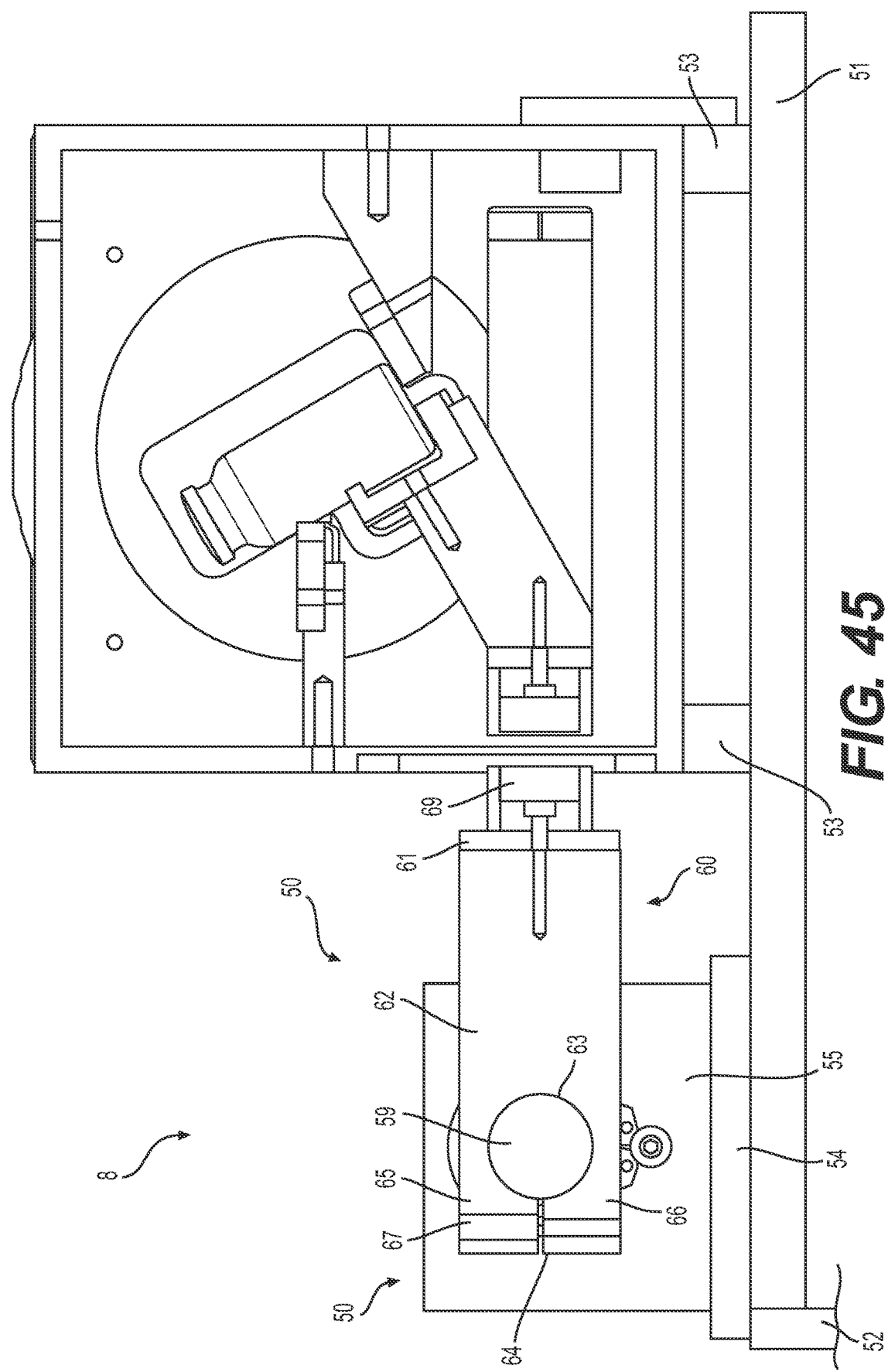
Figure 46:
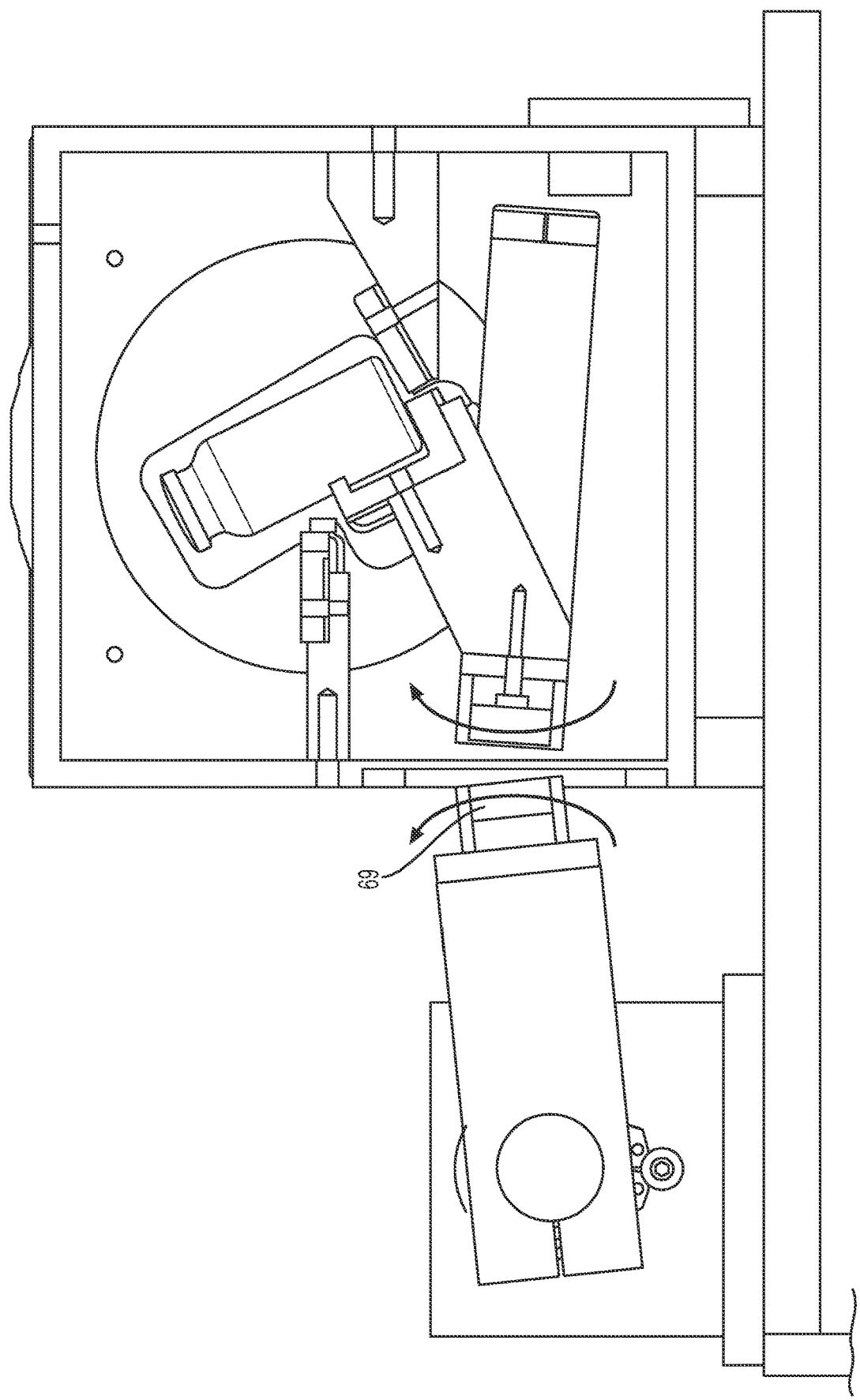
Figure 47:
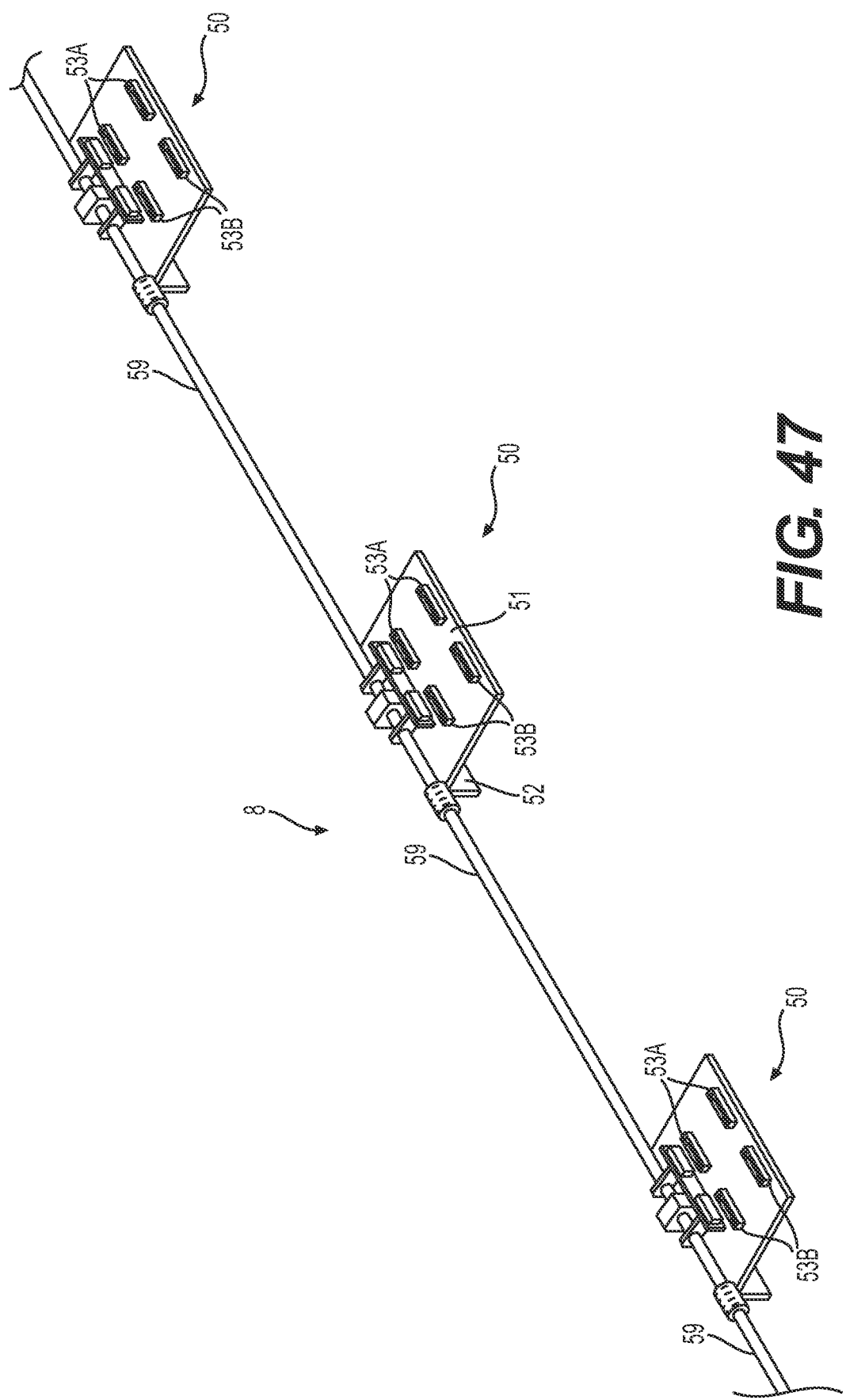
Figure 48A:
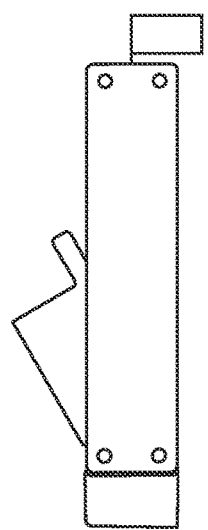
Figure 48B:
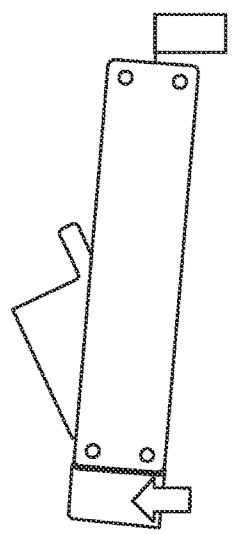
Figure 48C:
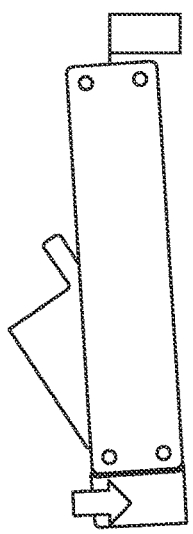
Figure 49C:
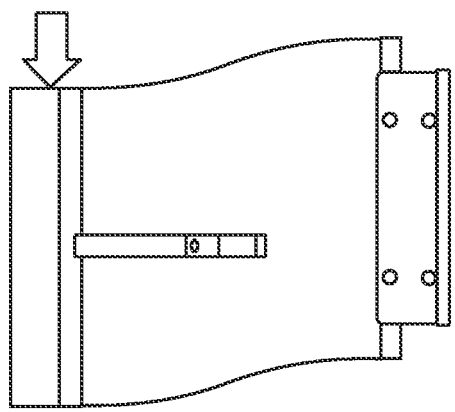
Figure 49B:
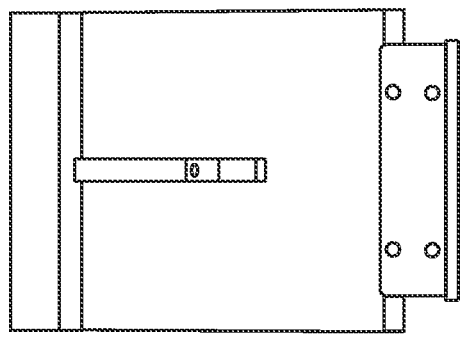
Figure 49A:
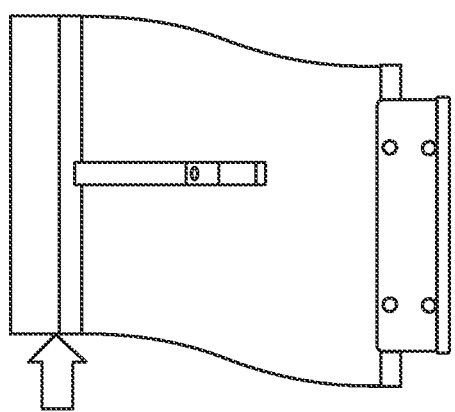
Figure 51:
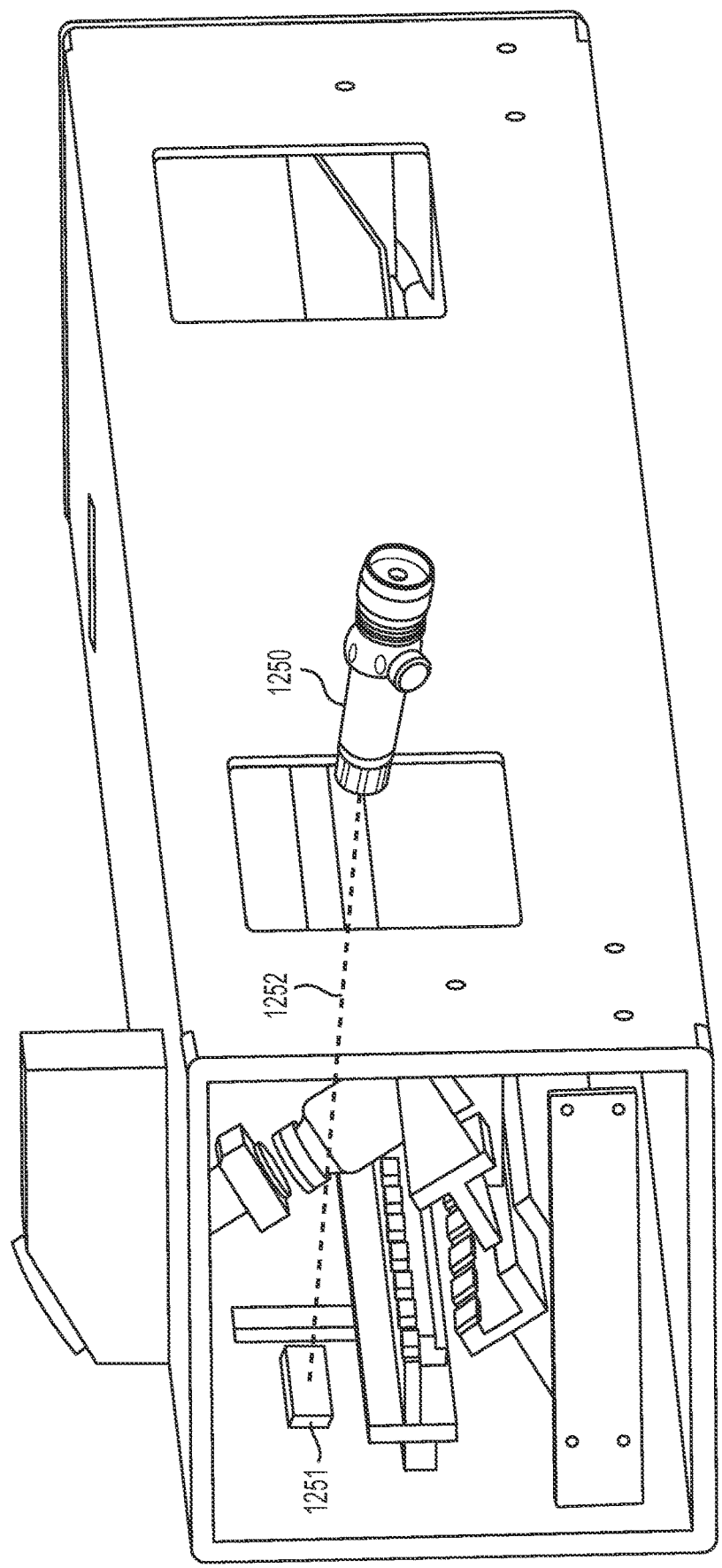
Figure 52:
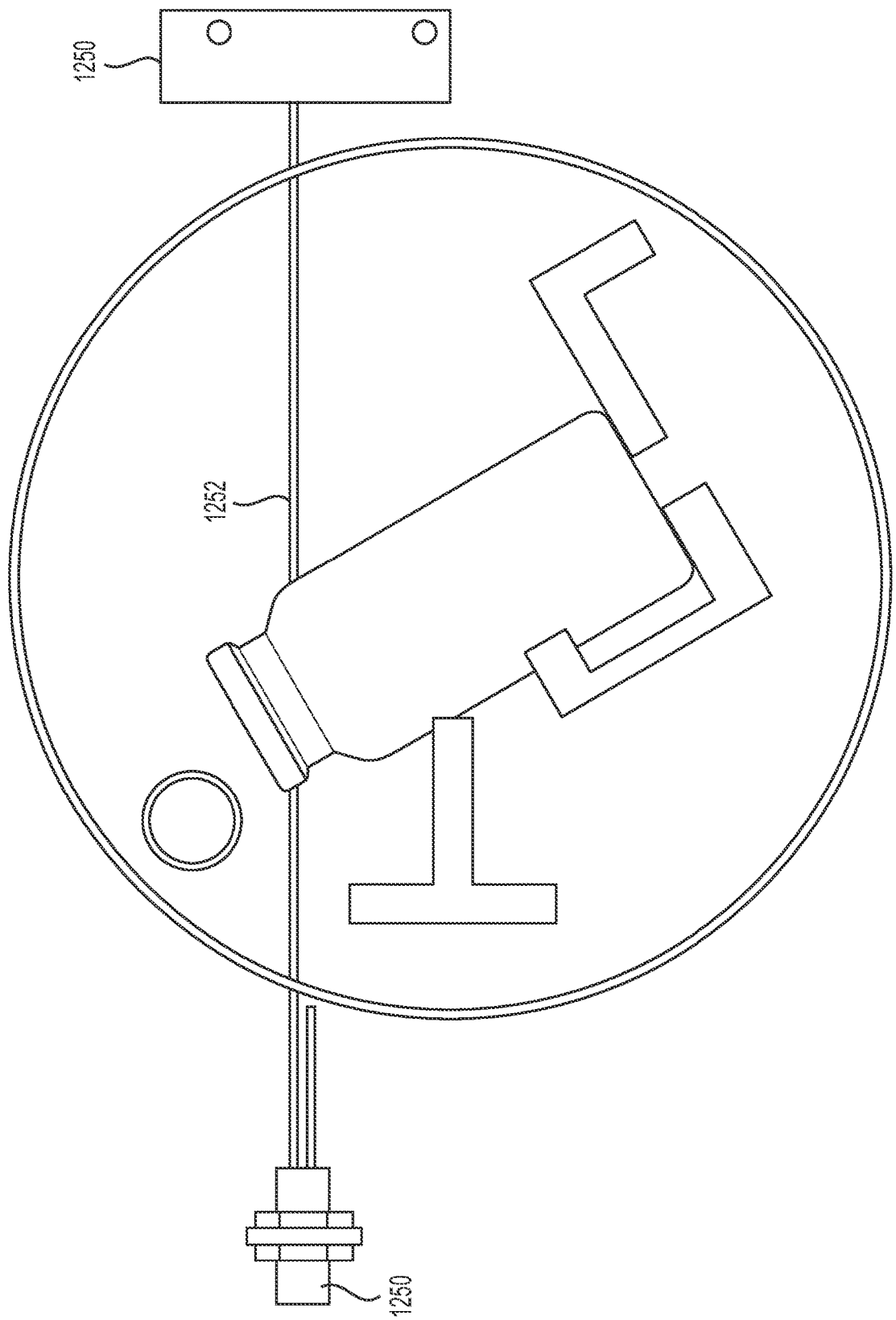
Figure 55:
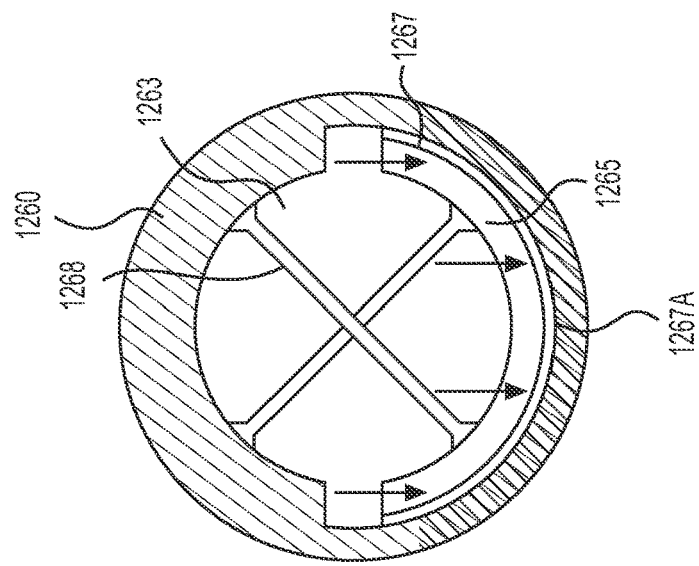
Figure 54:
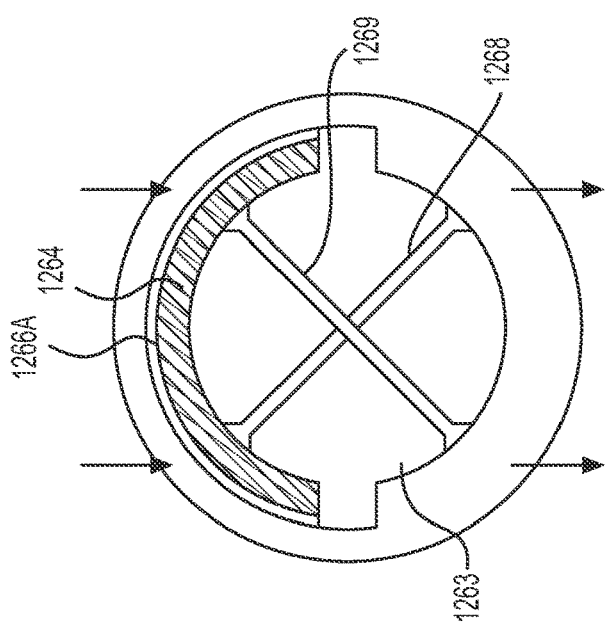
Figure 53:
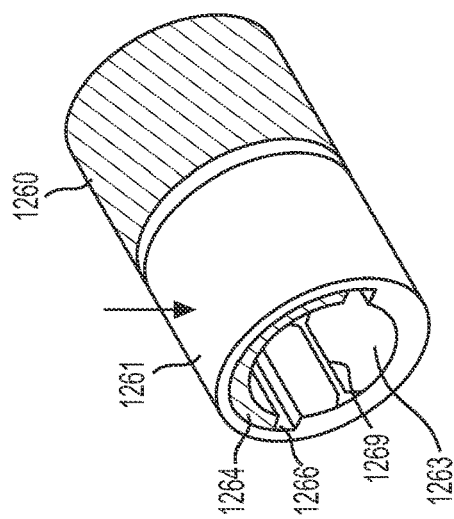
Figure 56:
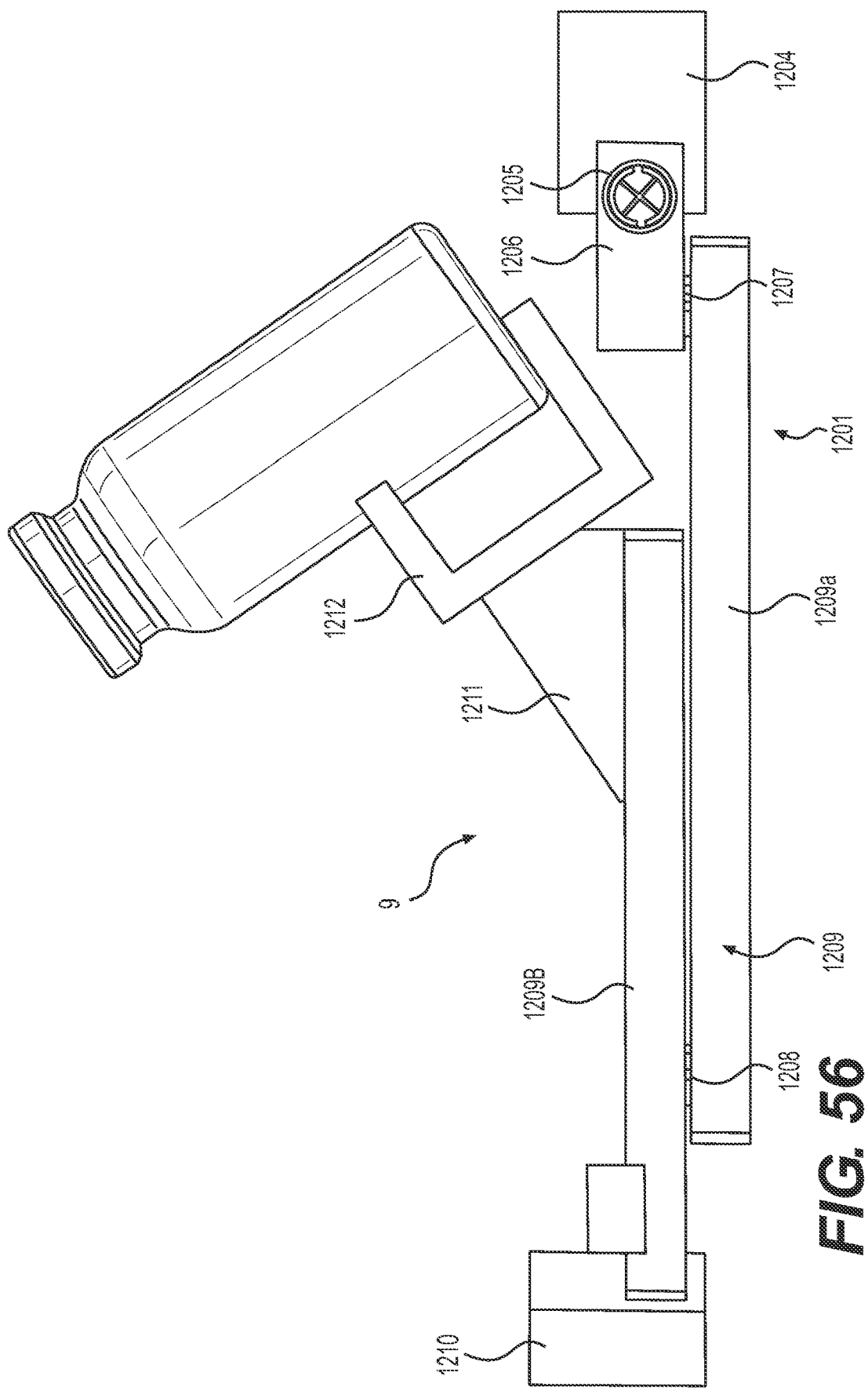
Figure 57:
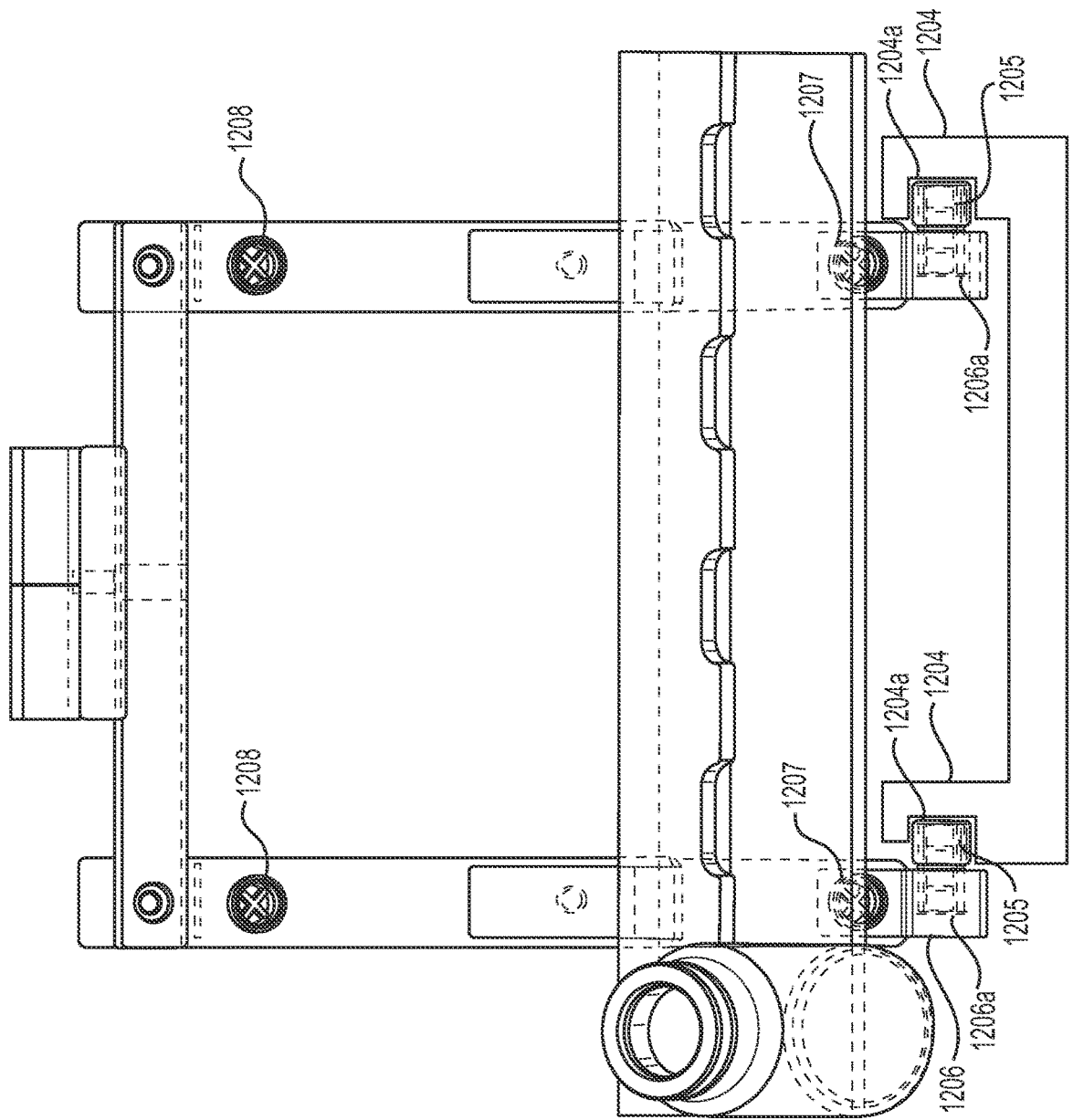
Figure 58:
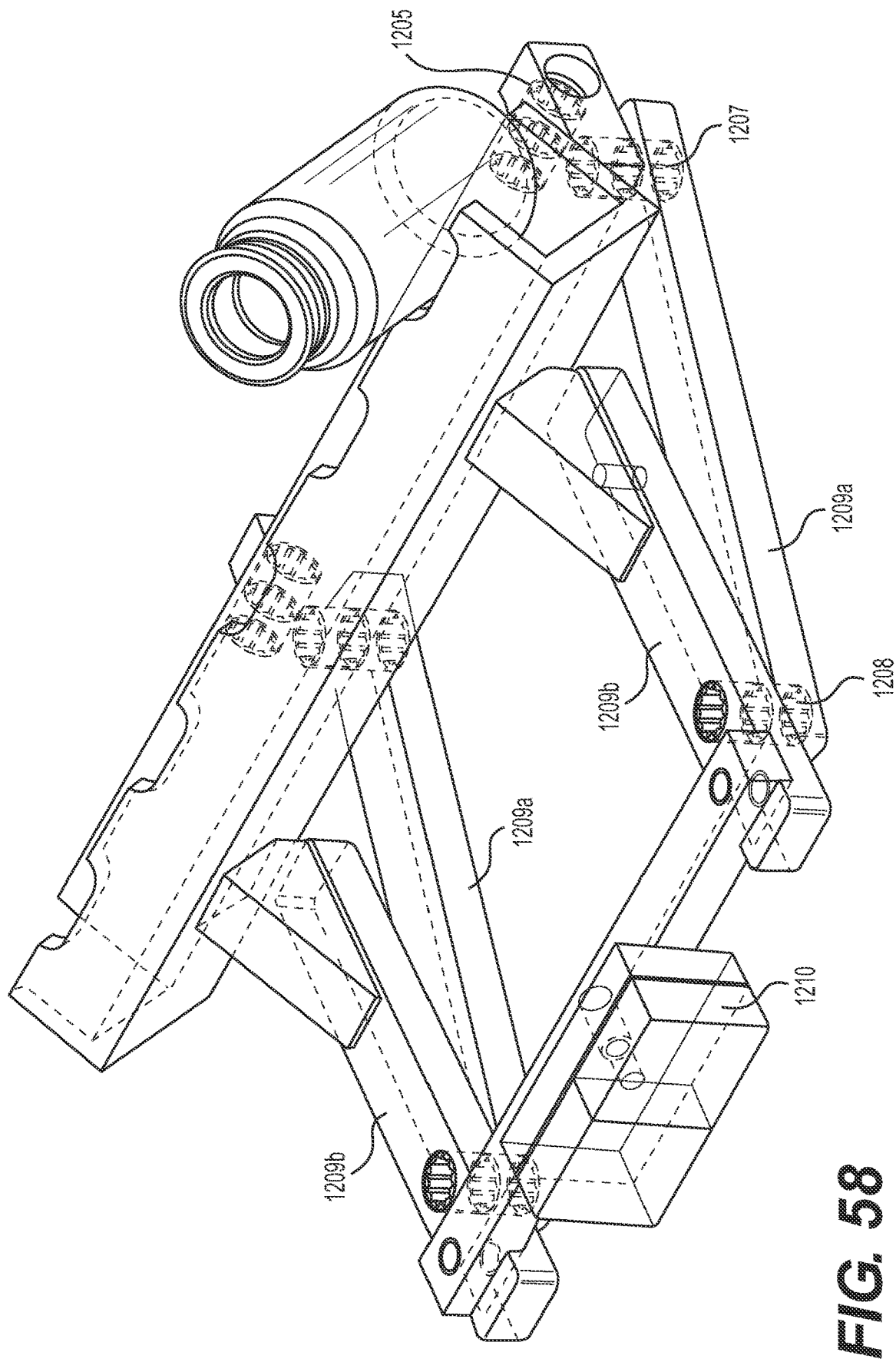

FIG. 13. is a front perspective view of production module in the form of a cooling module;

FIG. 14 is a cross-sectional, front perspective of the connection between a depyrogenation module and a cooling module;

FIG. 15 is a front exterior perspective of the connection depicted in FIG. 14;

FIG. 16. is a front cross-sectional perspective view of the cooling production module's distal end, showing operational components therein;

FIG. 17 is a depiction of a production module, in the form of a filling and closure module, connected to a closure feed mechanism;

FIG. 18 is a front perspective view of a filling and closure module, showing the exterior components thereof;

FIG. 19 is a depiction of a filling and closure module, with the exterior housing thereof rendered transparent, showing the internal components thereof;

FIG. 20 is a vertical, widthwise cross-sectional view on the filling portion of the module of FIG. 17, showing internal components thereof;

FIG. 21 is a vertical, widthwise cross-sectional view on the filling portion of the module of FIG. 20, with filling needle assembly attached, and filling needle withdrawn from the filling housing of the production module;

FIG. 22 is a vertical, widthwise cross-sectional view on the filling housing;

FIGS. 23 and 24 are vertical, widthwise cross-sectional views on the filling portion of the filling module, with filling needle assembly attached, and filling needle extending through the filling housing and into the internal cavity of the housing of the filling and closure module, over a container positioned for filling;

FIG. 25 is a needle assembly useful in the filling module;

FIG. 26 is a length wise cross-sectional view of a needle assembly of FIG. 25;

FIG. 27 is a length wise cross-sectional view of the lower end of the needle assembly;

FIG. 28-30 are vertical, widthwise cross-sectional views of the closure portion of the module, showing container closure;

FIG. 31-33 depicts the closure feed unit, detached from the stoppering unit;

FIG. 34 depicts a sealing mechanism for the closure feed unit;

FIG. 35 depicts a sterilisable bag for containing closure stoppers;

FIG. 36 is a cross-sectional view of the bag depicted in 35, being attached to the feed unit with the sealing mechanism engaged;

FIG. 37 is a cross-sectional view of an alternative embodiment, wherein the feed bag is replaced by a larger sterilisable fee drum;

FIG. 38 is an external view of a feed drum used in the FIG. 37 embodiment;

FIG. 39 is a cross-sectional view, perspective view of the neck of the feed drum;

FIG. 40A is a vertical cross-sectional exploded view of the neck/exit conduit of the feed drum;

FIG. 40B is a vertical cross-sectional view of the neck/exit conduit of the feed drum;

FIG. 41 is a cross sectional view taken through the closure feed and the portion of the filling housing and filling module, when the closure feed is connected to the filling housing, depicting various fluid flows;

FIG. 42 is an exterior view of the outfeed module of the system;

FIG. 43 depicts the outfeed module with housing walls being shown as transparent, showing internal components thereof;

FIG. 44 is an external view of the end housings of two adjoined modules, mounted upon the base of the external drive system;

FIG. 45-46 are a width wise, cross-sectional view of the embodiment of FIG. 44 showing the internal components thereof;

FIG. 47 is a perspective view of connected sections of the external drive mechanism with the module housings removed therefrom;

FIGS. 48A-48C depict the vertical movement of a drive frame employed within a module of the present modular system;

FIGS. 49A-49C depict the horizontal movement of a drive frame employed within a module of the present modular system;

FIGS. 50A-50I depict a portion of the internal drive frame operating through one cycle of vial movement;

FIG. 51 is a depiction of a module of the present invention with a sensor component;

FIG. 52 is a depiction of a further module type module of the present invention with an alternative positioning of sensor components;

FIGS. 53-55 depict one type of flexural bearing useful in the present invention; and FIGS. 56-58 depicts an alternative form of drive frame useful in the moveable support assembly of the internal transport system, employing flexural bearings.

DETAILED DESCRIPTION

In the description of the various aspects of the invention, descriptors, such as proximal and distal, front and back, forward, back, top and bottom, are intended to assist in orientation only are not intended to limit any aspect of the invention to such orientation, unless context suggest otherwise. For purposes of orientation, unless otherwise specified herein, the right side of the system, module or component of a module will be referred to as proximal; the left side will be referred to as distal. When used, the x-axis refers to the horizontal direction, right (proximal) and left (distal); the y-axis refers to the vertical direction, up and down; and the z-axis refers to depth, front/forward and rear/backward.

Modular Production System

Figure 1:
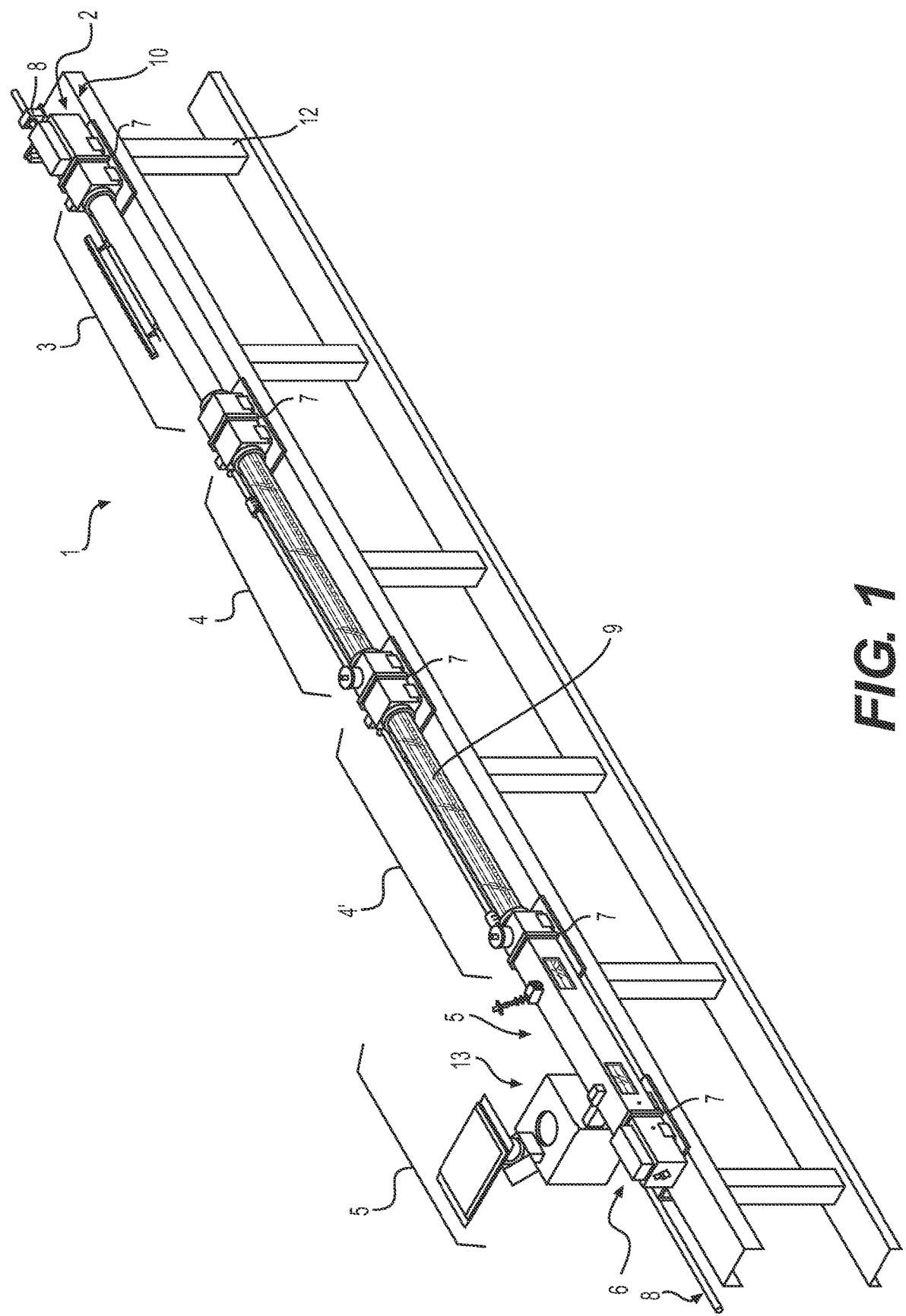
FIG. 1 depicts a modular production assembly forming an aseptic filling system, comprising individual production modules.
Figure 2:
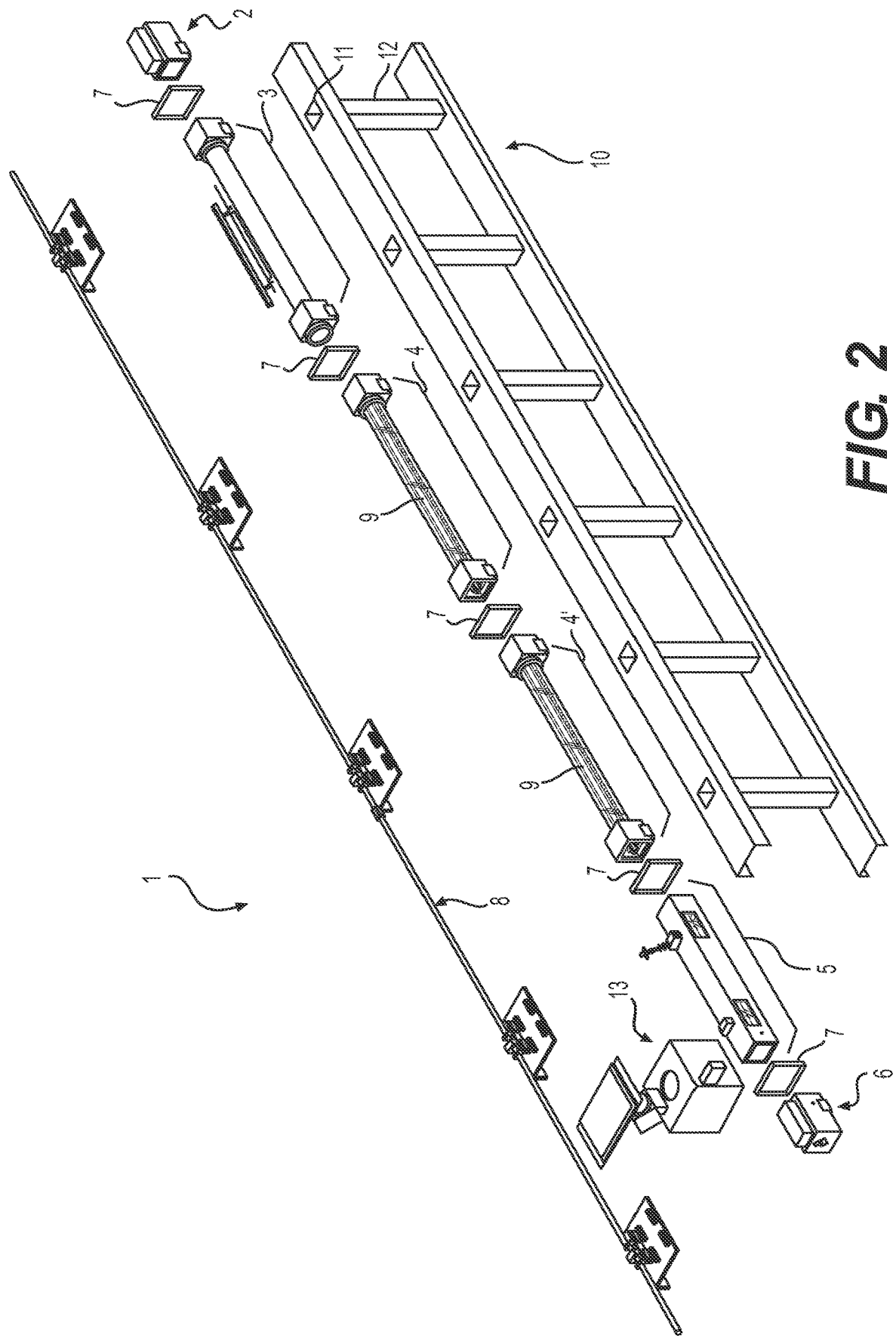
FIG. 2 is an exploded view of the modular production system of FIG. 1, with several of the sections of the external drive system (8) being operatively linked.

FIGS. 1 and 2. show a representative embodiment a modular production system (1), in the form of an aseptic filling system. The modular production systems of the present invention are made up of several function modules. Each module is considered to possess independently inventive features, and perform different functions. Modules may be arranged in multiple ways depending upon the requirements of the product being produced.

In the embodiment shown in FIGS. 1 and 2, modular production system comprises a plurality of individual subunits, each subunit having a housing, an article transport system, and operational components. In this representative embodiment, the modular system comprises an infeed module (2), a depyrogenation module (3), a pair of serially arranged cooling modules (4 and 4'), a combined filling and closure module (5), and an outfeed module (6). A closure feed (13) is associated with the closure module, which feeds container closures to a closure mechanism.

The interconnected modules, in the depicted embodiments in FIGS. 1 and 2, form a production line. In this production line, empty containers, such as fillable vials ("V"), or other articles capable of being filled with a material, are received into an infeed module, where they are positioned serially in a single line. The vials are passed via a transport system within the infeed to a transport system within the depyrogenation/sterilization module, where they are depyrogenated or sterilized. The depyrogenated/sterilized vials are passed to a transport system in one or more cooling module(s), where the temperature of the vial is reduced. The cooled articles are then passed to the internal transport system of a combined filling and closure module. In the filling portion of the module, the vials are moved to a filling mechanism and filled with a selected material. In this embodiment, the selected material is a liquid suspension or solution containing a pharmaceutically active compound. However, the filling system could also provide for deposition of any fluid (gas or liquid), or a solid material, such as a powder (e.g., particle compositions generated via micronization, lyophilization, spray drying, moulding, etc.), or solid articles of manufacture such as tablets, capsules, or other dosage form or device. The filled vials are then passed to a closure mechanism which seals the filled vial. The filled and sealed vials are then passed to the internal transport system of an outfeed module, where the passed out of the production line as a finished product.

Each of these interconnected production modules is composed of a housing, which defines individual interior chambers or cavities. When the modules are connected in a serial fashion, these interior chambers are linked forming a production channel which extends the length of the production line formed by the interconnected modules. A controllable internal environment is able to be created and maintained within the production channel, such that the internal environment may be sterilized, and this environment may be maintained through controlling the air flow through the production line. Due to its relatively small volume, non-complex structure, small number of components, and relatively inexpensive materials of construction, the production lines of the modular production system may be produced and maintained in a cost-effective fashion. The relatively compact nature of the system requires comparatively little in terms of manufacturing facility space. Operationally, the system highly efficient in terms of energy usage. The ease with which it may be assembles and disassembled affords significant cost savings in terms of construction and installation, as well as maintenance. These advantages, and others, are apparent from the discussion herein.

Individual modules within the system are connectable to each in a multitude of ways, which will be apparent to those of ordinary skill. By way of example only, and not of limitation, the ends of adjacent modules may be fitted within the opposing open sides of a connector sleeve (7), which slides over the adjacent ends and forms a seal therebetween. While the connector sleeves are shown in FIG. 2 as separate component from a module, it will be understood that the connector sleeve (7) may be formed as an integral component of an individual module, allowing it to be connected to an adjacent component in a sealed fashion. Alternatively, individual modules may be joined by positioning a traditional face seal (e.g., by an O-ring ring positioned between abutting module faces), with the compression of the seal being generated and maintained by fasteners, e.g., threaded screws/bolts.

Articles are transported through each module in the production line by the interaction between an external drive system coupled to an internal transport system. While this may take the form of a direct coupling by one or more drive shafts which extend thorough one or more of the housings and connect to the internal transport system(s), such an approach also requires the use of measures to avoid contamination with "viable" agents and the production of non-viable particulate matter in the enclosed environment of the production line. In an additional aspect of the invention, the external drive system (8) employs one or more externally situated drive magnets that are aligned with specific portions of the assembled production modules, and which are magnetically coupled to corresponding follower magnet components of an internal transport mechanism (9) present within the modules of the modular production line.

The individual modules and the external drive system are, in the depicted embodiment, affixed to a base (10) having conduits (11) formed within the support legs (12) thereof. These conduits provide access passages for associated wiring and, if desired may be used for ventilation. Further components, such as a closure feed system (13), involved in the production system may be attached as needed.

The individual modules and other components of the modular production system are now individually discussed:

1. Infeed Module

A. Infeed Housing

One embodiment of a module useful in the modular production system takes the form of an infeed module (2). As depicted with reference to FIGS. 3-5, the infeed module includes an infeed housing providing an interior chamber, an internal transport mechanism positioned within the chamber, and operational assembly, e.g., for facilitating article on loading and air flow control.

The infeed module includes an infeed housing (100) which possesses a top wall (101), a bottom wall (102), a front wall (103), a back wall (104), a proximal side wall (105) and an open distal side (106). Each of these walls include an interior and exterior surface. The interior surfaces of these walls define an infeed housing interior cavity (107).

The top wall (101) of the infeed housing (100) has an access port (108) defined therein, which provides access to the interior cavity (107). Attached to the exterior surface of the top wall (101), over the access port (108), is a filter housing (109). The filter housing includes a top wall (110), an open bottom (111), a front wall (112), a back wall (113), a proximal side wall (114) and a distal side wall (115). Each of these walls includes an interior and exterior surface.

The interior surfaces of the top, front, back, proximal side and distal side walls of the filter housing define a filter housing cavity (116). A ventilation port (117) is formed through the back wall (113) of filter housing (109), allowing access to the filter housing cavity (116).

A filter (119), (e.g., a HEPA filter) is positioned in the filter housing, covering access port (108), thus filtering and fluid passing from the filter housing cavity (116) into the infeed housing interior cavity (107). The HEPA filter, its housing and the vents are merely schematic in these drawings. Appropriate fixtures for the filter, their size etc., may be readily determined and selected by one of ordinary skill, and would depend, for example, on the amount of air in the system as to their shape and size.

The proximal side wall (105) of the infeed housing (100) defines an article access opening (118), which is formed as a "mouse hole." The mouse hole is shaped and sized to correspond to the containers or articles (e.g., vials "V") which are fed into the infeed module with the assistance of the infeed module' internal transport system section (200). The mouse hole corresponds to the silhouette of a vial "V", and is sized to permit movement of a moveable support rail component of the transport to extend to or from the house hole, to receive individual vials and bring each vial serially into the into the infeed module. The access opening also assists in regulating the flow of air into and out of the module cavity. Specifically, the size of the access opening is a constriction to airflow from the module, assist in maintaining the internal pressure of the module at a higher pressure than the atmosphere outside the module, yielding a net outflow of air/fluid from the module, and reducing the tendency of air to flow into the module, against this pressure gradient.

The bottom (102) of the infeed housing defines one or more elongate, lateral vents (120). These vents extend through the bottom wall of the infeed housing and form an egress channel from the infeed housing interior cavity (107). In the embodiment depicted, the vent(s) carry discharged airflow from the bottom of the infeed housing cavity. When the module is coupled to a base (10) as depicted in FIGS. 1-2, such ventilation may be routed through conduits (11) formed within the support legs (12) of base.

Figure 3:
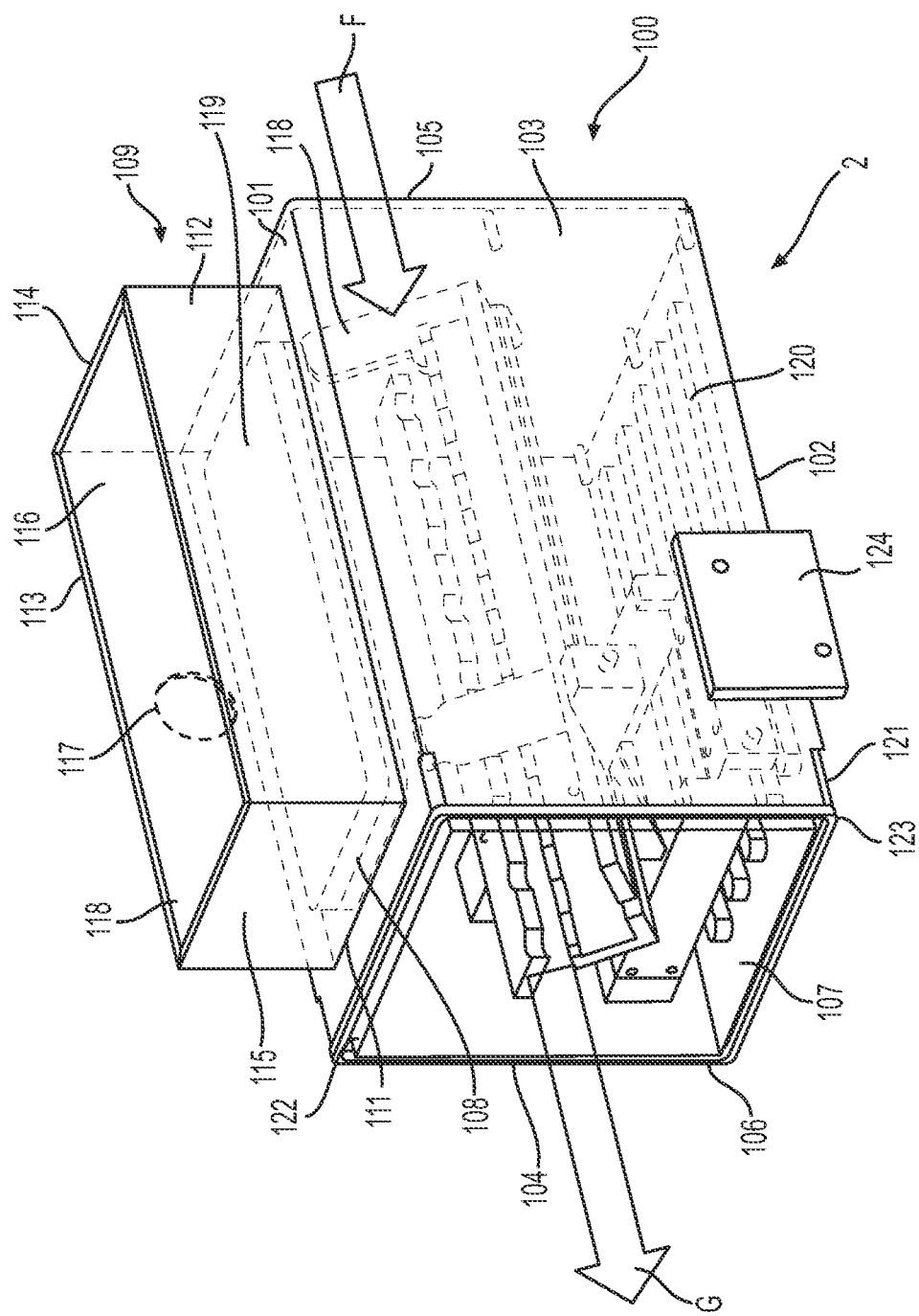
FIG. 3 depicts an embodiment of an infeed module, showing various interior components thereof in dashed lines.

As shown in FIG. 3, the distal end (106) of the infeed housing is open. The exterior surface of the top, front, bottom and back walls of the infeed housing, adjacent this open end, define a number of features involved in the connectability of the distal end of the infeed housing to the proximal end of the next module in the production line, such a one or more lateral elongate corner slots and one or more external circumferential O-rings.

Lateral elongate corner slots (121) are positioned in one or more of the corners of the infeed module, where top and front walls, front and bottom walls, bottom and back walls, and back and top walls meet. The elongate corner slots (121) extend from the distal face of the infeed housing in a proximal direction in the infeed housing's exterior surface.

An O-ring seat or recess) (122), is formed in the exterior faces of the top, front, bottom and back walls of the infeed housing, and extends around the infeed housing adjacent its distal end (106). An O-ring (123) is positioned in this O-ring recess, such that a portion of the O-ring faces the infeed housing interior cavity (107) resides within the O-ring recess (122), and an out-facing portion of the O-ring extends above the exterior surface of the top, front, bottom and back walls of the infeed housing.

Connection between individual modules in the system, as depicted in FIG. 1, may be accomplished in any suitable fashion. For example, by inserting the open distal end of the infeed housing (100) within the central opening of a connector sleeve (7). This is discussed in more detail below, with reference to FIG. 8. The connector sleeve (7) is slideable over the distal end of the infeed housing, such that the interior surface of the connector sleeve (7) compresses the out-facing portion of the O-ring (123), thus forming a resilient seal therebetween. So connected, the central opening of the distal side of the sleeve (7) is unoccupied and capable of connection to a distally positioned module.

Other connection arrangements are readily appreciable to those of ordinary skill. For example, an O-ring seat/recess could be formed in the interior surface of the connector sleeve (7), and the O-ring positioned therein, which would be compressed by the exterior surface of the module when positioned within the sleeve central opening. In such a case, a circumferential recess in the exterior surfaces of the walls of the infeed module may or may not be provided to interact with this connector sleeve mounted O-ring.

In a further alternative arrangement, a traditional face seal with the O-ring positioned between the distal face of the infeed module and the proximal face of an adjoined module could be employed. Compression of the O-ring face seal would be provided by appropriate fasteners, such as nuts and bolts. This sealing face approach may also be employed in addition to the connector sleeve (7), such as by positioning an O-ring face seal (or other gasket-type seal) between the distal face of the infeed and the proximal face of the distally positioned module housing, within the connector sleeve wherein the O-ring face seal/gasket occupied the gap between the distal face of the infeed and the proximal face of the distally positioned module.

With the connector sleeve (7) connection approach shown in FIG. 1, the connector sleeve's interior corners are guided by the corner slots (120) over the exterior distal end of the top, front, bottom and back walls of the infeed housing. The corner slots (120) may be of sufficient length to allow the connector sleeve to form such a resilient seal with the O-ring on the infeed housing. In the embodiment shown, the length of each corner slots is equal to or greater than the width of the connector sleeve. This slot length allows the sleeve to be slide in a proximal direction, such that the distal side of the sleeve disengages from a connected distal module. Once the sleeve is clear of the distally mounted module, the module may be lifted from an assembled production system without having to disconnecting the previously connected infeed module from the base. Thus, this feature advantageously facilitates the process of assembling and disassembling the production line by allowing modules to be individually removed from the assembled system, without having to also disconnect an adjoined module housing from the system base (10).

Figure 8:
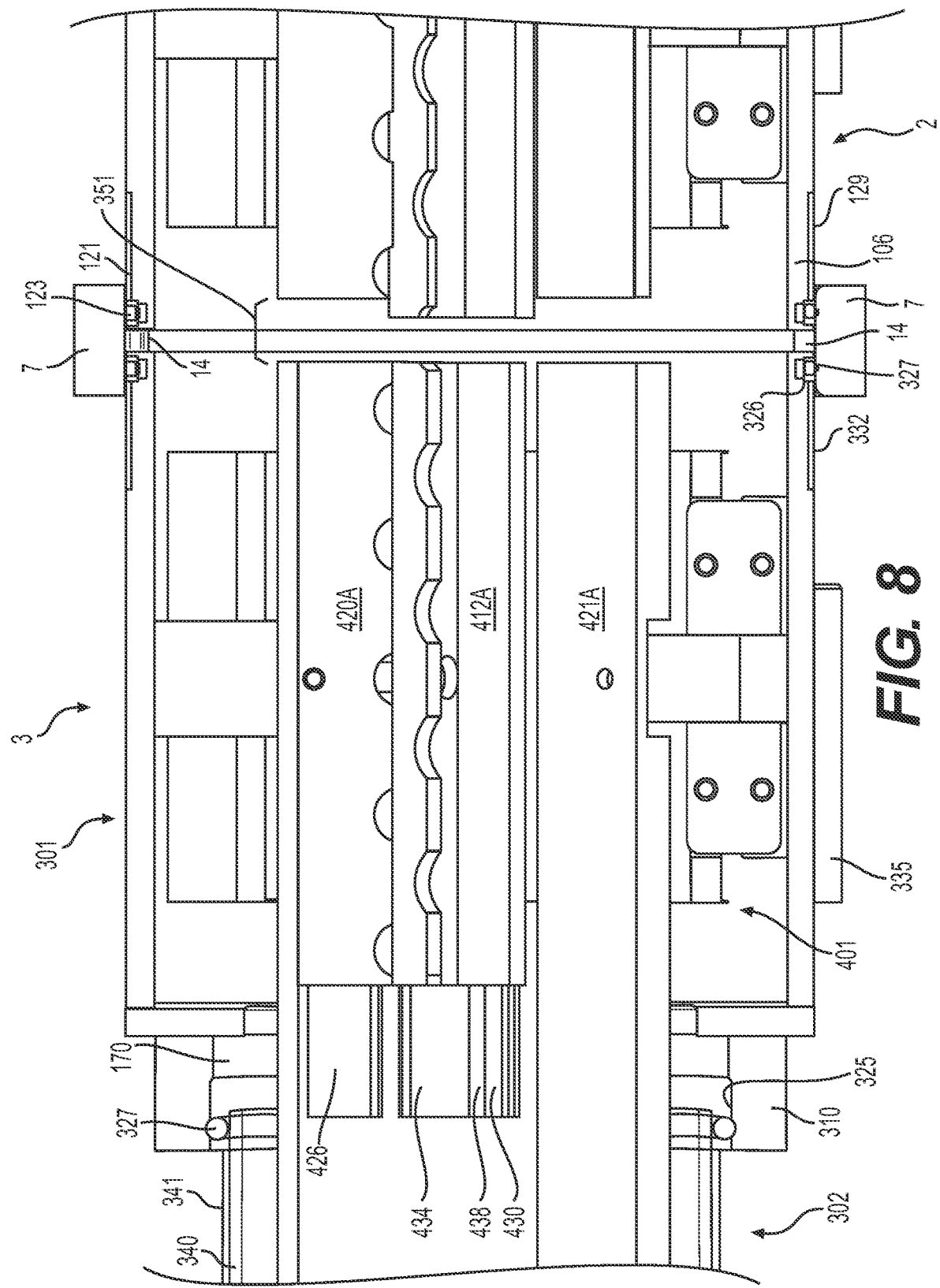
FIG. 8 is a cross-sectional view from above of the connection between infeed and depyrogenation modules.

As the distal end of the infeed module (2) is adapted to be connected to a further module, the distal ends of the stationary and moveable support rails of the infeed module are of a length which terminates at or near the proximal end of the infeed housing. The termination point of these rails are designed to provide a gap between the ends of the stationary and moveable support rails of the infeed module with the ends of the stationary and moveable support rails of the next attached module. This gap (such as is e.g., gap (351) in FIG. 8, is designed to accommodate any thermal expansion or contraction that may be experienced by the stationary and moveable support rails during operation. As will appreciated, the gap should be sufficiently large to allow expansion during heating, while at the same time not so large that transfer of an article being passed from the transport mechanism of one module to the transport mechanism of the next is impeded. The distance of this gap may be determined by the width of a connector sleeve gasket, or a spacing surface on the interior surface of a connector sleeve, or merely established by the relative lengths of the stationary and moveable support rails in adjacent modules.

The external surface of the front wall (103) of the infeed housing has attached thereto, or associated therewith, a mounting bracket (124), which may be employed to connect the internal article transport system (9) within the infeed housing, and/or connect the module housing to a component of the external drive system (8), and/or connect the module housing to the structure to which the module has been anchored, such as base (10), as depicted in FIGS. 1 and 2.

B. Internal Transport Mechanism: Infeed Housing

Transport of articles within the modules of the present invention is provided by an internal transport mechanism (9).

Figure 4:
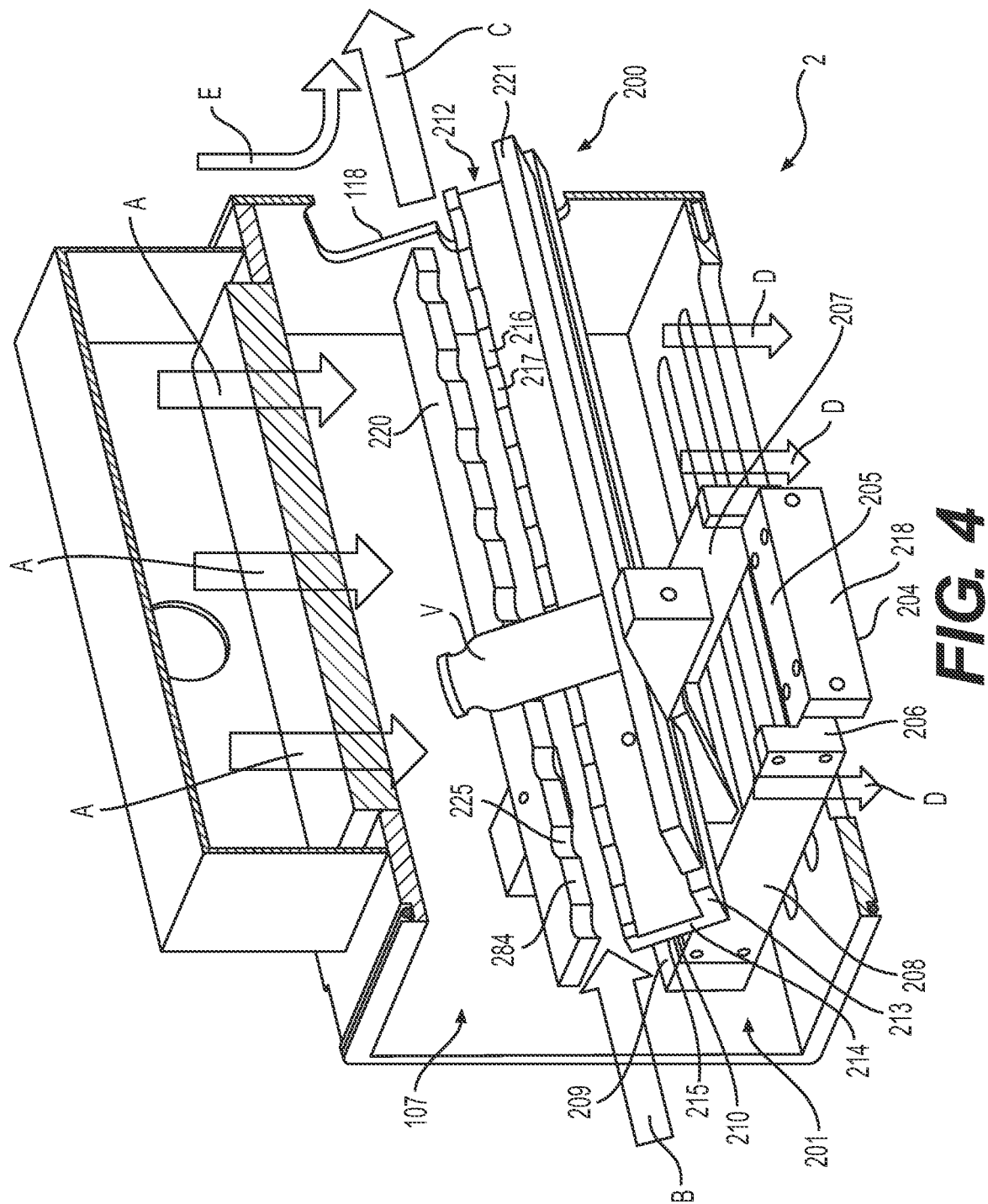
FIG. 4 is a lengthwise cross-sectional front view of the infeed module in FIG. 3, showing the internal components thereof.
Figure 5:
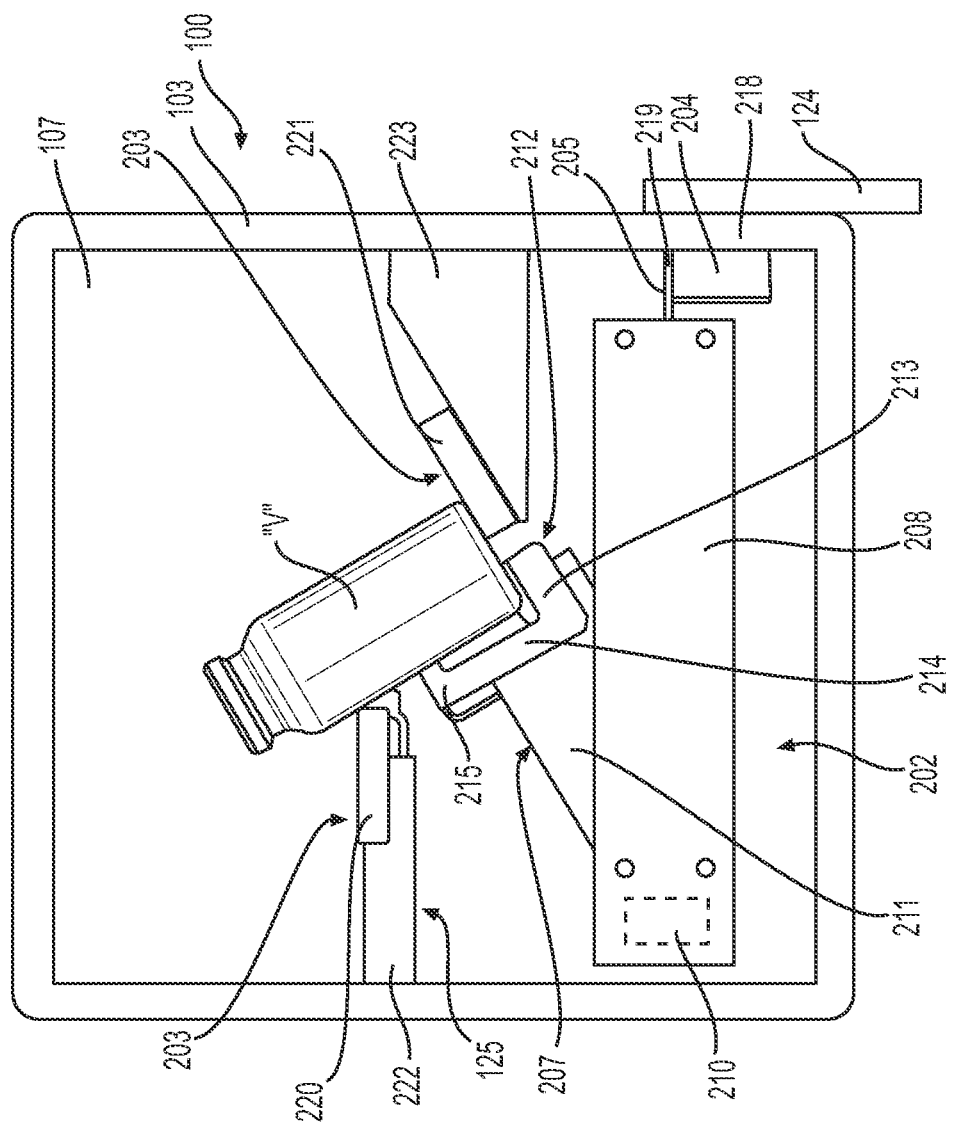
FIG. 5 is a widthwise, cross-sectional view of the infeed of FIG. 3, showing a side perspective view of the internal components thereof.

In the embodiment shown, in FIGS. 4 and 5, a section (200) of the internal transport mechanism (9) is positioned within the infeed module. Transport mechanism section (200) includes a movable support assembly (202), which includes a drive frame (201) connected to a movable support rail (212); and, a stationary support assembly (203), which includes a stationary back rail (220) and a stationary base rail (222).

This first embodiment of the drive frame (201) includes a wall mounting plate (204) having a front face (218) which contacts the interior of the front wall (103) of the infeed housing (100). This connection is made either directly to the front wall of the housing or by connection to the infeed mounting bracket (124) via a suitable fastening mechanism, including threaded fasteners (e.g., screws, nuts/bolts), pins, welds, or other suitable means.

Wall mounting plate (204) has a top surface (219) which is attached to the front end portion of a vertical lamella (205). The vertical lamella (205) extends rearwardly from the wall mounting plate, and is fixedly attached at its opposite end (in its rear-end portion) to an upwardly facing top surface of a front structural support (206), by any suitable means.

In this first embodiment, the vertical lamella is in the form of a thin, elongate plate having a top, bottom, and four sides (proximal, distal, front and back). The lamella is designed to be flexible in its thin, top-to-bottom dimension, such that it allows the vertical lamella to flex up and down. The sides of the lamella are thicker in their proximal side-to-distal side, and in their front-side to back-side dimensions. In these thicker dimensions, the lamella is relatively rigid and immovable when force is exerted in the proximal-to-distal or front-to-back direction.

Front structural support (206) includes a proximal side surface and a distal side surface. The proximal side surface of the front structural support (206) is fixedly connected to the front end portion of a first horizontal lamella (207). The distal side surface of the front structural support (206) is fixedly connected to the front end portion of a second horizontal lamella (208).

The proximal and distal horizontal lamella (207 and 208) extend rearwardly from the opposite sides of the front structural support (206), and are at their rear end portions (opposite their front ends) connected to opposing side surfaces of a rear structural support (209). The rear structural support (209) is generally rectangular, having a proximal side, a distal side, a top, a bottom, a front and a back. The rear end portion of the first/proximal horizontal lamella (207) is fixedly connected to the proximal side of the rear structural support (209), and the rear end portion of the second/distal horizontal lamella (208) is fixedly connected to the rear structural support's distal side face.

Each of the horizontal lamella (207 and 208) are in the form of a thin elongate plate having a top, a bottom, a proximal, a distal, a front, and a back side. Each horizontal lamella is flexible in its thin dimension, and is oriented such that the thin dimension is proximal-side to distal-side, thus allowing flexion directionally right and left. The horizontal lamella have thicker dimensions from top-to-bottom and front-to-back and are more ridged and stable in response to forces exerted in their thicker top-to-bottom, and front-to-back dimensions, thus limiting the up and down and forward and backward motion in these components.

The lamella may be composed of any suitably flexible material, having suitable structural characteristics to permit flexion in the necessary range of motion without being compromised by flexion-related stress, and which is heat tolerant to the range of temperatures to which it is exposed in use. Suitable lamella materials include metals, such as stainless steel, etc., and other materials identifiable by a those of ordinary skill.

The rear structural support (209) contains or has connected thereto one or more follower magnet(s) (210). In the depicted embodiment, the one or more follower magnet(s) is/are positioned within a housing on the back of the rear structural support.

The rear structural support (209) is attached, on its front side, to one end (the back end) of a moveable support connector arm (211). The movable support connector arm (211) extends upwardly and forwardly from the rear structural support, with the far end of the connector arm (211) adapted to connect to a movable support rail (212). The connection between the connector arm (211) and the rear structural support (209) and the movable support rail (212) may be fixed (through appropriate fasteners or by welding), or be such as to allow some movement between the connector arm and the moveable support rail, for example by a pin or other extension projecting from the connector arm or the movable support rail, which occupies a hole, groove or other recess formed in the corresponding interfacing component. In the embodiment shown in FIGS. 4, and 5, connection is of the more fixed nature and involves a fastener.

Moveable support rail (212) is L-shaped in cross-section and elongate in a proximal to distal dimension. The L-shaped rail includes a forwardly extending lower portion (213) having a front end and a back end. An upwardly extending back portion (214) rises from the back end of the lower portion (213). At the top of the upwardly extending back portion is a forwardly extending lip (215). The lip (215) of the L-shaped rail is shorter in length than the lower portion (213), and has a front face (216) in which are formed, at regular intervals, a plurality of notches or recesses (217).

The stationary article support assembly (203), of the embodiment shown in FIGS. 3-5 includes a back rail (220) and a base rail (221). The back rail (220) is mounted to the interior surface of the back wall (113) of the infeed housing by one or more back rail arm brackets (222). The stationary support base rail (221), on the other hand, is mounted to the interior surface of the front wall (103) of the infeed housing by one or more base rail arm brackets (222). The front end(s) of the back rail arm bracket(s) and the back end of the base rail arm bracket(s) are adapted to connect to a portion of their respective stationary rails.

Back rail (220) and base rail (221) are each elongate in their proximal to distal dimension, having proximal ends adjacent the interior surface of proximal side wall (105) of the infeed housing, and distal ends which terminate at or adjacent the open distal side (106) of the infeed housing. The back rail (215) has a front face (224) in which are formed, at regular intervals, a plurality of notches or recesses (225). The base rail (221) has an upper (or top) surface. These notched front face of the back rail, and the top surface of the base rail, form the support surfaces for supporting a container placed on the stationary support assembly by the moveable support rail.

As depicted, the top surface of the lower portion, the front surface of the upwardly extending back portion, and the front face of the lip of the L-shaped movable rail (212) form an article support surface of the moveable support rail for containers/vials (V) which are introduced into the infeed housing through the mouse hole. The movable rail's article support surface facilitates the positioning and repositioning of containers within the module. This process involves a container positioned on the movable rail's article support surface being lifted by the movable rail's upward motion, moved from a proximal position to a distal position by the moveable support rail's distal movement; and being placed onto the stationary support assembly's article support surfaces y the downward travel of the moveably support. The moveable support then descends below the base rail of the stationary support, causing the container to rest solely or primarily upon the stationary support assembly. Having disengaged from the container, the moveable support rail is able to move proximally below position of the container, such that upward movement of the moveable support rail once again engages the container at a further distal point on the elongate moveable support rail. Repetition of this motion of the moveable rail continues to move the container distally through the module, as indicated by arrows "F" and "G" in FIG. 3.

In the embodiment depicted in FIGS. 3-5, the containers take the form of vials having a closed base at their lower end, and annular side wall extending coaxially from the base. The upper end of the sides transition to an inwardly sloping annular shoulder portion. The shoulder narrows to an annular neck. The annular neck extends upwardly from the shoulders to form a top portion, having an underside, annular side surfaces and top face. The top face defines a centrally located mouth, which opens into the interior cavity of the container. The interior of the container is thus defined by the interior surfaces of the top portion, neck, shoulder, side walls and base of the vial. So structured, the vials may be stably positioned on support surfaces of the moveable rail, or the stationary support rails.

In this embodiment, the stationary support assembly rails and movable support assembly rail are positioned at an incline, such that containers placed thereon, are held at an angle, rather than being completely upright. This incline may be selected to be of any suitable degree, for example from 1 to 45 degrees off vertical, such as from 15-40 degrees, 20-35°, 25-35°, or about 30° off vertical. This incline advantageously allows the container to be stably positioned on an upper and lower portion of either the stationary rail assembly and/or the moveable rail assembly. This angled orientation also facilitates filling of the vials in the filling module, as will be discussed in further detail below.

An additional benefit associated with the notches or recesses in the front face of the back stationary support rail and the upper lip of the L-shaped support rail is that these features allow articles to be arranged serially in a single-line during transit through the production tunnel. The orderly positioning of vials during operation allows vials to be monitored at various points through the modular production system by, for example, a simple shift register in a commercially available Programmable Logic Controller (PLC), or other suitable mechanisms to automate machinery of this type, permitting vials identified as deficient during an in-production quality check to be tracked and removed at the system exit by an automated rejection system (not shown).

The mobility of the moveable support rail (212) is achieved through the follower magnet(s) (210) being coupled to the rear support structure. When a motive force is imparted on the rear support structure, the rear support structure moves relative to the wall mounting plate (204) attached to the front wall of the module. In the depicted embodiments, the follower magnet(s) in the rear structural support are magnetically coupled to drive magnets in the external drive system (8). Movement of a drive magnet in the external drive system (8) causes a complementary movement of the follower magnet in the drive frame, resulting in movement of the moveable support rail, as discussed in greater detail later herein.

It should be noted that the magnetic coupling between drive magnet and follower magnet affords certain benefits to the present system, in that the magnetic coupling avoids breaching the housing walls to install drive shafts to operate the drive frames, thus avoiding potential avenues for contaminant ingress within the modular system. That said, alternative embodiments are envisioned where one or more rear structural support(s) are attached to one or more drive shafts from an external drive source. In such alternative embodiment, vertical and horizontal movement of the drive shaft cause the vertical and horizontal motion of the rear support of the drive frame, and corresponding movement of the movable support rail. Such alternative mechanisms for providing motion to the internal transport system are considered within the scope of the present invention.

It will also be appreciated that the horizontal and vertical lamella may be susceptible to stress during flexion. Flexion beyond a certain material and construction-dependent maximum angle can result in fatigue stress which can cause structural failure in the lamella after repeated flexion. The relatively short length of the vertical lamella exacerbates the risk of stress failure, as the flexion in the lamella is confined to a very small area. The vertical lamella in the present embodiment is advantageously positioned at a distance from the rear support, allowing for a maximal the distance of vertical travel by the rear support by minimal angular flexion in the vertical lamella to achieve such distance of travel. So configured, structural compromise of the vertical lamella by structural stress forces is minimized.

The consideration of flexion related material stress is at play with the horizontal lamella, but structural compromise due to stress forces is somewhat dissipated as the horizontal lamella are much longer front to back than the vertical lamella. As such, the flexing forces are accommodated over a greater length of horizontal lamella, in less concentrated area, than when compared to the vertical lamella.

It is noteworthy that, because the components of the drive frame (201) are each fixedly connected to each other, the drive frame contains no parts having a frictional interaction. Movement of the moveable support rail occurs by lamellar flexion within the drive frame. Advantageously, this avoids creation of abrasionally-produced particulate material which could contaminate the internal environment of the infeed housing internal cavity (107) or the connected production tunnel formed by the internal cavities of distally connected production modules in a modular production assembly line. This frictionless interaction also reduces the wear and tear on the drive frame (201) itself, increasing the useful life of the module, decreasing the replacement costs for parts, and reducing the frequency of scheduled maintenance to replace worn parts, and the production down time associated therewith.

C. Operation Assembly: Air Flow Control within the Infeed]

The infeed module housing controls the flow of air in an assembled modular production line. Airflow within the infeed housing interior cavity (107) is controlled through various access ports in the infeed housing (100).

In the depicted embodiment, airflow (or other gas or gas mixture flow) provided by a compressed air source (not shown), enters the filter housing through the inlet port (117). A HEPA filter (119) is positioned to cover opening (108) in the top wall of the infeed housing, and the filter filters particulate and/or microbial matter from air flowing between the filter housing cavity and the interior of the infeed housing, as indicated by reference arrows "A" in FIG. 4. The air pressure in the infeed housing controlled in part with this incoming air flow. It will be appreciated by those of ordinary skill that air filtration may be achieved through any suitable means, and alternatives to the depicted embodiments may be employed in each of the module described herein and are considered within the scope of the present invention. Materials employed will be selected to withstand pre-operational depyrogenation/sterilization and operational thermal conditions.

The air pressure within the infeed interior cavity (and connected production tunnel) is maintained during operation at a higher pressure than the external environment. The filtered airflow "A" from the filter housing is augmented by airflow, indicated by reference arrow "B", from distally positioned module(s).

Due to this pressurization of the infeed by airflows "A" and "B", pressurized air flows outwardly from the infeed housing (100) through the article entry port/mouse hole (118), shown by reference arrow "C" in FIG. 3, and also through a series of elongate lateral vents (120), formed in the bottom of the infeed housing, as shown by reference arrows "D".

Airflows "C" and "D" achieve a common goal of reducing the risk presented by unfiltered air entering the interior of the infeed housing through mouse hole (118). Advantageously, external airflow at the mouse hole, shown by arrow "E", is largely redirected by the outgoing airflow from the mouse hole shown by arrow "C". To the extent that airflow "C" does not completely eliminate entry of unfiltered air through the mouse hole, which might arise due to turbulence at the mouse hole, the elongate lateral vents (120) in the floor of the infeed housing act as a vertical washout within the infeed module. Air vented through elongate vents (120) is taken away from the infeed module, by conduits, which may be routed through an access conduit (11) in a leg (12) of base (10), as shown in FIG. 2.

The infeed module is adapted to be connected to an adjacent module at it distal end. In the depict embodiment in FIGS. 1 and 2, such adjacent module is a depyrogenation and or sterilization module.

2. Depyrogenation/Sterilization Module (FIGS. 6-12)

In a further embodiment of a production module of the present invention, the module takes the form of a depyrogenation/sterilization module. The depyrogenation/sterilization module is useful as a component of various embodiments of the modular production system aspect of the present invention, including the embodiment of FIG. 1.

A. Housing Structure of Depyrogenation Module

An embodiment of a depyrogenation/sterilization module is shown in to FIGS. 6-12. Like the infeed module, the depyrogenation/sterilization module (3) also includes a housing (300) with an internal transport mechanism positioned therein and an operational assembly, in the form of an irradiation source, which allows for the depyrogenation and/or sterilization of articles being passed therethrough.

Depyrogenation/sterilization module housing (300) includes a proximal end housing (301), a middle, tubular housing (302) and a distal end housing (303).

The proximal end housing (301) includes a proximal end (304), a distal end wall (305), a top wall (306), bottom wall (307), a front wall (308), and a back wall (309), where the distal end, top, bottom, front, and back walls each possess exterior and interior surfaces. The interior surfaces of the distal end, top, bottom, front, and back walls define a proximal end housing interior cavity (310) within the proximal end housing (301).

The tubular housing (302), positioned between the proximal and distal end housings, includes a proximal end (311), a distal end (312), and an interior axial bore (313) which extends between the proximal and distal ends.

The distal end housing (303) includes a proximal end wall (314), an open distal end (315), a top wall (316), bottom wall (317), a front wall (318), and a back wall (319). The proximal end, top, bottom, front, and back walls each possess exterior and interior surfaces. The interior surfaces of the proximal end wall, top, bottom, front wall, and back wall define a distal end housing interior cavity (320) within the distal end housing (303).

The proximal end of the proximal end housing, and or the distal end of the distal end housing may be modified to regulate airflow through the module/or modular production system. To regulate the airflow through the module, the proximal and or distal ends may include and end wall defining an access opening, reducing the size of the opening into the module, as previously described in relation to the mouse hole the proximal wall of the infeed module.

An access opening (321) is defined through the distal wall of the proximal end housing (301) providing access between the proximal end housing interior cavity (320) and the axial bore (313) of the tubular housing. A further access opening (322) is defined through the proximal wall of the distal end housing (303), providing access between the distal end housing interior cavity (320) and the axial bore (313) of the tubular housing. Thus, the proximal end housing interior cavity (310), tubular housing axial bore (313), and the distal end housing interior cavity (320) collectively define the interior cavity (323) of the depyrogenation/sterilization module housing.

The exterior surface of the distal end wall (305) of the proximal end housing (301) has sealingly attached thereto a proximal ring-shaped mounting bracket (324). The proximal ring-shaped mounting bracket includes an inner circumferential surface (325), a distally directed face, a proximally directed face, and an outer circumferential surface. The proximal ring-shaped bracket (324) is sized slightly larger than the proximal end of the tubular housing, and is positioned on the exterior surface of the distal wall of the proximal end housing such that the proximal ring-shaped bracket encircles the access opening (321) extending through the distal wall of the proximal end housing. The seal between the external circumferential surface of the tubular housing and the ring-shaped bracket is facilitated by the inner circumferential surface of the ring-shaped bracket defining an O-ring recess (326) in which is positioned an O-ring (327). The O-ring (327) is sized such that a portion of the O-ring extends out of the O-ring recess, such than when the proximal end of the tubular housing is fitted within the ring shaped bracket and adjacent the exterior surface of the distal end wall of the proximal end housing encircled by the proximal ring-shaped bracket, the O-ring is compressed between the inner circumferential surface of the proximal ring-shaped bracket and exterior circumferential surface of the proximal end (311) of tubular housing (302). Sufficient space (a small gap) is left between the outer surface of the tubular housing and the inner surface of the ring-shaped bracket, and the proximal end of the tubular housing and the exterior face of the distal wall of the proximal end housing to accommodate thermally induced expansion and contraction during operations without breaching the O-ring seal therebetween. A corresponding connection is made between the distal end of the tubular housing and the exterior surface of the proximal end wall (314) of the distal end housing (303).

The distal end housing (303) proximal end wall (314) exterior surface also has sealingly attached thereto a distal ring-shaped mounting bracket (328). The distal ring-shaped mounting bracket includes an inner circumferential surface (329), a proximally directed front face, a distally directed rear face, and an outer circumferential surface. The distal ring-shaped bracket (324) is sized slightly larger than the distal end of the tubular housing, and is positioned on the proximal exterior surface of the distal end housing so as to encircle the access opening (322) extending through the proximal wall of the distal end housing. The seal between the external surface of the distal end of the tubular housing and the ring-shaped bracket is facilitated by the inner circumferential surface of the distal ring-shaped bracket defining an O-ring recess (330) in which is positioned an O-ring (331). The O-ring (331) is sized such that a portion of the O-ring extends out of the O-ring recess, such that when the distal end of the tubular housing is fitted within the distal ring-shaped bracket, and the distal face of the tubular housing is adjacent the exterior surface of the distal end wall of the proximal end housing surrounded by the rig-shaped bracket, the O-ring is compressed between the inner circumferential surface of the distal ring-shaped bracket and exterior surface of the distal end (312) of tubular housing (302). Again, sufficient space (a small gap) is left between the outer surface of the housing and the inner surface of the distal ring shaped bracket, and the distal end of the tubular housing and the exterior face of the proximal wall of the distal end housing to accommodate thermally induced expansion and contraction during operations without breaching the O-ring seal therebetween.

The proximal end (304) of the proximal end housing (301) is open, and the exterior surface of the top, front, bottom and back walls of the proximal end housing defines a number of features involved in the connectability of the proximal end of the proximal end housing to the previously described open distal end of the infeed module in the production line. In mirror image to the distal end of the infeed module, these features include lateral elongate corner slots (332) in selected or each of the corners where adjacent walls meet at the proximal end of the proximal end housing. The corner slots (332) extend from the proximal face of the proximal end housing and continue distally therefrom within the exterior corner surface of the proximal housing, as depicted in FIG. 6.

Figure 6:
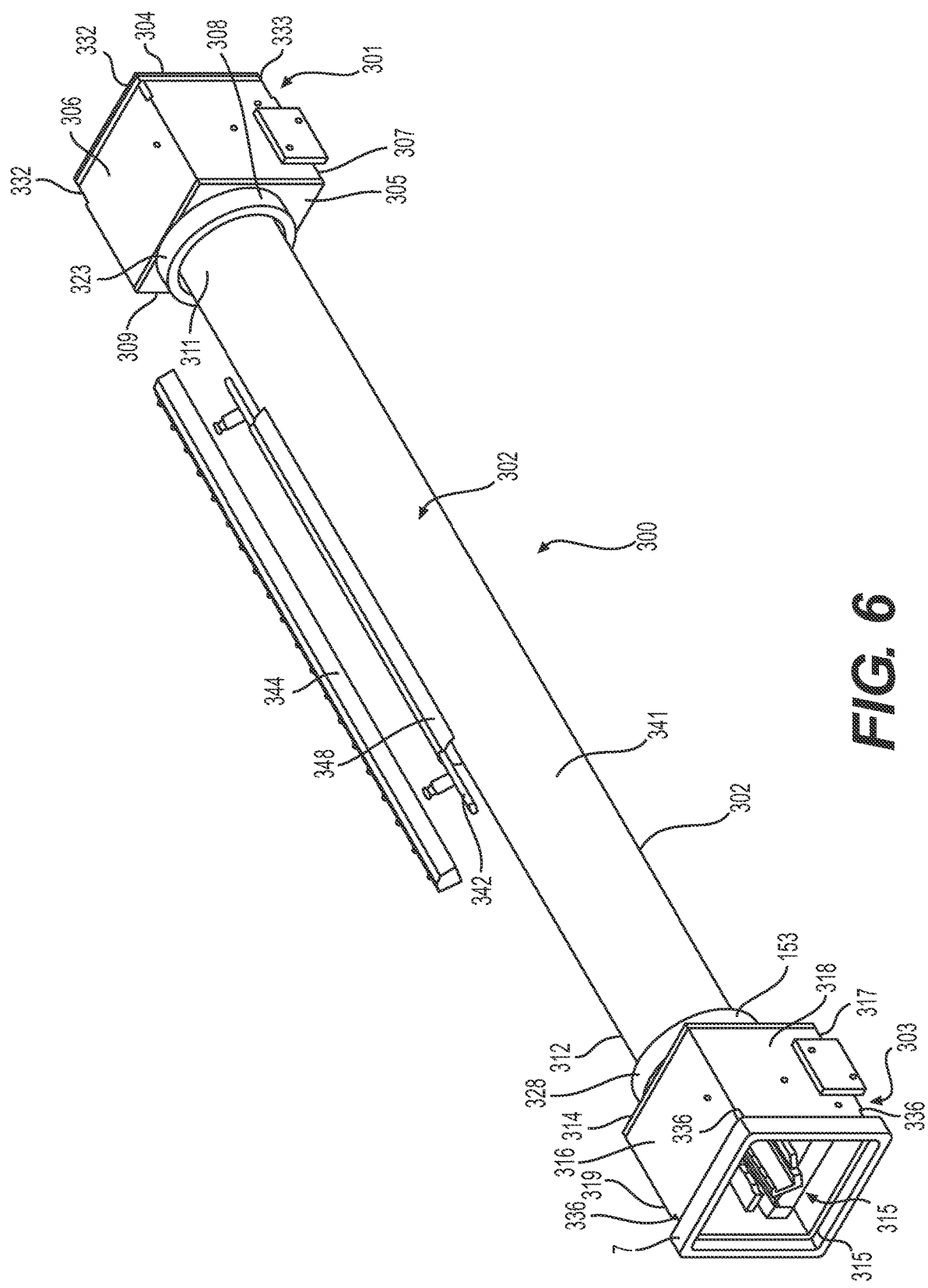
FIG. 6 is an exterior perspective view of an embodiment of a depyrogenation module of the present invention.

As shown in FIG. 6, the exterior faces of the top, front, bottom and back walls at the proximal end of the proximal end housing have formed therein an annular O-ring recess (333), which extends around the proximal end housing, adjacent its proximal end. An O-ring (334) is positioned in this proximal exterior O-ring recess, such that that portion of the O-ring that faces the proximal end housing exterior surface interior resides within the O-ring recess (22), and an outward-facing portion of the O-ring extends above the exterior surface of the top, front, bottom and back walls of the infeed housing. This open proximal end of the end housing is adapted to be inserted within the central opening of connector sleeve (7). To facilitate the connection between the distal end of the infeed module and the proximal end of the depyrogenation module, which is depicted in FIG. 8.

As shown in FIG. 8, the connector sleeve (7) is slideable over the distal end (106) of the infeed housing (2), such that the interior surface of a proximally facing portion the connector sleeve (7) compresses the out-facing portion of the O-ring (123), thus forming a resilient seal therebetween. The opposite end of the connector sleeve is (7) is slideable over the open proximal end (304) of the proximal end housing (301) of the depyrogenation module housing (300), such that the interior surface of a distally facing portion of the connector sleeve (7) compresses the out-facing portion of the O-ring (327) to form a resilient seal therebetween.

To further assist in sealing area between the distal end of the infeed and the proximal end of the proximal end housing of the depyrogenator, a connector sleeve gasket (14) may be positioned therebetween. So positioned, the connector sleeve gasket (14) occupies the space between the distal face of the infeed, the proximal face of the proximal housing, and the interior surface in the connector sleeve (7).

The connection between these adjacent modules (2) and (3) provides a small gap between the distal ends of the stationary support rails and moveable support rail of the infeed and the proximal ends of the stationary support rails and moveable support rail of the depyrogenation module. This gap it provided to accommodate thermal expansion of the support rails which may be experienced during operation. The gap (351) is designed to be large enough to achieve that function, and to be sufficiently small not to interfere with the orderly movement of vials over the gap, as articles move from one module to the next.

The connecter sleeve's interior corners may be guided by the corner slots (120) of the infeed over the exterior distal end portions of the top, front, bottom and back walls of the infeed housing, or by the corner slots (332) of the proximal end housing of the depyrogenator over the exterior distal end portions of the top, front, bottom and back walls of the proximal end housing. Both sets corner slots (120) and (332) may be of sufficient length to allow the connector sleeve to slid further in a proximally direction to completely be disconnected from the proximal end of the depyrogenator module, or distally, to completely be disconnected from the distal end of the infeed module, thus facilitating the process of assembling and disassembling the production line.

The external surface of the front wall (308) of the proximal end housing has attached thereto, or associated therewith, a mounting bracket (335), which may be employed in the connection of the internal article transport system (9) within the depyrogenator end housing, and/or assist in the connection of the depyrogenator housing to the external drive system (8) and or base structure (10), as shown in FIGS. 1 and 2.

The distal end (315) of the distal end housing (303) is structured nearly identical to the distal end of the infeed housing. The distal end (315) is open, and the exterior surface of the top, front, bottom and back walls of the distal end housing define the same features involved in the connectability of the distal end of the depyrogenator housing to the proximal end of the next module in the production line. These features include lateral elongate corner slots (336) in selected or each of the corners where adjacent wall meets at the distal end of the distal end housing. The corner slots (336) extend from the distal face of the end housing and continue proximally therefrom within the exterior surface of the corners of the end housing. The end housing further includes an annular O-ring recess (337), which extends circumferentially around the distal end housing adjacent its distal end (315). The annular O-ring recess (337) is defined in the exterior faces of the top, front, bottom and back walls of the distal end housing at the distal and the recess extends circumferentially around the distal end housing adjacent its distal end (315). The O-ring (338) is positioned in this O-ring recess, such that the portion of the O-ring that faces the surface of the end housing resides within the O-ring recess (337), and an out-facing portion of the O-ring extends above the exterior surface of the top, front, bottom and back walls of the distal end housing.

This open distal end of the distal end housing is adapted to be inserted within the central opening of a further connector sleeve (7), as previously described. The connector sleeve is slideable over the distal end of the end housing, such that the interior surface of the connector sleeve (7) compresses the out-facing portion of the O-ring (338), thus forming a resilient seal therebetween. A further connector sleeve gasket may be positioned within the sleeve to abut the distally facing edge of the distal end housing, to facilitate coupling with the next component of the modular production system. The corner slots (336) interact with the connector sleeve in the exact manner earlier described, to allow for convenient assembly and disassembly of the modular system.

The external surface of the front wall (318) of the distal end housing has attached thereto, or associated therewith, a mounting bracket (339), which may be employed in the connection of the drive frame of the internal article transport system (9) within the end housing, and/or assist in the connection of the module housing to the external drive system (8) and/or base structure (10), as described in relation to the infeed module above.

B. Internal Transport Mechanism of Depyrogenation Module

Internal transport system section (400) contains many similar if not identical features to those described for the section (200) of internal transport mechanism (9) in the infeed module (2) above. Due to these similarities, the reference numbering used in relation to the infeed transport will also be used to describe the internal transport system in the depyrogenation module. Reference numbers will however change in their hundreds digit, such that reference number (200) about the infeed internal transport system description, will be references as reference number (400) in this discussion of the depyrogenator module internal transport system. Moreover, where component is duplicated, such as with the drive frame, with a drive frame being positioned in both the proximal end housing and the distal end housing, components in the proximal housing are indicated with the standard reference number (e.g. 401) and components in the distal end housing will referenced with the same reference number with a prime character (e.g., 401'). A similar approach will be used in the discussion of the transport system in later modules.

With reference to FIGS. 8-12, the internal transport system section (400) in this depyrogenation production module embodiment includes a movable support assembly (402) having a pair of drive frames (401 and 401') and a movable support rail (412) attached at its proximal and distal end to the proximal and distally positioned drive frames (401 and 401'), respectively. The moveable support assembly interacts with a stationary article support assembly (403), as previously described for the infeed, lifting articles from the stationary support, distally moving those articles, and placing them back down on the stationary support surface, before extending below the stationary support surface and returning it its starting position.

Each drive frame includes a wall mounting plate (404/404'), having a front face which attaches to the interior front wall of its respective end housing. An inwardly directed vertical lamella (405/405') extends rearwardly from the top surface of wall mounting plate (404/404'), attaching to a front structural support (406/406'). A first (proximal) horizontal lamella (407/407') and a second (distal) horizontal lamella (408/408'), attach the front structural support (406/406') to the rear structural support (409/409'). The rear structural support (409/409') has associated with it a follower magnet (410/410') and a connector arm (411/411' (not shown)), which in turn is connected to a moveable support rail (412). Thus, as with the infeed module drive frame, each of the drive frames in the depyrogenator includes a first portion, e.g. wall mounting plate (404/404'), which is held in a fixed position within the housing channel, and a second portion, (e.g., a rear structural support (409/409') which is suspended within depyrogenator housing channel. The rear structural supports (409 and 409') support opposite ends of the moveable article support rail, which extends from the proximal end of the proximal end housing to the distal end of the distal end housing. The flexible lamella is positioned between the first portions and the second portions of the drive frames, and flexion of these lamella accommodates the movement of the second ends of the drive frames in response to a directional force, with movement of the second portions resulting in movement in the attached moveable article support surface.

So constructed, the first (proximal) drive frame (401) is mounted within the proximal end housing (301), and a second (distal) drive frame (401') is mounted within the proximal end housing (303) of the depyrogenator housing (300).

The drive frames (401 and 401') are mounted within their respective end housings (301 and 303, respectively) in the manner as previously discussed for the infeed, with connector plates (404 and 404') attaching to the interior surfaces of the front walls (308 and 318, respectively) of the proximal and distal end housings.

The proximal and distal movable support connector arms (411 and 411', respectively) carried by the proximal and distal drive frames are attached to portions of opposing ends of a single elongate moveable support rail (412) which extends between the end housings. Proximal end connector arm (411) is operatively connected a proximal portion of the moveable support rail (412) in the proximal end housing, and distal end connector arm (411') is operatively connected a distal portion of the moveable support rail (412) in the distal end housing (411').

In this way, the motion of the moveable support rail (412) is generated at the two extremities of the depyrogenator housing (300). The moveable transport rail (412) is suspended freely between these points of connection, and thus extends through the bore of the tubular housing of the module without connecting to or within the tubular hosing bore.

The stationary support assembly (402) mounted is a similarly paired arrangement as the moveable support. The stationary support assembly (402) includes a back rail (420) and a base rail (421). The back rail is connected within the depyrogenator housing (300) by a pair of back rail arm brackets (422 and 422'), which are connected to the back walls (309 and 319) of the proximal and distal end housings (301 and 303, respectively). The base rail (421) is connected within the depyrogenator housing (300) by a pair of base rail arm brackets (423 and 423', respectively), which are connected to the front walls (308 and 318, respectively) of the proximal and distal end housings (301 and 303, respectively).

The connection of the connector arms to their respective support rail may be accomplished in the manner described previously in relation to the infeed. In the depyrogenator, the connection of the connector arm to the given support rail is done in a manner which accommodates thermal expansion of components, as described in detail in discussion of the infeed module above.

Figure 10:
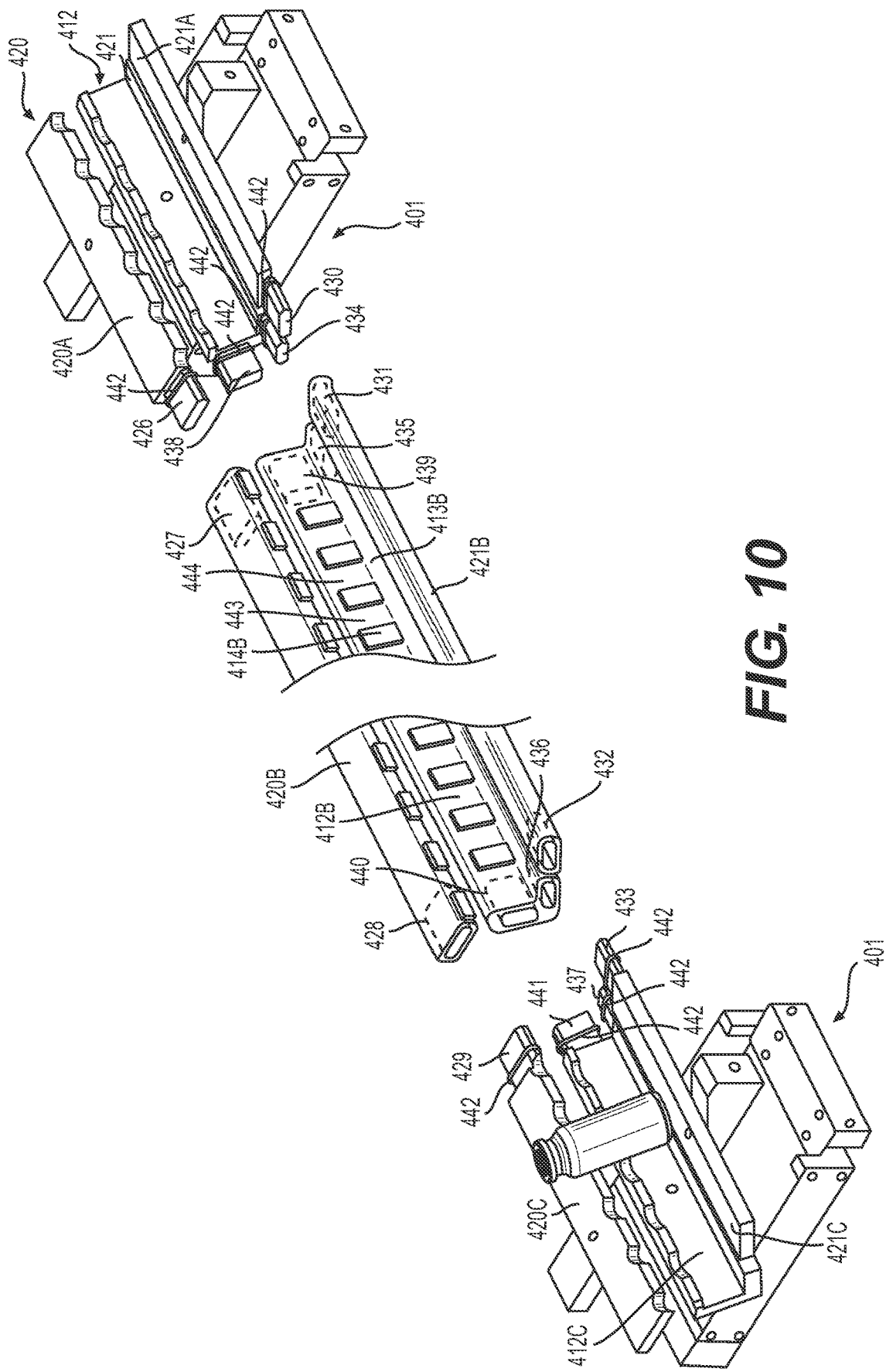
FIG. 10 is an exploded view of the article transport mechanism of FIG. 8.
Figure 11:
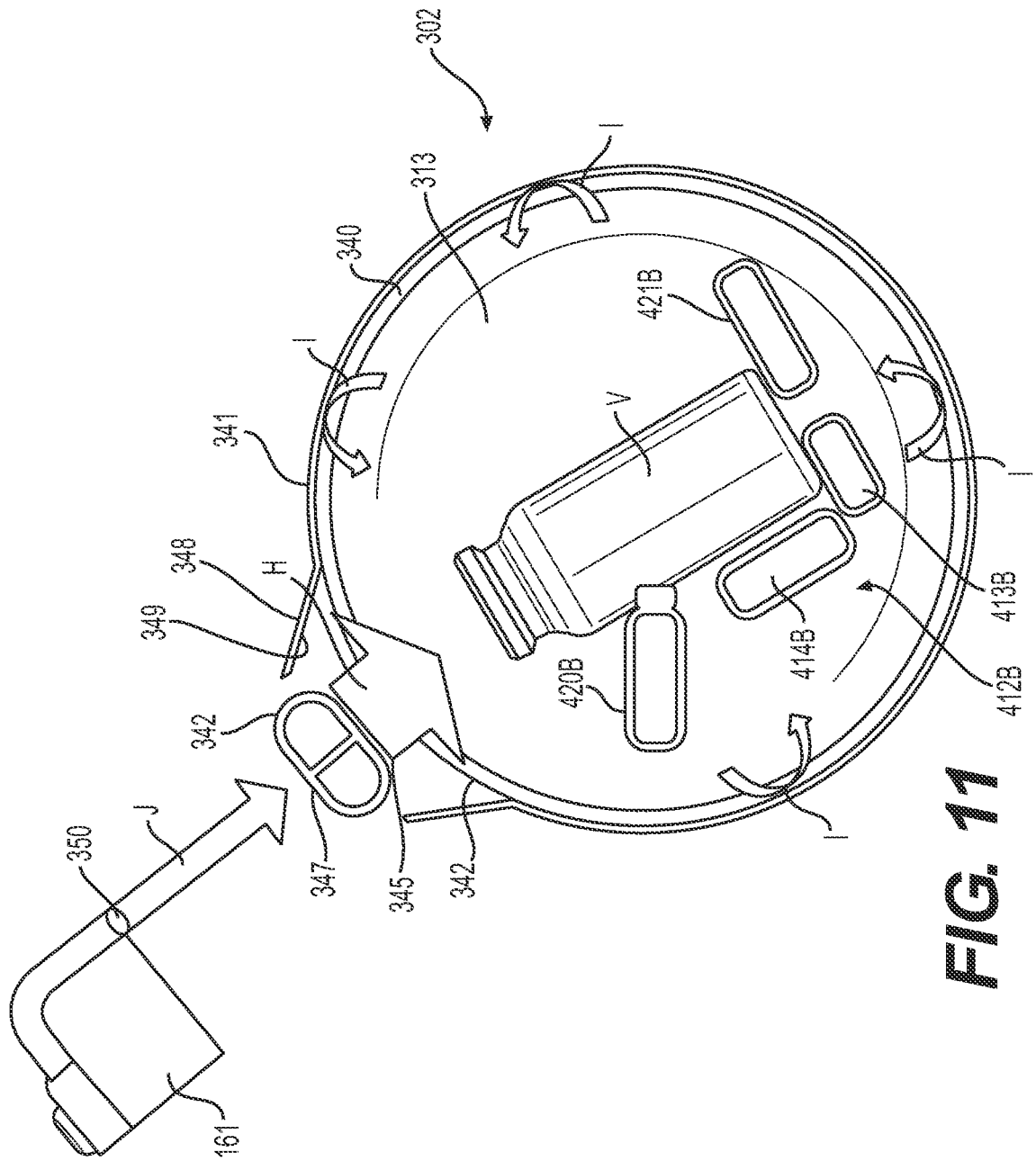
FIG. 11 is a widthwise, cross-sectional view of the depyrogenation module taken through the irradiation zone of the module, showing a side perspective view of the tubular housing, light fixture and cooling sparger.
Figure 12:
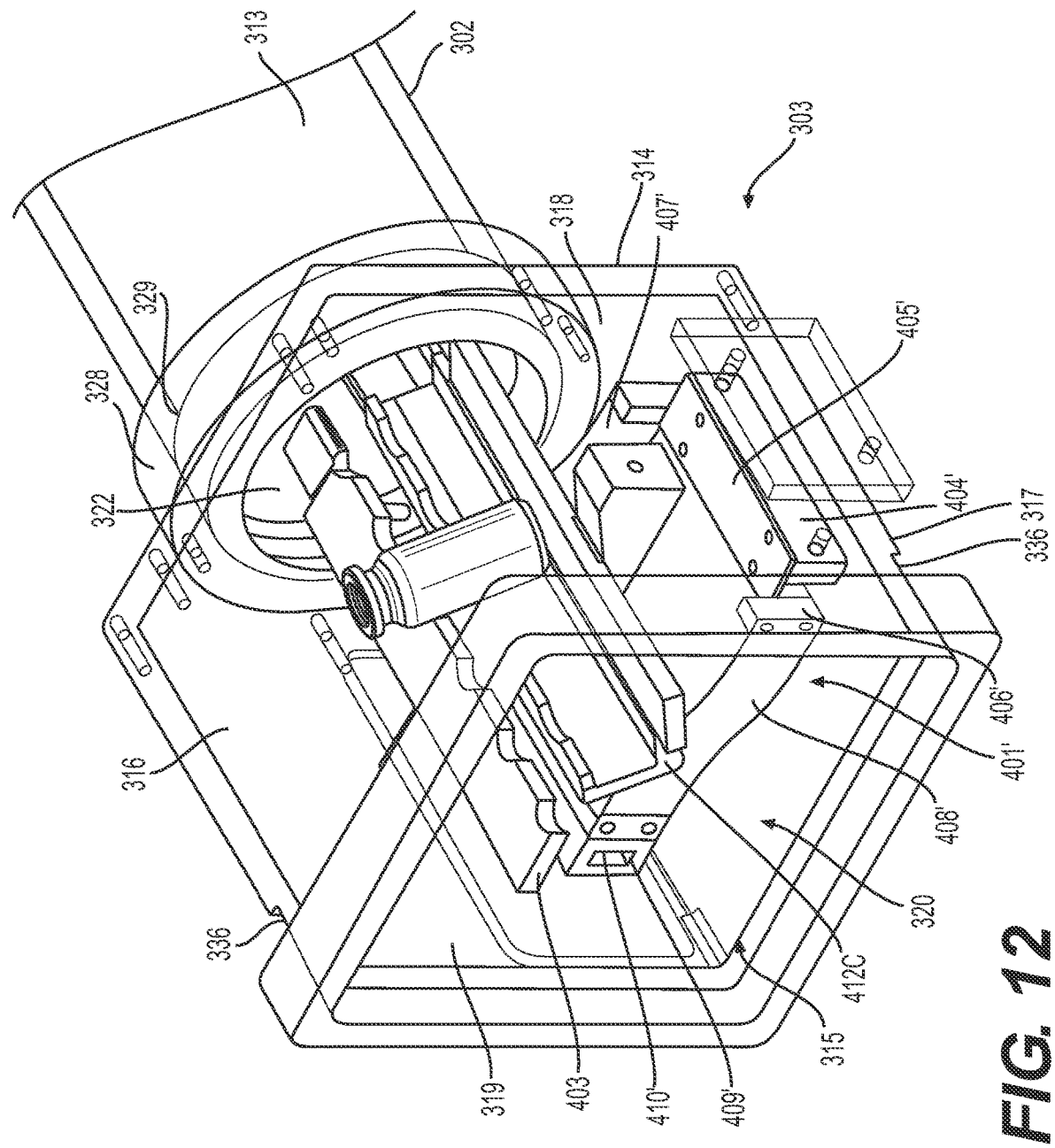
FIG. 12 depicts the distal end housing of the depyrogenation module, with the end housing rendered transparent.

The internal transport mechanism section (400) within the depyrogenator also differs from that describe for the infeed module in that the L-shaped movable support rail (412), the back rail (420), and the base rail (421) are each composed of three distinct sections: a proximal section, a medial extension section, and a distal section. As depicted in FIG. 10, the proximal, medial and distal sections of each rail are coupled to form a single rail section for each of the movable, back and base rails. Thus, the movable support rail (412), includes a proximal movable support rail section (412a), a medial movable support rail extension (412b), and a distal movable support rail section (412c). The back rail (420) of the stationary support assembly (403) includes a proximal back rail section (420a), a medial back rail extension section (420b), and a distal back rail section (420c). The base rail (421) of the stationary support assembly (403) includes a proximal base rail section (421a), a medial base rail extension section (421b), and a distal base rail section (421c).

The attachment between each rail's proximal section to its aligned medial extension section, and between the opposite side of the medial extension section and it's aligned distal section is accomplished by an adapter mechanism. The adapter mechanism in the depicted embodiment, takes the form a male and female connector pair, with one component having formed thereon a male connector member, for example a flange, and the other member being fitted with a female connector, for example a recess, which is sized to accept the flange.

For the moveable L-shaped support rail (412), a flanges and corresponding recesses are employed on both the lower arm (413) and the upwardly extending back portion (414) of L-shaped rail is provided to provide greater structural integrity of the interconnected rail pieces.

As shown in FIG. 10, the distal ends of the proximal rail section (412a) (420a), and (421a) define one or more flanges. Similarly, the proximal ends of the distal rail section (412c) (420c), and (421c) define one or more flanges. The medial extension section of each of the rails ((412b) (420b), and (421b)) define corresponding recesses at their proximal and distal ends. The attachment between the moveable support rail's proximal section's distally directed flange (412a) to the aligned proximally oriented recess of medial extension section (412b), and between the opposite side of the medial extension section and it's aligned distal section is accomplished by an adapter mechanism.

The stationary support back rail (420) is constructed by distally directed flange (426) of proximal back rail portion (420a) being inserted into proximally directed recess (427) of back rail medial extension (420b), and distally directed recess (428) of back rail medial extension (420b) receiving proximally directed flange (429) of distal back rail portion (420c).

The stationary support base rail (412) is constructed by distally directed flange (430) of proximal base rail portion (421a) being inserted into proximally directed recess (431) of base rail medial extension (421b); and distally directed recess (432) of base rail medial extension (421b) receiving proximally directed flange (433) of base rail portion (421c).

Figure 9:
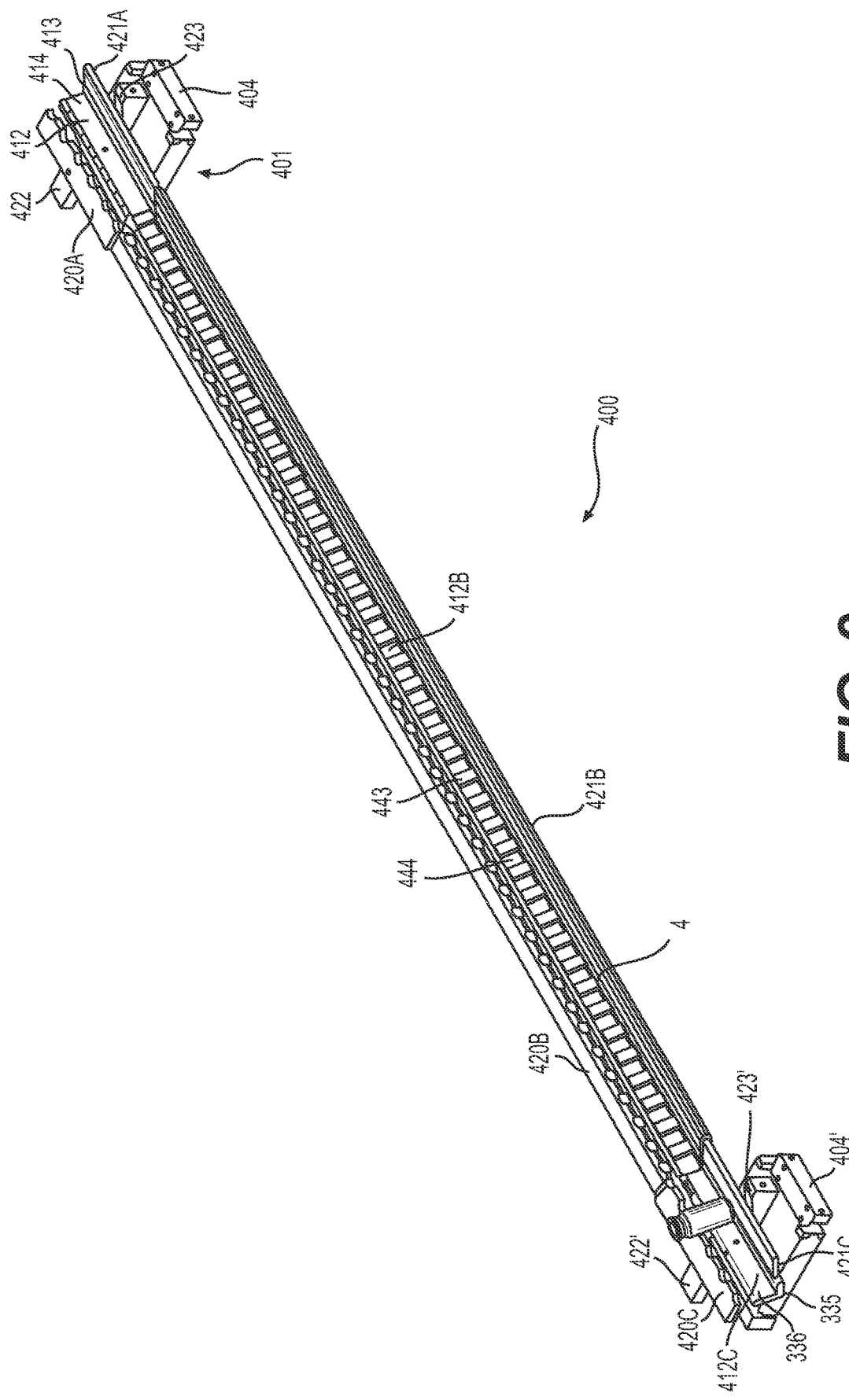
FIG. 9 depicts the internal article transport mechanism used within the depyrogenation module.

The moveable support base rail (412) is constructed by distally directed flange (434) of the lower arm of proximal movable rail (412a) portion being inserted into proximally directed recess (435) of the lower arm of movable rail medial extension (412b); distally directed flange (438) of the upwardly extending back portion of proximal movable rail (412a) portion being inserted into proximally directed recess (439) of the upwardly extending back portion of movable rail medial extension (412b), and; distally directed recess (436) of the lower arm of moveable rail medial extension (412b) receiving proximally directed flange (437) of the lower arm of distal movable rail portion (412c); and distally directed recess (440) of the upwardly extending back portion of moveable rail medial extension (412b) receiving proximally directed flange (441) of the upwardly extending back portion of distal movable rail portion (412c). The assembled internal transport system (400) is shown in FIG. 9.

Each of the rail flanges (426), (429), (430), (433), (434), (437), (438), and (441) and corresponding recesses (427), (428), (431), (432), (435), (436), (439) and (440) may be sized to accommodate thermal variation, such that a small amount of space is provide between the interconnected surface of the flange within the recess, such that thermal growth of the flange within the recess does not cause the extension rail to be damaged, such as by cracking.

A degree of cushioning may also be provided by each flange (426), (429), (430), (433), (434), (437), (438), and (441) of the rails being fitted with an O-ring (442), to absorb compressive forces between an end rail section and medial rail extension at a point where they interface, which may occur, for example, as a result of vibration during operation of the module, or by thermal expansion experienced by the component parts during operation.

By employing the medial extensions, the internal transport system is capable of expansion to a variety of lengths, thus providing great flexibility to the sizing of modules. In modules types where longer periods of exposure are desired, the module may be lengthened by use of a longer tubular housing, and a longer support rail extension, while using the same end housings and end housing components.

The extension rails allow the stationary and moveable supports rails to pass through the bore of the tubular housing between end housings without breaching or making contact with the internal surface of the tubular housing. In so doing, the design preserves the structural and environmental integrity of the tubular housing and the module itself.

As with the other O-rings mentioned above, these flange O-rings are composed of suitably a resilient, thermally stable material, such as a suitable rubber, elastomer or other material selectable by the skilled artisan to accommodate physical compression, thermally associated expansion and contraction in the ranges experienced during operation of the production system.

As can be seen in FIG. 10, the moveable rail extension, 412b, is structurally modified in comparison with that shown of the proximal (412a) and (412c) portions. The movable rail extension is L-shaped, having a lower arm (413b), and an upwardly extending back portion (414b), however, it lacks a upper lip portion such as those found on the proximal and distal moveable rail sections (412a) and (412c). The upwardly extending back portion (414b) of the moveable rail extension instead has a front face (443) having defined therein a series of spaced notches or recesses (444). Alternatively, these front faces may have a series of raised portions extending therefrom, achieving the same effect of providing a stationary platform for articles positioned thereon.

In an alternative form of the medial extensions ((412b) (420b), and (421b)) may be formed as individual hollow rectangular tubes where the recess at each end which forms the female coupling component, are formed by the hollow cavity that extends through each hollow rectangular tubular extension. In the case of the extension between the L-shaped rail, two separate rectangular tubes may be employed, one linking the lower extension arms of the proximal and distal movable rails (412a) and (412c), and the other linking the upwardly extending back portions of the proximal and distal movable rails (412a) and (412c). Such a configuration may advantageously provide a simpler construction for the extension bars, and providing a less expensive option than a L-shaped medial extension section.

The materials selected for the construction of the transparent elongate tubular housing component (340) of the tubular housing section (302), the support rail extensions (412b), (420b) and (421b), and the vials "V" in the depyrogenator, may each be optimized to facilitate effective sterilization within the depyrogenation/sterilization module. For example, they may each be composed of a light transparent and high heat tolerant material. As mentioned previously, the tubular housing is, in one embodiment, quartz. The support rail extensions (412b), (420b) and (421b), extending through the bore of the transparent tubular elongate housing, may be composed of any heat tolerant material, including metals (aluminium, stainless steel, etc.), or non-transparent ceramics, but in certain preferred embodiments, are transparent materials, such as quartz, borosilicate, etc. The vials too in certain embodiments may also be quartz or borosilicate, however, they may also be non-transparent, comprised of a suitable metal. When transparent, these materials are selected to be transparent with greater than 80% transparency, such as 90% transparent, e.g. 95% or greater, to short and/or medium wavelength light, so the light rays can travel through them.

Where the materials used for the rail extensions and/or vials are not transparent, it will be appreciated that the reflective layer applied to the outside of the tubular housing might be used to distribute the heat within the tubular housing and module.

C. Operational Assembly: Depyrogenation Module Function

The depyrogenation module functionality is described with reference to FIGS. 6, 7, 8 and 11, which collectively depict the tubular housing (302) of the depyrogenator module (3) as including a transparent tubular body (340) which defines axial bore (313) which extends lengthwise axially from the proximal end (311) to the distal end (312) of the tubular housing (302).

The transparent tubular body (340) may be composed of any suitable transparent material which is tolerant of temperatures of 200° C. degrees greater, such as 200° C. to 1000° C., and in certain embodiments, such as from 250° C. to 700° C., and will be dependent on the materials selected for the components of the module and containers passing therethrough. For example, with borosilicate, depyrogenation is usually at 300° C. and an exposure time of less than 5 minutes, such as 2-3 minutes, to achieve a desired reduction in the concentration of viable materials (e.g., 1000-fold reduction in pyrogens, such as endotoxins). This time and temperature correlation is dependent upon materials selected. Each material used in or passing through the depyrogenation module will respond differently to light irradiation, and generate a different temperature profile when exposed to the irradiation in the irradiation/heating zone. In the case of borosilicate, the range between 250° C. and 350° C. is considered acceptable. Suitable materials include, but are not limited to, tempered glass, borosilicate, and quartz. In one embodiment, the transparent tubular body comprises quartz.

A layer of an inwardly reflective material (341) substantially covers the exterior surface (342) of the transparent tubular housing, as shown in the cross-section of the tubular housing (302) of the depyrogenator module (3) is depicted in FIG. 8. This inwardly reflective material layer (341) may be composed of any reflective material suitable for the purpose of redirecting light radiation within the bore of the transparent tubular housing (340). The reflective layer may also be used to distribute heat more evenly, especially where non-transparent materials are used within the module for purposes of the vials, extension rails, and the like. The reflective layer may be a coating or a separate sheet of material laying over or adhered to the transparent tubular housing (340). For example, the reflective material may be or include a highly-polished metal, such as aluminium (e.g. AL1100), or gold, etc., whose reflective surface faces the exterior surface (342) of the transparent tubular housing (340) and the axial bore this transparent housing surrounds. Alternatively, the highly reflective coating layer can by composed of a coating having reflective properties, such as aluminized stainless steel or gold, nanocoating, and the like.

Figure 7:
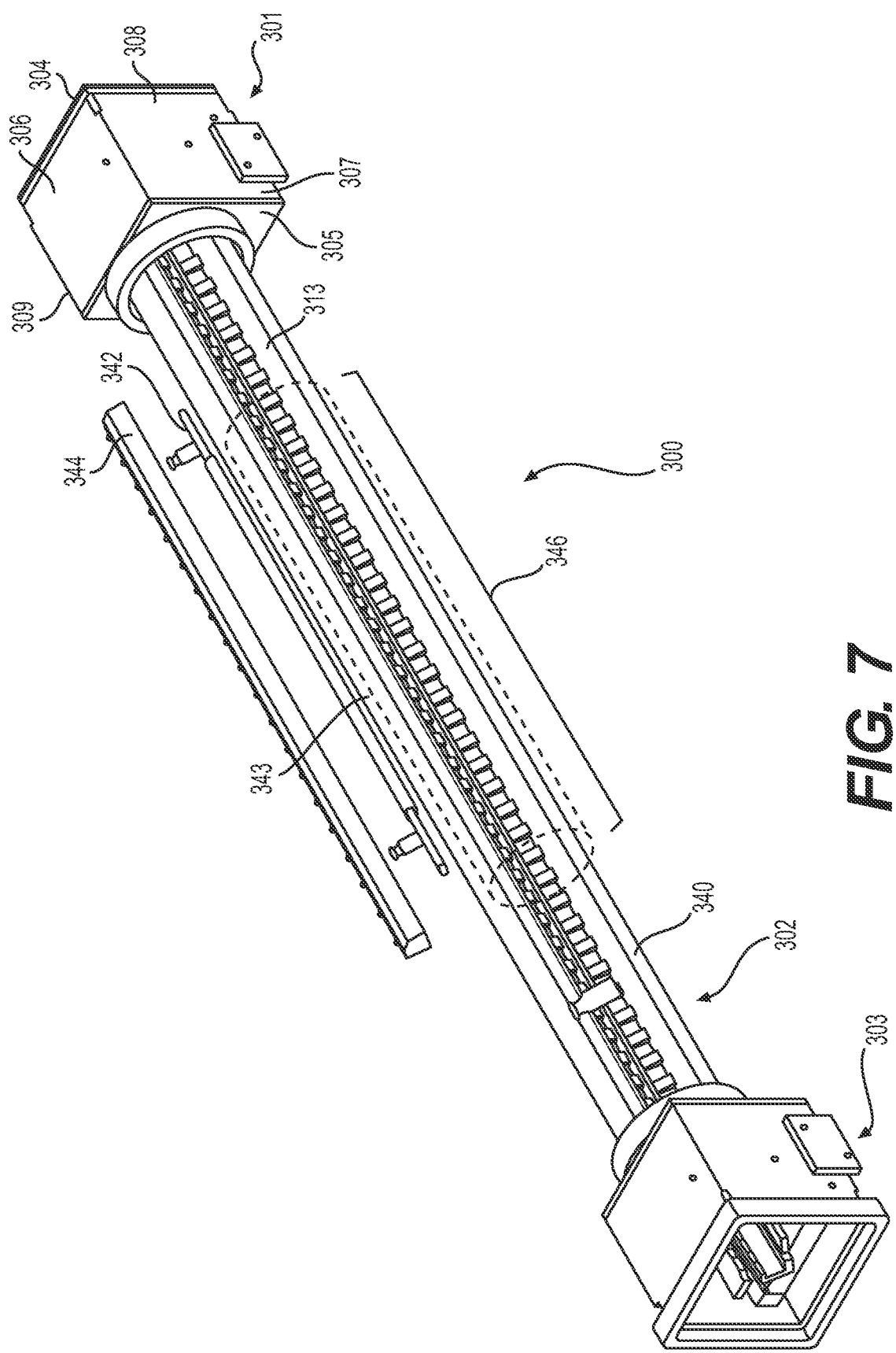
FIG. 7 is an exterior perspective view of an embodiment of a depyrogenation module, showing various internal components of the middle portion of the module.

The depyrogenator also includes an irradiation source, e.g., a light fixture (342), which, when activated, radiates light energy through its front face (345) toward an exposure window (343) in the exterior surface (342) of the transparent tubular housing, where the transparent tubular housing is not completely covered by the reflective layer/material, and the irradiated light may pass through the transparent housing and into the bore of the transparent housing. In the embodiment depicted in FIG. 6, the light fixture (342) is elongate in a proximal to distal direction. The corresponding exposure window is also elongate in a proximal to distal direction. The front face (345) of the light fixture, which faces the exposure window, includes one or more lighting elements. As shown in FIG. 7, the elongate lighting fixture and exposure window define a heating zone (346) within the depyrogenator tubular housing in the area under the light fixture. The light fixture may be of any suitable variety, but generally includes a lighting housing and bulb or other suitable emitter. Beneficially, the irradiation/lighting source may be of a standard variety, such as an infrared lamp, a halogen short wave lamp, or a medium wave (carbon) lamp. Examples of suitable light fixtures include, but are not limited to, the Heraeus, Shortwave #9751761 (twin tube); Heraeus, Carbon #45134868 (twin tube); Heraeus, Carbon #45134446 (single tube); Heraeus, Medium wave 9755255 (twin tube). Each of these possess a gold reflector in the back to direct the energy mostly towards the area to be irradiated.

A reflective apron (348) extends from the surface of the transparent tubular body toward and/or over the light fixture. Apron (348) may extend the length of the exposure window (343) also possesses a reflective underside (349) surface which faces the exposure window, so as to redirect light back toward the bore of the tubular housing. The apron also shields the light emitted from the light source from being directed to the generally away from the exposure window, thus increasing the efficiency of the lighting fixture in raising the temperature of the interior of the tubular housing in the heating zone (346).

When the irradiation source, e.g., light fixture, is turned on, the lighting element or elements in the fixture generate light energy, shown as reference arrow "H" in FIG. 8. This energy passes through the exposure window (343) into the interior bore of the tubular housing, where it is repeatedly reflected and redirected by the inwardly reflective material layer (341) and the reflective underside (349) of the reflective apron (348), as shown by reference arrows "I" in FIG. 8, into the interior bore of the tubular housing, and the components of the internal transport system extending therethrough.

The irradiation will be evenly dispersed, will heat up the contents of the tubular housing, including the support rails and containers themselves, (e.g., quartz pieces), but mostly will heat selectively heat any pyrogens or foreign materials, ensuring efficient destruction both inside and outside of the containers being present in the module. As this irradiation (e.g., light energy, such as Infra-red light energy, or other suitable wave length light) is converted to heat energy within the tubular housing, the internal temperature of the tubular housing within the irradiation zone rises to a pathogen/pyrogen destroying level, for example, 200° C. degrees and greater, such as 200° C. to 1000° C., and in certain embodiments, such as from 200° C. to 700° C., such as 250-350° C., and in so doing, sterilizing the contents of the housing bore exposed to such heat and light energy, including articles passing through this heating zone. Pyrogens and foreign materials will be preferentially heated by the infra-red IR, but the glass etc. will still reach depyrogenation/sterilization temperatures, especially on the surfaces.

A cold air sparger (344) is positioned adjacent the back of the light fixture, and is configured with a plurality of vents (350) which are directed toward the back of (347) of emitter (342) to blow cool air, indicated with reference arrow "J" in FIG. 8, onto the fixture housing and the exterior of the underlying tubular housing, to cool the fixture.

Transmission of the irradiation through the moveable and stationary rail extensions and the articles supported thereon is optimally accomplished when both transport components with in the tubular housing and the containers thereon, are transparent materials which allows short to medium wavelength light to pass through, while being tolerant to the temperatures and other environmental conditions that may be present in the modular production system. In this embodiment, the containers, "V", while they may comprise a metal (aluminium, stainless steel, etc.), or ceramic material, but are more preferably composed of a glass or glass-like material, or a transparent mineral material. In certain embodiments, containers are vials, made of a transparent quartz, borosilicate, or high-temperature resistant transparent glass.

The depyrogenation module (3) is designed to be connected to a module at its proximal end, and at its distal end. Between interconnected modules, the distal end of the stationary and moveable support rails of a proximal module and the proximal ends of the stationary and moveable support rails of the distally adjoining next module are each constructed for small gap to exist between the adjoining stationary top rail, stationary bottom rail, and movable L-shaped rails.

This gap, such as the e.g., gap (351) in FIG. 8., is designed to accommodate any thermal expansion or contraction that may be experienced by the stationary and moveable support rails during operation. As will appreciated, the gap should be sufficiently large to allow expansion during heating, while at the same time not so large that transfer of an article being passed from the transport mechanism of one module to the transport mechanism of the next is impeded.

Connection of the Infeed to the Depyrogenation Module:

FIG. 8 depicts the connection between the distal end (106) of the infeed unit (2), and the proximal end (305) of the proximal end housing (301) of the depyrogenator housing (300). In this embodiment, the distal end of the infeed unit (2) is fitted into the proximal side of a connector sleeve (7). The connector sleeve extends the around the exterior of the end of the infeed housing. The infeed housing (100) has an O-ring positioning recess (122) circumferentially extending around its distal end exterior surface, and O-ring (123) rests therein, compressed between the exterior surface of the housing and the interior surface of the connector bracket.

In like fashion, the exterior surface of the proximal end (147) of the proximal end housing (301) has an O-ring positioning recess (166) that extends around the exterior of the proximal end housing of the depyrogenation module, with O-ring (167) is positioned therein. The proximal end of the proximal end connector is fitted within the distal opening of the connecter sleeve (7), again with O-ring (167) being slightly compressed between the recess walls and the interior surface of the surrounding connector sleeve. The proximal end of the depyrogenator module acts as the male coupling, which is fitted within the distal end of the connector sleeve which acts as a female counterpart to this connection.

In this embodiment, a small gap (168) may be left between the facing surfaces of the end the lower infeed housing and the proximal end housing. This gap and a reliant washer (169) positioned in the gap, allows for thermal expansion of the housings due to the heat generated in the depyrogenator while the washer (169) and O-rings (145 and 167) act to maintain a seal between these connected components regardless their thermally induced state, thus preserving the closed nature of the system within the interior of these connected housings.

The proximal end of the light transparent tubular housing (157) is also held in a sealed fashion within the internal surface the ring-shaped bracket (153) at the distal end (148) of the proximal end housing by O-ring (168), which fits around the tubular housing, and into an annular recess (169) formed in the interior surface of the ring-shaped bracket (149). Again, a gap (generally 170) may be left between the end of the tubular housing and the distal face of the proximal end housing surrounded by the ring-shaped bracket, to allow for thermally induced expansion and contraction of components.

The elongate corner slots on the ends of the interfacing modules display a useful feature of the modular system, which may facilitate connection and disconnection. Connection of the interfacing ends of adjoining modules is achieved by inserting each within a portion of connector bracket (7), as shown in FIG. 13. As mentioned above, the connector bracket compresses O-rings on the ends of each module to achieve a seal therebetween. The lateral end grooves on each module however may be configured, by making them of a sufficient length, to allow the connector bracket to be received entirely over either of the module's ends. Specifically, the connector bracket in FIG. 13 may be slid proximally, such that the bracket's distal end is flush with, or is proximal to the distal end of the infeed housing, or alternatively, the connector bracket may be slid distally, such that the bracket's proximal end is flush with, or is distal to the proximal end of the depyrogenator housing, thus disconnecting the interfacing housings, and allowing the removal of a unit by lifting the unit out.

3. Cooling Module (FIGS. 13-16)

In a further embodiment of a production module of the present invention, the module takes the form of a cooling module. The depyrogenation module is useful as a component of various embodiments of the modular production system aspect of the present invention.

A. Cooling Module Housing

A still further embodiment of a production module useful in the modular production system takes the form of a cooling module, one embodiment of which is depicted with reference to FIGS. 13-16. Such modules include a housing providing an interior chamber, transport mechanism positioned within the chamber, and an operational assembly, in this case, a cooling source.

In the embodiment of a cooling module is depicted with reference to, the cooling housing (500) is similar to the depyrogenation module housing (300). Like terms are used to define like structures, with reference numbers changed from the 300 series to the 500 series where these features are shared. The discussion provided in relation to the depyrogenator in regards to reference number (300) to (329), are applicable to reference numbers 500-539, and may be imported into the discussion of this cooling module without be copied verbatim below. With these provisions in mind, the cooling module (4) includes a cooling housing (500) having a proximal end housing (501), connected to an elongate tubular housing (502) which is connected to a distal end housing (503).

The proximal end housing (501) includes an open proximal end (504), a distal end wall (505), a top wall (506), bottom wall (507), a front wall (508), and a back wall (509). The distal end, top, bottom, front, and back walls each possess exterior and interior surfaces. The interior surfaces of the distal end, top, bottom, front, and back walls define a proximal end housing interior cavity (510) within the proximal end housing (501).

The tubular housing (502) has a proximal end (511) a distal end (512), and an interior axial bore (513) which extends between the proximal and distal ends. The materials selected for the construction of tubular housing section (502) be of the same materials used for the depyrogenator, thus employing a standardized platform for the similar housing type. Alternatively, a different material may be employed.

The distal end housing (503) includes a proximal end wall (514), an open distal end (515), a top wall (516), bottom wall (517), a front wall (518), and a back wall (519). The proximal end, top, bottom, front, and back walls each possess exterior and interior surfaces. The interior surfaces of the proximal end wall, top, bottom, front wall, and back wall define a distal end housing interior cavity (520) within the distal end housing (503).

An access opening (521) is defined through the distal wall of the proximal end housing (501), providing access between the proximal end housing interior cavity (510) and the axial bore (513) of the tubular housing.

A further access opening (522) is defined through the proximal end wall of the distal end housing (503), providing access between the distal end housing interior cavity (520) and the axial bore (513) of the tubular housing.

The proximal end housing interior cavity (510), tubular housing axial bore (513), and the distal end housing interior cavity (520) are in fluid communication and collectively define the cooling module housing interior cavity (523).

The exterior surface of the distal end wall (505) of the proximal end housing (501) has sealingly attached thereto a proximal ring-shaped mounting bracket (524). The proximal ring-shaped mounting bracket includes an inner circumferential surface (525), a distally directed face, a proximally directed face, and an outer circumferential surface. The proximal ring-shaped bracket (524) is sized slightly larger than the proximal end of the tubular housing, and is positioned on the exterior surface of the distal wall of the proximal end housing such that the proximal ring-shaped bracket encircles the access opening (521) extending through the distal wall of the proximal end housing.

The seal between the external circumferential surface of the tubular housing and the ring-shaped bracket is facilitated by the inner circumferential surface of the ring-shaped bracket defining an O-ring recess (526) in which is positioned an O-ring (527). The O-ring (527) is sized such that a portion of the O-ring extends out of the O-ring recess, such than when the proximal end of the tubular housing is fitted within the ring shaped bracket and adjacent the exterior surface of the distal end wall of the proximal end housing encircled by the proximal ring-shaped bracket, the O-ring is compressed between the inner circumferential surface of the proximal ring-shaped bracket and exterior circumferential surface of the proximal end (511) of tubular housing (502). Sufficient space (a small gap) is left between the outer surface of the tubular housing and the inner surface of the ring-shaped bracket, and the proximal end of the tubular housing and the exterior face of the distal wall of the proximal end housing to accommodate potential thermally induced expansion and contraction during operations without breaching the O-ring seal therebetween.

A corresponding connection is made between the distal end (512) of the tubular housing and the exterior surface of the proximal end wall (514) of the distal end housing (503). The proximal end wall exterior surface of the distal end housing has sealingly attached thereto a distal ring-shaped mounting bracket (528). The distal ring-shaped mounting bracket includes an inner circumferential surface (529) defining a central opening, a proximally directed front face, (unless integrally formed on the proximal wall of the distal end housing) a distally directed rear face, and an outer circumferential surface.

The distal ring-shaped bracket (524) is sized slightly larger than the distal end of the tubular housing, and is positioned on the proximal exterior surface of the distal end housing so as to encircle the access opening (522) extending through the proximal wall of the distal end housing.

The seal between the external surface of the distal end of the tubular housing and the distal ring-shaped bracket is facilitated by the inner circumferential surface of the distal ring-shaped bracket defining an O-ring recess (530) in which is positioned an O-ring (531).

The O-ring (531) is sized such that a portion of the O-ring extends out of the O-ring recess, such that when the distal end of the tubular housing is fitted within the distal ring-shaped bracket, and the distal face of the tubular housing is adjacent the exterior surface of the distal end wall of the proximal end housing surrounded by the ring-shaped bracket, the O-ring is compressed between the inner circumferential surface of the distal ring-shaped bracket and exterior surface of the distal end (512) of tubular housing (502). Again, sufficient space (a small gap) may be left between the outer surface of the tubular housing and the inner surface of the distal ring-shaped bracket, and the distal end of the tubular housing and the exterior face of the proximal wall of the distal end housing to accommodate potential thermally induced expansion and contraction during operations without breaching the O-ring seal therebetween.

The proximal end (504) of the proximal end housing (501) is open, and the exterior surface of the top, front, bottom and back walls of the proximal end housing defines a number of features involved in the connectability of the proximal end of the proximal end housing to the previously described open distal end of previously described production modules. These features include lateral elongate corner slots (532) in selected or each of the corners where adjacent walls meet at the proximal end of the proximal end housing. The corner slots (532) extend from the proximal face of the proximal end housing and continue distally therefrom within the exterior corner surface of the proximal housing, as depicted in FIG. 13.

The exterior faces of the top, front, bottom and back walls at the proximal end (504) of the proximal end housing have formed therein an annular O-ring recess (533), which extends circumferentially around the proximal end housing adjacent its proximal end. An O-ring (534) is positioned in this proximal exterior O-ring recess. An inner circumferential portion of the O-ring (534) resides within the O-ring recess (533), and the outward-facing portion of the O-ring extends above the exterior surface of the top, front, bottom and back walls of the infeed housing, presenting a contact surface.

The open proximal end (504) of the proximal end housing of the cooling module is thus adapted to be inserted within the central opening of a connector sleeve (7).

The connector sleeves described in this embodiment have an exterior surface, a first (proximal) face, a second (distal) face, and an interior surface which defines the central opening of the connector sleeve. The central opening of the connector sleeve is sized to be only slightly larger than the size of the end housings it connects, and shaped to accommodate an end of a production module housing.

The interior circumferential surface of the of the connector sleeve (7) acts as a compression surface for an O-ring positioned on the end portion of a production module housing positioned within the central opening of the connector sleeve. Compression of the O-ring between the interior surface of the sleeve and the exterior surface of the end portion of the module housing effectively seals the connection between the two, thus facilitating the connection between the distal end of a proximally mounted module, such as the depyrogenator module shown and the proximal end of the cooling module, as depicted in FIGS. 13 and 14.

As shown in FIGS. 13 and 14, the connector sleeve (7) is slideable over the distal end (306) of the depyrogenation housing (3), such that the interior surface of a proximally facing portion the connector sleeve (7) compresses the out-facing contact surface of the O-ring (333), thus forming a resilient seal therebetween. The opposite end of the connector sleeve is (7) received the open proximal end (504) of the proximal end housing (501) of the cooling module housing (500), such that the interior surface of a distally facing portion of the connector sleeve (7) compresses the out-facing contact surface portion of the O-ring (534) to form a resilient seal therebetween.

To further assist in sealing area between the distal end of the proximally positioned production module (e.g. a depyrogenation module, as shown in FIGS. 1 and 2) and the proximal end of the proximal end housing of the cooling module, a connector sleeve gasket (14) may be positioned therebetween. So positioned, the connector sleeve gasket (14) occupies the space between the distal face of the proximally positioned module housing (e.g. a depyrogenator module), and the proximal open face of the proximal end housing of the cooling module, and the interior surface in the connector sleeve (7).

The connection between these adjacent modules (2) and (3) provides a small gap (551) between the distal ends of the stationary support rails and moveable support rail of the proximally positioned module housing (e.g., in the depyrogenator module distal end housing), and the proximal ends of the stationary support rails and moveable support rail of the distally positioned module (i.e. the cooling module). This gap is provided to accommodate potential thermal expansion of the support rails which may be experienced during operation. The gap (551) is designed to be large enough to achieve that function, and to be sufficiently small not to interfere with the orderly movement of vials over the gap as articles move from one module to the next by operation of the internal transport system (9).

Production module connection is also aided by the corner slots (536) of the proximal end housing of the cooling module, which allow the connector sleeve 7 to slip entirely over the end portion of the end housing, to completely be disconnected from the distal end of the depyrogenator module, thus facilitating the process of assembling and disassembling the production line.

The external surface of the front wall (508) of the proximal end housing has attached thereto, or associated therewith, a mounting bracket (535), which may be employed in the connection of the internal article transport system (9) within the cooling module end housing, and/or assist in the connection of the cooling module housing to the external drive system (8) and or base structure (10), as shown in FIGS. 1 and 2.

The open distal end (515) of the cooling end housing (503) is structured very similarly to the previously described open distal end of the depyrogenation module. The distal end (515) is open and the exterior surface of the top (516), front (518), bottom (517) and back (519) walls of the distal end housing define the same features involved in the connectability of the distal end of the depyrogenator housing. These features include lateral elongate corner slots (536) in selected or each of the corners where adjacent wall meets at the distal end of the distal end housing. The corner slots (536) extend from the distal face of the end housing and continue proximally therefrom within the exterior surface of the corners of the end housing. The end housing further includes an annular O-ring recess (537), which extends circumferentially around the distal end housing adjacent its distal end (515). The annular O-ring recess (537) is defined in the exterior faces of the top, front, bottom and back walls of the distal end housing at the distal and the recess extends circumferentially around the distal end housing adjacent its distal end (515). The O-ring (538) is positioned in this O-ring recess, such that the portion of the O-ring that faces the surface of the end housing resides within the O-ring recess (537), and an out-facing portion of the O-ring extends above the exterior surface of the top, front, bottom and back walls of the distal end housing.

This open distal end (515) of the distal end housing is adapted to be inserted within the central opening of a further connector sleeve (7), as previously described. The connector sleeve is slideable over the distal end of the end housing, such that the interior surface of the connector sleeve (7) compresses the out-facing portion of the O-ring (538) thus forming a resilient seal therebetween. A further connector sleeve gasket (not shown) may be positioned within the sleeve so as to abut the distally facing edge of the distal end housing, to facilitate coupling with the next component of the modular production system. The corner slots (536) interact with the connector sleeve in the exact manner earlier described, to allow for convenient assembly and disassembly of the modular system.

The external surface of the front wall (518) of the distal end housing has attached thereto, or associated therewith, a mounting bracket (539), which may be employed in the connection of the drive frame of the internal article transport system (9) within the end housing, and/or assist in the connection of the module housing to the external drive system (8) and/or base structure (10).

B. Internal Transport Mechanism of Cooling Module

The cooling module internal transport system section (600), is structured very similarly to that described for the internal transport system section (400) of the depyrogenation module (300) above. Internal transport system section (600) of cooling module (500) contains similar if not identical features to those described for the internal transport system section (400) the depyrogenation module (300). As the components for the drive frames of such moveable support assemblies are described in the above discussion of the depyrogenator module, they are not shown in detail in FIGS. 13-16. Where shown in FIGS. 13-16, reference numbering used for the transport section changes only the hundredths digit, i.e., (605) in this section, refers to the feature (405) in the discussion of the depyrogenation module above. Likewise, components of the transport system drive frame assembly within the proximal housing are indicated with the standard reference number (e.g. 601) and components of the section of the transport system within the distal end housing are referenced with the number plus prime (e.g., 601').

In the cooling module section (500), the internal transport system section (600) includes a moveable support assembly (602) possessing a proximal drive fame (601) and a distal drive frame (601'). The proximal and distal drive fames are fixedly connected by their wall mounting plates to the interior of the front walls (308 and 318, respectively) of proximal and distal end housings (501) and (503), respectively, in the manner as previously discussed for the depyrogenation module.

As before the proximal drive frame and distal drive frames each include a drive frame wall mounting plate (604/604'), from which extend inwardly directed vertical lamella (605/605'), which are attached to front structural support (606/606'). First (proximal) horizontal lamella (607/607'), and second (distal) horizontal lamella (608/608') attached the front structural supports to respective rear structural supports (609/609'). Each rear structural support contains or is attached to a respective follower magnet (610/610'), and each rear structural support is connected to a connector arm (611/611'). The connector arms operative attached to the proximal and distal rear structural supports to portions of opposing ends of an elongate moveable support rail (612) which extends through the bore of the tubular housing between the proximal and distal end housings.

The proximal end connector arm is operatively connected a proximal portion of the moveable support rail (612) in the proximal end housing, and the distal end connector arm is operatively connected a distal portion of the moveable support rail (612) in the distal end housing (503). Thus, as was described above with the depyrogenation module, the motion of the moveable support rail (612) is generated at the two extremities of the cooling housing (500), with the moveable transport rail (612) being suspended freely between its points of connection to these drive frames, extending through the bore of the tubular housing of the module without being connected to the tubular housing itself.

The stationary support assembly (602) in the depyrogenation module is similarly fashioned to the stationary support of the depyrogenation module described above. In the embodiment shown, the stationary support includes a back rail (620) and a base rail (621). The back rail is connected within the cooling module housing (500) by a pair of back rail arm brackets (622 and 622'), which are connected to the back walls (509 and 519) of the proximal and distal end housings, respectively. The base rail (621) is connected within the cooling housing (500) by a pair of base rail arm brackets (623 and 623', respectively), which are connected to the front walls (508 and 518, respectively) of the proximal and distal end housings (501 and 503, respectively).

The connection of the connector arms to their respective (moveable or stationary) support rail may be accomplished in the manner described previously in relation to the depyrogenation module. Again, the connection of the connector arm to the given support rail may be made in a manner which accommodates thermal expansion of components, as described in detail in discussion of the depyrogenation module above.

The internal transport mechanism section (600) within the cooling module differs from that describe for the depyrogenation module in that the L-shaped movable support rail (612), the back rail (620), and the base rail (621) are each composed of a single length of rail, which may be of unitary construction. As the stationary and movable supports are just one piece, and can be made of metal or ceramic, and are designed to absorb thermal expansions in two different ways: first, the stationary supports may be provided with straight, elongate slots in the surfaces where they attach to the connector brackets mounting them to the internal wall of the end housings. The brackets are fitted with a pin which extends in to the slots. The expansion is accommodated by the pin sliding in the slot. Alternatively, the stationary supports could rest on a small piece of slippery material such as ceramic, which would allow slippage during thermal size change. Thermal size change of the movable support rail is the accommodated by a flexible bearing (i.e., the flexibility of the horizontal lamella) which flex when needed.

As can be seen in FIG. 14, the moveable rail (612) is L-shaped, having a lower arm (613), and an upwardly extending back portion (614), and an upper lip portion (615), front vertical face (616), and notches or recesses (617) therein.

In an alternative embodiment, the internal transport mechanism (9) employed in the cooling housing may be structurally identical to that described for the depyrogenator above.

In this alternative form, the drive frames carrying the L-shaped movable transport support rail and the back and base stationary support rails are attached within the proximal and distal end housings in identical fashion as with the depyrogenator module. Extension rails extending through the bore of the elongate tubular housing connect the movable and structural support portions located in the end housings. It will be appreciated, though, that light irradiation offers no advantage in the cooling module, and thus, the materials selected for the extension rails through the elongate tubular housing (503), may differ than those select for the accordingly depyrogenator. In the appropriate case, such extension rails may comprise metal, (e.g., aluminium, stainless steel, etc.,), ceramic, if materials used in the depyrogenator are not employed in the transport internal mechanism of the cooling module.

C. Operational Assembly Cooling Module

FIG. 16 depicts features within the distal end housing (503) of the cooling module (4) which has operational functionality. As shown, cooling module distal end housing (503) has a top wall (516). The exterior surface of this top wall (516) forms the upper surface of the distal end housing. The interior surface of the top wall forms the ceiling within the interior chamber (520), with an access opening (555), extending upwardly from an opening the ceiling through the top wall, exiting through an opening in the exterior surface thereof.

Positioned on exterior surface of this top wall (516) of the cooling module end housing, over the access opening (555), is cold air filter housing (552). The cold air filter housing possesses a cylindrical, tubular filter body (553), which defines a vertical bore (554). The tubular filter body (553) is capped at its upper end by a removable lid (556), having a compressed air port connection (557), which is turn is attached to one end of a cold air feed tube (558), which is itself connected to an cold air source (559), e.g., a compressed air feed. An air filter (560) is positioned within vertical bore (554).

The air filter (560), may be of any suitable type, such as a single or double HEPA filter. The filter preferably made of sintered metal and can stand high temperatures, above 200° C. As with the Infeed module discussed above, the filter housing and filters are schematic representations or not exhaustive. Alternative configurations and systems may be employed without departing from the scope of the invention.

On the interior of the distal end housing (503), a sparger housing (561) is connected to the end housing ceiling. The sparger housing defines a vertical chamber interior conduit (562), whose upper end is in fluid communication with access opening (555). The sparger housing, at its lower proximal side, provides a sparger tube mounting passage (563) into which is positioned an elongate sparger tube (564), which defines a central channel (565). The elongate sparger tube extends proximally within axial bore (513) of the tubular housing (502). A plurality of spray holes or nozzles (566) are formed in the sparger tube (564).

In use, the cooling module (4) acts to cool air and articles passed on from the depyrogenator. Cold air is generated by the cold air source (559), and is pumped through cold air feed tube (558) port connection (557), into the vertical bore (554) of the cold air filter housing (552). This cold, pressurized air to is depicted with reference arrows "K" in FIG. 16.

Sterilizing filters (560) in cold air filter housing (552) act as a double filtration mechanism, and remove any "viable" and "non-viable" particles present in the air flow, before the airflow passes through access opening (555) and into the interior conduit (562) of the sparger housing (561), as depicted by reference arrow "L" in FIG. 16. Two filters are used in series to achieve traditional "double filtration".

From the interior conduit (562) of the sparger housing (561), the cold pressurized air is forced proximally within the sparger tube mounting passage (563), down the central channel (565) of elongate sparger tube (564), as depicted by reference arrow "M", before being blown out of the sparger tube through the plurality of spray holes or nozzles (566) formed in the sparger tube (564), as depicted by reference arrow "N".

The cold air distributed along the length of the cooling module tubular housing by the cold as sparger functions to reduces the temperature of the container coming out of the depyrogenating unit while passing through the cooling module. Some heat may also be removed through the walls of the cooling module housing.

When connected in a modular production system, such as the one shown FIGS. 1 and 2, such a cooling module would provide pressurized air to those modules connected proximally thereto, providing the airflow designated by arrow "B", which is also shown in FIG. 4, and which was described in the discussion of infeed module; and providing the airflow designated by arrow "P", which is also shown in FIG. 43, and which is described in the discussion of outfeed module.

The cold, pressurized air is used to facilitate internal cooling and to keep the internal pressure of the production tunnel/chamber within the interconnected system at a pressure greater than the ambient air pressure outside the modular system, to assist in maintaining an aseptic environment within the production tunnel. Only a small amount of air is used in this over pressurization, to avoid creating an undesirably high wind current inside the system. If desired, systems, such as a plug flow may be employed to regulate the desired pressure in the interconnected modules. In such cases, the systems would act, for example, prevent the internal air current from exceeding a desired air flow threshold, (e.g., 0.45 m/s).

As will be appreciated, in a modular production system employing a depyrogenation module, the reduction of the heat distal of the depyrogenation module (such as the aseptic filling system of the present invention), is a function of multiple factors. These factors include, but are not limited to, the temperature of the air or other cooling fluid employed; the length of time that the articles are present in the interior of the cooling module (which is a factor of both the speed at which articles are being passed through the transport system and the length of the cooling module itself); and the heat conducting properties of the internal components of the module(s) and the articles being transported therethrough. To accommodate adequate cooling in the aseptic filling system in the present embodiment, a second cooling module (4'), may be coupled to the first cooling module (4) as shown in FIGS. 1 and 2.

Other ways of reducing the temperature of materials within the production tunnel include decreasing the temperature of air being used; increasing the cooling surface area by employing still more cooling modules; lengthening the elongate tubular portions used; recirculating cold air within the system; employing an external heat exchanger; or by air removal through further filtration within the cooling module(s). As one of ordinary skill, the flexibility in the present modular approach permits easy modification of the systems by use of additional modules, or modification of those described herein.

The cooling modules are connectable as described for other modules herein. The connection between modules, facilitated via, a connector sleeve (7) interacting with O-rings present on the external surfaces of the end housings being connected, as depicted for example, in FIG. 8 and/or FIG. 14 and FIG. 15.

As one of ordinary skill will appreciate, the modular system described above has multiple advantages in comparison traditional depyrogenation tunnels. The size, weight, and footprint of the system is greatly reduced. The combined length of the infeed, depyrogenator and both cooling modules being less, for example, than 10 meters long (e.g., 8 meters or less) and approximately 0.3 meters in width and height. As will be appreciated in comparison to the available industrial manufacturing lines, the embodiments described herein involves merely a few kilograms of quartz tube, instead of a 1000 kilo stainless steel tunnel.

Use of sintered steel HEPA filters avoids problems associated with heat sensitivity of standard filters, which known to be delicate at high temperatures. The depyrogenator and cooling modules as avoids handling air at extremely high temperatures, thus offering a safety advantage. Moreover, this modular system involves an even distribution of heat through the cooling system. Very few sensors are needed in terms of internal control, allowing the use of a simple temperature control, without resorting to gate opening and closing, etc. that is experienced with known sterilization tunnels.

The modular system has a fast response time, as warm up is accomplished in minutes instead of hours, and may achieve fast sterilization cycle time, e.g., 6 minutes instead of the typical 30 needed with standard sterilization tunnels.

Further still, the present modular system can be switched off when not in use, whereas some standard tunnels must be kept at least at 150° C. to avoid damages to the filter sealing.

Additionally, the instant modular system is very simply sealed from the outside, thus easily reducing contamination risk of the systems.

The cooling module (4) is adapted to be connected to a proximally located module at its proximal end, and a further distally located module at its distal end. The proximal and distal ends of the stationary and moveable support rails of the cooling module are structured so as to provide a gap between the ends of the stationary and moveable support rails of one module with the ends of the stationary and moveable support rails of the next attached module.

This gap, e.g., gap (351) in FIG. 8 or (551) in FIG. 14, is designed to accommodate any thermal expansion or contraction that may be experienced by the stationary and moveable support rails during operation. As will appreciated, the gap should be sufficiently large to allow expansion during heating, while at the same time not so large that transfer of an article being passed from the transport mechanism of one module to the transport mechanism of the next is impeded.

4. Filling and Closure Module

In a still further embodiment of a production module of the present invention, the production module takes the form of a filling module, or a closure module, or a combined filling and closure module, such as the embodiment of such a module described below. The filling module, or closure module, or combined filling and closure module is useful as a component of various embodiments of the modular production system aspect of the present invention.

A. Filling and Closure Housing

A still further embodiment of a module useful in the present modular system takes the form of a combined filling and closure (e.g., capping) module. Similar to the depyrogenator and cooling modules, the combined filling and closure module includes a housing (700) including an interior chamber, an interior transport mechanism section (800) positioned within the interior chamber, and includes an operational assembly, in this case, two operational assemblies, the first acts to meter and fill a container presented by the transport system, and a second, subsequent container closure mechanism, operates to position a closure, such as a cap, on the filled container. It is to be understood that in alternative embodiments of this aspect of the invention, each of the operational functions may be performed in their own separate production module housing. In still further embodiments, more than two functions may be performed in a single modular housing, without departing from the scope of the present invention.

As shown in FIGS. 17-21, the filling and closure functions are combined in a single filling and closure module (5), as an alternative to separate, but joined modules preforming such functions. This is advantageous where for example, a particular filling process is adaptable to a particular closure process. The close proximity of operations reduces the number of module housings in an coupled modular production line, thus offering cost savings in module production.

The filling and closure housing (700) includes a proximal end (701), a distal end (702), a front wall (703), a back wall (704), a top wall (705), and a bottom wall (706). The front, back, top and bottom walls have an exterior surface and an interior surface. The interior surface of these walls encloses an interior cavity (707), which extends from the proximal end (701) to the distal end (702) of the housing.

Like the prior modules described above, the exterior faces of the top, front, bottom and back walls of the housing possess a number of features associated with connecting the housing to other module housings. Circumferential proximal and distal exterior O-ring recess (708) and (709) are formed in the exterior surfaces of the top, front, bottom and back walls at or adjacent to the proximal end and the distal end of the housing (700), respectively. A proximal O-ring (710) is positioned in the proximal O-ring recess (708), and a distal O-ring (711) is positioned in the distal O-ring recess (709).

As described previously, the portion of each of these the O-rings (710) and (711) that faces the filling and closure housing (700) resides within its respective O-ring recess (708) and (709) respectively. The outwardly-facing portion of the O-rings extends above the exterior surface of the top, front, bottom and back walls of the housing. Each end of the housing (700) is adapted to be inserted within the central opening of separate connector sleeves (7) which are slideable over the proximal and distal ends of the filling and closure housing, such that the interior surface of the connector sleeve (7) compresses the out-facing portion of the O-rings, thus forming resilient seal therebetween. Again, as will be appreciated, as an alternative to positioning the O-ring recess and O-ring on the exterior surface of the filling and closure module housing, the O-ring recess could be formed in the interior surface of each connector sleeve (7), and the O-ring positioned therein, and this resilient seal still be achieved.

The exterior proximal and distal ends of the top, front, bottom and back walls of the housing form corners where the top wall and front wall, front wall and bottom wall, bottom wall and back wall, and back wall and top walls meet. Proximal corner slots (712) are formed upon the exterior surface of the housing at these corners on the proximal end of the housing and extend distally therefrom. Distal corner slots (713) upon the exterior surface of the housing at these corners on the distal end of the housing and extend proximally therefrom.

When the proximal and distal ends of housing (700) are inserted into a separate connector sleeves (7), these proximal and distal corner slots (712) and (713), are designed to guide the connector sleeves over the exterior surface of the housing. The corner slots may be of sufficient length to allow the connector sleeve to form a resilient seal with the O-ring(s) (710) and (710) at each end of the housing. As in the descriptions of previous modules, the slots are sized to be roughly the width of the connector sleeve, such that the sleeve may be to slid even further over the end of the filling and closure housing at which it is attaches, such the end of the sleeve facing the adjacent module is retracted to be flush or nearly flush with the given end of the housing over which it is attached, thus facilitating the process of assembling and disassembling the production line by allowing adjacent modules to be lowered or raised without interference from the retracted connector sleeve.

A proximal mounting bracket (714) and distal mounting bracket (715), in the region of its proximal and distal ends, on housing (700) may be employed in the connection of the internal article transport system (9) within the interior walls of the module housing, and/or assist in the connection of the module housing to the external drive system (8) and/or base structure (10), as with prior modules.

It should be noted that airflow within a given module and between interconnected modules may be regulated through incorporating wall portions defining mouse holes at the proximal and/or distal end of a given module housing. The presence of wall portion at one end of a module impedes the flow of air therefrom, and encourages airflow in the opposite direction.

FIG. 19. depicts, for descriptive purposes only, a rendering of the module housing (700) with the top (705), bottom (706), front (703) and back (704) walls of the housing (700) shown as transparent, such that the various features of the housing and internal transport system section (800) are visible.

The top wall (705) of the module housing has attached thereto filling housing (716), which is aligned with proximal window (717), and a closure housing (718) toward the distal end of the housing, aligned with distal window (719).

An access port (720) for a component of a closure feed system (13) is formed in the back wall (704) of the module housing.

B. Internal Transport Mechanism of Filling and Closure Module

The filling and closure module internal transport system section (800), is structured very similarly to that described for the internal transport system section (600) of the cooling module (500) above, and is shown, in FIGS. 19-21, 23, 24, Where shown in reference numbering used for the transport section changes only the hundredths digit, i.e., (805) in this section, refers to the feature (605) in the discussion of the cooling module, or (405) in the depyrogenation module above. Components of the transport system drive frame assembly mounted proximally in the housing are indicated with the standard reference number (e.g. 805), whereas components of the transport system drive frame assembly mounted distally are indicated with the prime notation after the reference number (e.g. 805').

With this in mind, the internal transport system section (800) includes a movable support assembly (802), that includes proximal and distal drive frames (801 and 801' respectively) and a moveable article support rail (812), and; a stationary support assembly (803), which, in this embodiment, includes a back rail (820) and the base rail (821).

Toward the proximal end, proximal drive frame (801) includes a wall mounting plate (804), having a front face (818) which is attached to the interior surface of front wall (703) between the proximal end (701) and the proximal window (717) in the filing and closure housing (700). The top surface (819) of the proximal mounting plate connects to a front lower surface of an inwardly directed vertical lamella (805), which attaches at its opposite end to front structural support (806). The front structural support has a proximal and distal side surface, and a first (proximal) horizontal lamella (807) attaches to the proximal side of the front structural support, and a second (distal) horizontal lamella (808) extends from the distal side of the front structural support. The first and second horizontal lamella connect at their far ends to the proximal and distal sides of a proximal rear structural support (809). One or more follower magnet (810) is associated with the rear structural support (809). A proximal connector arm (811) attaches at one end to the proximal rear support, and at the other end is operatively connected to the moveable support rail (812).

Toward the distal end of the housing, the distal drive frame (801') includes a wall mounting plate (804'), having a front face (818') which is attached to the interior surface of front wall (703) between the distal end (702) and the distal window (719) of the filing and closure housing (700). The top surface (819') of the distal mounting plate (804') connects to a front lower surface of an inwardly directed vertical lamella (805'). Vertical lamella (805') attaches at its opposite end to front structural support (806'). The front structural support (806') has a proximal and distal side surface, and a first (proximal) horizontal lamella (807') attaches to the proximal side of the distal front structural support, and a second (distal) horizontal lamella (808') extends from the distal side of the distal front structural support. The first and second horizontal lamella connect at their far ends to the proximal and distal sides, respectively, of a distal rear structural support (809'). One or more follower magnet (810') is associated with the rear structural support (809'). One end of a distal connector arm (811') attaches at to the proximal rear support, and the opposite end is operatively connected to the moveable support rail (812).

As before, vertical lamella (805 and 805'), are thin, plate-like structures, flexible in their thin direction (i.e., up and down), while being relatively stable and immovable in their thicker dimensions (i.e., right and left and forward and backward), hence they are flex up and down, but generally not are inflexible and relatively right and left. Similarly, each of the horizontal lamellas (807, 807', 808 and 808') are thin plate-like structures, flexible in their thin direction (i.e., right and left) while being relatively and immovable in their thicker dimensions (i.e., up and down or forward and backward), hence being flexible right and left, but generally not flexible up and down.

As was described above with the cooling and depyrogenation modules, the motion of the moveable support rail (812) is generated by the proximal and distal drive frames (801 and 801') toward the proximal and distal ends of the housing (700), with the moveable transport rail (812) being suspended freely between its points of connection to the drive frames, extending the length of housing (700) of the module (5). The motion of the rail is due to the exterior of a motive force upon the follower magnets (810/810') by the external drive mechanism.

The moveable support rail (812) is formed as a single piece, akin to that described for the cooling module. The moveable support rail (812), includes a lower arm (813), an upwardly extending back portion (814), forwardly extending lip (815), having a front vertical face (816), with notches or recesses (817) being formed therein.

The internal transport mechanism section (800) within the filling and closure module (700) differs from that describe for the depyrogenation module (300), in that the L-shaped movable support rail (812), the back rail (820), and the base rail (821) are each composed of a single length of rail, which may be of unitary construction. As the stationary and movable supports, may be comprised of a suitable metal or ceramic material, and are designed to absorb thermal expansion.

As seen in FIGS. 19-21 show construction of the base and back supports of the internal transport mechanism (9) different than those previously described for other modules. In this alternative embodiment, the back structural support (820) and base structural support (821) of the stationary support (803), are each T-shaped. The T-shaped rail has a cross-bar portion (which would form the top of a T) having a side (the lower side of the top portion of the T) from which extends a medial extension (the elongate base of the T-shape). The T-shaped rail, when turned on its side, presented a downward facing section of the cross-bar portion. This downward facing section fits into a slot formed in proximal and distal arm brackets.

In this embodiment, the stationary support back rail (820) of the stationary support assembly is connected to interior wall of the back wall (704) by a proximal arm bracket (822) and a distal arm bracket (822'). The stationary support base rail (821) of the stationary support assembly is connected to interior wall of the front wall (703) by a proximal arm bracket (823) and a distal arm bracket (823').

The stationary back rail (820) thus includes a cross-bar portion (824) having a side (825) from which extends a medial extension (826). The T-shaped rail, when turned on its side, presented a downward facing section (827) of the cross-bar portion. This downward facing section (827) such that the medial extension extends toward the front wall (703) of the housing, fits into slots (828) and (828')) formed in the proximal and distal back rail arm brackets (822) and (822') respectively. The end of the medial extension (826) opposite to where it connects to the cross-bar portion (824) forms contact face (829), having formed therein a plurality of spaced recesses (830). This contact face (829) and the notches (830) formed therein operate to support and separate vials (V) being transported through the housing.

The stationary base rail (821) includes a cross-bar portion (831) having a side (832) from which extends a medial extension (833). The T-shaped rail, when turned on its side such that the medial extension extends toward the back wall (704) of the module housing, presents a downward facing section (834) of the cross-bar portion. This downward facing section (834) may fit into slots (835) and (835')) formed in proximal and distal base rail arm brackets (823) and (823') respectively. Or the slot may be in the rail, not the support, and the rail is supported as usual. The upwardly facing side (836) of the medial extension (833) forms an article support surface which supports articles when positioned upon the stationary base support rail during transport of articles through the module housing.

The base and/or back supports may be configured such that the base arm brackets (823/823') and back arm brackets (822/822') have slots ((828/828') and (835/835'), respectively, formed therein. So configured, the downward facing sections of the cross-bars of the base and back rails configured to merely slip into the slots of these bracket arms. The slots may be designed to permit for example, thermal expansion, or to ease assembly disassembly of the module, and other advantageous properties, as discussed below.

In this alternative form, the base rail arm brackets 823 and 823', each include a front face (837/837') which is fixedly abutted to the interior front surface of the housing module front wall, as described for previous modules. The top surface (838/838') has region having an angled face (839/839'), with slots (835/835') being formed therein. The slots may be configured to extend tangentially into the angled surface of the bracket arm.

This configuration of the base rail and the connector arm provides one or more potential advantages: (1) the configuration makes assembly and disassembly of the module more convenient, as there is no longer a need to use additional fasteners to attach the base support rail to its bracket arms, as connection is achieved by inserting the downwardly facing section of the T-shaped base rail into the slot formed in the arm bracket, whereas disassembly merely requires by lifting the rail out of the slot; (2) the slot and portion of the rail positioned therein can be formed with dimensions allowing some space therebetween, thus accommodating thermally induced materials expansion that might be experienced in use of the production system. Moreover a "slippery" material, such as ceramic, may be positioned between the two surfaces to facilitate such slippage.

In these various configurations, the rails can be lifted out (one pin fits perfectly, the other is loose longitudinally (groove) to be able to release thermal expansion), gravity keep the rail in. Ceramic may always be used as slippery material between the rail and the support.

As was mentioned with reference to prior modules, the ends of the stationary and moveable support rails of the filling and closure module are of a length which terminates at or near the proximal and distal ends of the housing. The termination points of these rails may be designed to provide a small gap between the ends of the stationary and moveable support rails of this module with the ends of the stationary and moveable support rails of the modules to be attached proximally or distally thereto. Again, this gap is designed to accommodate any thermal expansion or contraction that may be experienced by the stationary and moveable support rails during operation. As will appreciated, the gap should be sufficiently large to allow expansion during heating, while at the same time not so large that transfer of an article being passed from the transport mechanism of one module to the transport mechanism of the next is impeded. The distance of this gap may be determined by the relative lengths of the stationary and moveable support rails in adjacent modules, or by the spacing between adjacent modules which is provided by a component, such as a spacer, on the internal surface of a connector sleeve, or by a gasket positioned in such connector sleeve between two connected modules.

C. Operational Assembly

1) Filling Mechanism

A filling mechanism (721) of the module (5) includes filling housing (716) sealingly attached onto the exterior surface of the top wall (705) of the filling and closure module housing (700). As seen in FIGS. 18, 20-22, the filling housing (716) housing, having a top wall (724), bottom wall (728), front wall (723), back wall (725), proximal side wall (726) and distal side wall (727), wherein the walls each have internal and external surfaces, and together their internal surfaces define a main internal cavity (722).

An access passage (729) extends through the bottom wall (728) of the filling housing (716) and the top wall (705) of the module housing (700), providing a fluid communication path between the internal cavity (722) of the filling housing (716) and the internal cavity (707) of module housing (700).

In the upper portion of the back wall (725) of the filling housing (716) is positioned filling needle connector (730). The filling needle connector (730) has an upper connector surface (731) from which extends an angled filling needle channel (732). The angled filling needle channel (732) is a conduit which extends from the upper connector surface, through the filling needle connector and into a recess (733) formed in the back wall of the filling housing. The needle channel transitions between an upper larger diameter section (734) and a lower small diameter section (735) at a constriction seat (736).

As depicted in FIGS. 20 and 21, the front wall (703) of the filling housing defines a bellows receiving port (737), in which is positioned a retractable bellows (738). Toward the front end of the bellows, the sides (739) of the retractable bellows engage the interior walls (740) of the bellows receiving port and a front flange (743) on the bellows is presses against the exterior surface of the front wall of the filling housing, thus sealing the interior cavity of the filling housing from the environment exterior to the filling housing, precluding microbial and atmospheric transfer into the filling hosing cavity. As will be appreciated, a seal for this connection may also incorporate a common gasket or O-ring.

The bellows back end (741) provides one or more O-ring(s) presented on the back end of the annular exterior of bellows, forming a compression surface (742). These O-rings are generally heat tolerant and able to withstand exposure to high heat which may be employed to sterilize the housing when initially readying it for use.

The bellows are preferably a durable, high heat tolerant material, such as, but not limited to stainless steel, with the O-rings on the compression surface (742) being also high heat tolerant and resilient, both being able to withstand high temperature exposure that may be employed during initial sterilization of the module prior to use in production.

The bellows (738) may be extended or retracted, with the accordion like side region of the bellows lengthening without breaching the seal at the font region of the bellows where it interacts with the front wall of the filling housing to create an environmental seal therebetween. In an extended state, the bellows compression surface (742) covers the opening to the recess (733) in the interior back wall of the filling housing. In this extended state, the compression surface (742) is compressed against the interior surface of the back wall (725) of the filling housing, creating a seal between the internal cavity (722) and the recess (733). The heat tolerant O-ring(s) extending around the annular exterior of the compression face of the bellows assist in providing a seal between the interior back wall of the filling housing and the face bellows, thus separating the interior of the filling housing from the recess in the back wall of the filling housing.

In a retracted state, the bellows compression surface (744) is spaced away from the interior surface of the back wall, and the recess and filling housing cavity are open and in fluid communication with each other. In the retracted state, a filling needle may descend through the angled needle channel, recess, filling housing cavity, and into the filling and closure module (700) internal cavity (707).

On the opposite side of the filling housing from the bellows port, the lower portion of the back wall (725) of the filling housing defines a forwardly directed breather port channel (744) which extends through the back wall (725) of the filling housing, and converges with the angled needle channel (732) within the recess (733). The breather port channel (744) is defined by a larger diameter region (745), ending at an internal end wall (746), and a smaller diameter region (747). The breather port channel larger diameter region (745) extends into the exterior surface of the back wall and terminates at internal wall (746). The smaller diameter region (747) of the breather port channel extends generally centrally from the internal wall (746) into the recess (733).

A filter plug (748), having a front face (749), exterior side surfaces (750), a back flange portion (751), and a central passageway (752) is positioned in the breather port channel (744), such that a portion of the exterior side surfaces (750)

of the filter plug engage the interior walls of the larger diameter region (745) of the breather port channel, and the front face (749) of the filter plug is compressed against the internal wall (745) of the breather port channel. O-ring(s) (753) extending around the annular exterior of the filter plug assist in providing a seal between the filter plug and the interior walls and internal wall of the breather channel. The front face of the filter plug may comprise a sintered metal filter (breather), or similarly structured filter.

The filling system employed in the filling mechanism of the depicted module may use any suitable filling needle capable of extending through the filling needle connector (730). With a non-customized filling needle assembly, some form of environmental barrier would be required to preclude potential microbial contamination, etc., for example, in the area where the needle is inserted into the needle channel in the upper connector surface (731). Sterilization of the connected components would have to be maintained throughout use.

A specialized needle assembly (900) is described below, which is also considered a separate inventive aspect, which has use in the present filling module.

a) Needle Assembly

As shown, in FIG. 25-27, the customized needle assembly (900), includes a filling needle or filling tube (901) having an elongate external surface (902) and an internal lumen or channel (903) which extends from the top (904) of the needle to the bottom (905). In this customized needle assembly, the filling needle is enclosed within an accordion-like external sheath (906). The sheath extends from the lower end (907) of an assembly head (908) to a connector head (909). The assembly head (908) is connectable to supply of medicament, such as an outlet of a metering pump for a supply of fluid medicament. The connector head (909) includes a mounting surface, a gasket (910) at its lower end that is connectable to the filling needle connector (730) of the filling housing ((716)). An annular ridge (911) on the mounting surface assists in sealing contact of the gasket (910) and the upper connector surface (731) of the filling needle connector (730), such that the needle-receiving bore (912) of the connector head is aligned with the angled filling needle channel (732) of the filling needle connector (730). This is a standard tri-clamp, which is commonly employed in the industry.

A pierceable seal (913), e.g., a stainless steel disc, is positioned within the connector head (909), along of the needle-receiving bore (912). The pierceable seal (913) is positioned below a further gasket (910B), and the further gasket and pierceable seal separate the portion of the needle-receiving bore (912) above the seal from a portion of the needle-receiving bore below. When the filling needle bottom (905) is positioned above the pierceable seal, and the seal is intact, and the opening at the top of the needle assembly (904) is sealed, the portion of the needle surrounded by the sheath is positioned within a completely enclosed space (914). The enclosed space (914) is defined by the bottom of the assembly head (908), the interior surface of the accordion-like sheath, interior surface of the needle-receiving bore (912) above the seal (913), and the upper surface of the seal (913). So configured, the interior of the sleeve and therefor the needle may be sterilized (by gamma irradiation, and the like) and maintained in a sterile condition until ready to use.

Sterility of the needle assembly may be achieved and maintained in any conventional manner. For example, to assure a sterile connection between components, the needle top (904) may be connected to a silicon tube ending in a "single-use set-up".

Preparation of the Filling Module for Use

In preparing to use the filling module, compression surface (742) of the bellows (738) is compressed against the interior surface of the back wall of the filling housing, thus closing access of the recess (733) to the cavity of the filling housing and cavity of the (707) of the module housing (700). The filling and closure module would be internally sterilized as the system is brought on line. An additional sterilization process is undertaken to sterilize the regions of the filling housing not sealed by the compression surface (724) of the extended bellows (738).

In order to assure the sterility of the pathway into the filling housing and housing cavity (707) of the module housing (700), the mounting surface (910) of the connector head of the filling needle assembly is connected to the upper connector surface (731), such that the needle-receiving bore (912) of the connector head (909) is aligned with the filling needle channel (732). So connected, the area of the needle-receiving bore (912) below the pierceable seal (913), and the interior of the recess in the back wall of the filling housing, are isolated the external environment. This enclosed area, which includes the small diameter region (735) is then sterilized (by dry heat, and the like) prior to use. The filling module, in this configuration is shown in FIG. 20.

Once the connected portion of the connector head and filling housing are sterilized, the bellows (738) is retracted in the filling housing (716). Bellows retraction establishes an opening between the recess (733) and the internal cavity (722) into the filling housing. The filling needle may then be extended downward through the needle-receiving bore (912). Downward movement causes the needle to pierce the pierceable seal (913), enter the angled filling needle channel (732) of the filling housing, where the constriction seat (736) accommodates precise alignment of the filling needle through angled filling needle channel (732) and recess (733) in the interior surface of the back wall of the filling housing, and into an operable position in the interior chamber of the filling module housing. The movement of the needle being accommodated by the accordion-like sheath of the needle assembly, while the sterility of the needle is maintained by the barrier properties of the sheath. The filling module, in this configuration is shown in FIG. 19.

In certain embodiments, pierceable seal (913) is composed of stainless steel, aluminium or the like, of sufficient thickness (e.g., 1 to 3 thousandths of an inch thick), allowing it to be heat tolerant and shearable, while avoiding the creation of non-viable particulate matter. When the pierceable seal is pierced, the sheared portion remains attached, keeping the sheared portion from falling into the central cavity of the module. In certain embodiments, seals having both a preferential shear region, and a further region designed to remain intact upon shearing of the preferential shear region, thus precluding the sheared material from entering the production tunnel.

2) Closure Mechanism

As seen in FIGS. 18, 28-30, the closure mechanism (755) of the filling and closure module (5) includes a closure housing (718), which is sealingly attached onto the top (705) of the filling and closure module housing (700) operationally distal to the position of the filling housing (716).

The closure housing (718) includes a front wall (756), a top wall (757), a back wall (758), a proximal side wall (759), and a distal side wall (760) and a substantially open bottom (761). The internal surfaces of these walls front, back, top, proximal side and distal side walls, define an closure housing internal cavity (762). The top wall (705) of the module housing (700) defines an access opening (763) providing access through the open bottom (761) of the closure housing (718), connecting the closure housing internal cavity (762) and the interior cavity (707) of the module housing (700). The bottom (761) surface of the closure housing (718) abuts the exterior surface of the top wall (705) of the filling and closure module housing (700), and is sealingly attached thereto.

The rear of the top wall of the closure housing forms a rearward sloping face (764), in which is formed a plunger port opening (765). The plunger port opening (765) defines the upper end of a plunger channel (766). The lower end of the plunger channel opens into the internal closure housing cavity (762).

A plunger assembly (767) is positioned within the plunger channel (766). The plunger assembly (767) includes a sealing head (768), an accordion outer sleeve (769), and a piston body (770).

The sealing head (768) has an upper face (771) and a lower face (772). The lower face (772) abuts the rearwardly sloping face (764) of the closure housing (718).

The accordion-like outer sleeve (769) includes an upper end (773) and lower end (774) along its side surface. The upper end (773) of the accordion-like outer sleeve extends from the lower face (772) of the sealing head (768). The exterior side surface of the accordion outer sleeve at this upper end Includes an O-ring or gasket, (not shown) which compressively contacts the side surfaces of plunger channel (766) forming an effective seal therebetween.

The lower end (774) of the accordion-like sleeve is attached to the upper end (775) piston body (770). The portion of the piston body extending from the point of contact with the accordion sleeve, extends through the closure housing cavity (762) and into the internal cavity (707) of the housing module (700), forming at its lower end, a piston head (776).

As can be seen in FIG. 26-28, the piston body and piston head (776) are configured to be aligned with a closure holder (777).

Closure holder (777) has an upper portion (778), a side portion (779) and a lower portion (780), which together form a closure reception cavity (781).

The upper portion (778) of closure holder defines a piston entry opening (782), which is sized and positioned to receive the piston head (776). The rear facing side of side portion (779) of the closure holder (777) defines a vial closure reception opening (783).

The vial closure reception opening is adapted to receive vial closures ("VC") fed into the closure holder from the closure feed chute (953) of the closure feed (13) (discussed in detail below), when the closure feed is connected to the filling and closure module (5). A feed chute port (786) is formed in the back wall (704) of the module housing, through which the closure feed chute (953) passes, permitting the dispensing end of the closure feed chute to be aligned with the vial closure reception opening (783).

The lower portion (780) of closure holder (777) defines a closure ejection opening (784). The piston entry opening (782), the vial closure reception opening (783), and closure ejection opening (784) leads into or from the closure reception cavity (781).

The vial closures ("VC") shown in FIGS. 29-30 are standard vial closures and generally comprise a resilient material, for example, an elastomer or rubber, which are sufficiently heat tolerant to withstand sterilization while being resilient to withstand compression fitting in to vials to achieve a suitable seal for the vial. The vial closures are configured to a larger diameter top portion, having an underside from which extends a smaller diameter lower body portion. The top and lower portions of the vial closures are annular.

When the vial closures are received by the vial closure holder (777) from a component of the closure feed (13) which extends into the internal cavity (707) of the module housing (700) though the access port (720), the vial closures pass through vial closure reception opening (783) and pass into the closure reception cavity (781), as depicted in FIG. 28.

Vial closures are fed from the component of closure feed (13) oriented with the larger diameter top of the vial closure facing up, and the smaller diameter lower body portion facing down. When the vial closure is passed into the closure reception cavity (781), the smaller diameter lower body portion of the vial closure is transferred through the closure ejection opening (784), such that the underside of larger diameter top portion of the vial closure rests on "floor" (785) of the closure reception cavity (781), thus holding the vial closure within (VC) closure reception cavity.

The closure plunger assembly (768) operates by moving from a retracted position, shown in FIG. 28, to an extending position shown in FIG. 29, before returning to the retracted position, as shown in FIG. 30.

In the orientation shown in FIG. 28, the vial closure (VC) is positioned in the closure reception cavity (781) of the closure holder (777), such that the closure's top surface is aligned with the piston entry opening (782), and the lower portion of the vial closure is positioning in closure ejection opening (784). In this position, the lower end of the smaller diameter lower body portion of the vial closure is positioned directly over the open mouth of a vial ("V") which has been moved into position beneath the closure holder. The accordion sheath of the closure plunger assembly (768) is in a retracted state, and the piston head is positioned in the piston head opening (782), just above the top of the vial closure.

Activation of the closure plunger assembly (768) causes the piston body to be extended downward, with the accordion sheath extending to accommodate this motion. Downward motion of the piston body drives the piston head (776) through the piston head opening (782), the closure reception cavity (781) and closure ejection opening (784) of the closure holder (777), toward the open vial positioned therebelow. By this action, the lower surface of the closure top is pushed through closure ejection opening (784) and downward onto the open end of the vial. The piston motion causes the lower body portion of the vial closure to be pushed through the mouth of the vial into the neck of the vial, where compression of the sides of the vial closure lower body portion against the interior side surfaces of the neck of the vial, and the compression of the underside of the vial closure upper body portion against the upper surface of the vial, sealing the vial with the vial closure, as shown in FIG. 29.

Retraction of the piston head (776) to its starting position such that piston head (776) resides within the piston entry opening (782), resets the closure mechanism to its starting position, as shown in FIG. 30. From this returned position, the closure holder (777) is emptied and ready to receive the next vial closure from the closure feed (13). The now sealed vial is ready to be moved distally along the production line by the internal transport mechanism, while the next proximally located filled but unsealed vial is moved into the closure station oriented below the closure plunger assembly.

Filed and sealed vials are transported distally from the closure mechanism, and through the distal end of the filling and capping module, to the next desired module in the modular production system.

The distal end of the filling and capping module is connected, as described previously, via a connector sleeve (7) to the next desired module. In the depicted embodiment of the modular production system of FIG. 1, the next module comprises an outfeed module.

The Closure Feed System

The closure feed system (13) and various components thereof or usable therewith are depicted in FIGS. 31-41. The purpose of the closure feed system (13) is to present individual vial closures in an appropriate orientation the closure holder (777) and the stoppering plunger. The closure feed system (13) is positionable upon a simple pedestal base (not shown), which is positioned behind the closure module housing (700), so as to align the components with the closure feed system with the closure mechanism (755).

As depicted in FIG. 31, in this embodiment the closure feed system, the closure feed system (13) comprises a closure feed housing (950) having a front wall from which extends a feed chute enclosure (951), and a top wall which is connected to a closure transfer housing (952), as well as bottom, back and proximal and distal side walls, which form a sealed housing. The transfer housing is connectable to a container (953), in this depiction a bag, of sterilized vial closures.

A feed chute channel (954), defined by the walls of the feed chute enclosure (951), is configured to allow communication between the interior of the closer feed housing and the interior of the closure module housing (700). The feed chute enclosure has an open front end (955), from which protrudes the closure feed chute (956). The feed chute enclosure is connectable to the closure module housing (700) in a sealed fashion at this open front end, thus allowing the closure feed chute (956) to be aligned with the closure holder (777), as depicted in FIGS. 28-30.

The closure feed housing (950) houses a number of components of the are shown in FIGS. 32-33. The top of the closure feed housing contains a quartz window (957) which allows the interior cavity (958) of the housing to be viewed. In the depicted exemplar embodiment, a vibrating sorting bowl (959), is positioned within interior cavity (958), upon a base (960) which is connected to the floor of the closure feed housing by a number of flexible legs (961) via connector footings (962). Base (960) is positioned upon an armature (963), which sits upon an encapsulation housing (964), containing an oscillating electromagnet (965). A small air gap is provided between the magnet and the armature.

The bowl, the base and the armature (963) are all oscillating, while the remaining portion of the feed remain stationary. The oscillation is given to the armature (ferromagnetic material) by the oscillating electromagnet, which is basically a magnet that generates an oscillating magnetic field. This magnetic field makes the armature to oscillate, and this makes the bowl to oscillates. The specific structure of the leg creates a special pattern of oscillation that orient the closure and pushes them towards the plunger. The air gap keeps a distance between oscillating and stationary parts.

The materials selected for the components of the feed housing are suitably able to withstand high temperatures (e.g., 180° C.-200° C.) associated with sterilization of the system. For example, such components are composed of stainless steel, including the flexible legs (961). The flexible legs may, for example comprise a thin lamellar material (e.g., stainless steel), set at an angle between the bottom (floor) of the closure feed housing and the base (960), thus supporting the bowl while permitting the bowl to be vibrated. Alternatively, the flexible legs could be connected to the bottom (floor) of the closure feed housing and the base (960) by commercially available flexural bearings (e.g., C-flex). The encapsulation housing (964), would also be composed of a heat-tolerant material, for example, stainless steel.

Thermal damage to the electromagnet is preferably avoided. The electromagnet can be provided with insulation up to 250° C., but the encapsulation potentially offers the benefit of being able to use less expensive and more readily available electromagnetic materials.

The encapsulation housing acts as a barrier between the interior of the closure feed housing (958) and the interior of the encapsulation housing containing the oscillating electromagnet (965). As the oscillating electromagnet (965) generates heat during operation, ventilation holes (966 and 967) are positioned in and extend through the bottom of the closure feed housing allowing the circulation of cooling fluid (e.g., gas or liquid) through the encapsulation housing interior, as well as to provide an access conduit for any wiring.

As shown in FIG. 33, the closure transfer housing (952), has an input conduit (968) at its upper end, defining a channel. At its upper end, the input conduit defines standard tri-clamp connector/ferrule, having an open mouth (969) having an annular lip (970) extending around its exterior circumference. The lower end of the input conduit opens into a plug chamber (971). At the upper end of plug chamber (971) is formed a sealing face (972) and at the lower end of the plug chamber is a lower wall (973). Between the lower wall and the sealing face is positioned a retractable plug (974). The retractable plug includes a plug face (975) having an O-ring (976) positioned in a recess (977) formed in the plug face. The O-ring is configured and positioned such that when the plug is extended, the plug face O-ring is pressed against the sealing face at the upper end of the plug chamber, thus creating an effective barrier between the plug chamber and the input conduit. This barrier allows the interior of the closure feed housing to be sterilized as its separated the interior of the closure feed housing from the exterior environment, very similar as to that discussed previously with regard to the filling housing. A stainless steel bellows (978) surrounding a shaft (not shown) allows for the movement of the plug within the plug chamber while maintaining the integrity of the environment therein. Due to the material choice the closure feed housing, can withstand high temperatures (200° C.), thus allowing heat sterilization.

As shown in FIG. 34, The plug may be retracted such that the plug face is moved away from the sealing face of the plug chamber, and an access passage is opened through this portion of the plug chamber between the input conduit (968) and a lower access conduit (979) which opens into the interior of the closure feed housing above the vibrating sorting bowl (959).

Bulk quantities closures, such as vial closures, are fed into the open mouth (969) of input conduit (968) of the closure transfer housing (952).

It is an additional aspect of the present invention, to provide containers (953) which are sterilisable, and connectable to the annular lip (970) extending around of the open mouth (969) of the closure transfer housing (952). A first embodiment of such a container (953) is depicted in FIG. 35.

In this embodiment, the container (953) includes an exit conduit (980) having an outwardly flaring lip portion (981) which extends away from the exit conduit. A sealing disc (982) is affixed over the conduit lip in a sealed fashion. The container defines an interior (983), which contains a plurality of closures (VC).

The sealing disc (982) may be constructed of any heat tolerant material, capable of withstanding the sterilization process, but which is pressure shearable, such as a metal (e.g., stainless steel, aluminium, etc.). The container itself and the exit conduit, including the backside of the lip which is adhered to the sealing disc (982) may be composed of a suitable plastic material used for sterilizable bags (e.g., Tyvek™, etc . . . ). The lid and the disc will experience the sterilization temperature when connected, and thus should be heat resistant ((e.g. stainless steel or equivalent.)

This container type provides an alternative to commercially containers, such as those employing a DPTE® (Getinge AB, Sweden), Rapid Transfer Port System (RABS), used for transfer of aseptic or toxic products in isolators or RABS systems. The DPTE® transfer system enables the user to introduce material into, or to extract material from a closed barrier, or to connect two devices with identical environments (e.g. isolators) without affecting their ambient characteristics. The DPTE® system is based on the interaction of two separate units—"Alpha" and "Beta"—each fitted with a door, a lock and a sealing function. The Alpha unit is mounted on a support (e.g. an isolator surface), while the Beta unit is movable and seals off a container, a transfer isolator or any other suitable device. In the depicted embodiment, the Alpha door would be mounted on the box surrounding the bowl, and would be adapted to stand high temperatures. Examples of Alpha ports able to sustain pressure and temperature are known to those of ordinary skill, as for example in U.S. Pat. No. 6,537,509. The Alpha door would be sterilized with the modular production system, but after sterilization, the connection can happen at room temperature as commonly done. This allows the use common Beta doors available on the market.

In an alternative configuration, the vibrating bowl could be sterilized with dry heat alone leaving the electromagnet and the springs at ambient temperature by enclosing the bowl only and providing a seal with a very flexible silicone sleeve to the box, so to allow vibrations and at the same time taking the heat of sterilization when needed. The silicon seal prevents the spring/electromagnet from releasing particles into the critical zones, advantageously, it may also be used at high temperatures.

In contrast to the complex DPTE® closure system, the container configuration shown in FIG. 35 employs a simple sealing disc which acts as a closure. The container of the present invention may be filled with vial closures, sealed with the sealing plug, and sterilized. An additional cover can be provided to protect the sealing disc from damage during transport or handling, and it can be removed just prior to connecting.

FIG. 36 depicts the connection of the pre-sterilized container (953) to the input conduit (968). The sealing disc (982) of the container is compressed against the lip (970) of the input conduit, and held in position by any suitable means, e.g., a clamp and gasket (not shown). In this configuration, the sealing disc (982) of the pre-sterilized container seals the open mouth (969) of the input conduit.

At the input conduit's lower end, the plug face (975) of the plug (974), in its extended orientation, engages the sealing face (972) of the plug chamber (971). The interior of the closure feed housing is thus isolated, and sealed from the external environment, and it too would have undergone a sterilization process prior to connection of the container.

It will be appreciated that the interior of the input conduit sealed between the sealing disc and the plug face is isolated external environment. This isolated region can now be sterilized using for example, dry heat delivered in many ways, such as of infra-red (IR) irradiation through a small quartz window (not shown) in the input conduit, which advantageously starts from the inside, or an outside surface heater, or the like.

Heat in the input conduit (968) will be dissipated to the adjacent regions, such as the plug chamber (971) and connected container (953) and cooling can be enhanced with forced air. Low thermal conductivity gaskets may also be employed between adjacent components to act as heat barriers.

Pressure build up during heating within the input conduit is relieved by a sintered metal filter (984) positioned in a filter port (985) in the side of the input conduit. The sintered metal filter (984) may be held in the port by any suitable means, for example by use of sealing O-rings, but could also be welded in place for increased safety.

When the input conduit interior has gone through the sterilization process, and its interior is sterile, the application of pressure on the top of the container bag will break the shearable sealing disc (982), thus allowing the vial closures to be deposited into the input conduit.

Retraction of the plug allows the vial closures to pass from the input conduit to the bowl in the closure feed housing. The plug can be used to deliver the stoppers and the proper rate, avoiding jamming the bowl.

A second alternative embodiment of a closure container is depicted in FIG. 37-40B. In this alternative embodiment, the closure container is formed as a drum (984), defining an interior chamber (989).

The drum forms a multi-component exit conduit, which in the embodiment shown has a lower conduit portion (985) a valve housing portion (986) and an upper conduit portion (987).

The lower exit conduit (985), includes an upper lip portion (985A). On top of upper lip portion (985A) is positioned a gasket (985B). The gasket (985B) is sealingly positioned between the upper lip portion 985A and the lower lip portion (986A) of a valve body (986) in a typical triclamp fashion.

The valve body houses a butterfly valve (990). The butterfly valve is rotatably positioned within the exit conduit, and is rotatable about an axis extending through an axle (991). The axle is held at one end by a closed axle bracket (992) and its other end by an open axle bracket (993). A portion of the axle extends from the open end (994) of the open axle bracket to allow the butterfly valve to be rotated. The interface between the open axle bracket and the axle is maintained in a sealed fashion, for example by an O-ring (995), or other suitable means, to maintain the environmental integrity of the interior chamber of the drum when the sealing disc is in place.

The end of the valve body opposite the lower lip portion (986A) forms an upper lip portion (986B). On top of upper lip portion (986B) is sealingly positioned a further gasket (986C). Gasket (986C) is sealingly connected to the underside of a sealing disc (988). An annular portion of the upper side of the sealing disc (988) abuts the lower lip portion (987A) of the upper exit conduit body (987). The central portion of the sealing disc seals the channel extending through the exit conduit. The upper end of the upper exit conduit body (987) includes an upper lip portion (987B) which is sealingly connected to a further gasket (987C).

In this manner, the sealing disc (988) is positioned along the exit conduit of the drum, and and acts to seal the interior chamber (989) of the drum from the external environment. Like the container in the first embodiment, the sealing disc (988) may be constructed of a heat tolerant and shearable material, such as a metal (e.g., stainless steel, etc.).

To facilitate sterilization of the drum, and preclude prematurely shearing the sealing disc, during the heating and/or steam sterilization process), as a result of a steam pressure build up in the drum, a protective cap (987D) is insertable in the central opening of the upper exit conduit portion, as depicted in FIGS. 40A and 40B. During sterilization, the drum can be conveniently be held with the connector facing upward, and can then be inverted with the connector facing downward just before connecting it to the machine. The sterilization of the drum is generally achieved by saturated steam, which is generally conducted at temperature such as 121° C. at 2 bar for 15 min, followed by condensate removal and cooling, similar to the processes used for commercially available drum type containers, such as from Hanag, Getinge.

The protective cap (987D) is maintained in the upper exit conduit portion until after the sterilization is complete, and is removed prior to attachment to the open mouth (969) of the input conduit. Once the protective cap is removed, the gasket (987C) on the upper lip portion (987B) of the upper exit conduit portion of the drum may be positioned upon the annular lip (970) of the input conduit (968).

Following such positioning and sealing connection between the drum exit conduit and the annular lip (970) of the input conduit, the region between the sealing disc (988) and the plug face (975) of the retractable plug (974) may once more undergo a sterilization process. Once completed, the passage from the drum interior to the interior cavity (958) of the closure feed housing (950) is completely sterile.

The butterfly valve may then be rotated in exit conduit, whereby it contacts and shears the sealing disc (988). Specifically, rotation of the butterfly valve (990) about the axis of the axel (991) causes the butterfly valve to contact the sealing disc (988) and continued rotation of the butterfly valve ultimately shears the shearable disc. By opening the conduit from the drum to the closure feed input conduit, allowing the closures to pass to the bowl (959).

The connection of the drum containing bulk vial closures (or other articles) to the input conduit (968), as shown for example in FIG. 37, occurs as previously described for the container bag above. Heat sterilization of the isolated input conduit, is as described above for the first configuration of the container (bag). Advantageously, the butterfly valve keeps kept the vial closures away from the heat during sterilization of the isolated of the input conduit. It also keeps the closures away from the disc when the tank is turned upside down and connected.

Once the input conduit is sterilized, and the butterfly valve rotated to breach the sealing disc(s), and the retractable plug (974) is retracted, vial closures or other desired articles from the container drum may flow into the vibrating sorting bowl of the bowl of the closure feed. The butterfly valve or the retractable plug may also be used to regulate the flow of vial closures from the drum.

Vial closures are tumbled with in the vibrating sorting bowl, and appropriately aligned vial closures are passed into the closure feed chute, where they are passed into the closure module and fed to the closure mechanism as previously described. This feed system employed by the feed chute is of a standard variety, and would be readily employable by those of ordinary skill.

Vibration in the bowl is high enough that the functioning of the bowl undesirably generates particulate matter within the closure feed system (13). For this reason, the bowl is separated, and the connection to the closure module is through a sealed channel through the feed chute enclosure (951). As depicted in FIG. 41, air flow is directed from the closure module (5) through the feed chute enclosure (951), as depicted by reference arrow (AA). Air flow out of the closure feed housing is via appropriately sized sintered metal filters positioned in the input conduit, depicted by reference arrows (AB), and in the back wall of the closure feed housing (998), as depicted by reference arrows (AC), to keep any particulate matter created by the vibrating bowl within the closure feed housing (950). While the closure feed is constructed to minimize the risk of particulate material entering the closure module housing, any small amounts of particulate material which might potential flow from the closure feed into the central cavity of the closure module would be swept up in the distally venting gas flow, shown as arrow "P" and directed distally out of the module to the next distal module. This directional flow thus precludes potential particulate contamination of any open vials within the closure module.

5. Outfeed Module

A. Outfeed Housing

A further embodiment of module useful in the modular production system takes the form of an outfeed module (6). An embodiment of the outfeed module is depicted with reference to FIGS. 42 and 43.

The outfeed module (6) includes an outfeed housing (1000) providing an interior chamber, an internal transport mechanism positioned (1100) within the chamber. The housing's operational purpose relates to air flow control and facilitating article offloading.

In the depicted embodiment, the outfeed module (6) includes an outfeed housing (1000) having a top wall (1001), a bottom wall (1002), a front wall (1003), a back wall (1004), an open proximal side (1005) and a distal wall (1006). Each of top wall (1001), a bottom wall (1002), front wall (1003), back wall (1004), and distal wall (1006) include an interior and exterior surface. The interior surfaces of top, bottom, front, back, and distal walls define an outfeed housing interior cavity (1007).

The top wall (1001) of the outfeed housing (1000) has an access port (1008) defined therein, providing access to the outfeed housing interior cavity (1007) through the top wall (1001).

Attached to the exterior top wall (1001) of the outfeed housing (1000) over the access port (1008) is a filter housing (1009). The filter housing (1009) includes a top wall (1010), an open bottom (1011), a front wall (1012), a back wall (1013), a proximal side wall (1014) and a distal side wall (1015). Each of these walls include an interior and exterior surface. The interior surfaces of the top, front, back, proximal side and distal side walls of the filter housing define a filter housing cavity (1016). A ventilation port (1017) is formed through the back wall (1013) of filter housing (1009), which provides access into the filter housing cavity (1016), and via access port (1008) defined in the top wall of the outfeed housing, into the outfeed housing interior cavity (1007). A filter (1019) is positioned to cover access port (1008), thus separating the filter housing cavity (1016) and the outfeed housing interior cavity (1007).

The proximal side wall (1005) of the outfeed housing (1000) defines an article access opening (1018), which is formed as a "mouse hole," that is shaped, sized and positioned to correspond to articles to be processes within the module. In the instance of the present aseptic filling system embodiment of the modular production stem, the article access opening/mouse hole corresponds to the silhouette of a vial "V".

The bottom wall (1002) of the outfeed housing defines a number of elongate lateral vents (1020) that extend through the bottom wall of the outfeed housing, and form a egress channel from the outfeed housing interior cavity (1007) to below the outfeed housing.

The distal end (1006) of the outfeed housing is open, and the exterior surface of the top, front, bottom and back walls of the outfeed housing defines a number of features involved in the connectability of the distal end of the outfeed housing to the proximal end of the next module in the production line. These features include lateral elongate corner slots (1021) in selected or each of the corners where adjacent wall meets. The corner slots (1021) extend from the distal face of the outfeed housing and continue proximally therefrom within the exterior surface of the outfeed housing.

The exterior faces of the top, front, bottom and back walls of the outfeed housing, at the distal end of the outfeed housing, also have formed therein an annular O-ring recess (1022), which extends circumferentially around the outfeed housing adjacent its distal end (1006).

An O-ring (1023) is positioned in this O-ring recess, such that the portion of the O-ring that faces the outfeed housing interior cavity (1007) resides within the O-ring recess (1022), and an out-facing portion of the O-ring extends above the exterior surface of the top, front, bottom and back walls of the outfeed housing. This open distal end of the outfeed housing is adapted to be inserted within the central opening of a connector sleeve (7). As will be discussed in greater detail below, the connector sleeve is slideable over the distal end of the outfeed housing, such that the interior surface of the connector sleeve (7) compresses the out-facing portion of the O-ring (1022), thus forming a resilient seal therebetween. As will be appreciated, as an alternative to positioning the O-ring recess and O-ring on the exterior surface of the outfeed housing, the O-ring recess could be formed in the interior surface of the connector sleeve (7), and the O-ring positioned therein, and this resilient seal still be achieved.

The sleeve's interior corners are guided by the corner slots (1020) over the exterior distal end portions of the top, front, bottom and back walls of the outfeed housing. The corner slots (1020) may be of sufficient length to allow the connector sleeve to form such a resilient seal with the O-ring on the outfeed housing. In the embodiment shown, the slots are sized to be roughly the width of the connector sleeve, such that the sleeve may be to slid in a proximally direction over the end of the housing, thus facilitating the process of assembling and disassembling the production line.

The external surface of the front wall (1003) of the outfeed housing has attached thereto, or associated therewith, a mounting bracket (1024), which may be employed in the connection of the internal article transport system (9) within the outfeed housing, and/or assist in the connection of the outfeed housing to the external drive system (8) and or base structure (10).

B. Internal Transport Mechanism: Outfeed Module

The features on the internal support system of the outfeed module are identical to those of the infeed module, although connected at slightly different points. Like terms are used to name like features.

As shown in FIG. 43, open proximal side (1005) is the point of entry for articles being individually received into the outfeed housing interior. To receive and move such articles, the outfeed module (6) includes an internal transport mechanism section (1100). In the outfeed module shown, the internal transport mechanism section includes a movable support assembly (1102) having a drive frame (1101), connected to movable support rail (1112); and a stationary support assembly (1103). The drive frame has a number of connected parts. Where these parts are fixedly connected, the connections are made by threaded fasteners, pins, welds, or other suitable means.

In this embodiment, the drive frame (1101) includes a wall mounting plate (1104), having a front face (1118) which contacts the interior of the front wall (1103) of the outfeed housing (1000). This connection to the interior front wall of the outfeed housing is made either directly to the front wall of the housing via a suitable fastening mechanism, or the wall mounting plate is held in position by connection to the outfeed mounting bracket (1024) by bolts, or other suitable fastener, extending through the outfeed housing wall.

The top surface (1119) of the wall mounting plate (1104) forms the mounting surface for the front end portion of a vertical lamella (1105), which is attached thereto. In this embodiment, the vertical lamella (1105) is in the form of a thin, elongate plate having a top, bottom, and four sides (a proximal side, distal side, front and back) and is designed to be flexible in its thin, top-to-bottom dimension, allowing the vertical lamella to flex up and down. The sides of the lamella are, due to their thicker side-to-side and front to back dimensions relatively rigid and immovable when force is exerted in a proximal-distal or front-back direction.

The vertical lamella (1105) extends rearwardly from the wall mounting plate (1104), and is fixedly attached at its opposite end (in its rear-end portion) to an upwardly facing surface of a front structural support (1106).

The front structural support (1106) includes a proximal side surface and a distal side surface. The proximal side surface of the front structural support (1106) is fixedly connected to the front end portion of a first horizontal lamella (1107). The distal side surface of the front structural support (206) is fixedly connected to the front end portion of a second horizontal lamella (1108).

Each of these horizontal lamella (1107 and 1108) are, in this embodiment, in the form of a thin plate. Each elongate plate has a top, a bottom, a proximal side, a distal side and a front side and a back side. These plates too are designed to be flexible but in their thin proximal-side to distal-side dimension, allowing flexion directionally right and left. The horizontal lamella has thicker dimensions' top to bottom and front to back and are more ridged and stable in response to forces exerted in their thicker top-to-bottom, and front to-back dimensions, thus limiting up and down or forward and backward motion in these components.

The horizontal lamella (1107 and 1108) extend rearwardly from the sides front structural support, and at their rear end portions (opposite their front ends) are connected to opposing side surfaces of a rear structural support (209). Specifically, the rear end portion of the first/proximal horizontal lamella (1107) is fixedly connected to the proximal side face of the rear structural support (1109). The rear end portion of the second/distal horizontal lamella (1108) is fixedly connected to the distal side face of the rear structural support (209). The rear structural support (1109) is generally rectangular, having a proximal side, a distal side, a top, a bottom, a front and a back. The rear structural support is elongate in the proximal to distal direction, and is dimensionally smaller front to back, and top to bottom, relative to its length.

The rear structural support (1109) is made up of, contains, or is connected to one or more follower magnets (not shown).

In the depicted embodiment, the rear structural support (1109) is attached, on its front side, to one end of a connector arm (1111), which extends upwardly and forwardly therefrom. The end of the connector arm (1111) opposite this first end, forms a second end, which is adapted to be connected to movable support rail (1112). The connection between the connector arm and the rear structural support (1109) and the movable support rail (1112) may be fixed (through threaded connection or by weld. In some instances, though, the connection between the connector arm and the movable support rail (1112), may be less fixed, as by a pin or other extension projecting from one of the second end of the arm or the movable support rail, which occupies a hole, groove or recess formed in the other interfacing component.

The moveable support rail (1112) is L-shaped in cross-section, and elongate in a proximal to distal dimension. The L-shaped rail includes a forwardly extending lower portion (1113), having a front end and a back end. An upwardly extending back portion (1114) rises from the back end of the lower portion (1113). At the top of the upwardly extending back portion is a forwardly extending lip (1115). The lip (1115) of the L-shaped rail is shorter in length than the lower arm (1113), and has a front face (1116) in which are formed, at regular intervals, a plurality of notches or recesses (1117). The top surface of the lower portion, the front surface of the upwardly extending back portion, and the front face of the lip of the L-shaped rail (1112) form an article support surface of the moveable support rail. The moveable support rail forms the platform for articles (V) introduced into the outfeed housing internal cavity through the open proximal end moving them distally, out of the outfeed module.

The mobility of the moveable support rail (1112) is achieved through the follower magnet(s) (not shown) imparting a motive force on the rear support structure, moving the rear support structure relative to the wall mounting plate (1104). The follower magnet(s) are designed to track the motion of a corresponding drive magnet positioned in the external drive system (8), which will be discussed in greater detail later herein. As will be appreciated, the drive frame is solidly connected to the interior front wall of the housing and is immovable. The rear structural support (1109), containing the follower magnets (1110), is freely suspended within the outfeed housing interior cavity (1007). The structurally fixed flexible vertical lamella (1105) is flexible up and down to accommodate upward and downward motion of the rear structural support. The horizontal lamella (1107 and 1108) are flexible horizontally, in the proximal and distal directions, to accommodate proximal and distal motion of the rear structural support. This motion allows the moveable support rail to be raised, to lift an article placed there on upwardly, moved distally a given horizontal distance in the housing, to move the article thereon distally for this horizontal distance, and lowered, setting the article on the stationary support assembly, thus moving the article a distance along the stationary support. The moveable support rail support surface then descends further below the support rail, such that the article is no longer supported by the moveable article support. While the movable rail is below the base support rail support surface, it is moved proximally by movement of the drive follower magnets, then it ascends to be flush with the base support rail support surface, initiate the lift, move and place process over again. Repeating this cycle sequentially allows the article to be moved through the system. This movement is described in further detail in relation to the discussion of FIGS. 48A-48C, 49A-49C, 50A-50I below.

An advantage of the vertical lamella being attached to the drive frame at the front of the drive frame is that the point of flexion is at a distance from the rear support structure. Because of this, a relatively large distance of travel in the rear support structure is accommodated by a relatively small angular flex in the vertical lamella due to the distance between the rear support structure and flex point in the lamella in question. Thus, the lamella is not structurally compromised by stress force during operational movement of the moveable support rail. This same consideration is at play with the horizontal lamella, but structural compromise due to stress forces is somewhat dissipated as the horizontal lamella are much longer front to back than the vertical lamella, and the flexing forces are accommodated over a greater length of horizontal lamella, in less concentrated area, than when compared to the vertical lamella.

The surface onto which articles ("V") are picked up from and set down upon is provided by a stationary article support assembly (1103). In the embodiment shown in FIG. 43, the stationary article support assembly (1103) includes a back rail (1120) and a base rail (1121). The back rail (1120) and base rail (1121) are each elongate in their proximal to distal dimension, having proximal ends adjacent the interior surface of proximal end of the outfeed housing. The distal ends of the a back rail and a base rail terminate at or adjacent the distal side wall (1006) of the outfeed housing. The back rail (1115) has a front face (1124) in which are formed, at regular intervals, a plurality of notches or recesses (1125).

The top surface (1126) of the base rail (1121) and the notched front face of the back rail (1120) form the stationary article support surfaces of the depicted embodiment, from which the moveable support rail picks up vials, over which the movable support moves the vials, and onto which the movable support places the moved vials. As is the case of the movable support lip front face, the notches or recesses in the front face of the back rail allow for the more orderly spacing and stable positioning of vials during operation of the internal transport mechanism. The notches or recesses located on the movable support rail and on the stationary support rail allow vials to be spaced and maintained in a trackable order. The position of each vial may be tracked by an operator or appropriate control system through the modular production system. A suitable quality assurance system, may be incorporated which is capable of tracking and removing individual vials exiting the outfeed module if the vial is identified as deficient. This allows individual failing articles to be removed, as opposed to an entire batch being discarded to assure the one failing product is not released.

The back rail (1120) of the stationary support assembly is mounted to the back wall (1013) of the outfeed housing by one or more back rail arm brackets (1122). The back rail arm bracket(s) (1122) include a back end and a front end, and attach to the interior surface of the back wall of the outfeed housing at it's this back end. The base rail (1121) of the stationary support assembly is mounted to the front wall of the outfeed housing by one or more base rail arm brackets (1122). The base rail arm bracket(s) (1122) include a back end and a front end, and attach to the interior surface of the front wall of the outfeed housing at their front end. A single back rail arm bracket and base rail arm bracket are in this depicted embodiment.

The front end(s) of the back rail arm bracket(s) and the back end of the base rail arm bracket(s) are adapted to connect to a portion of their respective stationary rails.

Preferably, the respective connections between the connector arms and the L-shaped rail, the back rail and the base rail is on a portion of the rails which does not interfere with transport of articles through the module. The connection between the front end of the back rail arm bracket(s) and the back stationary support rail (1120), and between the back end(s) of the base rail arm bracket(s) and the base stationary support rail (1121), may be fixed in nature, through threaded connection or by weld or the like. Alternatively, the connections may provide a certain amount of "play" by interaction between a pin or other extension projecting from one of the end of the arm bracket or respective support rail, and a corresponding hole or groove formed in the other interfacing respective component. The hole or groove may be dimensionally configured to hold the support rail either tightly or loosely relative to the size of the pin/extension. A loose hold in this position may be employed by the hole or groove being dimensionally larger than the pin/extension, allowing some slippage between the bracket arm and the respective rail surface. Slippage may be further augmented by providing a slippery surface, such as a ceramic plate between the interconnected arm portion and rail. Such non-fixed configurations may be employed to accommodate any thermal expansion and contraction in stationary support assemblies experienced during operation of an assemble modular production line.

The movable article support assembly (1102) and the stationary article support assembly (1103) interact, to provide surfaces for supporting articles, such as vials ("V"), positioned thereon, which are moved by the moveable support through the interior cavity of the outfeed housing.

It is noteworthy that, because the components of the drive frame (1101) are each fixedly connected to each other, the drive frame contains no parts having a frictional interaction. Movement of the moveable support rail occurs by lamellar flexion within the drive frame. Advantageously, this avoids creation of abrasionally-produced particulate material which could contaminate the internal environment of the outfeed housing internal cavity (1007) or the connected production tunnel formed by the internal cavities of proximally connected production modules in a modular production assembly line. This frictionless interaction also reduces the wear and tear on the drive frame (1101) itself, increasing the useful life of the module, decreasing the replacement costs for parts, and reducing the frequency of scheduled maintenance to replace worn parts, and the production down time associated therewith.

As in the earlier discussed module, the stationary support assembly and movable support assembly rails are positioned at an incline, and their support surfaces are slightly angled in a rearward direction, such that the bottom surface of the base of a vial positioned thereon rests on the upper surface of the base rail and/or the lower arm of the L-shaped rail and is held at an incline, with the side of the vial resting against the front surface of the back rail and/or the front-facing surface of the upwardly extending portion or the lip portion of the L-shaped rail. The notches or recesses formed in these front surfaces permit the vial to be stably positioned in this fashion, making it less likely to fall of the given rails during transport within the module's interior. Further, as described below in relation to the filling and closure module, this inclined position may facilitate filling of the vials.

When the articles are vials or other open containers, they generally have a closed base at their lower end which is structured so that it may rest on the lower arm of the L-shaped rail and/or the upper support face of the stationary support base rail without falling over. Such vials have annular side walls extending coaxially from the base extending to an upper end where the sides transition to an annular coaxial inwardly sloping shoulder portion, which narrows to an annular coaxial neck. The annular neck portion of the vial extends upwardly from the shoulders to form the outwardly directed lip of the vial. The lip has lower, side and top surfaces. The top surface of the lip defines a central opening extending through the lip, neck, shoulder and into an interior cavity of the vial. The interior of the vial is therefore defined by the interior surfaces of the lip, neck, shoulder, side walls, and base of the vial.

Air Flow Control within the Outfeed

Airflow within the outfeed housing interior cavity (1007) is controlled through various access ports in the outfeed housing (1000). Air, provided by compressed air source (not shown), enters the filter housing (1009) through the inlet port (1017). A filter (1019) is positioned to cover opening (1008) in the top wall of the outfeed housing. The filter is employed to remove particulate and/or microbial matter from air flowing between the filter housing cavity and the interior of the infeed housing, as indicated by reference arrows "O" in FIG. 43. The air pressure in the outfeed housing controlled in part with this incoming air flow.

In this embodiment, the air pressure within the outfeed interior cavity (and connected production tunnel) is maintained during operation at a higher pressure than the external environment. The filtered airflow "O" from the filter housing is augmented by airflow, indicated by reference arrow "P", from proximally positioned module(s). Due to this pressurization of the outfeed by airflows "O" and "P", pressurized air flows outwardly from the outfeed housing (1000) through the article entry port/mouse hole (1018), shown by reference arrow "Q". Airflow also exists the outfeed housing interior cavity through elongate lateral vents (1020), formed in the bottom of the outfeed housing, as shown by reference arrows "R".

Airflows "Q" and "R" achieve a common goal of reducing the risk presented by unfiltered air entering the interior of the outfeed housing from mouse hole (1018). The airflow out of the mouse hole shown by arrow "Q." Airflow from the mouse hole redirects external airflow, as shown with arrows "S", creating an air current away from access hole (1018). Airflow "Q" however, may not eliminate the potential for entry of unfiltered air through the mouse hole, as such may still occur because of turbulence at the mouse hole opening. To address such turbulence-induced air ingress, air flow out of the elongate lateral vents (1020) in the floor of the outfeed housing act as a vertical washout within the outfeed module. Air vented from vents (1020) may, for example, be routed through access conduits (11) in a leg (12) of base (10), as shown in FIG. 2.

6. External Drive System:

In the embodiment of the present invention, the modular product system may include a magnetically coupled external drive system and internal transport system. In such embodiment, the external drive system (8) of the present invention provides the motive force which acts upon one or more of the internal transport system sections positioned in the module housings making up the production tunnel of the of the present modular system. While the external drive system (8) may take several forms, which provides motion to the internal transport system, the present application describes representative embodiments thereof.

A. Structure

In one embodiment of the external drive system (8), shown in FIGS. 44-47, the external drive system (8) is made up of one or more external drive system operative sections (50). Each operative section includes a horizontally oriented housing mounting plate (51). A downwardly extending vertical base mounting plate (52) is attached to the back side the housing mounting plate. The vertical base mounting plate (52) attaches to base (10), as shown in FIG. 1, by any suitable means, e.g., threaded fasteners, etc.

FIGS. 44-46 show the junction between an interconnected pair of modules. FIG. 44 is a perspective view from the back side of the external drive system, showing the back of the attached module housings anchored thereon. As shown in FIG. 44, the proximally attached module is the distal end housing (301) of the depyrogenation unit (3), which is connected via a connector sleeve (7) to the proximal end housing (501) of a cooling module (4). FIGS. 45 and 46 depict a cross sectional view through the proximal end housing on the cooling module. FIG. 47 depicts several the external drive system (8) operative sections (50) which have been interconnected, without any modules positioned thereon.

Each housing mounting plate (51) has a top surface to which are connected one or more raised module mounting surfaces (53). As may be best seen in FIG. 47, a first pair (53*a*) of the raised module mounting surfaces are connected on the proximal half of the top surface of the housing mounting plate, and a second pair (53*b*) of raised module mounting surfaces are attached on the distal half of the top surface of the housing mounting plate (51). In each of these pairs, one of the mounting surfaces is mounted in a forward position, and the other is mounted rearward thereof. Thus, as can be seen in FIG. 44, the first pair of raised mounting surfaces are positioned to support the exterior bottom surface, at both the front and back of the bottom wall, of the distal end of the proximally module. The second pair of raised mounting surfaces are positioned to support the exterior bottom surface, at both the front and back of the bottom wall, of the proximal end of the distal module connected thereto. The connector sleeve (7) which joins the two connected modules, is positioned at the midpoint of the housing mounting plate (51), thus advantageously assisting in the aligned positioning of the module housings in a desired fashion.

Rearward of raised mounting surfaces (53), the top surface of mounting plate (51) carries a drive axle mounting bracket base (54), on which is positioned a drive axle mounting bracket (55). A central bore opening (56) extends through the drive axle mounting bracket (55) in a proximal to distal direction. A ring-shaped axle bearing (57), having an annular central opening (58), through which a elongate drive axle (59) passes, is positioned in the central bore opening (56) of the drive axle mounting bracket (55).

So inserted, the elongate drive axle (59) extends horizontally parallel to the length of the connected modular housings attached to the housing mounting plate (51). The interior annular surface of the ring-shaped bearing is a low friction surface or a ball bearing casing, allowing elongate drive axle (59) to move smoothly in both rotational and horizontal right and left directions within the drive axle mounting bracket (54).

A drive magnet frame assembly (60) is attached to the elongate drive axle (59). The drive magnet frame assembly (60) includes a front (horizontally) elongate plate (61), having a rear surface from which extends a pair of rearwardly extending axle clamp arms (62*a* and 62*b*, respectively). The proximal axle clamp arm (62*a*) and a distal axle clamp arm a (62*b*) are positioned so as to be on either side of the drive axle mounting bracket (55). At the end of the axle clamp arms opposite the connection to the front elongate plate, each clamp arm (62) possess a horizontally extending axle reception passage (63), which receives the elongate drive axle (59).

The horizontal, forwardly directed slot (64) extends from the rear of each axle clamp arm to axle reception passage (63), thus dividing the rear portion of each clamp arm (62) into an upper (65) and lower (66) section. The upper surface of the upper section defines a fastener reception hole (67), which extends through the upper section and into or through the lower section. The interior of the fastener reception hole (67), at least in lower section (66) is threaded and is adapted to receive a complimentarily threaded bolt positioned in the fastener reception hole. When the bolt is tightly secured in the fastener reception hole, the upper and lower sections of the bracket arms are drawn together, to tightly hold to the drive magnet frame assembly (60) to the elongate axle (59).

The front surface of the front elongate plate (61) of the drive magnet frame assembly (60) has affixed, toward its proximal end, a proximal drive magnet (68), and, toward its distal end, a distal drive magnet (69).

As can be appreciated in FIGS. 45 and 46, the front surface of the front elongate plate (61) of drive magnet frame assembly (60) is held in close proximity to the rear side of the proximal and distal interconnected modules positioned on the housing mounting plate (51).

In this orientation, the proximal drive (68) magnet is held in close proximity to the follower magnet positioned in the distal end of the depicted proximal production module (301), and the distal drive magnet (69) is in close proximity to the follower magnet positioned in the proximal end of the distally attached production module, thus permitting the drive magnets (68 and 69) to be magnetically coupled to the follower magnets in drive frames mounted in these interconnected modules, as previously described.

The elongate axle (59) may be composed of a single length of axle, or separate lengths of axle linked together by an axle connector sleeve (70). The connector sleeve clamps over adjoining ends of separate axle sections, clamping them together by compression of the axle connector sleeve caused by the tightening of the threaded fasteners (71) in the sleeve, firmly binding the connector sleeve over each of the adjoined axle ends.

The elongate axle (59), is moveable both rotationally and horizontally. As the axle connected to the proximal and distal clamp arms (62), which are in turn mounted to the front elongate plate on which the drive magnets drive magnets (68 and 69) are connected, the movement of the elongate axle correlates to the movement of the drive magnets, which are magnetically coupled to the follower magnets in the aligned module housings.

Due to this magnetic coupling, the rotational movement of the of the elongate drive axle (59) results in the drive magnets being moved up and down, which in turn cause the follow magnets to be raised (as depicted by the arrows in FIG. 46) or lowered. This in turn results in the moveable connector rail to be raised and lowered, which is depicted in FIGS. 48A, 48B and 48C. In FIG. 48A, the drive frame is shown with the flexible vertical lamella (34) straight. In FIG. 48B, the rear structural support structure has been drawn to upward by the magnetically coupled drive magnet, shown by reference arrow, resulting in the upward movement of the arm bracket which connects to the movable support rail. In FIG. 48C, the rear structural support of the drive frame has been drawn downward (shown by reference arrow), moving the movable support arm bracket downward, along with the moveable support rail that would be attached thereto.

The total vertical movement of the rear support structure, measured in degrees of rotational turning of the axle (59) is generally 20 degrees or less, for example about 15 degrees or less, such as 10 degrees or less. For example, from a position where the moveable rail and lower support rail are aligned and a container contacts both, counter-clockwise rotation of the axle (59) (rotating the drive magnet upwards) may be 10 degrees or less (e.g., 2-7 degrees, 3-5 degrees, about 4 degrees). Similarly, from a position where the moveable rail and lower support rail are aligned and a container contacts both, clockwise rotation of the axle (59) (rotating the drive magnet downwards) may be 10 degrees or less (e.g., 2-7 degrees, 3-5 degrees, about 4 degrees).

Horizontal movement on the elongate drive axle (59) proximally, moves the drive magnets proximally, which in turn moves the magnetically coupled follower magnets proximally, and moves the moveable support rail in a proximal direction in the housing. Horizontal movement on the elongate drive axle (59) in a distal direction, results in the drive magnet being drawn distally and in turn, moves the magnetically coupled follower magnets distally. This distal movement results in the moveable transport rail being moved distally. The total horizontal movement of a given drive magnet is generally less than 5 cm (e.g. 1-5 cm, 2-4 cm, about 3 cm). For example, where the amount of travel of the drive magnet from its proximal most position to its distal most position is about 30 mm, the drive magnet would move 15 mm proximal and 15 mm distal of the point where the horizontal lamella is unflexed and relatively straight, resulting in a corresponding motion of the moveable support within a module housing.

It will be understood that the magnet centers of the drive and corresponding follower magnet are aligned. The distance between the drive and follower magnets decreases magnetic force coupling the two magnets, and thus the movement of the magnets should not be so far as to lose the magnetic coupling.

The choice of magnets will be dependent on multiple factors, including the weight of the movable support rails when loaded with vials or other containers, as well as the range of rotational and horizontal movement required for the drive magnets and follower magnets. Suitable magnets employable for both drive and follower magnets include but are not limited to, samarium-cobalt. Optimally, the magnets employed for follower magnets should be such that withstand the sterilization temperatures experienced within the production. Thus, the magnet materials may be selected to have a ferro-magnetic temperature capacity such that the magnet does not lose polarity and destroy magnetism at temperatures it is exposed to in the given module. As the temperatures experienced outside the module housings are less than those within the modules, drive magnets, may, be made of any suitable material, such as a rare earth magnetic material. In certain embodiments, the material selected may include, but not be limited to neodymium, Samarium-cobalt, etc., which may be safely used in temperatures below 150° C. without compromising the magnetic properties of the material.

The movement of the drive this first frame embodiment is shown in FIGS. 49A, 49B and 49C.

FIGS. 49A-C depict a representative drive frame, including the connector moveable support arm bracket, but bot the moveable support rail that would be attached thereto. FIG. 49A depicts the resulting movement on the drive frame when the drive axle of the external drive system is moved horizontally in a proximal direction. Using the fixed position of the vertical lamella as a reference point, the rear structural support has been drawn to the right (shown by reference arrow), moving the movable support bracket arm which is connected to the rear support structure to right, which would correspond to proximal movement of a moveable support rail attached thereto. FIG. 49B depicts the resulting movement of the drive frame when the drive axle of the external drive system is drawn horizontally distal from that in FIG. 49A. The rear structural support and connected moveable arm bracket has moved to the left, the proximal and distal horizontal lamella are unbent, with the moveable support arm bracket being centered in relation to the poistionalyl-fixed vertical lamella. A moveable support rail connected to the moveable arm bracket would be positioned in its midpoint of travel within the module housing. FIG. 49C, depicts the result of the drive axle being moved still further distally, which results in the rear structural support being drawn further to the far left (shown by reference arrow), moving the movable support bracket arm leftward, which would correspond to the distal movable support rail being moved distally.

FIGS. 50A to 50I depict the combined vertical and horizontal movement of the rear support structure, and how this impacts the movement of vials (V) positioned on the internal transport system. In this depiction, the movable support assembly from the distal end housing (301) of depyrogenator (3) distal end.

Figure 50A:
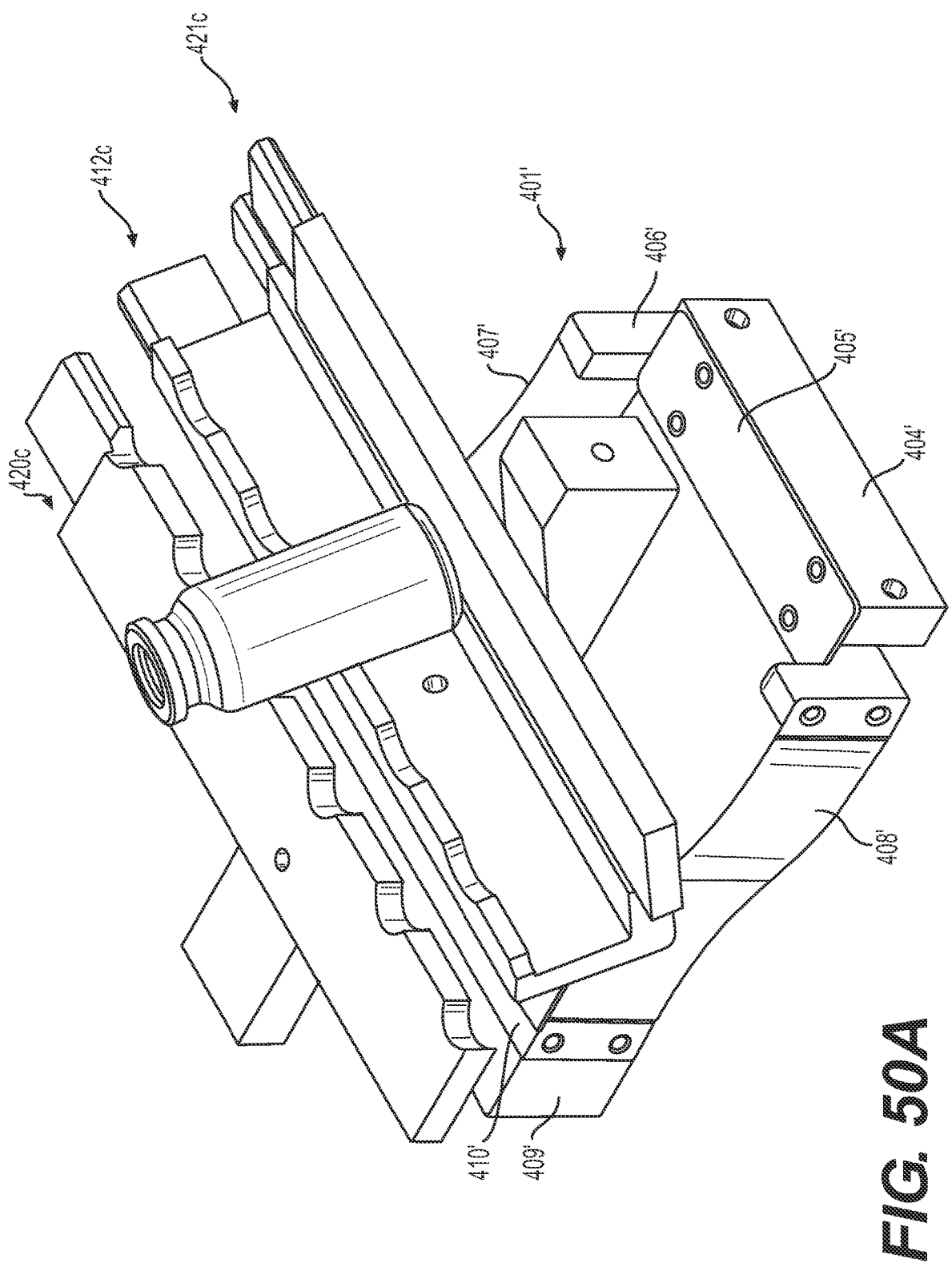

FIG. 50A reflects the orientation of the moveable and stationary supports when the axle (63) in FIG. 45 is occupies a rotational midpoint and is horizontally extended at the proximal end of its operational orientation. The top surface of the lower arm (413) of the L-shaped rail aligned with the top surface of the stationary support base rail, such that the base of the vial (V), which is positioned on an incline, is supported on both top surfaces. Due to the incline at which it is held, the vial is as also supported by the front surface of the back support rail, and is held in its lateral position on the rail within a recess formed in the back rail face. In terms of the vial's relative position on the rails, the vial occupies the fourth ($4^{th}$) recess from the left (distal) side in the front face of the back stationary support rail. In this orientation, the vertical lamella is unbent (as in FIG. 48A), while the horizontal lamella are shifted to the right (proximally) in the position akin to that shown in FIG. 49A.

Figure 50C:
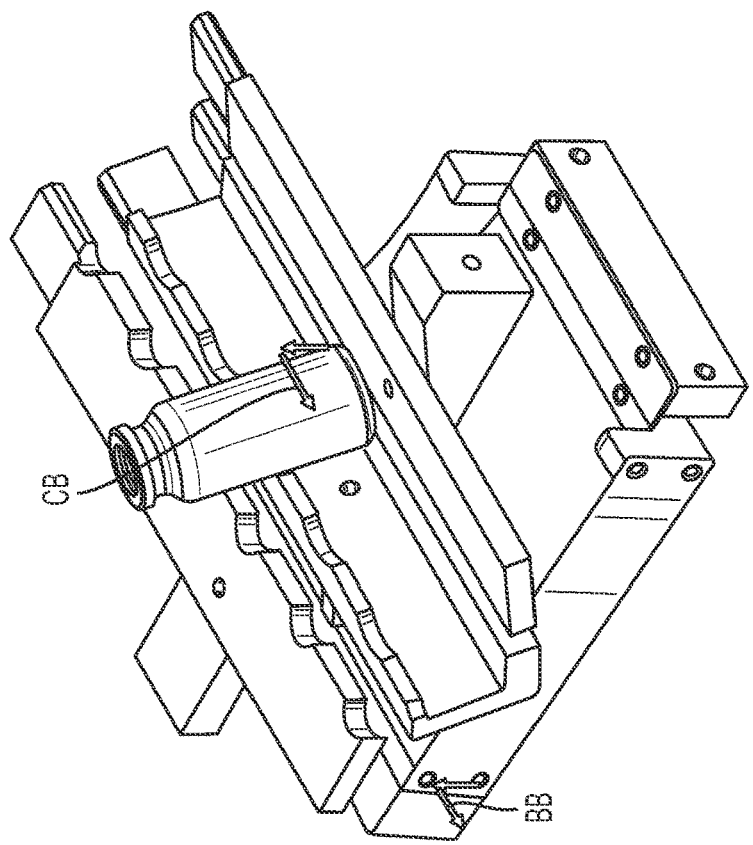
Figure 50B:
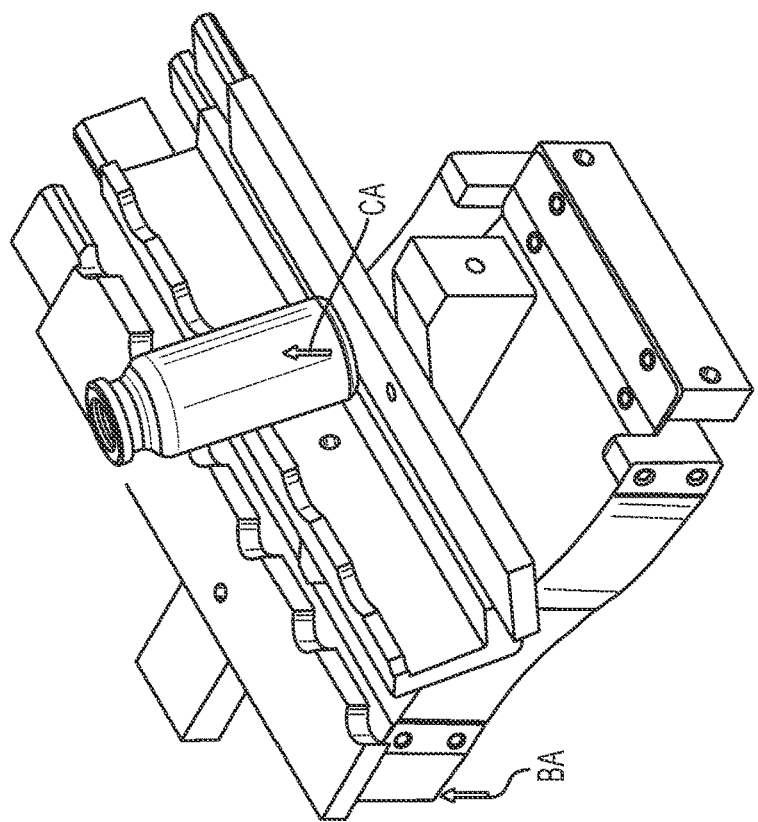

FIG. 50B, depicts what occurs when the axle (59) in FIG. 45 is rotated counter clockwise. The drive magnet (69) is moved upward, causing the follower magnet to lift the rear structural support vertically upward (as indicated by reference arrow "BA" in FIG. 50B). This raises the movable support rail within the module housing, causing the vertical lamella to be flexed upwardly. This flexion is accompanied by a degree of pivoting within a flexing/hinge region of the vertical lamella, such that the lower extension of the movable L-shaped is lifted above the upper face of the base rail, and the upper lip of the L-shape rail both rises and moves toward the housing front wall. The vial is thus simultaneously lifted from the upper surface of the stationary base rail, and out of the recess formed in the front face of the stationary back rail. In this position shown in 50B, the vial is held by the moveable support rail proximally above the stationary support surfaces. (as indicated by upwardly pointed reference arrow "CA" in FIG. 50B on the vial)

FIG. 50C depicts what occurs when the axle (59) in FIG. 45 is drawn distally while held in the raised orientation. As the drive magnet (69) is moved distally, this causes the follower magnet in the drive frame to move the raised rear structural support horizontally in a distal direction (as indicated by additional reference arrow "BB" in FIG. 50C). The L-shaped rail supporting the vial is moved in a horizontally distal direction within the module housing, causing the horizontal lamella to be straighten into a position midway between its proximal range, while the vertical lamella remains flexed in an upward direction, coinciding with the depictions shown in FIGS. 48B and 49B. In this manner, the vial is moved distally along the front face of the stationary back rail, such that it is now positioned between the fourth and third recesses in the back stationary support rail. (as indicated by additional horizontal reference arrow "CB" in FIG. 50C on the vial)

Figure 50E:
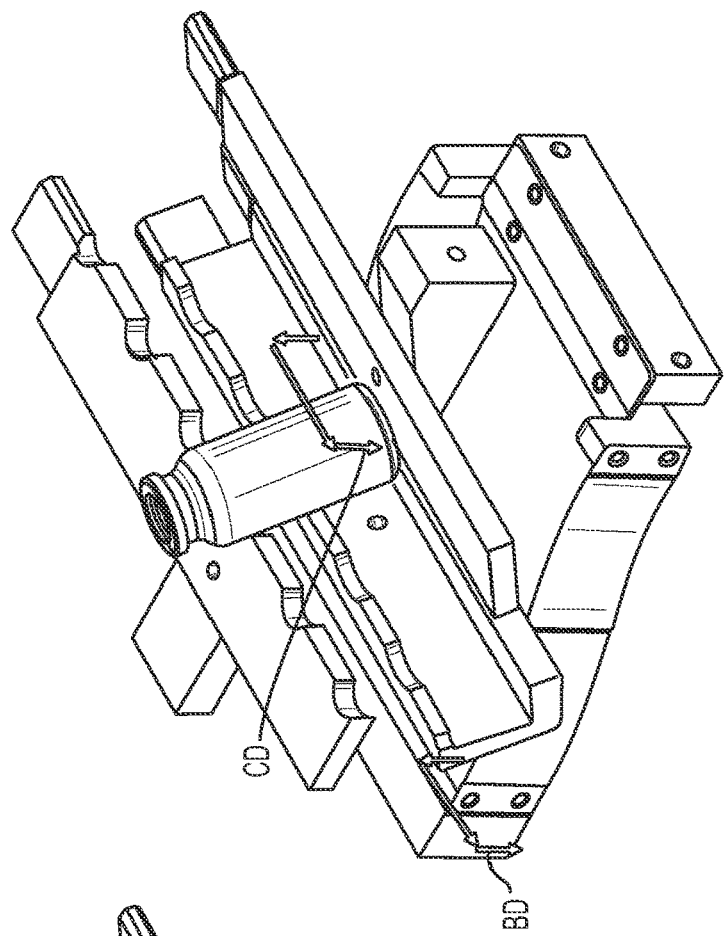
Figure 50D:
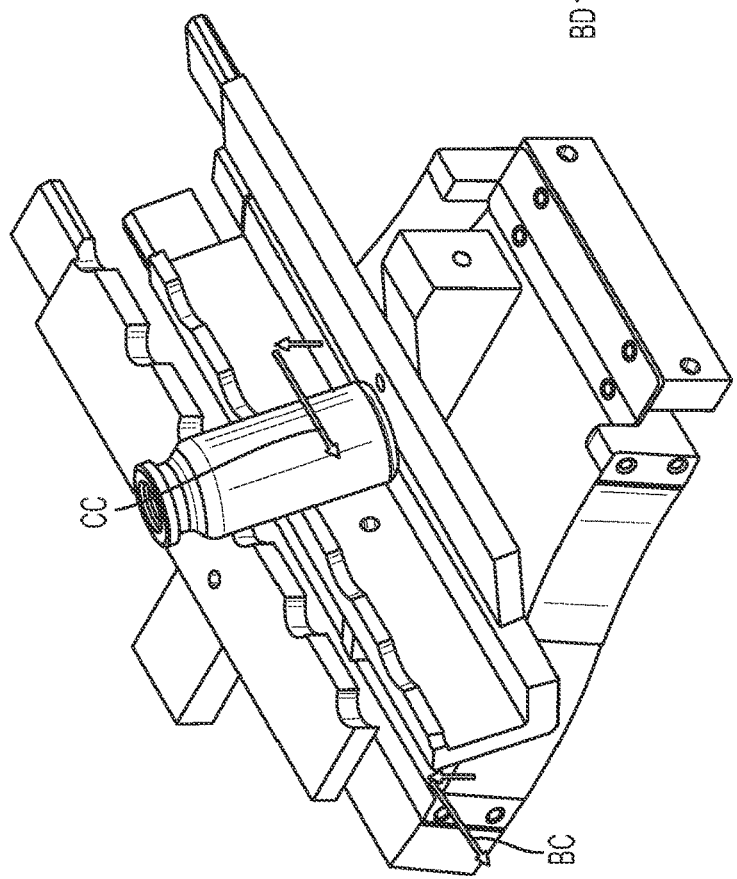

FIG. 50D depicts what occurs when the axle (59) in FIG. 45 is drawn further distally while held in the raised orientation. As the drive magnet (69) is moved horizontally further distal, the causes the follower magnet in the drive frame moves the raised rear structural support horizontally distal (as indicated by lengthened additional reference arrow "BC" in FIG. 50D off the drive frame). The L-shaped rail supporting the vial is moved in further horizontally distal within the module housing, causing the horizontal lamella to be flexed to its distal position, while the vertical lamella remains flexed in an upward direction, coinciding with the depictions shown in FIGS. 48B and 49C. In this manner, the vial is moved distally along the front face of the stationary back rail, such that it is now positioned over the third recess in the back, stationary support rail (as indicated by lengthened horizontal reference arrow "CC" in FIG. 50D on the vial).

FIG. 50E depicts what occurs when the axle (59) in FIG. 45 is rotated clockwise to it rotational midpoint in its operating range, while the held in its horizontally in a distal position. As the drive magnet (69) is rotated downwards, the follower magnet in the drive frame moves the rear structural support to a vertically neutral state, (as indicated by downward reference arrow "BD" in FIG. 50D off the drive frame). The L-shaped rail supporting the vial is moved downward, causing the vertical lamella to occupy a neutral unflexed (or only minorly flexed) state, while the horizontally lamella remains flexed in its distal operational orientation, coinciding with the depictions of the drive frames shown in FIGS. 48A and 49C. In this manner, the vial is moved vertically downward to resting upon both the top surface of the lower arm (413) of the L-shaped rail and the aligned top surface of the stationary support base rail, and is positioned in the third recess on the front face of the stationary back rail (as indicated by downward vertical reference arrow "CD" in FIG. 50E on the vial).

Figure 50G:
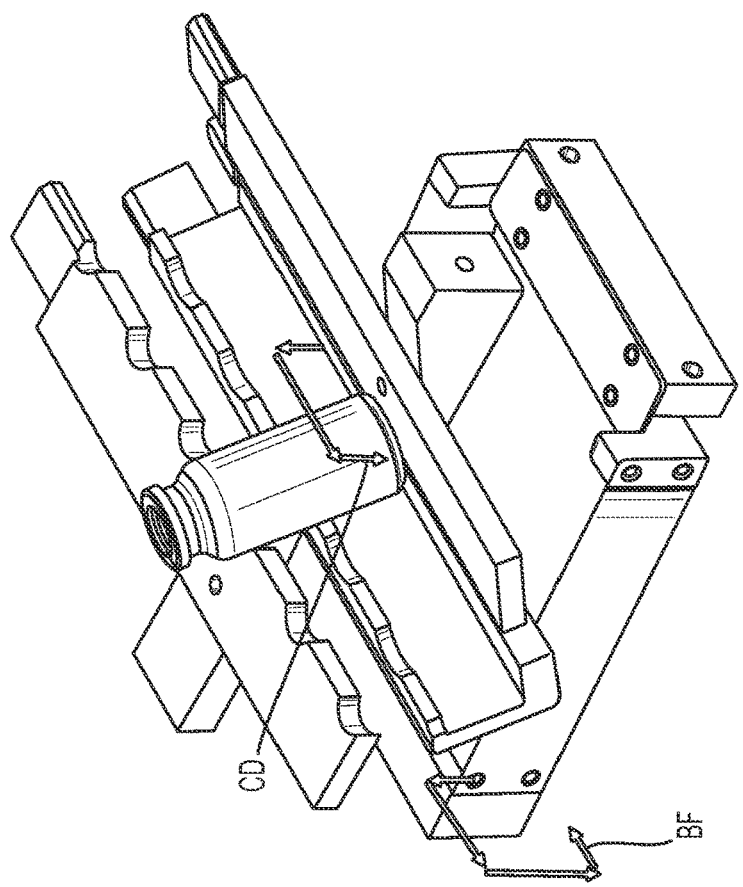
Figure 50F:
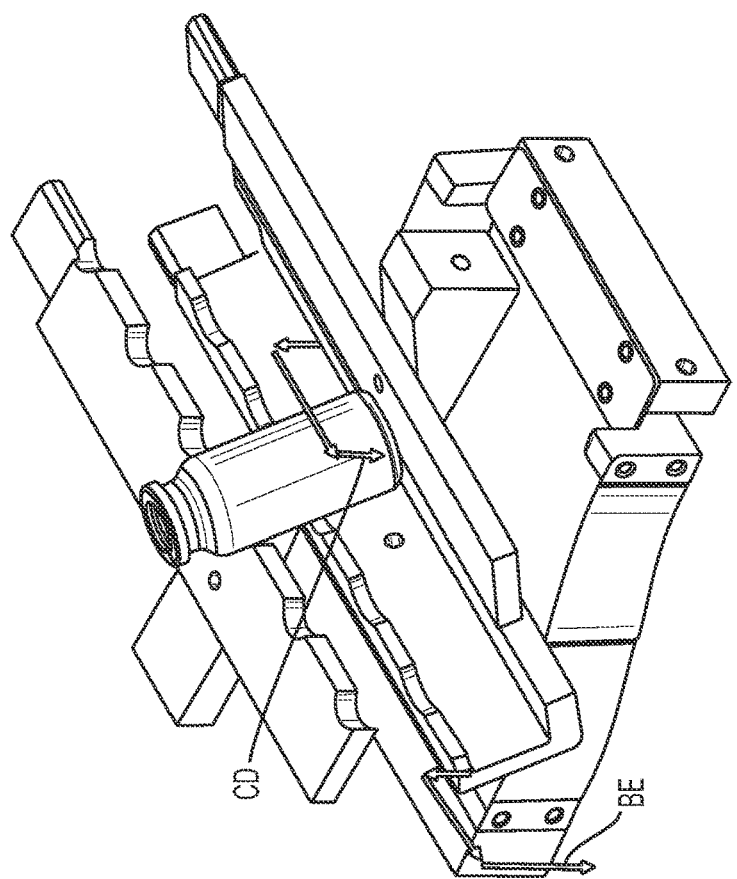

FIG. 50F, depicts what occurs when the axle (59) in FIG. 45 is rotated still further clockwise in its operating range, while being held in its horizontally in a distal position. As the drive magnet (69) is rotated downwards, the follower magnet in the drive frame lowers the rear structural support within the module housing (as indicated by lengthened downward reference arrow "BE" in FIG. 50F off the drive frame). The L-shaped rail supporting the vial is moved still downward, causing the vertical lamella to occupy a downwardly flexed state, while the horizontal lamella remains flexed its distal operational orientation, coinciding with the depictions of the drive frames shown in FIGS. 48C and 49C. In this manner, the vial remains in the exact same position (as indicated by reference arrows "CD" on the vial being identical to that in FIG. 50E). The vertical downward motion of the moveably support rail has, however, caused the vial to be wholly (or predominantly) supported by the stationary support, resting within the third recess of the front surface of the back support rail and the top surface of the base support rail. The support surfaces of the moveably support rail no longer support the vial.

FIG. 50G depicts what occurs when the axle (59) in FIG. 45 is drawn proximally while held in the lowered orientation. As the drive magnet (69) is moved proximally, this causes the follower magnet in the drive frame to move the lowered rear structural support horizontally in a proximal direction (as indicated by proximal reference arrow "BF" in FIG. 50G off the drive). As the L-shaped rail does not support the vial (as indicated by reference arrows "CD" on the vial being identical to that in FIGS. 50E and 50F), the moveable support rail moves horizontally in a proximal direction within the module housing, causing the horizontal lamella to be straighten into a position midway between its distal and proximal range, while the vertical lamella remains flexed in a downward orientation, coinciding with the depictions shown in FIGS. 48C and 49B.

Figure 50I:
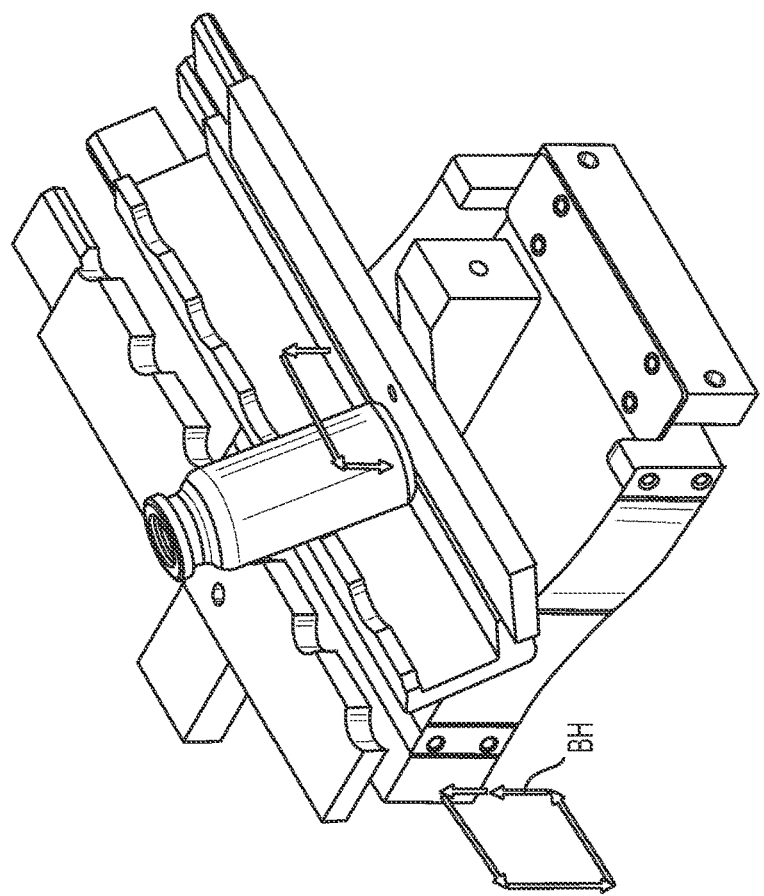
Figure 50H:
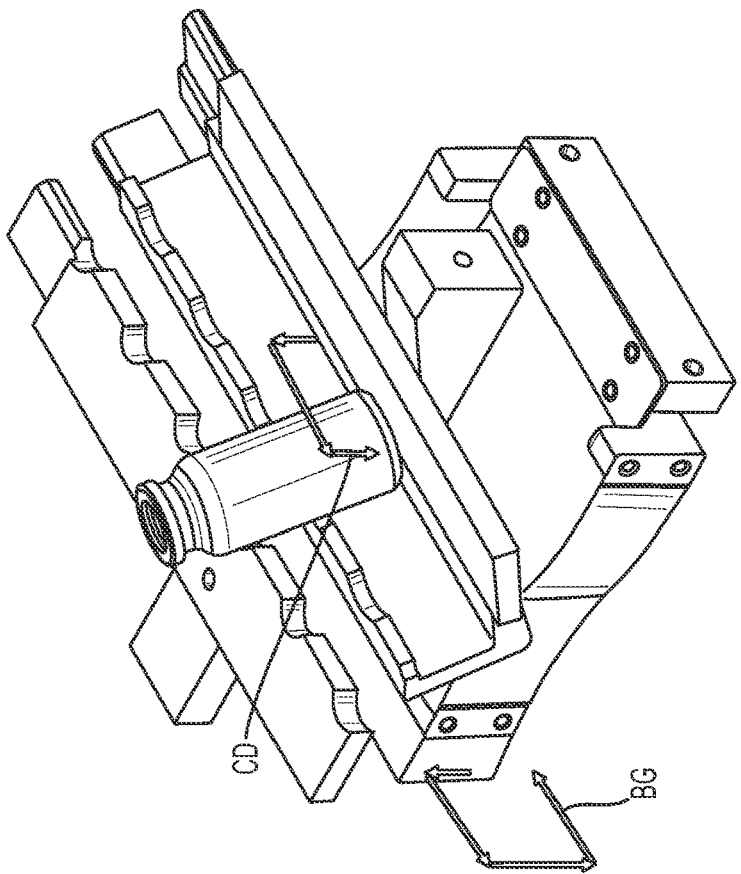

FIG. 50H, depicts what occurs when the axle (59) in FIG. 45 is drawn still further proximally while held in the lowered orientation. As the drive magnet (69) is moved still further proximally, this causes the follower magnet in the drive frame to move the lowered rear structural support horizontally further proximal (as indicated by proximal reference arrow "BG" in FIG. 50H off the drive). As the L-shaped rail continues to not support the vial or vials positioned above it (as indicated by reference arrows "CD" on the vial being identical to that in FIGS. 50E, 50F and 50G), the moveable support rail moves horizontally in a proximal direction within the module housing, causing the horizontal lamella to be straighten into a position midway between its distal and proximal range, while the vertical lamella remains flexed in a downward orientation, coinciding with the depictions shown in FIGS. 48C and 49C.

FIG. 50I depicts the counter clockwise rotation of the axle (59) in FIG. 45 back to its rotational midpoint (as represented by reference arrow "BH" in FIG. 50I), while occupying its proximal operative orientation, as shown initially in FIG. 50A. Once more, the top surface of the lower arm (413) of the L-shaped rail aligned with the top surface of the stationary support base rail, such that the base of the vial, which is positioned on an incline, is supported on both top surfaces. Due to the incline at which it is held, the vial is as also supported by the front surface of the back support rail, and is held in its lateral position on the rail within a the $3^{rd}$ recess formed in the back rail face. In this orientation, the vertical lamella is again unflexed, (as in FIG. 48A), while the horizontal lamella are shifted to the proximal orientation as shown in FIG. 49A.

Thus, FIGS. 50A-50I represent a single cycle of the moveable support assembly via the operation of the drive frame by the drive magnet of the external drive system, and the coincidental raising, distal movement, and lowering of such vial(s) positioned thereon. Repetition of this cycle provides for the movement of articles infeed into the modular system at its proximal end, to move through the system, have various operations imposed on it, such as depyrogenation and/or sterilization, filling, sealing, etc., before being outfeed from the processing line at its distal end.

An advantage of the system depicted in FIGS. 50A through 50I, is that for half of this cycle, i.e., those stages shown in 50E through 50I, each vial remains stationary, thus allowing, for example, vials positioned within the exposure window of the depyrogenation module, within the cooling module, within the filling station of the filling module, and beneath the closure mechanism in the closure module, to have some operation performed upon it for this established time period. Thus, this period of stationary positioning allows for operational coordination within each of the modules.

Repetition of this cycle thus results in the distal movement of the vial through the tunnel.

While the motion described above in reference to FIGS. 50A-50I is rectangular, it may be smoothed, as by incorporating a rounded arc in the corners of the rectangular motion, or performed as an elliptical motion.

The total vertical movement of the rear support structure, measured in degrees of rotational turning of the axle (59) is generally 20 degrees or less, for example about 15 degrees or less, such as 10 degrees or less. For example, from a position where the moveable rail and lower support rail are aligned and a container contacts both, counter-clockwise rotation of the axle (59) (rotating the drive magnet upwards) may be 10 degrees or less (e.g., 2-7 degrees, 3-5 degrees, about 4 degrees). Similarly, from a position where the moveable rail and lower support rail are aligned and a container contacts both, clockwise rotation of the axle (59) (rotating the drive magnet downwards) may be 10 degrees or less (e.g., 2-7 degrees, 3-5 degrees, about 4 degrees).

The total horizontal movement of a given drive magnet is generally minimal, e.g., less than 5 cm (e.g. 1-5 cm, 2-4 cm, or about 3 cm). For example, where the amount of travel of the drive magnet center from its proximal most position to its distal most position is about 30 mm, the drive magnet would move 15 mm proximal and 15 mm distal of the point where the horizontal lamella is unflexed and relatively straight, resulting in a corresponding motion of the moveable support within a module housing.

Testing and Monitoring of Modular Production System Environment

As will be appreciated from the above description, by employing environmental isolating features such as high temperature seals between and within modules, and metal bellows at various input points, the modular production system is rendered as a generally closed environment. Confirmation of the integrity of the production tunnel may be readily achieved by closing the connections to the utilities (e.g., cooling air) with a valve, and input ports, such as the mouse holes in the infeed and outfeed module with plugs, and pressure testing the interior of the system. A rapid pressure drop can thus indicate that the system is not completely sealed, and the internal environment could be in direct fluid contact with the external environment. Thus, the modular, sealed construction of the system permits easy pressure testing of the entire production line, between infeed and outfeed, allowing confirmation of that all seals are intact, and that the production system is ready to be safely operated.

Monitoring the system conditions in use is also readily achieved. In operation, sensors for temperature, etc., may be employed throughout the various modules in the production system. Advantageously, the modular production system provides a single internal transport system (interconnected portions which are operatively synchronized to form a unitary internal transport system) and all containers (vials) are in a single line on that system, and not many sensors to detect the location or orientation of containers/articles/vials, closures, etc. Where the module housing includes a quartz tube, as in FIG. 52, an optical emitter (1250) and an opposite optical detector (1251) may be positioned external to the tube, and the optical light beam (1252) travels through the transparent tube. Where the module is composed of a non-transparent material, such as metal (e.g., stainless steel), transparent, heat tolerant windows (e.g., quartz) may be used, as in FIG. 51, and the optical emitter (1250) and detector (1251) may each be located external to the module, as in a transparent tube, the emitted or detector could be located within the housing, and the other component could be located externally (as shown). Where windows are not feasible, fiber-optic components (sensors and detectors) may be employed on the interior of the module. In such instances, fiber optic components are selected to withstand the temperatures experienced within the module housing, for example some fiber optic heads can withstand 250° C.

Temperature and pressure sensors would be designed for high temperature, thus the temperature sensors can be on the exterior of, for example the transparent tubular housing of the module, including the depyrogenator and/or sterilization module, as well as in the cooling module. For example, temperature sensors could be placed between the outer reflective layer and the transparent tubular housing. Pressure sensors can be separated with a membrane from a hosing surface.

When the sensors are externally positioned/positionable in relation to the various module types, there are advantages in their ability to be serviced from the outside, without operators needing protective, clean-room type clothing. There is no need to disrupt the interior of the assembled production tunnel to intervene. Thus, contamination is avoided, and the risk of contamination of the environment within the module is avoided, thus realizing cost savings associated with protective measures to eliminate such contamination risks. Moreover, external mounting of sensors maintains the inside environment of the assembled modules extremely clean and simplified. Where sensors are mounted internally, each type of sensor is can withstand high temperatures experienced.

An additional feature of this system is that the small amount of air entering and exiting the system may be monitored and compared, such as by capturing and testing the air/gas escaping at the infeed/outfeed. As so few ingress and access points in the system exist, monitoring at these few points allowing for great portion of the entire environment of the system to be monitored. Such monitoring may be accomplished with the use of commercially available concentrators. Thus, the present modular production system permits refined ability to control the environmental content within the production tunnel than traditional filling lines where the air monitoring samples represents a minimal fraction of the entire air and surface environment.

7. Alternative Configuration of a Drive Frame

FIGS. 53-58 depicts an alternative drive frame (1200) embodiment useful in the internal transport system of the present invention. In this alternative form, the lamella (1201 and 1202) are incorporated within commercially available flexural/pivot bearings, such as C-Flex bearings, available from C-FLEX BEARING COMPANY, INC., Frankfort, New York, USA., as well as other commercial vendors, one type of which is shown in FIGS. 53-55). Pivot bearings, which may take various forms, and are described herein solely for purposes of example and not limitation. Suitable frictionless bearings may be employed for such purposes, and are considered within the scope of the invention.

FIG. 53 shows one example of a pivot bearing, in a perspective view. The opposite ends of the bearing are seen in a first side view and an opposite side view, In FIGS. 54 and 55. Such bearings allow for frictionless rotational movement about an axis of rotation by flexion of one or more lamella within the bearing. The bearings themselves comprise a first pivot housing (1260) and a second pivot housing (1261). Each of the pivot housings has a central bore (1263)

and a body projection. The body projection (1264) of the first pivot housing extends into the bore of the second pivot housing, and the body projection (1265) of the second pivot housing extends into the bore of the first pivot housing. Each of the pivot housings defines a recess (1266 and 1267) within its bore to accommodate the projection of the other pivot housing. It is noteworthy that the annular width of this recess is greater than the annular width of the projection it accommodates, thus to allow rotation of the pivot housings relative to each other.

Motion between one pivot housing portion and the body projection of the other pivot housing is achieved via lamella extending therebetween. In the depicted embodiments, a first lamella (1268) is bonded or connected to the inner surface of the first pivot housing and the inwardly facing surface of the projection of the second pivot housing, while a second lamella is bonded or connected to the interior surface of the second pivot housing and the inwardly facing surface of the projection of the first pivot housing. Gaps (1266A and 1267A) are maintained between the facing surfaces of the projections and opposite pivot housing surface by the first and second lamella, such that when one pivot housing is held stationary, the other housing is pivotable, via flexion of the first and second lamella, thus allowing a degree of rotation about a central axis through the pivot housings in a frictionless manner.

FIGS. 56, 57 and 58 depict a further alternative embodiment of the drive frame of the internal transport mechanism (9) useful in any given module of the present invention. In this alternative embodiment, the drive frame (1201) incorporates a number of vertically and horizontally operative pivot bearings to achieve vertical and horizontal motion. Again, due to the lamella within the pivot bearings, this motion is frictionless, and achieves the same desirable benefits therefrom as were described above.

The movable support includes a drive frame (1201), having a front structural support (1206), a rear structural support, 1209), which is attached to the moveable article support rail (1212), via a connector arm (1211). The movable rail (1212) may be constructed and attached to the drive frame as previously described for other embodiments of the internal drive systems.

In this alternative embodiment, the front structural support (1206) is attached to a wall mounting plate (1204). The wall mounting plate is attached in a fixed fashion (e.g., via threaded fasteners, etc.) to the interior wall of the module housing in which it resides, as previously described for the initial drive frame design discussed above. The front structural support (1206) is attached to the wall mounting plate via vertical lamella containing pivot bearings (1205). Attachment between the wall mounting plate and the front end of the front structural support is achieved by one portion the pivot bearing (1205) being positioned in a horizontally oriented recess (1204A) in the wall mounting plate, and the other pivot bearing body portion being positioned in an aligned horizontally oriented recess (1206A) situated in the front structural support.

The rear structural support in this embodiment has a lower portion (1209A) and an upper portion (2109B). The lower portion of the rear structural support is attached at its front end to the front structural support via a first pair of horizontal flexible lamella containing pivot bearings (1207). The lower portion of the rear structural support is attached at its back end to the upper portion of the rear structural support via a second pair of horizontal flexible lamella containing pivot bearings (1208). The horizontal lamella containing pivot bearings (1207 and 1208) are fixedly held in vertically oriented recesses in front structural support, and upper and lower portions of the rear structural support, as depicted. A follower magnet (1210) is positioned on the upper portion of the rear structural support and operates in the identical fashion described from previous drive frame embodiments.

In the depicted embodiment, the lower portion of the rear structural support comprises proximal and distal arms. Horizontal pivoting motion occurs both at the front of these arms, relative to the front structural support. Horizontal pivoting motion also occurs both at the rear of these arms, relative to the rear portion of the rear structural support. Vertical pivoting of the rear structural support is facilitated via the vertical lamella containing pivot bearing. So constructed, when coupled to an external drive system (e.g., by magnetic coupling) vertical and horizontal motion mage achieved in the same manner as described for the prior embodiments. Thus, this flexural bearing embodiment creates the same "walking beam" transport as the earlier embodiment of the drive frame described previously.

Dry Heat Sterilization

Key objectives of dry heat sterilization/depyrogenation in ovens include: the removal of moisture or residual moisture from the materials being sterilized thereby creating dry heat conditions; elevation of the temperatures of the entire load to the sterilization/depyrogenation temperature; attainment of uniform penetration of heat throughout all parts of the oven and the load during processing; maintenance of the specified sterilization/depyrogenation temperature within the load for the time specified to achieve satisfactory assurances of sterility/absence of pyrogens; protection of the load from contamination during processing; avoidance of compromising the sterility/absence of pyrogens during cooling; and provision of documentation from validation, preventative maintenance, and routine monitoring programs to confirm that the above key objectives are continually and consistently being achieved.

While dry heat is not necessarily the only manner for preparing the sterilization/depyrogenation system described herein for use, a significant advantage of the present production system is that the areas of the system which are required to be pyrogen free or sterile may be sterilized/depyrogenated entirely using dry heat. Dry heat sterilization/depyrogenation is advantageously employed as step in bring the completely assembled system on line prior to use. Alternatively, dry heat sterilization/depyrogenation can be conducted on individual components or groups of components that are then assembled under conditions prior to use to process articles in manufacture which are sterile/pyrogen-free. Thus, the materials selected for use in the system, as well as passing through the system, are selected to be heat resistant/heat stable.

Dry heat helps kill the organisms using the destructive oxidation method. It may be employed to depyrogenate, offering a significant advantage over moist heat processes, or the use of VHP (which is not accepted by regulators as a sterilization agent, but only for sanitization agent). As the thermal energy required to destroy pyrogens (including bacterial endotoxins, lipopolysaccharides) is significantly greater that that required to inactivate microorganisms, an effective depyrogenation process is also an effective sterilization process. Organisms are eradicated under dry heat as essential cell constituents are destroyed and the organism dies. This helps neutralize large contaminating bio-molecules such as proteins. Significantly though, materials, such as powders that are impermeable to moisture and anhydrous oils and fats are also capable of neutralized using dry heat sterilization. This process may also be used to kill resistant spores when the temperature employed in the process is maintained for the necessary amount of time.

The present invention includes a method for the depyrogenating and/or sterilizing a system or component(s) thereof, as set forth above, comprising the steps of:

a. providing a system or component(s) thereof; and
b. exposing at least the operative surfaces of said component(s) of such system (those coming into contact with the articles being processed in the system, and material used in such processing such as liquid formulations, seals/caps. etc.) to sufficient temperatures for a sufficient period of time to depyrogenate and/or sterilize said surface(s).

The sterilization temperatures in dry heat sterilization methods tend to be high, typically higher than 160° C., and more preferably 170° C. or 180° C. or greater, with an exposure time appropriate to achieve the desired level of sterility. Such temperatures are higher than those used in such techniques as moist heat sterilization. The temperature is maintained for a length of time which allows the destruction of undesirable organisms and materials that may pose a contamination threat.

For example, the World Health organization has established parameters for dry heat sterilization, stating:

"Preparations to be sterilized by dry heat are filled in units that are either sealed or temporarily closed for sterilization. The entire content of each container is maintained in the oven for the time and at the temperature given in the table below. Other conditions may be necessary for different preparations to ensure the effective elimination of all undesirable microorganisms.

| Temperature (° C.) | Minimum sterilization time (min) |
|---|---|
| 160 | 180 |
| 170 | 60 |
| 180 | 30 |

Specific conditions of temperature and time for certain preparations are stated in individual monographs.

One bioindicator strain proposed for validation of the sterilization process is: spores of *Bacillus subtilis* (e.g. var. niger ATCC 9372 or CIP 77.18) for which the D-value is 5-10 minutes at 160° C. using about 106 spores per indicator." (see, International Pharmacopoeia, Eighth Edition, 2018, "5.8 Methods of sterilization" (http://apps.who.int/phint/pdf/b/7.5.9.5.8-Methods-of-sterilization.pdf), although other suitable strains and organisms may be employed, as would be appreciated by those of ordinary skill.

The temperatures referred to for sterilization/depyrogenation should be those achieved in the system interior and in articles passing through the system and are viewed as temperature and time parameter starting points in processing. Settings in this pre-production phase, and in production will typically higher than these starting point temperatures, and be held for longer period of time, to assure sterility/freedom from pyrogens. The objective of dry heat sterilization is to achieve a Sterility Assurance Level of $10^6$ for the sterilization cycle. The objective of dry heat depyrogenation is to reduce ab endotoxin challenge by a factor of one thousand (three log reduction). As bacterial endotoxins require far greater thermal energy input for their destruction than viable microorganisms require for inactivation, any process that is capable of meeting the standard for bacterial endotoxin destruction also achieves satisfactory standards of sterility assurance. Bacterial endotoxin is not destroyed according to simple exponential kinetics, and practically no destruction takes place below 180° C.; US Pharmacopeia recommends temperatures in excess of 250° C.

For combined sterilization/depyrogenation, the temperature will be 200° C. or great for time periods 60 minutes or less, depending on the temperature selected. For example, depyrogenation may occur at greater than 200° C. for 60 min, or greater; 250° C. for 30 min, or greater, or 300° C. for 2 min, or greater. As will be recognized of ordinary skill, the temperature and time selected will be sufficient to allow for depyrogenation of areas of the system, without causing undue harm to the system components, especially under high thermal conditions.

Thus, dry heat may be employed to sterilize the system of the present invention, and is also capable of sterilizing article through the system in operation. In production, the system is capable of compliance with international standards. For example, Sterilization standards have been set forth in various national and international Pharmacopoeias and Guidance documents, such as the World Health Organization's International Pharmacopoeia, Eighth Edition, 2018, "5.8 Methods of sterilization" (http://apps.who.int/phint/pdf/b/7.5.9.5.8-Methods-of-sterilization.pdf); and US FDA's "Guidance for Industry, Sterile Drug Products Produced by Aseptic Processing—Current Good Manufacturing Practice (September 2004) Pharmaceutical CGMPs, https://www.fda.gov/downloads/Drugs/Guidances/ucm070342.pdf The modular production system described above is described in terms of preferred embodiments. Those of ordinary skill will appreciate that alternatives mechanisms to those described may be employed without departing from the scope of the present invention. It will be appreciated that alternatives to any of the described subsystems, including but not limited to the article transport system, air filtration system, filling systems, closure feed system, etc.

NUMBERED EMBODIMENTS

In embodiment 1, the invention is a modular production system comprising:

a plurality of production modules, each of said production housings comprising a module housing comprising a proximal end, a distal end, and a central cavity extending between said ends; and wherein the plurality of production modules are connected in a linear series to form a production tunnel, wherein the central cavities of each module housing collectively define a production channel, wherein the proximal end of most-proximal module housings defines the proximal end of the production tunnel, and the distal end of the most-distal module housing defines the distal end of the production tunnel, and wherein the proximal and distal ends of the production tunnel each comprise an article passage port;

at least one fluid inlet port defined along the production tunnel, said inlet port is in fluid communication with a pressurized fluid source, whereby influx of fluid from said fluid source through said fluid inlet port acts to maintain the fluid pressure within the production channel at a higher pressure than the atmospheric pressure outside of the production tunnel, such that fluid flows from both the proximal and distal article passage ports to minimize entry of air into the production channel from either the proximal or the distal article passage ports;

wherein one of said production modules positioned between said proximal-most and distal-most production modules comprises a depyrogenator module, said depyrogenator module comprising a transparent tubular body defining at least a portion of the central cavity of said production module, and an irradiation source positioned external to said transparent tubular body, said irradiation source capable of heating the internal environment of the depyrogenation module to a temperature sufficient to sterilize or depyrogenate articles passing therethrough.

In embodiment 2, the invention comprises the modular production system of embodiment 1 wherein the most proximal module housing further defines an exhaust vent positioned adjacent to said proximal article passage port, and forming vertical washout at the proximal end of the production tunnel.

In embodiment 3, the invention comprises the modular production system of embodiment 1 wherein the most distal module housing further defines an exhaust vent adjacent the distal article passage port which acts as a vertical washout for air passing into the production channel from the distal article passage port.

In embodiment 4, the invention comprises the modular production system of any of the preceding embodiments 1 to 3, wherein the irradiation source is a light source.

In embodiment 5, the invention comprises the modular production system of embodiment 4, wherein the light source is capable of heating the contents of the transparent tubular housing to at least 250° C.

In embodiment 6, the invention comprises the modular production system of embodiment 5, wherein the light source is selected from the group consisting a halogen short wave light emitter or a carbon medium wave emitter.

In embodiment 7, the invention comprises the modular production system of any of the preceding embodiments 1 to 6, wherein said transparent tubular housing comprises quartz.

In embodiment 8, the invention comprises the modular production system of any of the preceding embodiments 1 to 7, wherein the transparent tubular housing comprises an exterior surface that is at least partially covered or coated with an insulative, conductive or reflective material.

In embodiment 9, the invention comprises the modular production system of embodiment 8, wherein the reflective layer comprises a metallic coating or layer.

In embodiment 10, the invention comprises the modular production system of embodiment 9, wherein metallic coating or layer is selected from the group consisting aluminium foil, an aluminized or gold coating or nanocoating.

In embodiment 11, the invention comprises the modular production system of any one of embodiments 8 to 10, further comprising a reflecting apron extending from the external surface of the transparent tubular housing toward the irradiation source, the reflecting apron acting to redirect light toward the central cavity defined through the transparent tubular housing.

In embodiment 12, the invention comprises the modular production system of any one of the prior embodiments 1 to 11, further comprising at least one cooling module positioned distal to the depyrogenation or sterilization module, said cooling module comprising a cooling sparger in fluid communication with a cold fluid source, said cooling sparger positioned in relation to the tubular housing so as to reduce the temperature of materials present within the central cavity of the cooling channel.

In embodiment 13, the invention comprises the modular production system of embodiment 12, wherein said at least one cooling module comprises a transparent tubular housing, which defines at least portion of the central cavity of the cooling module, and said cooling sparger is positioned within said central cavity of said transparent tubular housing of said cooling module.

In embodiment 14, the invention comprises the modular production system of embodiment 13, wherein the transparent tubular housing of said at least one cooling module comprises an exterior surface, said exterior surface at least partially being covered or coated with a thermally conductive layer of material.

In embodiment 15, the invention comprises the modular production system of any one of preceding embodiments, further comprising one or more filling modules, said filling module positioned distal of the depyrogenation module and proximal of the distal-most production module, said one or more filling modules comprising one or more filling station at which containers is positioned to be filled with a material.

In embodiment 16, the invention comprises the modular production system of embodiment 15, wherein a filling module comprises a filling housing, said filling housing comprising a filling channel through which a material is passed to be positioned within a container, when the container is positioned at the one or more filling station.

In embodiment 17, the invention comprises the modular production system of embodiment 16, wherein the filling housing further comprises a channel closure, said channel closure being moveable between a first position, wherein said filling channel is sealed off from the central cavity of the filling module, and a second position, wherein the filling channel is in fluid communication with the central cavity of the filling module.

In embodiment 18, the invention comprises the modular production system of embodiment 17, wherein the channel closure comprises a metallic bellows.

In embodiment 19, the invention comprises the modular production system of embodiment 18, wherein the filing channel is in the form of a needle channel.

In embodiment 20, the invention comprises the modular production system of any one of embodiments 15 to 19, further comprising a filling mechanism attachable to the filling module, said filling mechanism adapted to deliver a material to a container positioned within the filling module.

In embodiment 21, the invention comprises the modular production system of embodiment 20, wherein the filling mechanism comprises a filling needle having a first end, a second end and a lumen extending therebetween, said first end being attached to a source of liquid to be delivered to a container, and a second end extendable into the central cavity of the filling module.

In embodiment 22, the invention comprises the modular production system of embodiment 21, wherein the filling channel is adapted to receive the filling needle.

In embodiment 23, the invention comprises the modular production system of embodiment 15, wherein the material is a fluid or a solid.

In embodiment 24, the invention comprises the modular production system of embodiment 23, wherein the fluid is a liquid.

In embodiment 25, the invention comprises the modular production system of embodiment 24, wherein the liquid is a medicament suspension or solution containing at least one active pharmaceutical ingredient.

In embodiment 26, the invention comprises the modular production system of embodiment 23, wherein the solid comprises a powder.

In embodiment 27, the invention comprises the modular production system of embodiment 26 wherein the powder comprises and active pharmaceutical or biological ingredient.

In embodiment 28, the invention comprises the modular production system of embodiment 23, wherein the fluid is an inert gas.

In embodiment 29, the invention comprises the modular production system of any of embodiments 15-28, comprising a plurality of filling mechanisms for filling materials into a container.

In embodiment 30, the invention comprises the modular production system of embodiment 29, wherein the plurality of filling mechanisms are adapted to deliver different materials.

In embodiment 31, the invention comprises the modular production system of embodiment 30, wherein the plurality of filling mechanisms are adapted to deliver different materials to the same container.

In embodiment 32, the invention comprises the modular production system of embodiment 15-30, comprising a plurality of filling modules.

In embodiment 33, the invention comprises the modular production system of embodiment 32, wherein each filling module delivers a single material, which may be the same or different from the single material delivered by another filling module in the production system.

In embodiment 34, the invention comprises the modular production system of any one of embodiments 15-33, further comprising a closure module positioned distal to said one or more filling modules, said closure module comprising a closure mechanism for sealing a container.

In embodiment 35, the invention comprises the modular production system of embodiment 34, wherein said sealing of the container is achieved by a closure, cap, crimp.

In embodiment 36, the invention comprises the modular production system of any one of embodiments 35, wherein said closure mechanism comprises a piston, having a sealing head, which acts upon a closure, to cause the closure to seal a container.

In embodiment 37, the invention comprises the modular production system of any one of embodiment 34-36, wherein the closure housing comprises a closure housing defining a piston channel, said piston channel containing said piston, further comprising an accordion like sleeve surrounding comprising a first end sealingly connected to a portion of said piston and a second end sealingly connected to a portion of the closure housing, the accordion like sleeve extending between a retracted and an extended start by movement of said piston.

In embodiment 38, the invention comprises the modular production system of any one of embodiment 34-37, further comprising a closure holder, said closure holder configured to hold closures in an aligned orientation with a container, to permit the piston to extend to press the closure into position on said container to effectuate a seal therebetween.

In embodiment 39, the invention comprises the modular production system of embodiment 38, wherein closures are fed into the closure holder by a closure feed.

In embodiment 40, the invention comprises the modular production system of embodiment 39, where said closure feed comprises a closure chute which extends into the central cavity of the closure module to feed closures into the closure holder.

In embodiment 41, the invention comprises the modular production system of any one of embodiments 1-40, further comprising an article transport system positioned within said linear production channel and extending between said proximal article passage port and said distal passage port, said article transport system configured to move containers entering the production channel from the proximal article passage port to said proximal article passage port.

In embodiment 42, the invention comprises the modular production system of embodiment 41, wherein said article transport system comprises a plurality of sections which act in a synchronized fashion.

In embodiment 43, the invention comprises the modular production system of any one of embodiments 41 and 42, wherein said article transport system comprises one or more moveable support rail sections, and one or more stationary support sections, wherein the moveable support section moves articles progressively along said one or more stationary support sections.

In embodiment 44, the invention comprises the modular production system of any one of embodiments 41-43, wherein the moveable support moves articles along the stationary support by lifting the article from the stationary support, moving the article a uniform horizontal distance in the distal direction, and lowering the article onto the stationary support.

In embodiment 45, the invention comprises the modular production system of any one of embodiments 41-44, wherein the moveable support moves vertically downward relative to the article positioned on the stationary support, so as to be below the article positioned on the stationary support, before the moveable rail moves proximal a horizontal distance, before rising vertically to once more contact the article.

In embodiment 46, the invention comprises the modular production system of any one of embodiments 45, wherein the moveable support moves in a rectangular, oval, or elliptical fashion relative to the stationary support.

In embodiment 47, the invention comprises the modular production system of any one of embodiments 45-46, wherein the moveable support is connected to a drive frame.

In embodiment 48, the invention comprises the modular production system of embodiment 41-47, wherein the drive frame comprises one or more flexible components which provide for frictionless movement of the moveable support.

In embodiment 49, the invention comprises the modular production system of embodiment 48, wherein the flexible component comprises a flexible lamella.

In embodiment 50, the invention comprises the modular production system of embodiment 49, wherein the flexible lamella is positioned within a pivot bearing.

In embodiment 51, the invention comprises the modular production system of embodiment 47, wherein said drive frame comprises one or more flexible vertical lamella, a front structural support, one or more horizontal flexible lamella, and a rear structural support;
   wherein said one or more vertical flexible lamella and one or more horizontal flexible lamella each comprise a first end and a second end; and
   wherein said front structural support defines a first portion distanced from a second portion,
   wherein said first end of said one or more vertical flexible lamella is held in a fixed position relative to an interior wall of said module housing, and said second end of said vertical lamella is connected to the first portion of said front structural support, whereby said first vertical lamella may flex vertically;

wherein said first end of said one or more horizontal flexible lamella is connected to the second portion of said front structural support, and said second end of said one or more horizontal lamella is connected to the rear structural support;

whereby flexion of the one or more vertical lamella allows vertical movement of the rear structural support, and flexion of the one or more horizontal lamella allows for horizontal movement of the rear structural support.

In embodiment 52, the invention comprises the modular production system of embodiment 51, the front and rear structural supports each define a proximal side surface and a distal side surface; and the one or more horizontal lamella comprise a first and a second horizontal lamella;

wherein the first end of the first horizontal lamella is connected to the proximal side surface of the front structural support, and the second end of the first horizontal lamella is connected to the proximal side surface of the rear structural support, and wherein the first end of the second horizontal lamella is connected to the distal side surface of the front structural support, and the second end of the second horizontal lamella is connected to the distal side surface of the rear structural support.

In embodiment 53, the invention comprises the modular production system of embodiment 51, wherein said one or more vertical and horizontal lamella are components of pivot bearings, each of said pivot bearings comprising a first pivot housing portion and a second pivot housing portion, and rotational movement of one of said pivot housings relative to the other of said pivot housings about a common axis being provided by lamellar flexion.

In embodiment 54, the invention comprises the modular production system of embodiment 53, comprising one or more vertical pivot bearings, wherein the first pivot housing portion of said one or more pivot bearing is fixedly held in relation to said interior surface of tubular housing of said production module, and the second pivot housing of said pivot bearing as fixedly held by the front structural support, such that flexion of the vertical lamella within said one or more pivot bearings allows rotational movement of the front structural support in a vertical fashion.

In embodiment 55, the invention comprises the modular production system of embodiment 53 or 54, comprising one or more horizontal pivot bearings, wherein the first pivot housing portion of said one or more pivot bearing is fixedly held in relation to said second portion of said front structural support, and the second pivot housing of said one or more pivot bearing is fixedly held by a portion of the structural support, such that flexion of the horizontal lamella within said one or more pivot bearings allows rotational movement of the rear structural support in a horizontal fashion.

In embodiment 56, the invention comprises the modular production system of embodiment 55, wherein the rear structural support comprises proximal and distal lower arms having a front portion and a rear portion, wherein front portion of the proximal lower arm firmly holds the second pivot housing of a first front horizontal pivot bearing, and wherein the front portion of the distal lower arm firmly holds the second pivot housing of a second front horizontal pivot bearing, said pivot bearing being oriented to provide rotational pivoting at said front end of said lower proximal and distal arms to provide horizontal movement of said lower arms at their rear portions.

In embodiment 57, the invention comprises the modular production system of embodiment 56, further comprising: a proximal rear horizontal pivot bearing firmly held by the rear portion of the proximal lower arm; a distal rear horizontal pivot bearing firmly held by the rear portion of the distal lower arm: and wherein the rear structural support further comprises an upper frame, said upper frame comprising a front portion adapted to connect to the moveable support rail of the internal transport system, and a rear portion defining a proximal portion which firmly secures the second pivot housing of the proximal rear horizontal pivot bearing, and a distal portion which firmly secures the second pivot housing of the distal rear horizontal pivot bearing, horizontal movement of the drive frame is accommodated by pivotal flexion in the pivot bearings fixedly held by the proximal and distal lower arms at their front and rear portions.

In embodiment 58, the invention comprises the modular production system of embodiment 57, wherein the upper frame of the rear structural support comprises:

a proximal upper arm, comprising a front portion and a rear portion;

a distal upper arm, comprising a front portion and a rear portion; and a rear support bar, comprising a proximal end portion and a distal end portion;

wherein the proximal end portion of the rear support bar is fixedly connected to the rear portion to the proximal upper arm, and the distal end portion of the rear support bar is fixedly connected to the rear portion to the distal upper arm, and wherein the proximal portion of rear portion of the upper frame is defined by the rear portion of the proximal upper arm;

wherein the distal portion of rear portion of the upper frame is defined by the rear portion of the distal upper arm; and wherein said front portion of the upper frame adapted to connect to the moveable support rail of the internal transport system, is defined by one or both of the front portions of the proximal and distal upper arms.

In embodiment 59, the invention comprises the modular production system of embodiment 50-58, wherein the rear structural support comprises a follower magnet.

In embodiment 60, the invention comprises the modular production system of embodiment 59, wherein the follower magnet comprises material which maintains is magnetic properties at temperatures of from 200° C. to 300° C.

In embodiment 61, the invention comprises the modular production system of embodiment 59 or 60, wherein the follower magnet comprises Samarium-cobalt.

In embodiment 62, the invention comprises the modular production system of any one of embodiments 59-61, further comprising one or more drive magnet positioned outside the modular housing within which is positioned said follower magnet, said drive and follower magnets being aligned, so as to allow magnetic coupling therebetween, whereby movement of said one or more drive magnet causes corresponding movement of an aligned and magnetically coupled follower magnet.

In embodiment 63, the invention comprises the modular production system of embodiment 62, further comprising, wherein said one or more drive magnet is associated with one or more elongate drive axle, whereby movement of the one or more elongate drive axle results in movement of the one or more drive magnet.

In embodiment 64, the invention comprises the modular production system of embodiment 63, wherein said one or more drive axles extend parallel to the external length the modular production system.

In embodiment 65, the invention comprises the modular production system of embodiment 64, wherein said one or more drive axles are capable of rotational movement, and linear movement, such that rotational movement causes the vertical movement of the drive magnet, and linear movement of the one or more drive axles result in the horizontal movement of the one or more drive magnets.

In embodiment 66, the invention comprises the modular production system of any one of embodiments 62 to 65, wherein the one or more drive magnet comprises a Rare Earth magnet material.

In embodiment 67, the invention comprises the modular production system of embodiment 66, wherein the one or more drive magnet comprises Samarium cobalt or Neodymium.

In embodiment 68, the invention comprises the modular production system of any one of embodiments 41 to 67, wherein the moveable support of internal transport system comprising a drive frame, a moveable support connector and a movable support rail.

In embodiment 69, the invention comprises the modular production system of embodiment 67, wherein the drive frame comprises one or more flexible member(s) allowing for frictionless directional motion in the drive frame.

In embodiment 70, the invention comprises the modular production system of embodiment 67, wherein the drive frame includes a first flexible member allowing frictionless vertical motion, and at least one second flexible member allowing frictionless horizontal motion.

In embodiment 71, the invention comprises the modular production system of embodiment 69 or 70, wherein the flexible members comprises flexible plate-like lamella.

In embodiment 72, the invention comprises the modular production system of embodiment 69 or embodiment 70, the flexible members comprise frictionless flex pivot bearings.

In embodiment 73, the invention comprises the modular production system of embodiment 72, wherein frictionless flex pivot bearings are selected from the group consisting cantilevered pivot bearings, double ended pivot bearings, or lamellar pivot bearings.

In embodiment 74, the invention comprises the modular production system of embodiment 68, wherein said moveable support connector, comprises a first end fixedly mounted to the drive frame, and a second end fixedly mounted to the movable support rail.

In embodiment 75, the invention comprises the modular production system of embodiment 68, wherein said moveable support connector, comprises a first end fixedly mounted to the drive frame, and a second end supporting, in a non-fixed manner, the movable support rail.

In embodiment 76, the invention comprises the modular production system of embodiment 75, wherein one of the second end of the support connector or the movable support rail defines an extension and the other of the second end of the support connector or the movable support rail defines a recess for receiving such extension, so as a non-fixedly connect the support connector and the movable support rail.

In embodiment 77, the invention comprises the modular production system of embodiment 76, wherein the extension comprises a raised portion, a post, or a pin.

In embodiment 78, the invention comprises the modular production system of embodiment 76 or embodiment 77, wherein said recess is shaped to correspond to the shape of the extension.

In embodiment 79, the invention comprises the modular production system any one of embodiments 76-78, wherein the recess is shaped as a groove or channel which is larger than the extension positioned therein, such that a degree of slippage is accommodated.

In embodiment 80, the invention comprises the modular production system any one of embodiments 76-78, the recess is elongate, and the extension comprises a pin or post, such that the extension may move in the elongate recess.

In embodiment 81, the invention comprises the modular production system any one of embodiments 76-80, further comprising a low friction material on or between one or more of the support connector and the movable support rail to permit slippage therebetween.

In embodiment 82, the invention comprises the modular production system any one of embodiments 68-81, wherein the movable support rail comprises a single length of support rail.

In embodiment 83, the invention comprises the modular production system any one of embodiments 68-81, wherein the movable support rail is composed of individual lengths of support rail, connected together.

In embodiment 84, the invention comprises the modular production system of embodiment 83, wherein said individual lengths of rail are connected to form a movable support rail surface by a flange on one portion of rail being positioned in a groove in an adjacent portion of rails to be joined thereto.

In embodiment 85, the invention comprises the modular production system of embodiment 84, wherein the rail portions comprising the movable support rail are constructed of independently selected materials, wherein the materials of construction may be the same or different.

In embodiment 86, the invention comprises the modular production system of embodiment 85, wherein a rail portion of the moveable support rail comprise borosilicate or quartz.

In embodiment 87, the invention comprises the modular production system of embodiment 84, where a gap exists between adjacent portions of rail to accommodate thermal expansion of the materials of construction.

In embodiment 88, the invention comprises the modular production system of embodiment 84, further comprising an elastomeric o-ring positioned around said flange, within said gap exists between adjacent portions of rail section.

In embodiment 89, the invention comprises the modular production system of any one of embodiments 41 to 80, wherein the internal transport system further comprises to a stationary support defining one or more article support surfaces.

In embodiment 90, the invention comprises the modular production system of embodiment 89, wherein the internal transport system comprises to a first stationary support defining one or more article support surfaces, and a second stationary support defining one or more article support surfaces, wherein and article positioned upon the stationary support is supported by each of the first and second support surfaces.

In embodiment 91, the invention comprises the modular production system of embodiment 90, wherein the stationary support comprises a base stationary support rail for supporting the base of an article, and a back stationary support rail which supports a further region of the article positioned thereon.

In embodiment 92, the invention comprises the modular production system of embodiment 89, wherein said stationary support further comprises one or more a support connectors having a first end fixedly mounted to the module housing, and a second end fixedly mounted to a stationary support rail.

In embodiment 93, the invention comprises the modular production system of embodiment 89, wherein said stationary support connector, comprises a first end fixedly mounted to the module housing, and a second end supporting, in a non-fixed manner, the a stationary support rail.

In embodiment 94, the invention comprises the modular production system of embodiment 93, wherein one of the second end of the stationary support connector or the stationary support rail defines an extension and the other of the second end of the stationary support connector or the stationary support rail defines a recess for receiving such extension, so as a non-fixedly connect the stationary support connector and the stationary support rail.

In embodiment 95, the invention comprises the modular production system of embodiment 94, wherein the extension comprises a raised portion, a post, or a pin.

In embodiment 96, the invention comprises the modular production system of embodiment 94 or embodiment 95, wherein said recess is shaped to correspond to the shape of the extension.

In embodiment 97, the invention comprises the modular production system any one of embodiments 94 to 96, wherein the recess is shaped as a groove or channel which is larger than the extension positioned therein, such that a degree of slippage is accommodated.

In embodiment 98, the invention comprises the modular production system any one of embodiments 94 to 97, wherein the recess is elongate, and the extension comprises a pin or post, such that the extension may move in the elongate recess.

In embodiment 99, the invention comprises the modular production system any one of embodiments 94-98, further comprising a low friction material on or between one or more of the support connector and the movable support rail to permit slippage therebetween.

In embodiment 100, the invention comprises the modular production system any one of embodiments 89-99, wherein the stationary support rail comprises a single length of support rail.

In embodiment 101, the invention comprises the modular production system any one of embodiments 89-99, wherein the stationary support rail is composed of individual lengths of support rail, connected together.

In embodiment 102, the invention comprises the modular production system of embodiment 101, wherein said individual lengths of stationary support rail are connected to form a movable support rail surface by a flange on one portion of stationary support rail being positioned in a groove in an adjacent portion of stationary support rail to be joined thereto.

In embodiment 103, the invention comprises the modular production system of embodiment 102, wherein the stationary support rail portions comprising the stationary support rail are constructed of independently selected materials, wherein the materials of construction may be the same or different.

In embodiment 104, the invention comprises the modular production system of embodiment 103, wherein a stationary support rail portion of the stationary support rail comprises borosilicate or quartz.

In embodiment 105, the invention comprises the modular production system of any one of embodiments 101-104, where a gap exists between adjacent portions of stationary support rail to accommodate thermal expansion of the materials of construction.

In embodiment 106, the invention comprises the modular production system of embodiment 105, wherein the stationary support comprises an elastomeric O-ring positioned around said flange, and positioned within said gap between adjacent portions of rail section.

In embodiment 107, the invention comprises the modular production system of any one of embodiments 74 to 106, wherein the movable support is movable relative to the stationary support surface to reposition articles positioned on the stationary support surface.

In embodiment 108, the invention comprises the modular production system of embodiment 107, wherein the moveable support moves in a plurality of dimensions relative to a support surface of the stationary support.

In embodiment 109, the invention comprises the modular production system of embodiment 107, wherein the moveable support defines one or more article positioning recesses.

In embodiment 110, the invention comprises the modular production system of embodiment 107 or 109, wherein the stationary support defines one or more article positioning recesses.

In embodiment 111, the invention comprises the modular production system of any one of embodiments 74 to 110, wherein the moveable support rail comprises a L-shaped rail, comprising a lower arm, and an upwardly extending back portion.

In embodiment 112, the invention comprises the modular production system of embodiment 111, wherein the L-shaped rail is positioned at an angle, so as to hold an article positioned thereon in an inclined orientation.

In embodiment 113, the invention comprises the modular production system of any one of embodiments 112, wherein the stationary base rail support surface is oriented at an angle other than horizontal, so as to hold an article positioned thereon in an inclined orientation.

In embodiment 114, the invention comprises a production module for the performance of at least one operation useful in the production of products comprising:
  a) a module housing defining an internal cavity, said module housing comprising a first end and a second end, said ends of said housing each comprising an opening, said end openings being in communication with said internal cavity, forming a channel through said housing,
  b) an internal transport system positioned within the housing, the internal transport system comprising:
  i.) a drive frame,
  ii.) a moveable article support surface attached to said drive frame, and
  iii.) a stationary article support surface, wherein the drive frame comprises
    (a) a first portion held in a fixed position within the housing channel,
    (b) a second portion suspended within said channel, and supporting the moveable article support surface,
    (c) at least one flexible lamella positioned between the first portion and the second portion of the drive frame, wherein flexion of the lamella permits movement of the second end of the drive frame in response to a directional force; and
  c) an operational assembly associated with said housing for performing an operation therein.

In embodiment 115, the invention comprises the production module according of embodiment 114, wherein said housing defines an end wall, having formed therein an article access opening.

In embodiment 116, the invention comprises the production module of embodiment 115, wherein article access opening is in the form of a mouse hole size to accommodate an article being passed into said channel.

In embodiment 117, the invention comprises the production module of any one of embodiments 114 to 116, wherein at least one of said ends is adapted for attachment to a further production module.

In embodiment 118, the invention comprises the production module of embodiment 117, wherein said housing comprises interconnected walls having interior and exterior surfaces, and said exterior surfaces having a first end portion adjacent the first end of said housing and a second end portion adjacent the second end of said housing, and at least one of said first or second end portions is adapted for attachment to a further production module.

In embodiment 119, the invention comprises the production module of embodiment 118, wherein at least one of said housing wall end portions further includes a sealing surface extending circumferentially around the housing.

In embodiment 120, the invention comprises the production module of embodiment 119, wherein said sealing surface is provided by an O-ring In embodiment 121, the invention comprises the production module of embodiment 120, wherein at least one of said housing wall end portions, defines a circumferential O-ring recess extending around the exterior surface of said housing, within which is positioned said O-ring.

In embodiment 122, the invention comprises the production module of embodiment 117, wherein said housing comprises interconnected walls having interior surfaces defining said housing cavity and exterior surfaces, and said walls each having a first end portion adjacent the first end of said housing and a second end portion adjacent the second end of said housing, and said first and second end portions are each adapted for attachment to a further production module.

In embodiment 123, the invention comprises the production module of embodiment 121, wherein said housing wall end portions each further comprise a sealing surface extending circumferentially around the exterior of housing.

In embodiment 124, the invention comprises the production module of embodiment 123, wherein one or both of said sealing surfaces is provided by one or more O-rings.

In embodiment 125, the invention comprises the production module of embodiment 117, wherein one or both of said housing wall end portions include a circumferential O-ring recess extending around the exterior surface of said housing, within which is positioned an O-ring, said O-ring providing said sealing surface.

In embodiment 126, the invention comprises the production module of embodiment 117, wherein said housing comprises interconnected walls having interior and exterior surfaces, and said exterior surfaces having a first end portion adjacent the first end of said housing and a second end portion adjacent the second end of said housing, wherein one of said end said portions further comprises an integral mounding sleeve, having an inner sealing surface adapted to facilitate connection to a further production module.

In embodiment 127, the invention comprises the production module of embodiment 126, wherein said integral mounting sleeve inner sealing surface defines an O-ring recess extending around the inner circumference of said sleeve.

In embodiment 128, the invention comprises the production module of embodiment 114-127, wherein the channel of the module housing is maintained at a higher air pressure than the atmosphere outside the module housing, such that net air flow is from the channel.

In embodiment 129, the invention comprises the production module of embodiment 128, wherein the module housing further comprises an air inlet, connectable to a pressurized air source to provide air flow to the channel.

In embodiment 130, the invention comprises the production module of any one of embodiments 128 or 129, wherein the module housing further comprises a filter housing, said filter housing defining said air inlet.

In embodiment 131, the invention comprises the production module of embodiment 129, further comprising an air filter positioned between said air inlet and said module housing channel.

In embodiment 132, the invention comprises the production module of embodiment 131, wherein the module housing further comprises a filter housing, said filter housing defining said air inlet, and an air filter positioned between said air inlet and said module housing channel.

In embodiment 133, the invention comprises the production module of embodiment 114, wherein the housing is defined by one or more wall portions having interior and exterior surfaces, wherein the interior surfaces of the wall portions define the channel.

In embodiment 134, the invention comprises the production module of embodiment 114, comprising a proximal end housing defining a proximal end housing internal cavity, a distal end housing defining a distal end housing internal cavity, and a tubular housing defining an axial bore therethrough, wherein the tubular housing is positioned between the proximal end housing and distal end housing, wherein the proximal end housing internal cavity, axial bore and distal end housing internal cavity are in fluid communication and collectively define the channel through the production module.

In embodiment 135, the invention comprises the production module of embodiment 134, wherein the tubular housing comprises a light radiation transparent material.

In embodiment 136, the invention comprises the production module of embodiment 135, wherein the light radiation transparent material is tolerant of heat of 250 degrees Celsius or greater.

In embodiment 137, the invention comprises the production module of embodiment 136, wherein the light radiation transparent material is selected from the group consisting quartz, borosilicate, and heat tolerant glass.

In embodiment 138, the invention comprises the production module of embodiment 137, wherein the light radiation transparent material is quartz.

In embodiment 139, the invention comprises the production module of embodiment 138, wherein the tubular housing comprises metal, glass or ceramic.

In embodiment 140, the invention comprises the production module of embodiment 139, wherein one or more of the end housings comprise metal.

In embodiment 141, the invention comprises the production module of any one of embodiments 134 to 140, wherein the proximal end housing and the distal end housing are each adapted for attachment to a further production module.

In embodiment 142, the invention comprises the production module of embodiment 141, wherein (a) the proximal end housing comprises an open proximal end, and top, front, bottom, and back walls, the walls having interior and exterior surfaces, and the exterior surfaces of the walls of the proximal end housing comprise a proximal end portion; and; (b) the distal end housing comprises an open end, and top, front, bottom, and back walls, the walls having interior and exterior surfaces, and the exterior surfaces of walls of the distal end housing comprises a distal end portion, and (c)

wherein the proximal end portion of the proximal end housing and the distal end portion of the distal end housing are each adapted for attachment to a further production module.

In embodiment 143, the invention comprises the production module of embodiment 142, wherein at least one of said proximal or distal end portions further includes a sealing surface to create a seal between adjacent modules.

In embodiment 144, the invention comprises the production module of embodiment 143, wherein said sealing surface is provided by an O-ring In embodiment 145, the invention comprises the production module of embodiment 144, wherein at least one of said proximal or distal end portions defines a circumferential O-ring recess extending around the exterior surface of said end housing, within which is positioned said O-ring.

In embodiment 146, the invention comprises the production module of embodiment 142, wherein both of said proximal or distal end portions further include a sealing surface extending circumferentially around the respective end housing.

In embodiment 147, the invention comprises the production module of embodiment 146, wherein said sealing surface is provided by an O-ring In embodiment 148, the invention comprises the production module of embodiment 144, wherein each of said proximal and distal end portions define a circumferential O-ring recess extending around the exterior surface of said end housing, within which is positioned a respective O-ring.

In embodiment 149, the invention comprises the production module of embodiment 134, wherein one of the proximal end portion or distal end portion further comprises an integral mounting sleeve, having an inner sealing surface adapted to facilitate connection to a further production module.

In embodiment 150, the invention comprises the production module of embodiment 104, wherein said integral mounting sleeve inner sealing surface defines an O-ring recess extending around the inner circumference of said sleeve.

In embodiment 151, the invention comprises the production module of embodiment 150, wherein a resilient O-ring is positioned the inner sealing surface O-ring recess.

In embodiment 152, the invention comprises the production module of any one of embodiments 134-151, further comprising an irradiation source for irradiating the tubular housing, such that articles passing through the tube are sterilized thereby.

In embodiment 153, the invention comprises the production module of any one of embodiments 152, wherein the irradiation source is a light source.

In embodiment 154, the invention comprises the production module of embodiment 153, wherein the light source generates light radiation in the infrared range.

In embodiment 155, the invention comprises the production module of embodiment 152-154, wherein the tubular housing has an exterior surface, and inner surface and the irradiation source is positioned adjacent the outer surface to direct radiation through the exterior surface of the tubular housing and the interior surface to irradiate the bore of the axial tubular housing.

In embodiment 156, the invention comprises the production module of embodiment 152-155, wherein the tubular housing has an exterior surface and further comprises a reflective layer on or adjacent the exterior surface of the tubular housing, said reflective layer having a reflective surface facing the central bore of the tubular housing, such that radiation from the irradiation source passing through the housing and into the bore is redirected by the reflective surface back toward the bore of the tubular housing.

In embodiment 157, the invention comprises the production module of embodiment 156, where the reflective layer defines an exposure window between the irradiation source and the external surface of the transparent tubular housing.

In embodiment 158, the invention comprises the production module of embodiment 156 or 157, wherein the tubular housing further includes a reflective apron comprising a reflective underside, the reflective apron extending outward from the surface of the tubular housing adjacent the exposure window and toward the irradiation source, and such that radiation from the irradiation source exiting the tubular housing through the exposure window is redirected by the reflective underside of the reflective apron back toward the bore of the tubular housing.

In embodiment 159, the invention comprises the production module of any one of embodiments 152 to 158, further comprising a cold air sparger positioned adjacent the irradiation source, the cold air sparger being in fluid communication with a cold air source, said cold air sparger comprising one of more sparger vents for directing the cold air from the cold air source onto the irradiation source to cool the irradiation source.

In embodiment 160, the invention comprises the production module of any one of embodiments 134 to 159, wherein the proximal end housing comprises a distal side wall, said distal side wall defining an access opening extending through the distal side wall, providing fluid communication between said proximal end housing internal cavity and the central bore of the tubular housing; and
    wherein the distal end housing comprises a proximal side wall, said proximal side wall side wall defining an access opening extending through the proximal side wall, providing fluid communication between said distal end housing internal cavity and the central bore of the tubular housing.

In embodiment 161, the invention comprises the production module of embodiment 160, further comprising:
    a proximal ring shaped bracket comprising an inner circumferential surface, said an inner circumferential surface defining a central opening, said bracket being sealingly connected to the distal wall of the proximal end housing such that the ring-shaped bracket surrounds the access opening extending through the distal side wall; and
    a distal ring shaped bracket comprising an inner circumferential surface, said inner circumferential surface defining a central opening, said distal ring shaped bracket being sealingly connected to the proximal wall of the proximal end housing such that the distal ring shaped bracket surrounds the access opening extending through the distal side wall; and
    wherein said tubular housing comprises
    an external surface;
    a proximal end, the proximal end of the tubular housing sealingly positioned within the central opening of the proximal ring-shaped bracket; and
    a distal end, the distal end of the tubular housing sealingly positioned within the central opening of the distal ring-shaped bracket; and
    wherein the tubular housing is sealingly connected to each end housing, and the access openings in the distal side wall of the proximal end housing and the proximal side wall of the distal end housing provide fluid communication between the internal cavities of the end housings and axial bore of the tubular housing.

In embodiment 162, the invention comprises the production module of embodiment 161, further comprising:
a first O-ring, said first O-ring being compressed between the inner circumferential surface of the proximal ring shaped bracket and the exterior surface of the tubular housing at the proximal end of the tubular housing; and
a second O-ring, said second O-ring being compressed between the inner circumferential surface of the distal ring-shaped bracket and the exterior surface of the tubular housing at the distal end of the tubular housing.

In embodiment 163, the invention comprises the production module of embodiment 162, wherein the inner circumferential surface of the proximal ring-shaped bracket defines and O-ring recess in which is positioned a portion of the first O-ring; and the inner circumferential surface of the distal ring-shaped bracket defines an O-ring recess in which is positioned a portion of the second first O-ring.

In embodiment 164, the invention comprises the production module of embodiment 152 to 163, further comprising a cold air sparger positioned adjacent the irradiation source, the cold air sparger being in fluid communication with a cold air source, said cold air sparger comprising one of more sparger vents for directing the cold air from the cold air source onto the irradiation source to cool the irradiation source.

In embodiment 165, the invention comprises the production module of any one of embodiments 134-151, further comprising a cold air sparger comprising a cold air sparger tube, said cold air sparger tube being positioned in the internal cavity of the module housing, said sparger tube having an external body defining an internal bore and one or more exit ports extending through said sparger body; said cold air sparger being in fluid communication with a cold air source to provide cold air through said internal bore of said sparger and out of said one or more exit ports in said sparger body and into the internal cavity of the module housing.

In embodiment 166, the invention comprises the production module of embodiment 165, further comprising an air filter positioned between the cold air source and the one or more exit ports in said sparger body.

In embodiment 167, the invention comprises the production module of embodiment 166 further comprising a filter housing containing the air filter.

In embodiment 168, the invention comprises the production module of embodiment 167, wherein a filter housing is affixed to or a component of the module housing.

In embodiment 169, the invention comprises the production module of any one of embodiment 166 to 168, wherein the filter is a HEPA filter In embodiment 170, the invention comprises the production module of any one of embodiments 134 to 151, wherein the operational assembly is a filling mechanism for depositing an amount of a material into a container which is positioned upon the internal transport system within said module.

In embodiment 171, the invention comprises the production module of embodiment 170, wherein the material delivered by the filing mechanism comprises a liquid, a gas or a solid.

In embodiment 172, the invention comprises the production module of embodiment 171, wherein the material delivered by the filling mechanism comprises an active pharmaceutical ingredient.

In embodiment 173, the invention comprises the production module of embodiment 171, wherein the material delivered by the filling mechanism comprises a liquid suspension or a liquid solution.

In embodiment 174, the invention comprises the production module of embodiment 173, wherein the material delivered by the filling mechanism comprises an active pharmaceutical ingredient.

In embodiment 175, the invention comprises the production module of any one of embodiments 170-174, further comprising:
a container defining a material containment cavity, wherein said container is positionable upon a portion of said internal transport system, and is transported by the internal transport system through said channel within said module housing;
wherein said filling mechanism further comprises a filling housing, said housing defining a filling needle channel defined therethrough and in fluid communication with said channel within said module housing, said needle channel being adapted to receive a filling needle;
wherein said filling needle comprises an elongate body comprising a first end, a second end, and a central lumen extending therebetween to allow fluid to flow from said first end to said second end through said filling needle;
wherein said filling needle is positionable in said filling channel such that the second end of said filling needle is positionable over or within said material containment cavity of said container.

In embodiment 176, the invention comprises the production module of any one of embodiments 114 to 128, wherein the operational assembly comprises a closure mechanism for sealing a container positioned therein.

In embodiment 177, the invention comprises the production module of embodiment 176, wherein said sealing of the container is achieved by a closure, cap, crimp.

In embodiment 178, the invention comprises the production module of embodiment 130, wherein said closure mechanism comprises a piston, having a sealing head, which acts upon a closure, to cause the closure to seal a container.

In embodiment 179, the invention comprises the production module of embodiment 178, wherein the module further comprises a closure housing defining a piston channel, and said piston channel containing said piston, further comprising an accordion like sleeve surrounding comprising a first end sealingly connected to a portion of said piston and a second end sealingly connected to a portion of the closure housing, the accordion like sleeve extending between a retracted and an extended start by movement of said piston.

In embodiment 180, the invention comprises the production module of any one of embodiments 176 to 179, further comprising a closure holder, said closure holder configured to hold closures in an aligned orientation with a container, to permit the piston to extend to press the closure into position on said container to effectuate a seal therebetween.

In embodiment 181, the invention comprises the production module of any one of embodiments 176 to 180, wherein closures are fed into the closure holder by a closure feed.

In embodiment 182, the invention comprises the production module of embodiment 181, where said closure feed comprises a closure chute which extends into the central cavity of the closure module to feed closures into the closure holder.

In embodiment 183, the invention comprises the production module of any one of embodiments 114 to 182, further comprising an article transport system positioned within said linear production channel and extending between said proximal article passage port and said distal passage port, said article transport system configured to move containers entering the production channel from the proximal article passage port to said proximal article passage port.

In embodiment 184, the invention comprises the production module of embodiment 183, wherein said article transport system comprises a plurality of sections which act in a synchronized fashion.

In embodiment 185, the invention comprises the production module of any one of embodiments 183 and 184, wherein said article transport system comprises one or more moveable support rail sections, and one or more stationary support sections, wherein the moveable support section moves articles progressively along said one or more stationary support sections.

In embodiment 186, the invention comprises the production module of any one of embodiments 183-185, wherein the moveable support moves articles along the stationary support by lifting the article from the stationary support, moving the article a uniform horizontal distance in the distal direction, and lowering the article onto the stationary support.

In embodiment 187, the invention comprises the production module of any one of embodiments 183-166, wherein the moveable support moves vertically downward relative to the article positioned on the stationary support, so as to be below the article positioned on the stationary support, before the moveable rail moves proximal a horizontal distance, before rising vertically to once more contact the article.

In embodiment 188, the invention comprises the production module of embodiment 187, wherein the moveable support moves in a rectangular, oval, or elliptical fashion relative to the stationary support.

In embodiment 189, the invention comprises the production module of any one of embodiments 187-188, wherein the moveable support is connected to a drive frame.

In embodiment 190, the invention comprises the production module of embodiment 183-189, wherein the drive frame comprises one or more flexible components which provide for frictionless movement of the moveable support.

In embodiment 191, the invention comprises the production module of embodiment 190, wherein the flexible component comprises a flexible lamella.

In embodiment 192, the invention comprises the production module of embodiment 191, wherein the flexible lamella is positioned within a pivot bearing.

In embodiment 193, the invention comprises the production module of embodiment 189, wherein said drive frame comprises one or more flexible vertical lamella, a front structural support, one or more horizontal flexible lamella, and a rear structural support;
- wherein said one or more vertical flexible lamella and one or more horizontal flexible lamella each comprise a first end and a second end; and
- wherein said front structural support defines a first portion distanced from a second portion,
- wherein said first end of said one or more vertical flexible lamella is held in a fixed position relative to an interior wall of said module housing, and said second end of said vertical lamella is connected to the first portion of said front structural support, whereby said first vertical lamella may flex vertically;
- wherein said first end of said one or more horizontal flexible lamella is connected to the second portion of said front structural support, and said second end of said one or more horizontal lamella is connected to the rear structural support;
- whereby flexion of the one or more vertical lamella allows vertical movement of the rear structural support, and flexion of the one or more horizontal lamella allows for horizontal movement of the rear structural support.

In embodiment 194, the invention comprises the production module of embodiment 193, the front and rear structural supports each define a proximal side surface and a distal side surface; and the one or more horizontal lamella comprise a first and a second horizontal lamella;
- wherein the first end of the first horizontal lamella is connected to the proximal side surface of the front structural support, and the second end of the first horizontal lamella is connected to the proximal side surface of the rear structural support, and
- wherein the first end of the second horizontal lamella is connected to the distal side surface of the front structural support, and the second end of the second horizontal lamella is connected to the distal side surface of the rear structural support.

In embodiment 195, the invention comprises the production module of embodiment 193, wherein said one or more vertical and horizontal lamella are components of pivot bearings, each of said pivot bearings comprising a first pivot housing portion and a second pivot housing portion, and rotational movement of one of said pivot housings relative to the other of said pivot housings about a common axis being provided by lamellar flexion.

In embodiment 196, the invention comprises the production module of embodiment 195, comprising one or more vertical pivot bearings, wherein the first pivot housing portion of said one or more pivot bearing is fixedly held in relation to said interior surface of tubular housing of said production module, and the second pivot housing of said pivot bearing as fixedly held by the front structural support, such that flexion of the vertical lamella within said one or more pivot bearings allows rotational movement of the front structural support in a vertical fashion.

In embodiment 197, the invention comprises the production module of embodiment 195 or 196, comprising one or more horizontal pivot bearings, wherein the first pivot housing portion of said one or more pivot bearing is fixedly held in relation to said second portion of said front structural support, and the second pivot housing of said one or more pivot bearing is fixedly held by a portion of the structural support, such that flexion of the horizontal lamella within said one or more pivot bearings allows rotational movement of the rear structural support in a horizontal fashion.

In embodiment 198, the invention comprises the production module of embodiment 197, wherein the rear structural support comprises proximal and distal lower arms having a front portion and a rear portion, wherein front portion of the proximal lower arm firmly holds the second pivot housing of a first front horizontal pivot bearing, and wherein the front portion of the distal lower arm firmly holds the second pivot housing of a second front horizontal pivot bearing, said pivot bearing being oriented to provide rotational pivoting at said front end of said lower proximal and distal arms to provide horizontal movement of said lower arms at their rear portions.

In embodiment 199, the invention comprises the production module of embodiment 198, further comprising: a proximal rear horizontal pivot bearing firmly held by the rear portion of the proximal lower arm; a distal rear horizontal pivot bearing firmly held by the rear portion of the distal lower arm: and wherein the rear structural support further comprises an upper frame, said upper frame comprising a front portion adapted to connect to the moveable support rail of the internal transport system, and a rear portion defining a proximal portion which firmly secures the second pivot housing of the proximal rear horizontal pivot bearing, and a distal portion which firmly secures the second pivot housing of the distal rear horizontal pivot bearing, horizontal movement of the drive frame is accommodated by pivotal flexion in the pivot bearings fixedly held by the proximal and distal lower arms at their front and rear portions.

In embodiment 200, the invention comprises the production module of embodiment 199, wherein the upper frame of the rear structural support comprises:
- a proximal upper arm, comprising a front portion and a rear portion;
- a distal upper arm, comprising a front portion and a rear portion; and
- a rear support bar, comprising a proximal end portion and a distal end portion;
- wherein the proximal end portion of the rear support bar is fixedly connected to the rear portion to the proximal upper arm, and the distal end portion of the rear support bar is fixedly connected to the rear portion to the distal upper arm, and
- wherein the proximal portion of rear portion of the upper frame is defined by the rear portion of the proximal upper arm;
- wherein the distal portion of rear portion of the upper frame is defined by the rear portion of the distal upper arm; and
- wherein said front portion of the upper frame adapted to connect to the moveable support rail of the internal transport system, is defined by one or both of the front portions of the proximal and distal upper arms.

In embodiment 201, the invention comprises the production module of embodiment 192-200, wherein the rear structural support comprises a follower magnet.

In embodiment 202, the invention comprises the production module of embodiment 201, wherein the follower magnet comprises material which maintains is magnetic properties at temperatures of from 200° C. to 300° C.

In embodiment 203, the invention comprises the production module of embodiment 201 or 202, wherein the follower magnet comprises Samarium-cobalt.

In embodiment 204, the invention comprises the production module of any one of embodiments 201 to 203, further comprising one or more drive magnet positioned outside the modular housing within which is positioned said follower magnet, said drive and follower magnets being aligned, so as to allow magnetic coupling therebetween, whereby movement of said one or more drive magnet causes corresponding movement of an aligned and magnetically coupled follower magnet.

In embodiment 205, the invention comprises the production module of embodiment 204, further comprising, wherein said one or more drive magnet is associated with one or more elongate drive axle, whereby movement of the one or more elongate drive axle results in movement of the one or more drive magnet.

In embodiment 206, the invention comprises the production module of embodiment 205, wherein said one or more drive axles extend parallel to the external length the production module.

In embodiment 207, the invention comprises the production module of embodiment 206, wherein said one or more drive axles are capable of rotational movement, and linear movement, such that rotational movement causes the vertical movement of the drive magnet, and linear movement of the one or more drive axles result in the horizontal movement of the one or more drive magnets.

In embodiment 208, the invention comprises the production module of any one of embodiments 204 to 207, wherein the one or more drive magnet comprises a Rare Earth magnet material.

In embodiment 209, the invention comprises the production module of embodiment 208, wherein the one or more drive magnet comprises Samarium cobalt or Neodymium.

In embodiment 210, the invention comprises the production module of any one of embodiments 183 to 209, wherein the moveable support of internal transport system comprising a drive frame, a moveable support connector and a movable support rail.

In embodiment 211, the invention comprises the production module of embodiment 209, wherein the drive frame comprises one or more flexible member(s) allowing for frictionless directional motion in the drive frame.

In embodiment 212, the invention comprises the production module of embodiment 209, wherein the drive frame includes a first flexible member allowing frictionless vertical motion, and at least one second flexible member allowing frictionless horizontal motion.

In embodiment 213, the invention comprises the production module of embodiment 211 or embodiment 212, wherein the flexible members comprise flexible plate-like lamella.

In embodiment 214, the invention comprises the production module of embodiment 211 or embodiment 212, the flexible members comprise frictionless flex pivot bearings.

In embodiment 215, the invention comprises the production module of embodiment 214, wherein frictionless flex pivot bearings are selected from the group consisting cantilevered pivot bearings, double ended pivot bearings, or lamellar pivot bearings.

In embodiment 216, the invention comprises the production module of embodiment 210, wherein said moveable support connector, comprises a first end fixedly mounted to the drive frame, and a second end fixedly mounted to the movable support rail.

In embodiment 217, the invention comprises the production module of embodiment 210, wherein said moveable support connector, comprises a first end fixedly mounted to the drive frame, and a second end supporting, in a non-fixed manner, the movable support rail.

In embodiment 218, the invention comprises the production module of embodiment 217, wherein one of the second end of the support connector or the movable support rail defines an extension and the other of the second end of the support connector or the movable support rail defines a recess for receiving such extension, so as a non-fixedly connect the support connector and the movable support rail.

In embodiment 219, the invention comprises the production module of embodiment 218, wherein the extension comprises a raised portion, a post, or a pin.

In embodiment 220, the invention comprises the production module of embodiment 218 or embodiment 219, wherein said recess is shaped to correspond to the shape of the extension.

In embodiment 221, the invention comprises the production module any one of embodiments 218 to 220, wherein the recess is shaped as a groove or channel which is larger than the extension positioned therein, such that a degree of slippage is accommodated.

In embodiment 222, the invention comprises the production module any one of embodiments 218 to 220, the recess is elongate, and the extension comprises a pin or post, such that the extension may move in the elongate recess.

In embodiment 223, the invention comprises the production module any one of embodiments 218 to 222, further comprising a low friction material on or between one or more of the support connector and the movable support rail to permit slippage therebetween.

In embodiment 224, the invention comprises the production module any one of embodiments 218 to 223, wherein the movable support rail comprises a single length of support rail.

In embodiment 225, the invention comprises the production module any one of embodiments 218 to 223, wherein the movable support rail is composed of individual lengths of support rail, connected together.

In embodiment 226, the invention comprises the production module of embodiment 225, wherein said individual lengths of rail are connected to form a movable support rail surface by a flange on one portion of rail being positioned in a groove in an adjacent portion of rails to be joined thereto.

In embodiment 227, the invention comprises the production module of embodiment 226, wherein the rail portions comprising the movable support rail are constructed of independently selected materials, wherein the materials of construction may be the same or different.

In embodiment 228, the invention comprises the production module of embodiment 227, wherein a rail portion of the moveable support rail comprise borosilicate or quartz.

In embodiment 229, the invention comprises the production module of any one of embodiment 226 to 229, where a gap exists between adjacent portions of rail to accommodate thermal expansion of the materials of construction.

In embodiment 230, the invention comprises the production module of any one of embodiments 226 to 229, further comprising an elastomeric O-ring positioned around said flange, within said gap exists between adjacent portions of rail section.

In embodiment 231, the invention comprises the production module of any one of embodiments 183 to 222, wherein the internal transport system further comprises to a stationary support defining one or more article support surfaces.

In embodiment 232, the invention comprises the production module of embodiment 231, wherein the internal transport system comprises to a first stationary support defining one or more article support surfaces, and a second stationary support defining one or more article support surfaces, wherein and article positioned upon the stationary support is supported by each of the first and second support surfaces.

In embodiment 233, the invention comprises the production module of embodiment 232, wherein the stationary support comprises a base stationary support rail for supporting the base of an article, and a back stationary support rail which supports a further region of the article positioned thereon.

In embodiment 234, the invention comprises the production module of embodiment 231, wherein said stationary support further comprises one or more a support connectors having a first end fixedly mounted to the module housing, and a second end fixedly mounted to a stationary support rail.

In embodiment 235, the invention comprises the production module of embodiment 231, wherein said stationary support connector, comprises a first end fixedly mounted to the module housing, and a second end supporting, in a non-fixed manner, the stationary support rail.

In embodiment 236, the invention comprises the production module of embodiment 235, wherein one of the second end of the stationary support connector or the stationary support rail defines an extension and the other of the second end of the stationary support connector or the stationary support rail defines a recess for receiving such extension, so as a non-fixedly connect the stationary support connector and the stationary support rail.

In embodiment 237, the invention comprises the production module of embodiment 236, wherein the extension comprises a raised portion, a post, or a pin.

In embodiment 238, the invention comprises the production module of embodiment 236 or embodiment 237, wherein said recess is shaped to correspond to the shape of the extension.

In embodiment 239, the invention comprises the production module any one of embodiments 236 to 238, wherein the recess is shaped as a groove or channel which is larger than the extension positioned therein, such that a degree of slippage is accommodated.

In embodiment 240, the invention comprises the production module any one of embodiments 236 to 239, wherein the recess is elongate, and the extension comprises a pin or post, such that the extension may move in the elongate recess.

In embodiment 241, the invention comprises the production module any one of embodiments 236 to 240, further comprising a low friction material on or between one or more of the support connector and the movable support rail to permit slippage therebetween.

In embodiment 242, the invention comprises the production module any one of embodiments 231 to 241, wherein the stationary support rail comprises a single length of support rail.

In embodiment 243, the invention comprises the production module any one of embodiments 231 to 241, wherein the stationary support rail is composed of individual lengths of support rail, connected together.

In embodiment 244, the invention comprises the production module of embodiment 243, wherein said individual lengths of stationary support rail are connected to form a movable support rail surface by a flange on one portion of stationary support rail being positioned in a groove in an adjacent portion of stationary support rail to be joined thereto.

In embodiment 245, the invention comprises the production module of embodiment 244, wherein the stationary support rail portions comprising the stationary support rail are constructed of independently selected materials, wherein the materials of construction may be the same or different.

In embodiment 246, the invention comprises the production module of embodiment 245, wherein a stationary support rail portion of the stationary support rail comprises borosilicate or quartz.

In embodiment 247, the invention comprises the production module of any one of embodiments 243 to 246, where a gap exists between adjacent portions of stationary support rail to accommodate thermal expansion of the materials of construction.

In embodiment 248, the invention comprises the production module of embodiment 247, wherein the stationary support comprises an elastomeric O-ring positioned around said flange, and positioned within said gap between adjacent portions of rail section.

In embodiment 249, the invention comprises the production module of any one of embodiments 216 to 248, wherein the movable support is movable relative to the stationary support surface to reposition articles positioned on the stationary support surface.

In embodiment 250, the invention comprises the production module of embodiment 249, wherein the moveable support moves in a plurality of dimensions relative to a support surface of the stationary support.

In embodiment 251, the invention comprises the production module of embodiment 249, wherein the moveable support defines one or more article positioning recesses.

In embodiment 252, the invention comprises the production module of embodiment 249 or 251, wherein the stationary support defines one or more article positioning recesses.

In embodiment 253, the invention comprises the production module of any one of embodiments 216 to 252, wherein the moveable support rail comprises a L-shaped rail, comprising a lower arm, and an upwardly extending back portion.

In embodiment 254, the invention comprises the production module of embodiment 253, wherein the L-shaped rail is positioned at an angle, so as to hold an article positioned thereon in an inclined orientation.

In embodiment 255, the invention comprises the production module of embodiment 254, wherein the stationary base rail support surface is oriented at an angle other than horizontal, so as to hold an article positioned thereon in an inclined orientation.

In embodiment 256, the invention comprises the a filling needle assembly comprising:
  an elongate filling needle, comprising a needle body having first end, a second end opposite the first end, and a central lumen extending axially through the body between the first and second end;
  a top portion, comprising a body which surrounds the first end of the elongate needle;
  an elongate, extendable sheath having a first end and a second end, an exterior surface and an interior surface, wherein the first end of the elongate sheath is sealingly connected to the top portion of the filling needle assembly and extends therefrom, such that the sheath surrounds the elongate needle; and
  a bottom portion sealingly connected to the second end of the sheath, the bottom portion comprising a body having an upper end, a lower end, and defining a needle channel extending through the upper end and the lower end, said needle channel sized to allow the elongate filling needle to extend therethrough;
    wherein the bottom portion further comprises a pierceable seal, bisecting the needle channel; so as to form a sealed environment defined by the interior surface of the elongate, extendable sheath.

In embodiment 257, the invention comprises the filling needle assembly of embodiment 256, wherein the elongate, extendable sheath is formed as an accordion, wherein alternating folds of the accordion allow the elongate sheath to occupy i) an extended position, wherein the top portion is distanced from the bottom portion, and the second end of the needle is within a sealed environment formed by the upper portion, sheath interior surface, needle channel of the lower portion, and pierceable metal seal, and ii) a retracted position, wherein the top portion is in closer proximity to the bottom portion, and the second end of the needle extends through the needle channel so as to have pierced the pierceable seal.

In embodiment 258, the invention comprises a sterilizable container for containing articles comprising:
  a container defining an interior chamber and an exit conduit comprising a mouth;
  a sealing disc positioned along the exit conduit, wherein the sealing disc seals the interior chamber of the container;
  a butterfly valve rotatable about an axle positioned within the exit conduit, between the sealing disc and the mouth,
  wherein rotation of the butterfly valve about the axle acts to shear the sealing disc, to open a passageway through the conduit between the mouth and the interior chamber of the sterilizable container.

In embodiment 259, the invention comprises the sterilizable container of embodiment 258, wherein the container and/or sealing disc comprise a heat-tolerant material, capable of withstanding sterilization conditions.

In embodiment 260, the invention comprises the sterilizable container of embodiment 258, wherein the sealing disc is metal.

In embodiment 261. The sterilizable container of embodiment 258, wherein the sealing disc is aluminium.

In embodiment 262, the invention comprises the sterilizable container of embodiment 260, wherein butterfly valve comprises a round body having a first face and second face and an annular periphery, and said axle comprises a first axle portion and a second axle portion, said first and second axle portions extending from opposite sides of the annular periphery of the body of the valve on a common axis.

In embodiment 263, the invention comprises the sterilizable container of embodiment 262, wherein said conduit comprises a first axle portion recess, and a second axle portion recess opposite the first axle portion recess, wherein the first axle portion is positioned within said first axle portion recess, and the second axle portion is positioned within said second axle portion recess, so as to permit rotation of said butterfly valve round body.

In embodiment 264, the invention comprises the process for producing a sterile container for material, comprising:
  providing production tunnel comprising interconnected operational modules having interior cavities which together form a contained environment, and at least one container, wherein the production tunnel comprises i) an infeed module providing a pressurized air source; ii) a transparent tubular housing including an irradiation source which irradiates the transparent tubular housing to a depyrogenation/sterilization temperature; and iii) an outfeed module providing a pressurized air source; and an internal drive mechanism extending through the production tunnel for transporting articles positioned thereon;
  positioning a container onto the internal transport system and passing said container into the infeed module;
  transporting said containers upon the internal transport mechanism into the transparent tubular housing;
  positioning container in the irradiated transparent tubular housing for a sufficient period depyrogenate and/or sterilize the container, to generate an irradiated container;
  and transport the sterilized container to the outfeed module on the internal transport mechanism.

In embodiment 265, the invention comprises the process of embodiment 264, wherein the production tunnel further comprises a cooling module comprising a pressurized cold air source, wherein said positioned between the transparent tubular housing including the irradiation source and the outfeed module; and the process further includes the steps of:

transporting the irradiated container from the transparent tubular housing including the irradiation source to the cooling module, and reducing the temperature of the irradiated container within the cooling module, to generate a cooled container.

In embodiment 266, the invention comprises the process of any one of embodiments 264 or 264, wherein the production tunnel further comprises a filling module comprising a filling mechanism for delivering a material to the irradiated and/or cooled container; and the process further includes the steps of:

transporting the irradiated and/or cooled container to the filling module and delivering a material from the filling mechanism to the container to generate a filled container.

In embodiment 267, the invention comprises the process of embodiment 266, wherein the filling mechanism is adapted to deposit a material into a container.

In embodiment 268, the invention comprises the process of embodiment 267, wherein material is a fluid, In embodiment 269, the invention comprises the process of embodiment 268, wherein fluid is a gas.

In embodiment 270, the invention comprises the process of embodiment 269, wherein the gas is inert.

In embodiment 271, the invention comprises the process of embodiment 268, wherein fluid is a liquid.

In embodiment 272, the invention comprises the process of embodiment 271, wherein the liquid comprises medicament containing suspension or solution.

In embodiment 273, the invention comprises the process of embodiment 267, wherein material is a solid.

In embodiment 274, the invention comprises the process of embodiment 273, wherein the solid is a powder.

In embodiment 275, the invention comprises the process of embodiment 274, wherein the powder is a medicament.

In embodiment 276, the invention comprises the process of embodiment 275, wherein the medicament is selected from the group consisting a micronized powder, spray dried powder, and a lyophilized powder.

In embodiment 277, the invention comprises the process of embodiment 267, wherein material is a capsules or tablet.

In embodiment 278, the invention comprises the process of embodiment 267, wherein material is an article of manufacture.

In embodiment 279, the invention comprises the process of any one of embodiments 264 to 278, wherein the production tunnel further comprises a closure module, comprising a closure mechanism, and the process further includes the steps of:

transporting a filled container to the closure module, and sealing the filled container to generate a filled sealed container.

In embodiment 280, the invention comprises the process of embodiment 279, wherein the closure is a cap compressed into an opening in the container;

In embodiment 281, the invention comprises the process of embodiment 279, wherein the closure is a seal over an opening of the container.

In embodiment 282, the invention comprises the process of embodiment 279, wherein the closure is a crimp around or of a portion of the container.

In embodiment 283, the invention comprises the process of any one of embodiments 264 to 282, further comprising the step of transporting the irradiated, filed or sealed container to the outfeed module.

In embodiment 284, the invention comprises the process of embodiment 283, further comprising the step of offloading the irradiated, filed or sealed container from the outfeed module.

In embodiment 285, the invention comprises the process of any one of embodiments 264 to 284, wherein the internal transport system is coupled to an external dive mechanism, wherein operation of external drive mechanism results in the internal drive system moving the container within the production tunnel from the infeed module to the outfeed module.

In embodiment 286, the invention comprises the process of embodiment 285, wherein the external drive mechanism comprises at least one drive magnet, and the internal transport system comprises at least one follower magnet, wherein said drive magnet and said follower magnet are magnetically coupled, such that movement of the drive magnet causes movement of the follower magnet, results in movement of the container by internal transport system.

In embodiment 287, the invention comprises a method for the depyrogenating and/or sterilizing a modular production system prior to its use in a manufacturing articles comprising the steps of:

a. providing a modular production system according of any one of embodiments 1 to 113; and b. exposing those portions of said modular production system defining said production channel to dry heat for a period of time, and at a temperature, sufficient to render the said portions free from pyrogen causing agents and/or sterile.

In embodiment 288, the invention comprises the method of embodiment 287 further comprising step of maintaining said production channel modular production system in a sterile and/or pyrogen free state.

In embodiment 289, the invention comprises a method for the depyrogenating and/or sterilizing a production module comprising the steps of:

a. providing one or more production module according of any one of embodiments 114 to 254; and b. exposing said one or more production module to dry heat for a period of time, and at a temperature, sufficient to render said one or more module so exposed free from pyrogen causing agents and/or sterile.

In embodiment 290, the invention comprises the method of embodiment 289, further comprising step of maintaining each exposed module in an environment to maintain its sterile and/or pyrogen free state.

What is claimed is:

1. A process for producing at least one sterile container for material, comprising the steps of:
 a) providing at least one container to be sterilized;
 b) providing a modular production system comprising: an infeed module having a housing defining an entrance, an exit, and an internal cavity between said infeed housing entrance and infeed housing exit; a sterilization module comprising a transparent tubular housing defining an entrance and exit and an interior cavity extending between said sterilization module entrance and sterilization module exit; and an outfeed module having a housing defining an entrance, an exit and an internal cavity between said outfeed housing entrance and infeed housing exit; wherein the infeed housing exit is operatively connected to the transparent tubular housing entrance, and the transparent tubular housing exit is operatively connected the entrance of the outfeed module, whereby the interior cavities the infeed module, sterilization module and outfeed modules are operatively interconnected and together form a production tunnel;

wherein each of said infeed, sterilization, and outfeed modules comprises a transport system, comprising a drive mechanism, and an internal transport mechanism, which operatively engaged to said drive mechanism having a container support surface;

the at least one container and internal transport mechanism engage to transport the at least one container from a module's entrance to the module's exit, and allows transport of the at least one container from one module to the next, allowing passage of the at least one container from the infeed module entrance to the outfeed module exit;

wherein the production system further comprises: a pressurized fluid source, operatively connected to the production tunnel, said fluid source providing pressurized air or other gas or gas mixture to maintain atmospheric pressure within the production tunnel of the production system at a level which exceeds the ambient atmospheric pressure within which the production system is housed; and wherein said sterilization module further comprises; an irradiation source which is positioned to irradiate the transparent tubular housing to a sterilization temperature;

c) positioning the at least one container for material in operational engagement with the internal support surface of the internal transport system of the infeed module, and within the greater atmospheric pressure therein, and transporting the at least one container through the infeed module internal cavity along the production tunnel and into the internal cavity of the transparent tubular housing;

d) irradiating the at least one container within the interior cavity of the transparent tubular housing at a time and temperature sufficient to sterilize the at least one container; and e) transporting the sterilized at least one container to the container support surface of the internal transportation mechanism extending through the internal cavity of the outfeed module.

2. The process of claim 1, wherein the process further comprises:

providing at least one cooling module, said at least one cooling module each comprising:

a housing, said housing having defined therein an entrance port, an exit port, and an internal cavity extending between said cooling module housing entrance and exit ports;

a transport system, comprising a drive mechanism, and an internal support surface which operatively engages a container within the cooling module which permits transport of the at least one container from the cooling module's entrance port to its exit port; and a cold air source, for providing cold air, said cold air source operatively connected to the interior cavity of the cooling module, said cold air, emerging from the cold air source acts to maintain the temperature of the cooling module internal cavity below that of the internal temperature of the internal cavity of the sterilization module;

wherein each of said at least one cooling module is positioned between said sterilization module exit, and the entrance of the outfeed module, the internal cavity of one of the at least one cooling module defines a portion of the production tunnel of the production system;

and further includes between steps d and e the step of:

transporting the sterilized at least one container from the sterilization module to the interior cavity of said cooling module, allow said sterilized at least one container to be exposed to the cold air within the cooling module interior cavity to reduce the temperature of the sterilized at least one container to a desired temperature, to generate at least one sterilized and cooled container.

3. The process of claim 2, further comprising the steps of:

providing a filling module positioned between the at least one cooling module and the outfeed module, said filling module comprising a housing having an entrance, and an exit, and a central cavity extending there between, and a filling mechanism for delivering a material to the cooled container, and a transport system, comprising a drive mechanism, and an internal transport mechanism positioned within the filling module central cavity, said internal transport mechanism comprising a container support surface; said internal transport mechanism operatively engaged with said drive mechanism; the at least one container and internal transport mechanism engage to transport the at least one container from the filling module's entrance to its exit which facilitates transport of the at least one container from one module to the next, allowing passage of the at least one container from the infeed module entrance to the outfeed module exit; and transporting the sterilized and cooled at least one container to the filling module and delivering a material from the filling mechanism to the at least one container to generate at least one filled container.

4. The process of claim 3, wherein the production tunnel further comprises: a closure module comprising a closure mechanism for sealing a container, and the process further includes the steps of:

transporting the at least one filled container to the closure module, and sealing the at least one filled container with a closure to generate at least one filled sealed container.

5. The process of claim 4, wherein the closure is a cap compressed into an opening in the at least one container.

6. The process of claim 4, wherein the closure is a seal over an opening of the at least one container.

7. The process of claim 4, wherein the closure is a crimp around or of a portion of the at least one container.

8. The process of claim 4, further comprising; the step of transporting the sterilized, filled and sealed at least one container to the outfeed module.

9. The process of claim 8, further comprising; the step of offloading the sterilized, filled and sealed at least one container from the exit port of the outfeed module.

10. The process of claim 1, wherein the drive mechanism of the infeed module, the sterilization module, and the outfeed module are external to the production tunnel and comprise at least one drive magnet, and the internal transport mechanism of each of said modules comprise at least one follower magnet, wherein said drive magnet and said follower magnet are magnetically coupled, such that movement of the drive magnet causes movement of the follower magnet, and results in movement of the at least one container by internal transport system.

11. The process of claim 3, wherein the filling mechanism is adapted to deposit a material into a container.

12. The process of claim 11, wherein the material is a fluid.

13. The process of claim 12, wherein the fluid is a liquid.

14. The process of claim 13, wherein the liquid comprises a medicament containing suspension or solution.

15. The process of claim 11, wherein the material is a solid.

16. The process of claim 15, wherein the solid is a powder.

17. The process of claim 11, wherein the powder is a medicament.

18. The process of claim 17, wherein the medicament is selected from the group consisting of a micronized powder, a spray dried powder, and a lyophilized powder.

* * * * *